United States Patent
Tanabe et al.

(10) Patent No.: US 12,370,143 B2
(45) Date of Patent: *Jul. 29, 2025

(54) COMPOUND OR SALT THEREOF AND LIPID PARTICLES

(71) Applicant: FUJIFILM Corporation, Tokyo (JP)

(72) Inventors: Shintaro Tanabe, Ashigarakami-gun (JP); Masahiko Yamamoto, Ashigarakami-gun (JP); Kimihiko Sato, Ashigarakami-gun (JP); Motomasa Takahashi, Ashigarakami-gun (JP); Kazuhiro Tsuna, Ashigarakami-gun (JP); Yasutaka Tasaki, Ashigarakami-gun (JP); Taisuke Endo, Ashigarakami-gun (JP); Issei Doi, Ashigarakami-gun (JP); Hirofumi Fukunaga, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/443,959

(22) Filed: Feb. 16, 2024

(65) Prior Publication Data
US 2024/0315970 A1    Sep. 26, 2024

Related U.S. Application Data

(63) Continuation of application No. 17/112,239, filed on Dec. 4, 2020, which is a continuation of application No. PCT/JP2019/022833, filed on Jun. 7, 2019.

(30) Foreign Application Priority Data

Jun. 8, 2018   (JP) .................................. 2018-110709

(51) Int. Cl.
A61K 9/1272 (2025.01)
A61K 9/1278 (2025.01)
(Continued)

(52) U.S. Cl.
CPC .......... A61K 9/1272 (2013.01); A61K 9/1278 (2013.01); C07C 219/06 (2013.01); C12N 15/88 (2013.01)

(58) Field of Classification Search
CPC ................ A61K 9/1272; A61K 9/1278; A61K 31/7088; A61K 9/127; A61K 9/5123;
(Continued)

(56) References Cited

U.S. PATENT DOCUMENTS 5,047,540 A    9/1991   Kamata et al.
2010/0324120 A1   12/2010   Chen et al.
(Continued)

FOREIGN PATENT DOCUMENTS

CA   3 102 985 A1   12/2019
CA   3 143 865 A1   12/2020
(Continued)

OTHER PUBLICATIONS

Office Action dated Oct. 10, 2024 issued by the United States Patent and Trademark Office in U.S. Appl. No. 17/457,793.
(Continued)

*Primary Examiner* — Joseph K McKane
*Assistant Examiner* — Meghan C Heasley
(74) *Attorney, Agent, or Firm* — Sughrue Mion, PLLC

(57) ABSTRACT

An object of the present invention is to provide a compound or a salt thereof constituting lipid particles that can achieve a high nucleic acid encapsulation rate and excellent delivery of nucleic acids, and to provide lipid particles that can achieve a high nucleic acid encapsulation rate and excellent delivery of nucleic acids. According to an aspect of the present invention, a compound represented by Formula (1) or a salt thereof is provided.

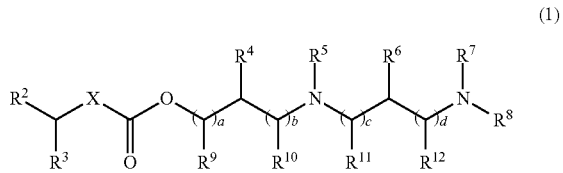

(1)

In the formula, X represents $-NR^1-$ or $-O-$, $R^1$ represents a hydrogen atom, a hydrocarbon group, or the like, $R^2$ and $R^3$ each independently represent a hydrogen atom, a hydrocarbon group, or the like, $R^4$, $R^5$, $R^6$, $R^7$, $R^8$, $R^9$, $R^{10}$, $R^{11}$, and $R^{12}$ each independently represent a hydrogen atom or an alkyl group, groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other to form a 4- to 7-membered ring which may contain an O atom, a, b, c, and d are each independently represent an integer of 0 to 3, a+b is equal to or greater than 1, and c+d is equal to or greater than 1.

28 Claims, No Drawings

(51) Int. Cl.
*C07C 219/06* (2006.01)
*C12N 15/88* (2006.01)

(58) Field of Classification Search
CPC ...... A61K 9/5192; A61K 9/107; A61K 47/14; A61K 48/0033; C07C 219/06; C07C 219/16; C07C 229/16; C07C 271/12; C07C 271/16; C07C 271/22; C07C 2601/02; C07C 2601/14; C12N 15/88; C12N 15/113; C07D 211/42; C07D 211/46; C07D 295/13
See application file for complete search history.

(56) References Cited

U.S. PATENT DOCUMENTS

| | | | |
|---|---|---|---|
| 2011/0311582 | A1 | 12/2011 | Manoharan et al. |
| 2013/0245107 | A1 | 9/2013 | de Fougerolles et al. |
| 2014/0045913 | A1 | 2/2014 | Kuboyama et al. |
| 2014/0371293 | A1 | 12/2014 | Brown et al. |
| 2015/0030667 | A1* | 1/2015 | Kaufman ............ A61K 9/127 514/114 |
| 2015/0174261 | A1 | 6/2015 | Kuboyama et al. |
| 2016/0257951 | A1 | 9/2016 | Koizumi et al. |
| 2016/0317458 | A1 | 11/2016 | Brito et al. |
| 2017/0137409 | A1 | 5/2017 | Brown |
| 2017/0137490 | A1 | 5/2017 | Brebcgley et al. |
| 2017/0157268 | A1 | 6/2017 | Ansell et al. |
| 2018/0051285 | A1 | 2/2018 | Koizumi et al. |
| 2021/0085604 | A1 | 3/2021 | Tanabe et al. |
| 2022/0096381 | A1 | 3/2022 | Endo et al. |
| 2022/0273817 | A1 | 9/2022 | Sekiguchi et al. |

FOREIGN PATENT DOCUMENTS

| | | |
|---|---|---|
| CN | 102625696 A | 8/2012 |
| CN | 104159615 A | 11/2014 |
| CN | 104873464 A | 9/2015 |
| CN | 106008272 A | 10/2016 |
| CN | 107207428 A | 9/2017 |
| CN | 112262122 A | 1/2021 |
| CN | 113924128 A | 1/2022 |
| JP | 6-298712 A | 10/1994 |
| JP | 2012-530059 A | 11/2012 |
| JP | 5288254 B2 | 9/2013 |
| JP | 2014-529328 A | 11/2014 |
| JP | 2015-501309 A | 1/2015 |
| JP | 2017-522376 A | 8/2017 |
| JP | 7178409 B2 | 11/2022 |
| TW | 201813632 A | 4/2018 |
| WO | 2007/130073 A2 | 11/2007 |
| WO | 2009/127060 A1 | 10/2009 |
| WO | 2010/054401 A1 | 5/2010 |
| WO | 2010/054405 A1 | 5/2010 |
| WO | 2010/144740 A1 | 12/2010 |
| WO | 2012/170952 A2 | 12/2012 |
| WO | 2013/059496 A1 | 4/2013 |
| WO | 2014/007398 A1 | 1/2014 |
| WO | 2015/005253 A1 | 1/2015 |
| WO | 2015/095340 A1 | 6/2015 |
| WO | 2015/095346 A1 | 6/2015 |
| WO | 2016/081029 A1 | 5/2016 |
| WO | 2018/078053 A1 | 5/2018 |
| WO | 2018/087753 A1 | 5/2018 |
| WO | 2019235635 A1 | 12/2019 |
| WO | 2020/246581 A1 | 12/2020 |

OTHER PUBLICATIONS

Office Action dated Nov. 17, 2023 issued by the United States Patent and Trademark Office in U.S. Appl. No. 17/112,239.
Extended European Search Report issued Aug. 22, 2024, in European Patent Application No. 24150973.6, corresponding to U.S. Appl. No. 17/743,584.
Advisory Action issued Aug. 22, 2024 in U.S. Appl. No. 17/112,239.
Office Action dated Jan. 28, 2025 issued in U.S. Appl. No. 17/457,793.
Office Action issued May 1, 2024 in U.S. Appl. No. 17/457,793.
Office Action issued May 7, 2024 in U.S. Appl. No. 17/112,239.
Office Action issued Jun. 4, 2024 in Japanese Application No. 2023-094459, corresponding to U.S. Appl. No. 17/743,584.
Written Opinion of the International Searching Authority issued Jul. 28, 2020 in International Application No. PCT/JP2020/022279, corresponds to U.S. Appl. No. 17/457,793.
U.S. Appl. No. 17/743,584, filed May 13, 2022 (Sekiguchi et al.).
Xue et al., "Highlighting the Role of Polymer Length, Carbohydrate Size, and Nucleic Acid Type in Potency of Glycopolycation Agents for pDNA and siRNA Delivery", Biomacromolecules, 2013, vol. 14, pp. 3903-3915 (13 pages).
Office Action dated Mar. 21, 2023 issued in Korean patent application No. 10-2020-7037881.
Chinese Office Action issued Jul. 1, 2023 in Application No. 202080079111.X.
RN 2003930-61-6, Oct. 2, 2016, Registry [online], American Chemical Society, [retrieved on Aug. 14, 2019], Retrieved from STN (1 page).
RN 2030447-26-6, Nov. 13, 2016, Registry [online], American Chemical Society, [retrieved on Aug. 14, 2019], Retrieved from STN (1 page).
International Preliminary Report on Patentability dated Dec. 8, 2020, issued by the International Bureau in application No. PCT/JP2019/022833.
International Search Report issued Jul. 28, 2020 in International Application No. PCT/JP2020/022279, corresponds to U.S. Appl. No. 17/457,793.
Written Opinion of the International Searching Authority issued Jan. 26, 2021 in International Application No. PCT/JP2020/042513, corresponds to U.S. Appl. No. 17/743,584.
Srikanth et al., "Synthesis of dihydrosterculic acid-based monoglucosyl diacylglycerol and its analogues and their biological evaluation", European Journal of Medicinal Chemistry, 2016, vol. 109, pp. 134-145 (12 pages).
Office Action issued Jun. 27, 2023 in Canadian Application No. 3,158,293.
RN 2001788-05-0, Sep. 29, 2016, Registry [online], American Chemical Society, [retrieved on Aug. 14, 2019], Retrieved from STN (1 page).
RN 2024626-33-1, Nov. 3, 2016, Registry [online], American Chemical Society, [retrieved on Aug. 14, 2019], Retrieved from STN (1 page).
RN 2155113-73-6, Dec. 10, 2017, Registry [online], American Chemical Society, [retrieved on Aug. 14, 2019], Retrieved from STN (1 page).
Written Opinion dated Aug. 27, 2019, issued by the International Searching Authority in application No. PCT/JP2019/022833.
International Search Report issued Jan. 26, 2021 in International Application No. PCT/JP2020/042513, corresponds to U.S. Appl. No. 17/743,584.
Akinc et al., "Development of Lipidoid-siRNA Formulations for Systemic Delivery to the Liver", Molecular Therapy, May 2009, vol. 17, No. 5, pp. 872-879 (8 pages).
Greene et al., Greene's Protective Groups in Organic Synthesis, Fourth Edition, 2007, pp. 697-926 (118 pages).
RN 2005720-56-7, Oct. 5, 2016, Registry [online], American Chemical Society, [retrieved on Aug. 14, 2019], Retrieved from STN (1 page).
RN 2016779-95-4, Oct. 21, 2016, Registry [online], American Chemical Society, [retrieved on Aug. 14, 2019], Retrieved from STN (1 page).
International Search Report dated Aug. 27, 2019, issued by the International Searching Authority in application No. PCT/JP2019/022833.
International Preliminary Report on Patentability issued Dec. 7, 2021 in International Application No. PCT/JP2020/022279, corresponds to U.S. Appl. No. 17/457,793.
Semple et al., "Rational design of cationic lipids for siRNA delivery", Nature Biotechnology, Feb. 2010, vol. 28, No. 2, pp. 172-176 (9 pages).

(56) References Cited

OTHER PUBLICATIONS

RN 2001907-05-5, Sep. 29, 2016, Registry [online], American Chemical Society, [retrieved on Aug. 14, 2019], Retrieved from STN (1 page).
RN 2012853-22-2, Oct. 16, 2016, Registry [online], American Chemical Society, [retrieved on Aug. 14, 2019], Retrieved from STN (1 page).
RN 2169605-81-4, Jan. 4, 2018, Registry [online], American Chemical Society, [retrieved on Aug. 14, 2019], Retrieved from STN (1 page).
Extended European Search Report dated Jun. 16, 2021, issued by the European Patent Office in European application No. 19814985.8.
Extended European Search Report dated Jul. 21, 2022 in European Application No. 20818988.6, which corresponds to U.S. Appl. No. 17/457,793.
Office Action dated Jan. 14, 2023, in Canadian Application No. 3,143,865.
Office Action dated May 24, 2022 from the Japanese Patent Office in JP Application No. 2020-523214.
Office Action issued Mar. 7, 2023 in Japanese Application No. 2022-011921.
Communication dated Feb. 17, 2022, issued by the Canadian Patent Office in Canadian application No. 3,102,985.
Office Action issued Oct. 18, 2022 in Japanese Application No. 2021-524926, corresponds to U.S. Appl. No. 17/457,793.
RN 2001651-45-0, Sep. 28, 2016, Registry [online], American Chemical Society, [retrieved on Aug. 14, 2019], Retrieved from STN (1 page).
Office Action dated Nov. 30, 2021 issued in Japanese Patent Application No. 2020-523214.
Office Action issued Nov. 1, 2022 in Chinese Application No. 201980038935.X.
Office Action issued Jul. 26, 2023 in Chinese Application No. 202080041980.3.
Office Action dated Apr. 11, 2023 issue in Japanese Patent Application No. 2021-556193.
International Preliminary Report on Patentability issued May 17, 2022 in International Application No. PCT/JP2020/042513, corresponds to U.S. Appl. No. 17/743,584.

* cited by examiner

COMPOUND OR SALT THEREOF AND LIPID PARTICLES

CROSS-REFERENCE TO RELATED APPLICATIONS

This application is a Continuation of application Ser. No. 17/112,239 filed Dec. 4, 2020, which is a Continuation of PCT International Application No. PCT/JP2019/022833 filed on Jun. 7, 2019, which claims priority under 35 U.S.C § 119(a) to Japanese Patent Application No. 2018-110709 filed on Jun. 8, 2018. Each of the above application(s) is hereby expressly incorporated by reference, in its entirety, into the present application.

BACKGROUND OF THE INVENTION

1. Field of the Invention

The present invention relates to a compound or a salt thereof and lipid particles using the compound or a salt thereof.

2. Description of the Related Art

Nucleic acid drugs have a clear mechanism of action on diseases, have few side effects, and are regarded as promising next-generation medicines. For example, a nucleic acid drug using small interfering RNA (siRNA) can inhibit the expression of a target gene in a cell in a sequence-specific manner. As a result, this drug can relieve or treat the diseases and symptoms caused by the abnormal expression of a specific gene or gene group. In order for these nucleic acids to perform their functions, the nucleic acid drugs need to be delivered into cells.

One of the methods for efficiently delivering nucleic acids into cells is a method using a viral vector such as a retrovirus or an adenovirus. The method using a viral vector brings a high gene transfer efficiency. However, the size of genes to be transferred by this method is limited, and there is a concern over immunogenicity and safety of this method. On the other hand, in a case where lipid particles are used, any gene can be transferred without limitation, and the above problems can be solved. Therefore, the lipid particles are being developed vigorously.

As a compound to be incorporated into the lipid particles, WO2010/054401A and WO2010/144740A disclose a compound having an ester group, an acetal group, or the like as a linking group that links an aliphatic group to an amino group. WO2010/054405A discloses a compound having a vinyloxy group, an amide group, an oxime group, or the like as a linking group that links an aliphatic group to an amino group. In WO2014/007398A, a compound is exemplified in which a tertiary aminoalkyl group and an aliphatic group are linked to each other by a carbamate group or the like. US2016/0317458A discloses a compound having a methylpiperazyl group, a carbonate group, and an ester group, and the like. WO2015/005253A discloses a compound having a carbonate group or the like as a linking group that links an aliphatic group to an amino group. WO2013/059496A discloses a compound having a cyclic or acyclic diamino group and the like.

SUMMARY OF THE INVENTION

The lipid particles that can function as vectors and the compounds that constitute the lipid particles are further sought for, and there is a demand for the development of compounds that can achieve a high nucleic acid encapsulation rate and excellent delivery of nucleic acids.

The present invention has been made under such circumstances, and an object thereof is to provide a compound or a salt thereof constituting lipid particles that can achieve a high nucleic acid encapsulation rate and excellent delivery of nucleic acids, and to provide lipid particles that can achieve a high nucleic acid encapsulation rate and excellent delivery of nucleic acids.

In order to achieve the above object, the inventors of the present invention have conducted intensive studies. As a result, the inventors have found that lipid particles prepared using a compound represented by Formula (1) or a salt thereof have a high nucleic acid encapsulation rate and excellently deliver nucleic acids. Based on the finding, the inventors have accomplished the present invention. According to the present invention, the following inventions are provided.

<1> A compound represented by Formula (1) or a salt thereof.

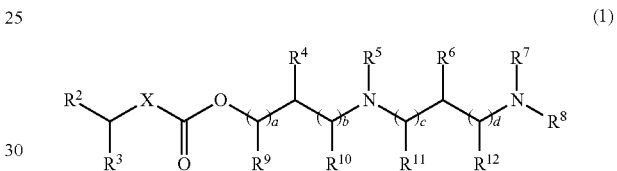
(1)

In the formula, X represents —NR$^1$— or —O—,

R$^1$ represents a hydrogen atom, a hydrocarbon group having 6 to 24 carbon atoms, or a group represented by R$^{21}$-L$^1$-R$^{22}$—, R$^{21}$ represents a hydrocarbon group having 1 to 24 carbon atoms, L$^1$ represents —O(CO)O—, —O(CO)—, —(CO)O—, —O—, or a group represented by the following formula,

R$^{22}$ represents a divalent hydrocarbon linking group having 1 to 18 carbon atoms, R$^2$ and R$^3$ each independently represent a hydrogen atom, a hydrocarbon group having 3 to 24 carbon atoms, or a group represented by R$^{31}$-L$^2$-R$^{32}$—, R$^{31}$ represents a hydrocarbon group having 1 to 24 carbon atoms, L$^2$ represents —O(CO)O—, —O(CO)—, —(CO)O—, —O—, or a group represented by the following formula,

R$^{32}$ represents a divalent hydrocarbon linking group having 1 to 18 carbon atoms, R$^4$, R$^5$, R$^6$, R$^7$, R$^8$, R$^9$, R$^{10}$, R$^{11}$, and R$^{12}$ each independently represent a hydrogen atom or an alkyl group having 1 to 18 carbon atoms that may be substituted, groups in any one or more pairs among R$^4$ and R$^5$, R$^{10}$ and R$^5$, R$^5$ and R$^{12}$, R$^4$ and R$^6$, R$^5$ and R$^6$, R$^6$ and R$^7$, R$^6$ and $R^{10}$, $R^{12}$ and $R^7$, and $R^7$ and $R^8$ may be linked to each other to form a 4- to 7-membered ring which may contain an O atom, a substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —$O(CO)O$—$R^{41}$, —$O(CO)$—$R^{42}$, —$(CO)O$—$R^{43}$, or —$O$—$R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —$O(CO)O$—$R^{41}$, —$O(CO)$—$R^{42}$, —$(CO)O$—$R^{43}$, or —$O$—$R^{44}$, $R^{41}$, $R^{42}$, $R^{43}$, $R^{44}$, $R^{45}$, and $R^{46}$ each independently represent a hydrocarbon group having 1 to 18 carbon atoms, a, b, c, and d each independently represent an integer of 0 to 3, a+b is equal to or greater than 1, and c+d is equal to or greater than 1.

<2> The compound or a salt thereof described in <1>, in which X represents —$NR^1$—, and $R^1$ has the same definition as $R^1$ in <1>.

<3> The compound or a salt thereof described in <1>, in which X represents —$NR^1$—, $R^1$ represents a hydrocarbon group having 6 to 24 carbon atoms, or a group represented by $R^{21}$-$L^1$-$R^{22}$—, $R^{21}$, $L^1$, and $R^{22}$ have the same definitions as $R^{21}$, $L^1$, and $R^{22}$ in <1> respectively;

one of $R^2$ and $R^3$ represents a hydrogen atom and the other represents a hydrocarbon group having 3 to 24 carbon atoms or a group represented by $R^{31}$-$L^2$-$R^{32}$—, and $R^{31}$, $L^2$, and $R^{32}$ have the same definitions as $R^{31}$, $L^2$, and $R^{32}$ in <1> respectively.

<4> The compound or a salt thereof described in <1>, in which the compound represented by Formula (1) is a compound represented by Formula (1-1).

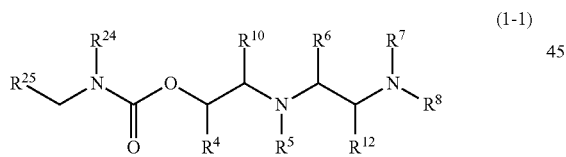

(1-1)

$R^{24}$ represents a hydrogen atom, a hydrocarbon group having 6 to 24 carbon atoms, or a group represented by $R^{21}$-$L^1$-$R^{22}$—, $R^{21}$ represents a hydrocarbon group having 1 to 24 carbon atoms, $L^1$ represents —$O(CO)O$—, —$O(CO)$—, —$(CO)O$—, —$O$—, or a group represented by the following formula,

$R^{22}$ represents a divalent hydrocarbon linking group having 1 to 18 carbon atoms, $R^{25}$ represents a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —$O(CO)O$—, —$O(CO)$—, —$(CO)O$—, —$O$—, or a group represented by the following formula,

$R^{32}$ represents a divalent hydrocarbon linking group having 1 to 18 carbon atoms, $R^4$, $R^5$, $R^6$, $R^7$, $R^8$, $R^{10}$, and $R^{12}$ each independently represent a hydrogen atom or an alkyl group having 1 to 18 carbon atoms that may be substituted, groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other to form a 4- to 7-membered ring which may contain an O atom, a substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —$O(CO)O$—$R^{41}$, —$O(CO)$—$R^{42}$, —$(CO)O$—$R^{43}$, or —$O$—$R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —$O(CO)O$—$R^{41}$, —$O(CO)$—$R^{42}$, —$(CO)O$—$R^{43}$, or —$O$—$R^{44}$, and $R^{41}$, $R^{42}$, $R^{43}$, $R^{44}$, $R^{45}$, and $R^{46}$ each independently represent a hydrocarbon group having 1 to 18 carbon atoms.

<5> The compound or a salt thereof described in <1>, in which X represents —$O$—.

<6> The compound or a salt thereof described in <1>, in which X represents —$O$—, $R^2$ and $R^3$ each independently represent a hydrocarbon group having 3 to 24 carbon atoms or a group represented by $R^{31}$-$L^2$-$R^{32}$—, and $R^{31}$, $L^2$, and $R^{32}$ have the same definitions as $R^{31}$, $L^2$, and $R^{32}$ in <1> respectively.

<7> The compound or a salt thereof described in any one of <1> to <3>, <5>, and <6>, in which $R^4$, $R^6$, $R^9$, $R^{10}$, $R^{11}$, and $R^{12}$ each represent a hydrogen atom.

<8> The compound or a salt thereof described in any one of <1> to <7>, in which $R^2$ and $R^3$ each independently represent a hydrogen atom, a hydrocarbon group having 6 to 24 carbon atoms, or a group represented by $R^{31}$-$L^2$-$R^{32}$—.

<9> The compound or a salt thereof described in <1>, in which X represents —$O$—, $R^2$, $R^3$, $R^{31}$, $L^2$, and $R^{32}$ have the same definitions as $R^2$, $R^3$, $R^{31}$, $L^2$, and $R^{32}$ in <1> respectively, $R^4$, $R^5$, $R^6$, $R^7$, $R^8$, $R^9$, $R^{10}$, $R^{11}$, and $R^{12}$ each independently represent a hydrogen atom or an alkyl group having 1 to 18 carbon atoms that may be substituted, a substituent on the alkyl group having 1 to 18 carbon atoms that may be substituted and the substituent on the substituted or unsubstituted aryl group and on the substituted or unsubstituted heteroaryl group have the same definitions as those in <1>, a+b is 1, and c+d is 1 or 2.

<10> The compound or a salt thereof described in <1>, in which the compound represented by Formula (1) is a compound represented by Formula (2).

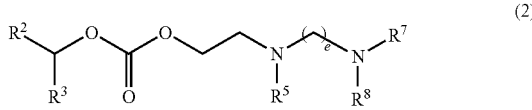

In the formula, $R^2$ and $R^3$ each independently represent a hydrogen atom, a hydrocarbon group having 3 to 24 carbon atoms, or a group represented by $R^{31}$-$L^2$-$R^{32}$—,
  $R^{31}$ represents a hydrocarbon group having 1 to 24 carbon atoms,
  $L^2$ represents —O(CO)O—, —O(CO)—, —(CO)O—, —O—, or a group represented by the following formula,

$R^{32}$ represents a divalent hydrocarbon linking group having 1 to 18 carbon atoms,
  $R^5$ represents a hydrogen atom or an alkyl group having 1 to 18 carbon atoms that may be substituted,
  $R^7$ and $R^8$ each independently represent a hydrogen atom or an alkyl group having 1 to 18 carbon atoms that may be substituted,
  a substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms,
  a substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, and
  e represents 2 or 3.
<11> The compound or a salt thereof described in <10>, in which $R^7$ and $R^8$ each independently represent a hydrogen atom or an alkyl group having 1 to 18 carbon atoms,
  a substituent on the alkyl group having 1 to 18 carbon atoms that may be substituted is a hydroxyl group, a substituted or unsubstituted aryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$ and $R^{46}$ each independently represent a hydrocarbon group having 1 to 18 carbon atoms,
  a substituent on the substituted or unsubstituted aryl group is an alkyl group having 1 to 18 carbon atoms, a hydroxyl group, a carboxyl group, an amino group represented by —$NR^{45}R^{46}$ or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$ and $R^{46}$ each independently represent a hydrocarbon group having 1 to 18 carbon atoms.
<12> The compound or a salt thereof described in <10>, in which $R^2$ and $R^3$ each independently represent a hydrocarbon group having 3 to 24 carbon atoms or a group represented by $R^{31}$-$L^2$-$R^{32}$—,
  $L^2$ represents —O(CO)— or —(CO)O—,
  $R^7$ and $R^8$ each independently represent a hydrogen atom or an alkyl group having 1 to 18 carbon atoms,
  a substituent on the alkyl group having 1 to 18 carbon atoms that may be substituted is an unsubstituted aryl group, —O(CO)—$R^{42}$, or —(CO)O—$R^{43}$, and $R^{42}$ and $R^{43}$ each independently represent a hydrocarbon group having 1 to 18 carbon atoms.
<13> The compound or a salt thereof described in <10>, in which $R^2$ and $R^3$ each independently represent a hydrogen atom or a hydrocarbon group having 3 to 24 carbon atoms,
  $R^7$ and $R^8$ each independently represent a hydrogen atom or an alkyl group having 1 to 18 carbon atoms,
  a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.
<14> The compound or a salt thereof described in <10>, in which at least one of $R^2$ or $R^3$ represents a group represented by $R^{31}$-$L^2$-$R^{32}$—,
  $L^2$ represents —O(CO)— or —(CO)O—,
  $R^7$ and $R^8$ each independently represent a hydrogen atom or an alkyl group having 1 to 18 carbon atoms,
  a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.
<15> The compound or a salt thereof described in <10>, in which $R^2$ and $R^3$ each independently represent a group represented by $R^{31}$-$L^2$-$R^{32}$—,
  $L^2$ represents —O(CO)— or —(CO)O—,
  $R^7$ and $R^8$ each independently represent a hydrogen atom or an alkyl group having 1 to 18 carbon atoms,
  a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.
<16> The compound or a salt thereof described in <10>, in which one of $R^2$ and $R^3$ represents a group represented by $R^{31}$-$L^2$-$R^{32}$— and the other represents a hydrocarbon group having 3 to 24 carbon atoms,
  $L^2$ represents —O(CO)— or —(CO)O—,
  $R^7$ and $R^8$ each independently represent a hydrogen atom or an alkyl group having 1 to 18 carbon atoms,
  a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.
<17> The compound or a salt thereof described in <10>, in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^7$ and $R^8$ each independently represent a hydrogen atom or an alkyl group having 1 to 18 carbon atoms, a substituent on the alkyl group having 1 to 18 carbon atoms that may be substituted is a group represented by —O(CO)—$R^{42}$ or —(CO)O—$R^{43}$, and $R^{42}$ and $R^{43}$ each independently represent a hydrocarbon group having 1 to 18 carbon atoms.

<18> The compound or a salt thereof described in <10>, in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or an alkyl group having 1 to 18 carbon atoms, and $R^7$ and $R^8$ each independently represent a hydrogen atom or an alkyl group having 1 to 18 carbon atoms.

<19> The compound or a salt thereof described in <10>, in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or an alkyl group having 1 to 18 carbon atoms, $R^7$ and $R^8$ each independently represent a hydrogen atom or an alkyl group having 1 to 18 carbon atoms, and e represents 2.

<20> The compound or a salt thereof described in <10>, in which one of $R^2$ and $R^3$ represents a group represented by $R^{31}$-$L^2$-$R^{32}$— and the other represents a hydrocarbon group having 3 to 5 carbon atoms, $L^2$ represents —O(CO)— or —(CO)O—, $R^5$ represents a hydrogen atom or an alkyl group having 1 to 18 carbon atoms, and $R^7$ and $R^8$ each independently represent a hydrogen atom or an alkyl group having 1 to 18 carbon atoms.

<21> The compound or a salt thereof described in <10>, in which one of $R^2$ and $R^3$ represents a group represented by $R^{31}$-$L^2$-$R^{32}$— and the other represents a hydrocarbon group having 3 to 5 carbon atoms, $L^2$ represents —O(CO)— or —(CO)O—, $R^5$ represents a hydrogen atom or an alkyl group having 1 to 18 carbon atoms, $R^7$ and $R^8$ each independently represent a hydrogen atom or an alkyl group having 1 to 18 carbon atoms, and e represents 2.

<22> The compound or a salt thereof described in <10>, in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or a substituted alkyl group having 1 to 18 carbon atoms, $R^7$ and $R^8$ each independently represent a hydrogen atom or an alkyl group having 1 to 18 carbon atoms, a substituent on the substituted alkyl group having 1 to 18 carbon atoms is a group represented by —O(CO)—$R^{42}$ or —(CO)O—$R^{43}$, and $R^{42}$ and $R^{43}$ each independently represent a hydrocarbon group having 1 to 18 carbon atoms.

<23> The compound or a salt thereof described in <10>, in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or a substituted alkyl group having 1 to 18 carbon atoms, $R^7$ and $R^8$ each independently represent a hydrogen atom or an alkyl group having 1 to 18 carbon atoms, a substituent on the substituted alkyl group having 1 to 18 carbon atoms is a group represented by —O(CO)—$R^{42}$ or —(CO)O—$R^{43}$, $R^{42}$ and $R^{43}$ each independently represent a hydrocarbon group having 1 to 18 carbon atoms, and e represents 2.

<24> A compound or a salt thereof selected from the following compounds:

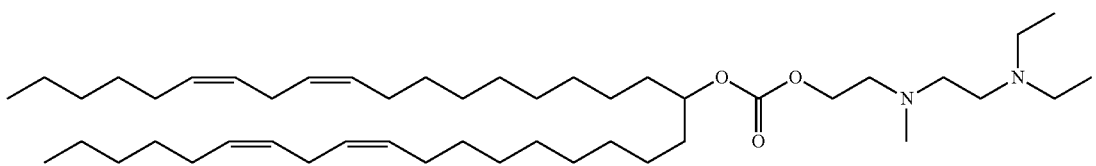

2-((2-(diethylamino)ethyl)(methyl)amino)ethyl((6Z,9Z,28Z,31Z)-heptatriaconta-6,9,28,31-tetraen-19-yl)carbonate

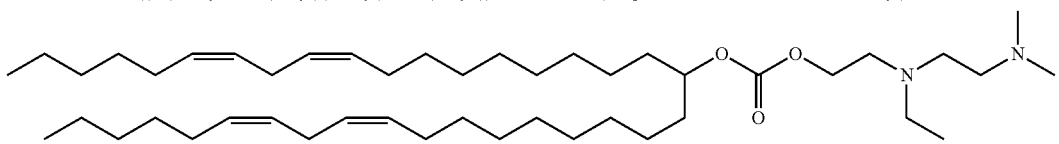

2-((2-(dimethylamino)ethyl)(ethyl)amino)ethyl((6Z,9Z,28Z,31Z)-heptatriaconta-6,9,28,31-tetraen-19-yl)carbonate

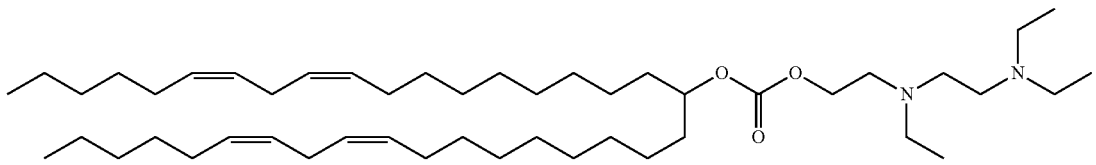

2-((2-(diethylamino)ethyl)(ethyl)amino)ethyl((6Z,9Z,28Z,31Z)-heptatriaconta-6,9,28,31-tetraen-19-yl)carbonate

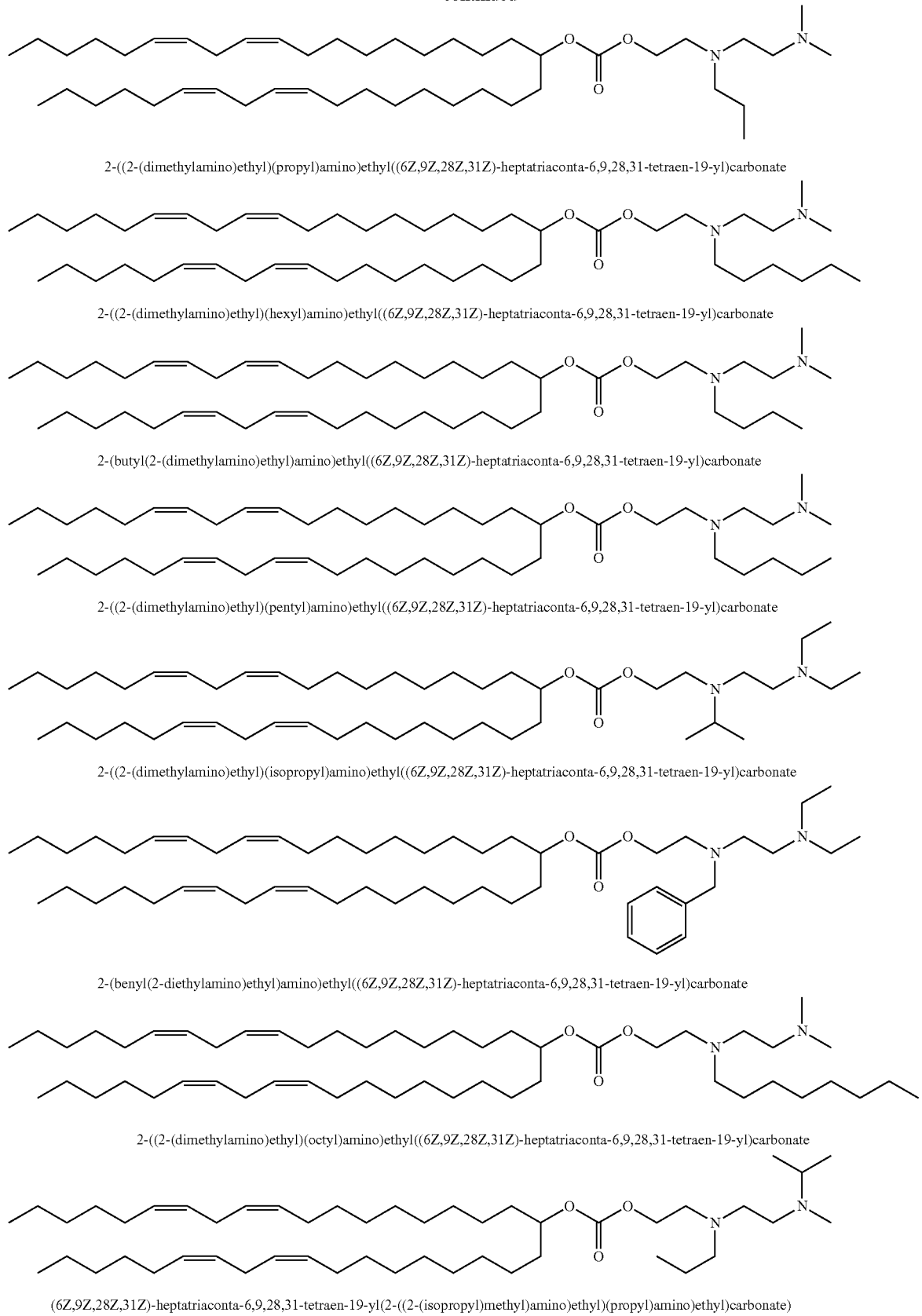

2-((2-(dimethylamino)ethyl)(propyl)amino)ethyl((6Z,9Z,28Z,31Z)-heptatriaconta-6,9,28,31-tetraen-19-yl)carbonate 2-((2-(dimethylamino)ethyl)(hexyl)amino)ethyl((6Z,9Z,28Z,31Z)-heptatriaconta-6,9,28,31-tetraen-19-yl)carbonate 2-(butyl(2-(dimethylamino)ethyl)amino)ethyl((6Z,9Z,28Z,31Z)-heptatriaconta-6,9,28,31-tetraen-19-yl)carbonate 2-((2-(dimethylamino)ethyl)(pentyl)amino)ethyl((6Z,9Z,28Z,31Z)-heptatriaconta-6,9,28,31-tetraen-19-yl)carbonate 2-((2-(dimethylamino)ethyl)(isopropyl)amino)ethyl((6Z,9Z,28Z,31Z)-heptatriaconta-6,9,28,31-tetraen-19-yl)carbonate 2-(benyl(2-diethylamino)ethyl)amino)ethyl((6Z,9Z,28Z,31Z)-heptatriaconta-6,9,28,31-tetraen-19-yl)carbonate 2-((2-(dimethylamino)ethyl)(octyl)amino)ethyl((6Z,9Z,28Z,31Z)-heptatriaconta-6,9,28,31-tetraen-19-yl)carbonate (6Z,9Z,28Z,31Z)-heptatriaconta-6,9,28,31-tetraen-19-yl(2-((2-(isopropyl)methyl)amino)ethyl)(propyl)amino)ethyl)carbonate)

<25> Lipid particles containing the compound or a salt thereof described in any one of <1> to <24> and a lipid.

<26> The lipid particles described in <25>, in which the lipid is at least one kind of lipid selected from the group consisting of a neutral lipid and a lipid having a nonionic hydrophilic polymer.

<27> The lipid particles described in <25> or <26>, further containing a sterol.

<28> The lipid particles described in any one of <25> to <27>, further containing a nucleic acid.

By using the compound according to an aspect of the present invention, it is possible to manufacture lipid particles that can achieve a high nucleic acid encapsulation rate and excellent delivery of nucleic acids. The lipid particles according to an aspect of the present invention can achieve a high nucleic acid encapsulation rate and excellent delivery of nucleic acids.

DESCRIPTION OF THE PREFERRED EMBODIMENTS

Hereinafter, the present invention will be specifically described.

In the present specification, "to" shows a range including numerical values described before and after "to" as a minimum value and a maximum value respectively.

Compound According to Embodiment of the Present Invention

The compound according to an embodiment of the present invention is represented by Formula (1).

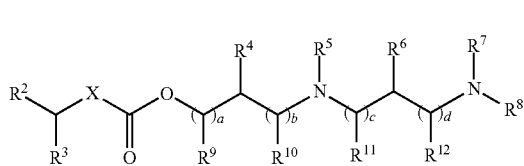

In the formula, X represents —NR$^1$— or —O—,

R$^1$ represents a hydrogen atom, a hydrocarbon group having 6 to 24 carbon atoms, or a group represented by R$^{21}$-L$^1$-R$^{22}$—, R$^{21}$ represents a hydrocarbon group having 1 to 24 carbon atoms, L$^1$ represents —O(CO)O—, —O(CO)—, —(CO)O—, —O—, or a group represented by the following formula,

R$^{22}$ represents a divalent hydrocarbon linking group having 1 to 18 carbon atoms, R$^2$ and R$^3$ each independently represent a hydrogen atom, a hydrocarbon group having 3 to 24 carbon atoms, or a group represented by R$^{31}$-L$^2$-R$^{32}$—, R$^{31}$ represents a hydrocarbon group having 1 to 24 carbon atoms, L$^2$ represents —O(CO)O—, —O(CO)—, —(CO)O—, —O—, or a group represented by the following formula,

R$^{32}$ represents a divalent hydrocarbon linking group having 1 to 18 carbon atoms, R$^4$, R$^5$, R$^6$, R$^7$, R$^8$, R$^9$, R$^{10}$, R$^{11}$, and R$^{12}$ each independently represent a hydrogen atom or an alkyl group having 1 to 18 carbon atoms that may be substituted, groups in any one or more pairs among R$^4$ and R$^5$, R$^{10}$ and R$^5$, R$^5$ and R$^{12}$, R$^4$ and R$^6$, R$^5$ and R$^6$, R$^6$ and R$^7$, R$^6$ and R$^{10}$, R$^{12}$ and R$^7$, and R$^7$ and R$^8$ may be linked to each other to form a 4- to 7-membered ring which may contain an O atom, the substituent on the alkyl group having 1 to 18 carbon atoms that may be substituted is a hydroxyl group, a carboxyl group, an amino group represented by —NR$^{45}$R$^{46}$, a substituted or unsubstituted aryl group, a substituted or unsubstituted heteroaryl group, or a group represented by —O(CO)O—R$^{41}$, —O(CO)—R$^{42}$, —(CO)O—R$^{43}$, or —O—R$^{44}$, R$^{41}$, R$^{42}$, R$^{43}$, R$^{44}$, R$^{45}$, and R$^{46}$ each independently represent a hydrocarbon group having 1 to 18 carbon atoms, the substituent on the substituted or unsubstituted aryl group and on the substituted or unsubstituted heteroaryl group is an alkyl group having 1 to 18 carbon atoms, a hydroxyl group, a carboxyl group, an amino group represented by —NR$^{45}$R$^{46}$, or a group represented by —O(CO)O—R$^{41}$, —O(CO)—R$^{42}$, —(CO)O—R$^{43}$, or —O—R$^{44}$, R$^{41}$, R$^{42}$, R$^{43}$, R$^{44}$, R$^{45}$, and R$^{46}$ each independently represent a hydrocarbon group having 1 to 18 carbon atoms, a, b, c, and d each independently represent an integer of 0 to 3, a+b is equal to or greater than 1, and c+d is equal to or greater than 1.

As the hydrocarbon group having 6 to 24 carbon atoms that is represented by R$^1$ and the hydrocarbon group having 3 to 24 carbon atoms that is represented by R$^2$ and R$^3$, an alkyl group, an alkenyl group, or an alkynyl group is preferable, and an alkyl group or an alkenyl group is more preferable. The alkyl group having 6 to 24 carbon atoms and the alkyl group having 3 to 24 carbon atoms may be linear or branched or may be chainlike or cyclic. The alkyl group having 6 to 24 carbon atoms is preferably an alkyl group having 6 to 20 carbon atoms, and the alkyl group having 3 to 24 carbon atoms is more preferably an alkyl group having 6 to 20 carbon atoms. Specifically, examples thereof include a hexyl group, a heptyl group, an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, a nonadecyl group, an icosyl group, and the like. The alkenyl group having 6 to 24 carbon atoms and the alkenyl group having 3 to 24 carbon atoms may be linear or branched or may be chainlike or cyclic. The alkenyl group having 6 to 24 carbon atoms is preferably an alkenyl group having 6 to 20 carbon atoms, and the alkenyl group having 3 to 24 carbon atoms is more preferably an alkenyl group having 6 to 20 carbon atoms. Specifically, examples thereof include a hexenyl group, a heptenyl group, an octenyl group, a nonenyl group, a decenyl group, an undecenyl group, a dodecenyl group, a dodecadienyl group, a tridecenyl group, a tetradecenyl group, a pentadecenyl group, a hexadecenyl group (preferably a (Z)-hexadec-9- enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), a nonadecenyl group, an icosenyl group (preferably a (Z)-icos-11-enyl group), an icosadienyl group (preferably a (11,14)-icosa-11,14-dienyl group), and the like. The alkynyl group having 6 to 24 carbon atoms is preferably an alkynyl group having 6 to 20 carbon atoms, and the alkynyl group having 3 to 24 carbon atoms is more preferably an alkynyl group having 6 to 20 carbon atoms. Specifically, examples thereof include a hexynyl group, a heptynyl group, an octynyl group, a nonynyl group, a decynyl group, an undecynyl group, a dodecynyl group, a tetradecynyl group, a pentadecynyl group, a hexadecynyl group, a heptadecynyl group, an octadecynyl group, and the like. All of the above alkenyl groups preferably have one double bond or two double bonds. All of the above alkynyl groups preferably have one triple bond or two triple bonds.

The hydrocarbon group having 1 to 24 carbon atoms that is represented by $R^{21}$ and $R^{31}$ is preferably an alkyl group having 10 to 24 carbon atoms, an alkenyl group having 10 to 24 carbon atoms, or an alkynyl group having 10 to 24 carbon atoms. The alkyl group having 10 to 24 carbon atoms may be linear or branched or may be chainlike or cyclic. The alkyl group having 10 to 24 carbon atoms is preferably an alkyl group having 12 to 24 carbon atoms. Specifically, examples thereof include a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, a 2-butylhexyl group, a 2-butyloctyl group, a 1-pentylhexyl group, a 2-pentylheptyl group, a 3-pentyloctyl group, a 1-hexylheptyl group, a 1-hexylnonyl group, a 2-hexyloctyl group, a 2-hexyldecyl group, a 3-hexylnonyl group, a 1-heptyloctyl group, a 2-heptylnonyl group, a 2-heptylundecyl group, a 3-heptyldecyl group, a 1-octylnonyl group, a 2-octyldecyl group, a 2-octyldodecyl group, a 3-octylundecyl group, a 2-nonylundecyl group, a 3-nonyldodecyl group, a 2-decyldodecyl group, a 2-decyltetradecyl group, a 3-decyltridecyl group, a 2-(4,4-dimethylpentan-2-yl)-5,7,7-trimethyloctyl group, and the like. The alkenyl group having 10 to 24 carbon atoms may be linear or branched or may be chainlike or cyclic. Specifically, examples thereof include a decenyl group, an undecenyl group, a dodecenyl group, a dodecadienyl group, tridecenyl group (preferably a (Z)-tridec-8-enyl group), a tetradecenyl group (preferably a tetradec-9-enyl group), a pentadecenyl group (preferably a (Z)-pentadec-8-enyl group), a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), and the like. The alkynyl group having 10 to 24 carbon atoms may be linear or branched or may be chainlike or cyclic. Specifically, examples thereof include a decynyl group, an undecynyl group, a dodecynyl group, a tetradecynyl group, a pentadecynyl group, a hexadecynyl group, a heptadecynyl group, an octadecynyl group, and the like. All of the above alkenyl groups preferably have one double bond or two double bonds. All of the above alkynyl groups preferably have one triple bond or two triple bonds.

The divalent hydrocarbon linking group having 1 to 18 carbon atoms that is represented by $R^{22}$ and $R^{32}$ is preferably an alkylene group having 1 to 18 carbon atoms or an alkenylene group having 2 to 18 carbon atoms. The alkylene group having 1 to 18 carbon atoms may be linear or branched or may be chainlike or cyclic. The number of carbon atoms in the alkylene group is preferably 1 to 12, more preferably 1 to 10, and even more preferably 2 to 10. Specifically, examples thereof include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, and the like. The alkenylene group having 2 to 18 carbon atoms may be linear or branched or may be chainlike or cyclic. The number of carbon atoms in the alkenylene group is preferably 1 to 12, and more preferably 2 to 10.

—O(CO)O—, —O(CO)—, and —(CO)O— are in a preferred range of $L^1$, and —O(CO)— and —(CO)O— are in a more preferred range of $L^1$.

—O(CO)O—, —O(CO)—, and —(CO)O— are in a preferred range of $L^2$, and —O(CO)— and —(CO)O— are in a more preferred range of $L^2$.

The alkyl group which is represented by $R^4$, $R^6$, $R^9$, $R^{10}$, $R^{11}$, and $R^{12}$ and has 1 to 18 carbon atoms that may be substituted may be linear or branched or may be chainlike or cyclic. The number of carbon atoms in the alkyl group is preferably 1 to 12. Specifically, examples thereof include a methyl group, an ethyl group, a propyl group, an isopropyl group, a cyclopropyl group, a butyl group, an isobutyl group, a tert-butyl group, a cyclobutyl group, a pentyl group, a cyclopentyl group, a hexyl group, a cyclohexyl group, a heptyl group, an octyl group, a nonyl group, a decyl group, an undecyl group, a dodecyl group, and the like. In a case where the alkyl group has a substituent, as the substituent, a hydroxyl group, a carboxyl group, or a group represented by —O(CO)O—$R^{41}$, —O(CO)—$R^{42}$, —(CO)O—$R^{43}$, or —O—$R^{44}$ is preferable, and a group represented by —O(CO)—$R^{42}$ or —(CO)O—$R^{43}$ is more preferable.

The alkyl group which is represented by $R^5$, $R^7$, and $R^8$ and has 1 to 18 carbon atoms that may be substituted may be linear or branched or may be chainlike or cyclic. The number of carbon atoms in the alkyl group is preferably 1 to 12, and more preferably 1 to 8. Specifically, examples thereof include a methyl group, an ethyl group, a propyl group, an isopropyl group, a cyclopropyl group, a butyl group, an isobutyl group, a tert-butyl group, a cyclobutyl group, a pentyl group, a cyclopentyl group, a hexyl group, a cyclohexyl group, a heptyl group, an octyl group, a nonyl group, a decyl group, an undecyl group, a dodecyl group, and the like. In a case where the alkyl group has a substituent, the substituent is preferably a hydroxyl group, a carboxyl group, or a group represented by —O(CO)O—$R^{41}$, —O(CO)—$R^{42}$, —(CO)O—$R^{43}$, or —O—$R^{44}$, and more preferably a group represented by —O(CO)—$R^{42}$ or —(CO)O—$R^{43}$.

Examples of the 4- to 7-membered ring which may contain an O atom include an azetidine ring, a pyrrolidine ring, a piperidine ring, a morpholine ring, and an azepane ring. The 4- to 7-membered ring is preferably a 6-membered ring which is preferably a piperidine ring or a morpholine ring.

In a case where the alkyl group which is represented by $R^4$, $R^5$, $R^6$, $R^7$, $R^8$, $R^9$, $R^{10}$, $R^{11}$, and $R^{12}$ and has 1 to 18 carbon atoms that may be substituted has a substituted or unsubstituted aryl group as a substituent, the number of carbon atoms in the aryl group is preferably 6 to 22, more preferably 6 to 18, and even more preferably 6 to 10. Specifically, examples of the aryl group include a phenyl group, a naphthyl group, an anthracenyl group, a phenanthrenyl group, and the like. As the substituent on the aryl group, an alkyl group having 1 to 18 carbon atoms, a hydroxyl group, a carboxyl group, an amino group represented by —$NR^{45}R^{46}$, or a group represented by —$O(CO)$ $O-R^{41}$, —$O(CO)-R^{42}$, —$(CO)O-R^{43}$, or —$O-R^{44}$ is preferable, and a hydroxyl group or a carboxyl group is more preferable. Specifically, examples of the substituted aryl group include a hydroxyphenyl group, a carboxyphenyl group, and the like.

In a case where the alkyl group which is represented by $R^4$, $R^5$, $R^6$, $R^7$, $R^8$, $R^9$, $R^{10}$, $R^{11}$, and $R^{12}$ and has 1 to 18 carbon atoms that may be substituted has a substituted or unsubstituted heteroaryl group as a substituent, the number of carbon atoms in the heteroaryl group is preferably 1 to 12, and more preferably 1 to 6. Specifically, examples of the heteroaryl group include a pyridyl group, a pyrazolyl group, an imidazolyl group, a benzimidazolyl group, a thiazolyl group, an oxazolyl group, and the like. As the substituent on the heteroaryl group, an alkyl group having 1 to 18 carbon atoms, a hydroxyl group, a carboxyl group, an amino group represented by —$NR^{45}R^{46}$, or a group represented by —$O(CO)O-R^{41}$, —$O(CO)-R^{42}$, —$(CO)O-R^{43}$, or —$O-R^{44}$ is preferable, and a hydroxyl group or a carboxyl group is more preferable. Specifically, examples of the substituted or unsubstituted heteroaryl group include a hydroxypyridyl group, a carboxypyridyl group, a pyridonyl group, and the like.

As hydrocarbon group having 1 to 18 carbon atoms that is represented by $R^{41}$, $R^{42}$, $R^{43}$, $R^{44}$, $R^{45}$, and $R^{46}$, an alkyl group having 1 to 18 carbon atoms, an alkenyl group having 2 to 18 carbon atoms, or an alkynyl group having 2 to 18 carbon atoms is preferable, and an alkyl group having 1 to 18 carbon atoms or an alkenyl group having 2 to 18 carbon atoms is more preferable. The alkyl group having 1 to 18 carbon atoms may be linear or branched or may be chainlike or cyclic. The number of carbon atoms in the alkyl group is preferably 3 to 18, and more preferably 5 to 18. Specifically, examples thereof include a propyl group, an isopropyl group, a cyclopropyl group, a butyl group, an isobutyl group, a tert-butyl group, a cyclobutyl group, a pentyl group, a cyclopentyl group, a hexyl group, a cyclohexyl group, a heptyl group, an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a heptadecyl group, an octadecyl group, and the like. The alkenyl group having 2 to 18 carbon atoms may be linear or branched or may be chainlike or cyclic. The number of carbon atoms in the alkenyl group is preferably 3 to 18, and more preferably 5 to 18. Specifically, examples thereof include an allyl group, a prenyl group, a pentenyl group, a hexenyl group, a heptenyl group, an octenyl group, a nonenyl group (preferably a (Z)-2-nonenyl group or an (E)-2-nonenyl group), a decenyl group, an undecenyl group, a dodecenyl group, a dodecadienyl group, a tridecenyl group (preferably a (Z)-tridec-8-enyl group), a tetradecenyl group (preferably a tetradec-9-enyl group), a pentadecenyl group (preferably a (Z)-pentadec-8-enyl group), a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), and the like. The alkynyl group having 2 to 18 carbon atoms may be linear or branched or may be chainlike or cyclic. The number of carbon atoms in the alkynyl group is preferably 3 to 18, and more preferably 5 to 18. Specifically, examples thereof include a propargyl group, a butynyl group, a pentynyl group, a hexynyl group, a heptynyl group, an octynyl group, a nonynyl group, a decynyl group, an undecynyl group, a dodecynyl group, a tetradecynyl group, a pentadecynyl group, a hexadecynyl group, a heptadecynyl group, an octadecynyl group, and the like.

In a case where X represents —$NR^1$—, $R^1$ preferably represents a hydrocarbon group having 6 to 24 carbon atoms or a group represented by $R^{21}$-$L^1$-$R^{22}$—. In this case, it is preferable that one of $R^2$ and $R^3$ represents a hydrogen atom and the other represents a hydrocarbon group having 6 to 24 carbon atoms or a group represented by $R^{31}$-$L^2$-$R^{32}$—.

In a case where X represents —O—, it is preferable that $R^2$ and $R^3$ each independently represent a hydrocarbon group having 6 to 24 carbon atoms or a group represented by $R^{31}$-$L^2$-$R^{32}$—.

It is preferable that $R^4$, $R^6$, $R^9$, $R^{10}$, $R^{11}$, and $R^{12}$ each represent a hydrogen atom.

$R^5$ is preferably a hydrogen atom, an alkyl group having 1 to 18 carbon atoms, an alkyl group having 1 to 18 carbon atoms that may be substituted with —$O(CO)-R^{42}$ or —$(CO)O-R^{43}$, an alkyl group having 1 to 18 carbon atoms that may be substituted with an aryl group, or an alkyl group having 1 to 18 carbon atoms that may be substituted with a hydroxyl group. In a case where $R^5$ is an alkyl group, $R^5$ may be linked to $R^4$, $R^6$, $R^{10}$, and $R^{12}$ so as to form a ring which may contain an O atom. Particularly, $R^5$ is preferably an alkyl group having 1 to 18 carbon atoms, an alkyl group having 1 to 18 carbon atoms that may be substituted with —$O(CO)-R^{42}$ or —$(CO)O-R^{43}$, an alkyl group having 1 to 12 carbon atoms that may be substituted with an aryl group, or an alkyl group having 1 to 8 carbon atoms that may be substituted with a hydroxyl group, and more preferably an alkyl group having 1 to 18 carbon atoms or an alkyl group having 1 to 18 carbon atoms that may be substituted with —$O(CO)-R^{42}$ or —$(CO)O-R^{43}$.

$R^7$ and $R^8$ preferably each independently represent a hydrogen atom, a hydrocarbon group having 1 to 18 carbon atoms, an alkyl group having 1 to 18 carbon atoms that may be substituted with —$O(CO)-R^{42}$ or —$(CO)O-R^{43}$, an alkyl group having 1 to 8 carbon atoms that may be substituted with an aryl group, or an alkyl group having 1 to 8 carbon atoms that may be substituted with a hydroxyl group. Alternatively, it is preferable that $R^7$ and $R^8$ are linked to each other so as to form a 4- to 7-membered ring which may contain an O atom.

$R^5$ is not linked to $R^7$ or $R^8$ and does not form a ring with $R^7$ or $R^8$.

a+b is preferably 1 or 2, and more preferably 1. c+d is preferably 1 or 2, and more preferably 1.

The compound represented by Formula (1) is preferably a compound represented by Formula (1-1).

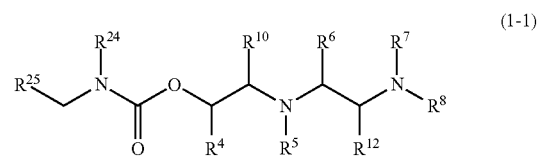

(1-1)

R²⁴ represents a hydrogen atom, a hydrocarbon group having 6 to 24 carbon atoms, or a group represented by R²¹-L¹-R²²—, R²¹ represents a hydrocarbon group having 1 to 24 carbon atoms, L¹ represents —O(CO)O—, —O(CO)—, —(CO)O—, —O—, or a group represented by the following formula,

R²² represents a divalent hydrocarbon linking group having 1 to 18 carbon atoms.

R²⁵ represents a hydrogen atom, a hydrocarbon group having 3 to 24 carbon atoms, or a group represented by R³¹-L²-R³²—, R³¹ represents a hydrocarbon group having 1 to 24 carbon atoms, L² represents —O(CO)O—, —O(CO)—, —(CO)O—, —O—, or a group represented by the following formula,

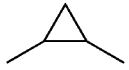

R³² represents a divalent hydrocarbon linking group having 1 to 18 carbon atoms.

R⁴, R⁵, R⁶, R⁷, R⁸, R¹⁰, and R¹² each independently represent a hydrogen atom or an alkyl group having 1 to 18 carbon atoms that may be substituted, and groups in any one or more pairs among R⁴ and R⁵, R¹⁰ and R⁵, R⁵ and R¹², R⁴ and R⁶, R⁵ and R⁶, R⁶ and R⁷, R⁶ and R¹⁰, R¹² and R⁷, and R⁷ and R⁸ may be linked to each other so as to form a 4- to 7-membered ring which may contain an O atom. However, it is preferable that R⁵ is not linked to R⁷ or R⁸ and does not form a ring with R⁷ or R⁸.

The substituent on the alkyl group having 1 to 18 carbon atoms that may be substituted is a hydroxyl group, a carboxyl group, an amino group represented by —NR⁴⁵R⁴⁶, a substituted or unsubstituted aryl group, a substituted or unsubstituted heteroaryl group, or a group represented by —O(CO)O—R⁴¹, —O(CO)—R⁴², —(CO)O—R⁴³, or —O—R⁴⁴, R⁴¹, R⁴², R⁴³, R⁴⁴, R⁴⁵, and R⁴⁶ each independently represent a hydrocarbon group having 1 to 18 carbon atoms.

The substituent on the substituted or unsubstituted aryl group and on the substituted or unsubstituted heteroaryl group is an alkyl group having 1 to 18 carbon atoms, a hydroxyl group, a carboxyl group, an amino group represented by —NR⁴⁵R⁴⁶, or a group represented by —O(CO)O—R⁴¹, —O(CO)—R⁴², —(CO)O—R⁴³, or —O—R⁴⁴, and R⁴¹, R⁴², R⁴³, R⁴⁴, R⁴⁵, and R⁴⁶ each independently represent a hydrocarbon group having 1 to 18 carbon atoms.

The definitions and preferred ranges of R⁴, R⁵, R⁶, R⁷, R⁸, R¹⁰, and R¹² in Formula (1-1) are the same as those of R⁴, R⁵, R⁶, R⁷, R⁸, R¹⁰, and R¹² in Formula (1).

R²⁴ in Formula (1-1) is preferably an alkyl group or an alkenyl group having 6 to 24 carbon atoms. The alkyl group having 6 to 24 carbon atoms may be linear or branched or may be chainlike or cyclic. The alkyl group having 6 to 24 carbon atoms is preferably an alkyl group having 8 to 20 carbon atoms. Specifically, examples thereof include an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, a nonadecyl group, an icosyl group, and the like. The alkenyl group having 6 to 24 carbon atoms may be linear or branched or may be chainlike or cyclic. The alkenyl group having 6 to 24 carbon atoms is preferably an alkenyl group having 8 to 20 carbon atoms. Specifically, examples thereof include an octenyl group, a nonenyl group, a decenyl group, an undecenyl group, a dodecenyl group, a dodecadienyl group, a tridecenyl group, a tetradecenyl group, a pentadecenyl group, a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), a nonadecenyl group, an icosenyl group (preferably a (Z)-icos-11-enyl group), an icosadienyl group (preferably a (11,14)-icosa-11,14-dienyl group), and the like.

It is preferable that all of the above alkenyl groups have one double bond or two double bonds.

R²⁵ in Formula (1-1) is preferably an alkyl group or an alkenyl group having 6 to 24 carbon atoms. The alkyl group having 6 to 24 carbon atoms may be linear or branched or may be chainlike or cyclic. The alkyl group having 6 to 24 carbon atoms is preferably an alkyl group having 7 to 20 carbon atoms. Specifically, examples thereof include a hexyl group, a heptyl group, an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, and the like. The alkenyl group having 6 to 24 carbon atoms may be linear or branched or may be chainlike or cyclic. The alkenyl group having 6 to 24 carbon atoms is preferably an alkenyl group having 8 to 20 carbon atoms. Specifically, examples thereof include an octenyl group, a nonenyl group, a decenyl group, an undecenyl group, a dodecenyl group, a dodecadienyl group, a tridecenyl group, a tetradecenyl group, a pentadecenyl group, a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), a nonadecenyl group, an icosenyl group (preferably a (Z)-icos-11-enyl group), an icosadienyl group (preferably a (11,14)-icosa-11,14-dienyl group), and the like.

It is preferable that all of the above alkenyl groups have one double bond or two double bonds.

In a preferred embodiment,

X represents —O—;

R², R³, R³¹, L², and R³² have the same definitions as R², R³, R³¹, L², and R³² in Formula (1) respectively, R⁴, R⁵, R⁶, R⁷, R⁸, R⁹, R¹⁰, R¹¹, and R¹² each independently represent a hydrogen atom or an alkyl group having 1 to 18 carbon atoms that may be substituted, the substituent on the alkyl group having 1 to 18 carbon atoms that may be substituted and the substituent on the substituted or unsubstituted aryl group and on the substituted or unsubstituted heteroaryl group have the same definitions as those in Formula (1), a+b is 1, and c+d is 1 or 2.

In a more preferred embodiment, the compound represented by Formula (1) is a compound represented by Formula (2).

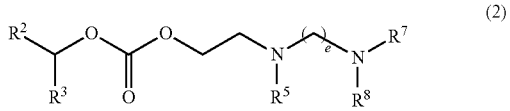

(2)

In the formula, $R^2$ and $R^3$ each independently represent a hydrogen atom, a hydrocarbon group having 3 to 24 carbon atoms, or a group represented by $R^{31}$-$L^2$-$R^{32}$—.

$R^{31}$ represents a hydrocarbon group having 1 to 24 carbon atoms, $L^2$ represents —O(CO)O—, —O(CO)—, —(CO)O—, —O—, or a group represented by the following formula,

$R^{32}$ represents a divalent hydrocarbon linking group having 1 to 18 carbon atoms, $R^5$ represents a hydrogen atom or an alkyl group having 1 to 18 carbon atoms that may be substituted, $R^7$ and $R^8$ each independently represent a hydrogen atom or an alkyl group having 1 to 18 carbon atoms that may be substituted, the substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, the substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms, and e represents 2 or 3.

$R^2$, $R^3$, $R^5$, $R^7$, and $R^8$ have the same definitions as $R^2$, $R^3$, $R^5$, $R^7$, and $R^8$ in Formula (1) respectively.

Formula (2) preferably represents a compound in which $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is a hydroxyl group, a substituted or unsubstituted aryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, the substituent on the substituted or unsubstituted aryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms.

Formula (2) more preferably represents a compound in which $R^2$ and $R^3$ each independently represent a hydrocarbon group having 3 to 24 carbon atoms or a group represented by $R^{31}$-$L^2$-$R^{32}$—, $L^2$ represents —O(CO)— or —(CO)O—, $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is an unsubstituted aryl group, —O(CO)—$R^{42}$, or —(CO)O—$R^{43}$, and $R^{42}$ and $R^{43}$ each independently represent a hydrocarbon group having 1 to 18 carbon atoms.

Formula (2) even more preferably represents a compound in which $R^2$ and $R^3$ each independently represent a hydrogen atom or a hydrocarbon group having 3 to 24 carbon atoms, $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) preferably represents a compound in which at least one of $R^2$ or $R^3$ represents a group represented by $R^{31}$-$L^2$-$R^{32}$—, $L^2$ represents —O(CO)— or —(CO)O—, $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) more preferably represents a compound in which $R^2$ and $R^3$ each independently represent a group represented by $R^{31}$-$L^2$-$R^{32}$—, $L^2$ represents —O(CO)— or —(CO)O—, $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) preferably represents a compound in which one of $R^2$ and $R^3$ represents a group represented by $R^{31}$-$L^2$-$R^{32}$— and the other represents a hydrocarbon group having 3 to 24 carbon atoms, $L^2$ represents —O(CO)— or —(CO)O—, $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) even more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or an alkyl group having 1 to 18 carbon atoms, and $R^7$ and $R^8$ each independently represent a hydrogen atom or an alkyl group having 1 to 18 carbon atoms.

Formula (2) still more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or an alkyl group having 1 to 18 carbon atoms, $R^7$ and $R^8$ each independently represent a hydrogen atom or an alkyl group having 1 to 18 carbon atoms, and e represents 2.

Formula (2) yet more preferably represents a compound in which one of $R^2$ and $R^3$ represents a group represented by $R^{31}$-$L^2$-$R^{32}$— and the other represents a hydrocarbon group having 3 to 5 carbon atoms, $L^2$ represents —O(CO)— or —(CO)O—, $R^5$ represents a hydrogen atom or an alkyl group having 1 to 18 carbon atoms, and $R^7$ and $R^8$ each independently represent a hydrogen atom or an alkyl group having 1 to 18 carbon atoms.

Formula (2) more preferably represents a compound in which one of $R^2$ and $R^3$ represents a group represented by $R^{31}$-$L^2$-$R^{32}$— and the other represents a hydrocarbon group having 3 to 5 carbon atoms, $L^2$ represents —O(CO)— or —(CO)O—, $R^5$ represents a hydrogen atom or an alkyl group having 1 to 18 carbon atoms, $R^7$ and $R^8$ each independently represent a hydrogen atom or an alkyl group having 1 to 18 carbon atoms, and e represents 2.

Formula (2) even more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or a substituted alkyl group having 1 to 18 carbon atoms, $R^7$ and $R^8$ each independently represent a hydrogen atom or an alkyl group having 1 to 18 carbon atoms, the substituent on the substituted alkyl group having 1 to 18 carbon atoms is a group represented by —O(CO)—$R^{42}$ or —(CO)O—$R^{43}$ and $R^{42}$ and $R^{43}$ each independently represent a hydrocarbon group having 1 to 18 carbon atoms.

Formula (2) still more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or a substituted alkyl group having 1 to 18 carbon atoms, $R^7$ and $R^8$ each independently represent a hydrogen atom or an alkyl group having 1 to 18 carbon atoms, the substituent on the substituted alkyl group having 1 to 18 carbon atoms is a group represented by —O(CO)—$R^{42}$ or —(CO)O—$R^{43}$, $R^{42}$ and $R^{43}$ each independently represent a hydrocarbon group having 1 to 18 carbon atoms, and e represents 2.

The compound according to the embodiment of the present invention may form a salt.

Examples of the salt in a basic group include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salt in an acidic group include salts with alkali metals such as sodium and potassium; salts with alkaline earth metals such as calcium and magnesium; ammonium salts; salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine, and the like.

Among the above salts, for example, pharmacologically acceptable salts are preferable.

Specifically, as the compound according to the embodiment of the present invention, for example, the compounds described in Examples 1 to 133 which will be described later are preferable. However, the present invention is not limited thereto.

The compounds described in Examples 1 to 133 are called compounds 1 to 133 respectively.

Among the above compounds, the compounds 1, 3, 4, 7, 9, 20, 23 to 27, 29, 30, 31, 33, 36, 40, 41, 43, 45 to 48, 50 to 53, 56, 60, 61, 64, 66 to 70, 72 to 76, 78, 84, 87, 88, 93, 94, 100 to 107, 109 to 113, 116, 118 to 122, and 129 are preferable.

Among the above compounds, from the viewpoint of the delivery of an encapsulated nucleic acid, the compounds 1, 4, 7, 9, 20, 23, 25 to 27, 29, 30, 31, 33, 36, 40, 41, 43, 45 to 47, 50 to 53, 56, 60, 61, 64, 66 to 70, 72 to 76, 78, 84, 87, 88, 93, 94, 100 to 107, 109, 110, 112, 113, 116, and 118 to 122 are preferable.

Among these, the compounds 1, 4, 7, 9, 20, 25, 29, 30, 33, 36, 40, 41, 43, 45 to 47, 50, 52, 53, 56, 60, 61, 64, 66, 67, 69, 70, 73 to 76, 78, 88, 93, 100, 102 to 105, 107, 109, 110, 112, 113, 116, 120, and 122 are more preferable.

Furthermore, the compounds 23, 24, 30, 31, 37, 38, 40 to 43, 45 to 48, 50 to 52, 56, 58, 59, 61, 62, 64 to 78, 83, 86 to 89, 91, 93, 94, 98 to 100, 103 to 113, 117 to 122, 124 to 126, 129, 130, and 133 are preferable.

In addition, the compounds 30, 31, 37, 38, 40 to 43, 45 to 48, 50 to 52, 56, 58, 59, 61, 62, 64 to 78, 83, 86 to 89, 91, 93, 94, 98 to 100, 103 to 113, and 117 to 122 are preferable.

<Manufacturing Method>

The method for manufacturing the compound according to an embodiment of the present invention will be described.

The compound according to the embodiment of the present invention can be manufactured using known methods in combination. For example, the compound can be manufactured by the following manufacturing method.

[Manufacturing Method 1]

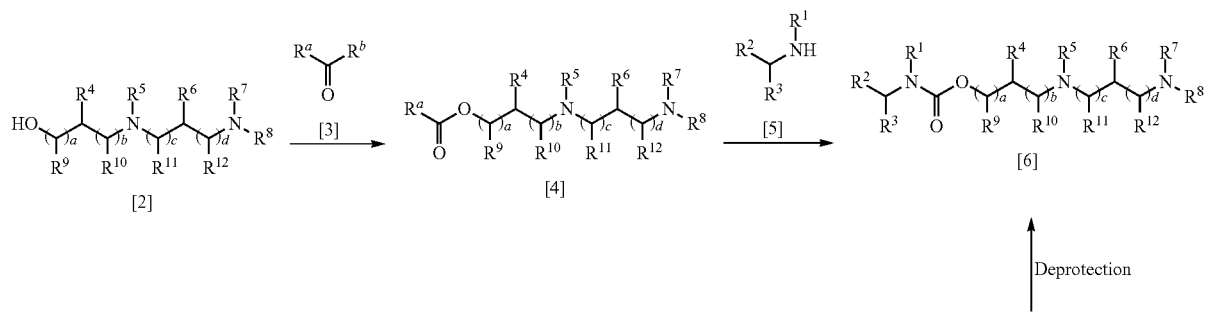

[2] [3] [4] [5] [6]

Deprotection

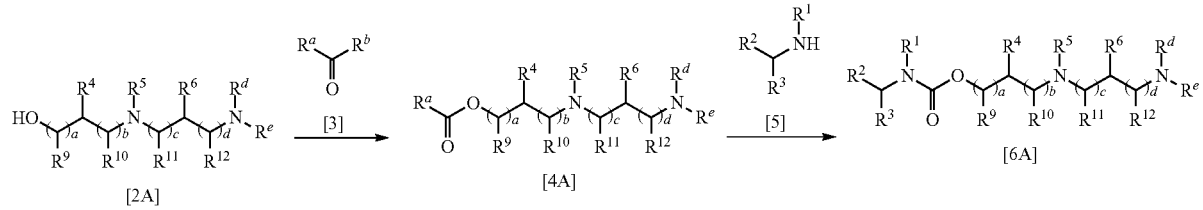

[2A] [3] [4A] [5] [6A]

"In the formula, $R^a$ and $R^b$ each represent a leaving group; $R^c$, $R^d$, and $R^e$ each represent an amino protecting group or an imino protecting group; and $R^1$, $R^2$, $R^3$, $R^4$, $R^5$, $R^6$, $R^7$, $R^8$, $R^9$, $R^{10}$, $R^{11}$, and $R^{12}$ have the same definitions as $R^1$, $R^2$, $R^3$, $R^4$, $R^5$, $R^6$, $R^7$, $R^8$, $R^9$, $R^{10}$, $R^{11}$, and $R^{12}$ described above." Examples of the leaving group include a chloro group, a fluoro group, a bromo group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4-oxadiazolidyl group, a N-hydroxysuccinimidyl group, and the like. Examples of the amino protecting group and the imino protecting group include a tert-butoxycarbonyl group, a benzyloxycarbonyl group, a 2-nitrobenzenesulfonyl group, a benzyl group, and the like.

(1-1)

As the compound represented by Formula [3], for example, 4-nitrophenyl chloroformate, 1,1'-carbonyldiimidazole, triphosgene, phosgene, and the like are known.

The compound represented by Formula [4] can be manufactured by reacting the compound represented by Formula [2] with the compound represented by Formula [3] in the presence of a base.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [2].

Examples of the base used in this reaction include an inorganic base and an organic base. As the base, an organic base is preferable. Specifically, examples thereof include triethylamine, N,N-diisopropylethylamine, 4-methylmorpholine, pyridine, 4-dimethylaminopyridine, and the like.

The amount of the base used may be 1 to 50 times and preferably 1 to 10 times the molar amount of the compound represented by Formula [2].

The amount of the used compound represented by Formula [3] is not particularly limited, but may be 0.3 to 10 times (v/w) the amount of the compound represented by Formula [2].

This reaction may be carried out at −30° C. to 150° C. preferably at 0° C. to 100° C. for 5 minutes to 48 hours.

(1-2)

As the compound represented by Formula [5], for example, (9Z,12Z)-di((9Z,12Z)-octadeca-9,12-dien-1-yl) amine, dihexadecylamine, and the like are known.

The compound represented by Formula [6] can be manufactured by reacting the compound represented by Formula [4] with the compound represented by Formula [5] in the presence of a base.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [4].

Examples of the base used in this reaction include an inorganic base and an organic base. As the base, an organic base is preferable. Specifically, examples thereof include triethylamine, N,N-diisopropylethylamine, 4-methylmorpholine, pyridine, 4-dimethylaminopyridine, and the like.

The amount of the base used may be 1 to 50 times and preferably 1 to 10 times the molar amount of the compound represented by Formula [4].

The amount of the used compound represented by Formula [5] is not particularly limited, but may be 1 to 10 times (v/w) the amount of the compound represented by Formula [4].

This reaction may be carried out at −30° C. to 150° C. preferably at 0° C. to 100° C. for 5 minutes to 48 hours.

(1-3)

As the compound represented by Formula [2A], for example, tert-butyl(2-((tert-butoxycarbonyl)amino)ethyl)(2-hydroxyethyl)carbamate, tert-butyl(2-((2-hydroxyethyl)(methyl)amino)ethyl)carbamate, and the like are known.

The compound represented by Formula [6A] can be manufactured by reacting the compound represented by Formula [2A] with the compound represented by Formula [3] in the presence of a base, and then reacting the compound represented by Formula [4A] with the compound represented by Formula [5] in the presence of a base.

This reaction may be performed based on the manufacturing methods (1-1) and (1-2).

(1-4)

The compound represented by Formula [6] can be manufactured by deprotecting the compound represented by Formula [6A].

This reaction may be performed, for example, based on the method described in "Protective Groups in Organic Synthesis, T. W. Greene et al., 4th Edition, pp. 696-926, 2007, John Wiley & Sons, INC".

[Manufacturing Method 2]

oxadiazolidyl group, a N-hydroxysuccinimidyl group, and the like. Examples of the amino protecting group and the imino protecting group include a tert-butoxycarbonyl group, a benzyloxycarbonyl group, a 2-nitrobenzenesulfonyl group, a benzyl group, and the like.

(2-1)

As the compound represented by Formula [3], for example, 4-nitrophenyl chloroformate, 1,1'-carbonyldiimidazole, triphosgene, phosgene, and the like are known.

The compound represented by Formula [8] can be manufactured by reacting the compound represented by Formula [7] with the compound represented by Formula [3] in the presence of a base.

This reaction may be performed based on the manufacturing method (1-1).

(2-2)

The compound represented by Formula [9] can be manufactured by reacting the compound represented by Formula [8] with the compound represented by Formula [2] in the presence of a base.

The solvent used in this reaction is not particularly limited as long as the solvent does not affect the reaction. Examples of the solvent include halogenated hydrocarbons, ethers,

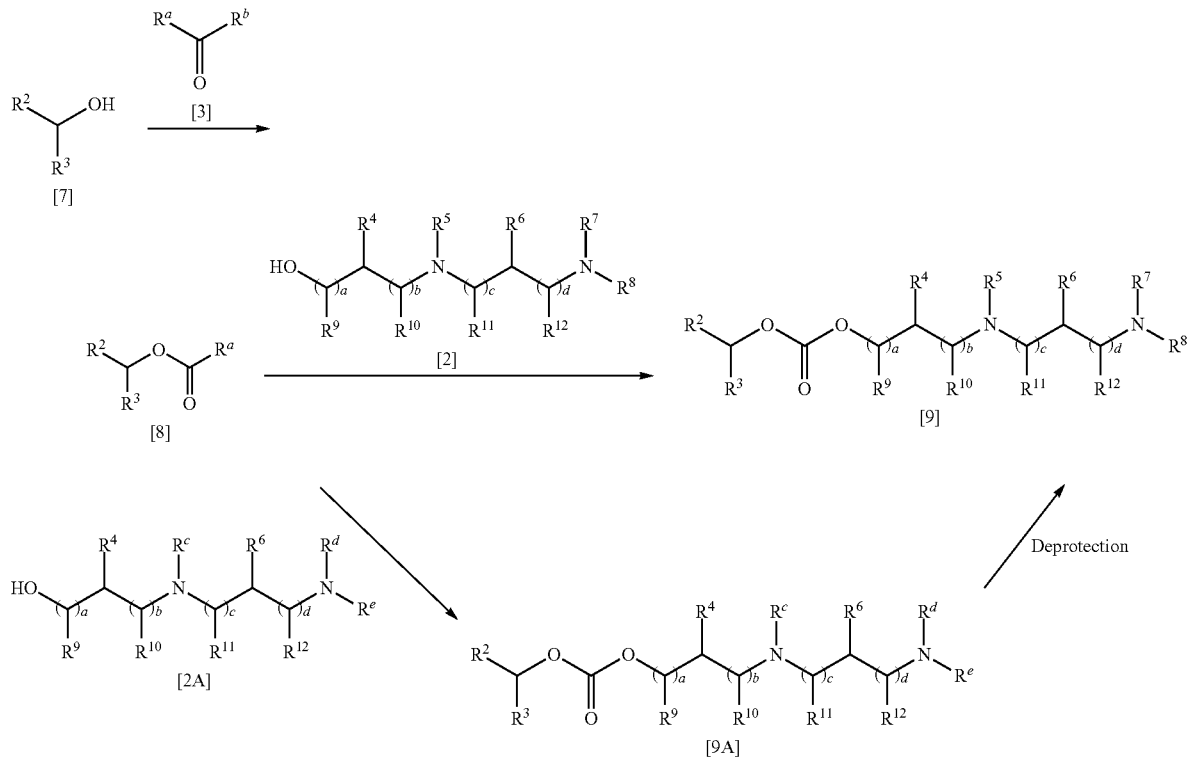

"In the formula, $R^a$ and $R^b$ each represent a leaving group; $R^c$, $R^d$, and $R^e$ each represent an amino protecting group or an imino protecting group; and $R^1$, $R^2$, $R^3$, $R^4$, $R^5$, $R^6$, $R^7$, $R^8$, $R^9$, $R^{10}$, $R^{11}$, and $R^{12}$ have the same definitions as $R^1$, $R^2$, $R^3$, $R^4$, $R^5$, $R^6$, $R^7$, $R^8$, $R^9$, $R^{10}$, $R^{11}$, and $R^{12}$ described above." Examples of the leaving group include a chloro group, a fluoro group, a bromo group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4- esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [8].

Examples of the base used in this reaction include an inorganic base and an organic base. As the base, an organic base is preferable. Specifically, examples thereof include triethylamine, N,N-diisopropylethylamine, 4-methylmorpholine, pyridine, 4-dimethylaminopyridine, and the like.

The amount of the base used may be 1 to 50 times and preferably 1 to 10 times the molar amount of the compound represented by Formula [8].

The amount of the used compound represented by Formula [2] is not particularly limited, but may be 1 to 10 times (v/w) the amount of the compound represented by Formula [8].

This reaction may be carried out at −30° C. to 150° C. preferably at 0° C. to 100° C. for 5 minutes to 48 hours.

(2-3)

As the compound represented by Formula [2A], for example, tert-butyl(2-((tert-butoxycarbonyl)amino)ethyl)(2-hydroxyethyl)carbamate, tert-butyl(2-((2-hydroxyethyl)(methyl)amino)ethyl)carbamate, and the like are known.

The compound represented by Formula [9] can be manufactured by reacting the compound represented by Formula [8] with the compound represented by Formula [2A] in the presence of a base, and then deprotecting the compound represented by Formula [9A] in the presence of a base.

This reaction may be performed based on the manufacturing methods (2-2) and (1-4).

[Manufacturing Method 3]

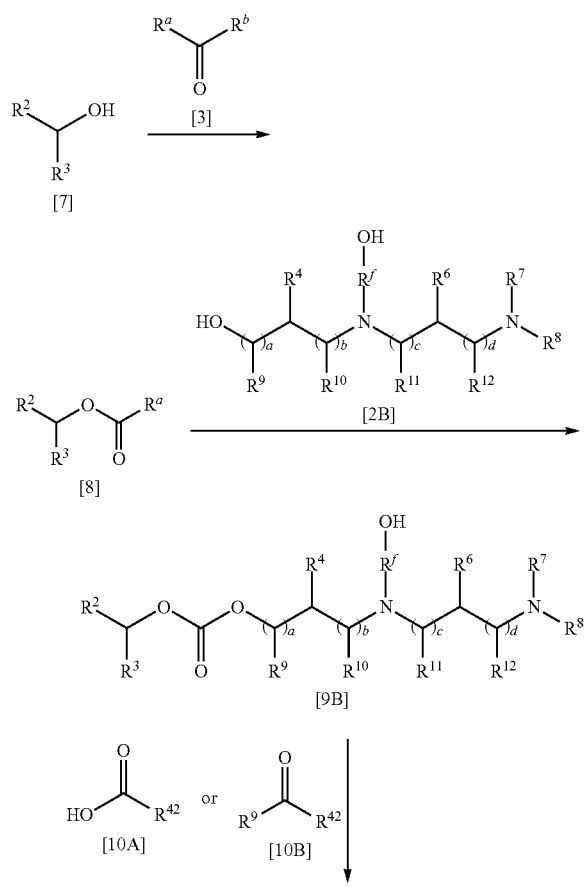

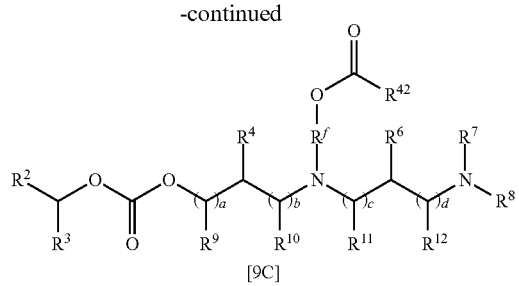

[9C]

"In the formula, $R^a$, $R^b$, and $R^9$ each represent a leaving group; $R^f$ represents an alkyl group having 1 to 18 carbon atoms; and $R^1$, $R^2$, $R^3$, $R^4$, $R^5$, $R^6$, $R^7$, $R^8$, $R^9$, $R^{10}$, $R^{11}$, $R^{12}$, and $R^{42}$ have the same definitions as $R^1$, $R^2$, $R^3$, $R^4$, $R^5$, $R^6$, $R^7$, $R^8$, $R^9$, $R^{10}$, $R^{11}$, $R^{12}$, and $R^{42}$ described above."

Examples of the leaving group include a chloro group, a fluoro group, a bromo group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4-oxadiazolidyl group, a N-hydroxysuccinimidyl group, and the like.

(3-1)

As the compound represented by Formula [3], for example, 4-nitrophenyl chloroformate, 1,1'-carbonyldiimidazole, triphosgene, phosgene, and the like are known.

The compound represented by Formula [8] can be manufactured by reacting the compound represented by Formula [7] with the compound represented by Formula [3] in the presence of a base.

This reaction may be performed based on the manufacturing method (1-1).

(3-2)

As the compound represented by Formula [2B], for example, 2,2'-((2-(diethylamino)ethyl)azanediyl)bis(ethan-1-ol), 2,2'-((3-(diethylamino)propyl)azanediyl)bis(ethan-1-ol), and the like are known.

The compound represented by Formula [9B] can be manufactured by reacting the compound represented by Formula [8] with the compound represented by Formula [2B] in the presence of a base.

This reaction may be performed based on the manufacturing method (2-2).

(3-3)

As the compound represented by Formula [10A], for example, dodecanoic acid, decanoic acid, nonanoic acid, octanoic acid, and the like are known.

The compound represented by Formula [9C] can be manufactured by reacting the compound represented by Formula [9B] with the compound represented by Formula [10A] in the presence of a condensing agent or an acid halide or in the presence of a base.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [9B].

Examples of the base used in this reaction include an inorganic base and an organic base. As the base, an organic base is preferable. Specifically, examples thereof include triethylamine, N,N-diisopropylethylamine, 4-methylmorpholine, pyridine, 4-dimethylaminopyridine, and the like.

The amount of the base used may be 1 to 50 times and preferably 1 to 10 times the molar amount of the compound represented by Formula [9B].

Examples of the condensing agent used in this reaction include carbodiimides such as N,N'-dicyclohexylcarbodiimide and 1-ethyl-3-(3-dimethylaminopropyl)carbodiimide; carbonyls such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium=hexafluorophosphate, O-(7-azabenzotriazol-1-yl)-1,1,3,3-tetramethyluronium=hexafluorophosphate, and the like.

Examples of the acid halide used in this reaction include carboxylic acid halides such as acetyl chloride and trifluoroacetyl chloride; sulfonic acid halides such as methanesulfonyl chloride and tosyl chloride; chloroformic acid esters such as ethyl chloroformate and isobutyl chloroformate, and the like.

The amount of the used compound represented by Formula [10A] is not particularly limited, but may be 1 to 10 times (v/w) the amount of the compound represented by Formula [9B].

esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [9B].

Examples of the base used in this reaction include an inorganic base and an organic base.

The amount of the base used may be 1 to 50 times and preferably 1 to 10 times the molar amount of the compound represented by Formula [9B].

The amount of the used compound represented by Formula [10B] is not particularly limited, but may be 1 to 10 times (v/w) the amount of the compound represented by Formula [2B].

This reaction may be carried out at −30° C. to 150° C. preferably at 0° C. to 100° C. for 5 minutes to 48 hours.

Next, the synthesis of the compound represented by Formula [2], which is a raw material for manufacturing the compound according to the embodiment of the present invention, will be described.

[Manufacturing Method 4]

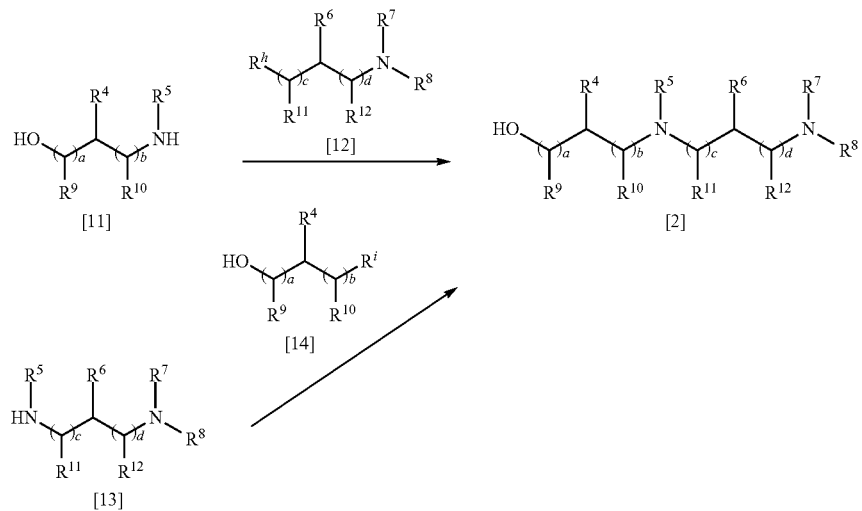

This reaction may be carried out at −30° C. to 150° C. preferably at 0° C. to 100° C. for 5 minutes to 48 hours.
(3-4)

As the compound represented by Formula [10B], for example, dodecanoic acid chloride, decanoic acid chloride, nonanoic acid chloride, octanoic acid chloride, and the like are known.

The compound represented by Formula [9C] can be manufactured by reacting the compound represented by Formula [9B] with the compound represented by Formula [10B] in the presence of a base.

The compound represented by Formula [10B] can be manufactured by reacting the compound represented by Formula [10A] with thionyl chloride, oxalyl chloride, or the like.

The solvent used in this reaction is not particularly limited as long as the solvent does not affect the reaction. Examples of the solvent include halogenated hydrocarbons, ethers, "In the formula, $R^h$ and $R^i$ each represent a leaving group; and $R^4$, $R^5$, $R^6$, $R^7$, $R^8$, $R^9$, $R^{10}$, $R^{11}$, and $R^{12}$ have the same definitions as $R^4$, $R^5$, $R^6$, $R^7$, $R^8$, $R^9$, $R^{10}$, $R^{11}$, and $R^{12}$ described above." Examples of the leaving group include a chloro group, a bromo group, an iodo group, a methanesulfonyl group, a 4-toluenesulfonyl group, a chloromethanesulfonyl group, a trifluoromethanesulfonyl group, and the like.
(4-1)

As the compound represented by Formula [12], for example, 2-chloro-N,N-dimethylethan-1-amine, 4-(2-chloroethyl)morpholine, 2-chloro-N,N-diethylethan-1-amine, 2-bromo-N,N-diethylethan-1-amine, 3-chloro-N,N-diethylethan-1-amine, and the like are known.

The compound represented by Formula [2] can be manufactured by reacting the compound represented by Formula [11] with the compound represented by Formula [12] in the presence or absence of a base.

The solvent used in this reaction is not particularly limited as long as the solvent does not affect the reaction. Examples of the solvent include alcohols, halogenated hydrocarbons, ethers, esters, amides, nitriles, sulfoxides, aromatic hydrocarbons, and water. These solvents may be used by being mixed together.

The amount of the solvent used is not particularly limited, but may be 1 to 500 times (v/w) the amount of the compound represented by Formula [11].

Examples of the base used in this reaction include an inorganic base and an organic base. The amount of the base used may be 1 to 10,000 times and preferably 1 to 5,000 times the molar amount of the compound represented by Formula [11].

The amount of the used compound represented by Formula [12] is not particularly limited, but may be 1 to 10 times (v/w) the amount of the compound represented by Formula [11].

This reaction may be carried out at −30° C. to 150° C. preferably at 0° C. to 100° C. for 5 minutes to 48 hours.

(4-2)

As the compound represented by Formula [14], for example, 2-bromoethan-1-ol, 3-bromopropan-1-ol, and the like are known.

The compound represented by Formula [2] can be manufactured by reacting the compound represented by Formula [13] with the compound represented by Formula [14] in the presence or absence of a base.

This reaction may be performed based on the manufacturing method (4-1).

[Manufacturing Method 5]

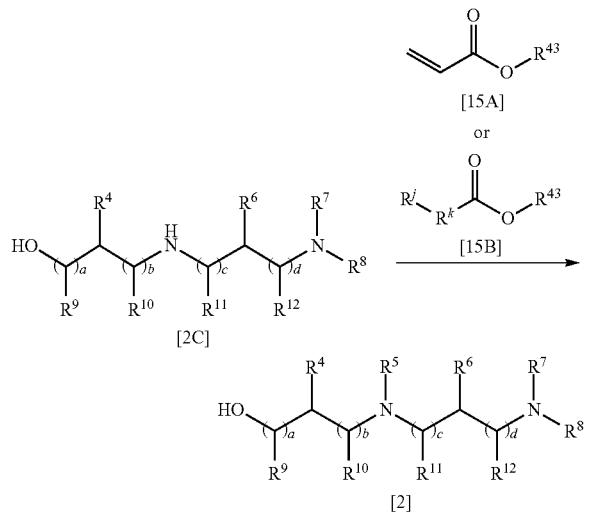

"In the formula, $R^j$ represents a leaving group; $R^k$ represents an alkyl group having 1 to 18 carbon atoms; and $R^4$, $R^5$, $R^6$, $R^7$, $R^8$, $R^9$, $R^{10}$, $R^{11}$, $R^{12}$, and $R^{43}$ have the same definitions as $R^4$, $R^5$, $R^6$, $R^7$, $R^8$, $R^9$, $R^{10}$, $R^{11}$, $R^{12}$, and $R^{43}$ described above." Examples of the leaving group include a chloro group, a bromo group, an iodo group, a methanesulfonyl group, a 4-toluenesulfonyl group, a chloromethanesulfonyl group, a trifluoromethanesulfonyl group, and the like.

(5-1)

As the compound represented by Formula [15A], for example, heptyl acrylate and the like are known.

The compound represented by Formula [2] can be manufactured by reacting the compound represented by Formula [2C] with the compound represented by Formula [15A] in the presence or absence of a base.

The solvent used in this reaction is not particularly limited as long as the solvent does not affect the reaction. Examples of the solvent include alcohols, halogenated hydrocarbons, ethers, esters, amides, nitriles, sulfoxides, aromatic hydrocarbons, and water. These solvents may be used by being mixed together.

As the solvent, for example, ethers or nitriles are preferable. Among these, tetrahydrofuran or acetonitrile is more preferable.

The amount of the solvent used is not particularly limited, but may be 1 to 500 times (v/w) the amount of the compound represented by Formula [2C].

Examples of the base used in this reaction include an inorganic base and an organic base.

The amount of the base used may be 1 to 10,000 times and preferably 1 to 5,000 times the molar amount of the compound represented by Formula [2C].

The amount of the used compound represented by Formula [15A] is not particularly limited, but may be 1 to 10 times (v/w) the amount of the compound represented by Formula [13].

This reaction may be carried out at −30° C. to 150° C. preferably at 0° C. to 100° C. for 5 minutes to 48 hours.

(5-2)

As the compound represented by Formula [15B], for example, heptyl 3-chloropropanoate and the like are known.

The compound represented by Formula [2] can be manufactured by reacting the compound represented by Formula [2C] with the compound represented by Formula [15B] in the presence or absence of a base.

This reaction may be performed based on the manufacturing method (4-1).

[Manufacturing Method 6]

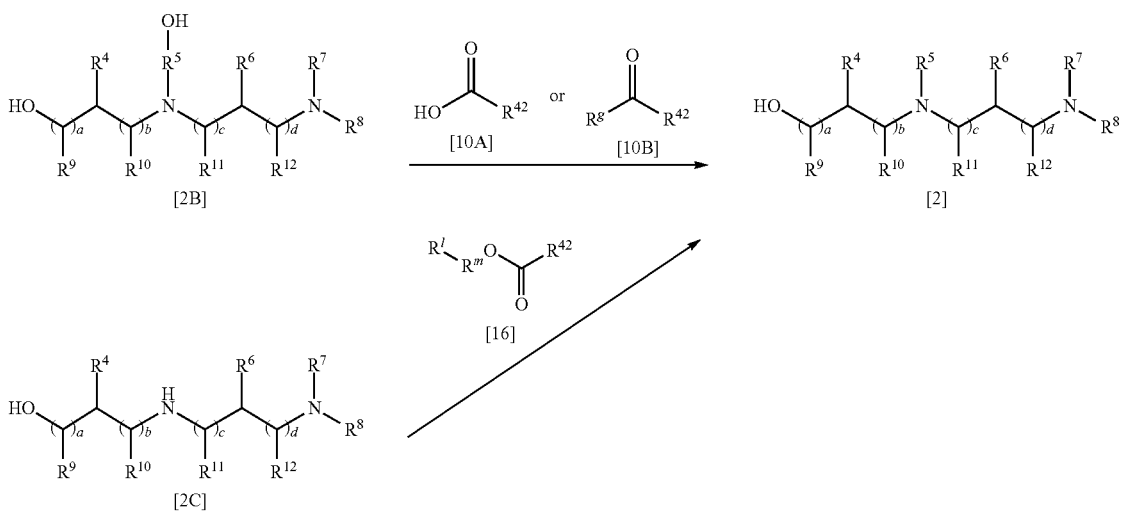

"In the formula, $R^g$ and $R^l$ each represent a leaving group; $R^m$ represents an alkyl group having 1 to 18 carbon atoms; and $R^4$, $R^5$, $R^6$, $R^7$, $R^8$, $R^9$, $R^{10}$, $R^{11}$, $R^{12}$, and $R^{42}$ have the same definitions as $R^4$, $R^5$, $R^6$, $R^7$, $R^8$, $R^9$, $R^{10}$, $R^{11}$, $R^{12}$, and $R^{42}$ described above." Examples of the leaving group include a chloro group, a bromo group, an iodo group, a methanesulfonyl group, a 4-toluenesulfonyl group, a chloromethanesulfonyl group, a trifluoromethanesulfonyl group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4-oxadiazolidyl group, a N-hydroxysuccinimidyl group, and the like.

(6-1)

As the compound represented by Formula [10A], for example, dodecanoic acid, decanoic acid, nonanoic acid, octanoic acid, and the like are known.

The compound represented by Formula [2] can be manufactured by reacting the compound represented by Formula [2B] with the compound represented by Formula [10A] in the presence of a condensing agent or an acid halide or in the presence of a base.

This reaction may be performed based on the manufacturing method (3-3).

(6-2)

As the compound represented by Formula [10B], for example, dodecanoic acid chloride, decanoic acid chloride, nonanoic acid chloride, octanoic acid chloride, and the like are known.

The compound represented by Formula [2] can be manufactured by reacting the compound represented by Formula [2B] with the compound represented by Formula [10B] in the presence of a base.

This reaction may be performed based on the manufacturing method (3-4).

(6-3)

As the compound represented by Formula [16], for example, heptyl 3-chloropropanoate and the like are known.

The compound represented by Formula [2] can be manufactured by reacting the compound represented by Formula [2C] with the compound represented by Formula [16] in the presence or absence of a base.

This reaction may be performed based on the manufacturing method (4-1).

[Manufacturing Method 7]

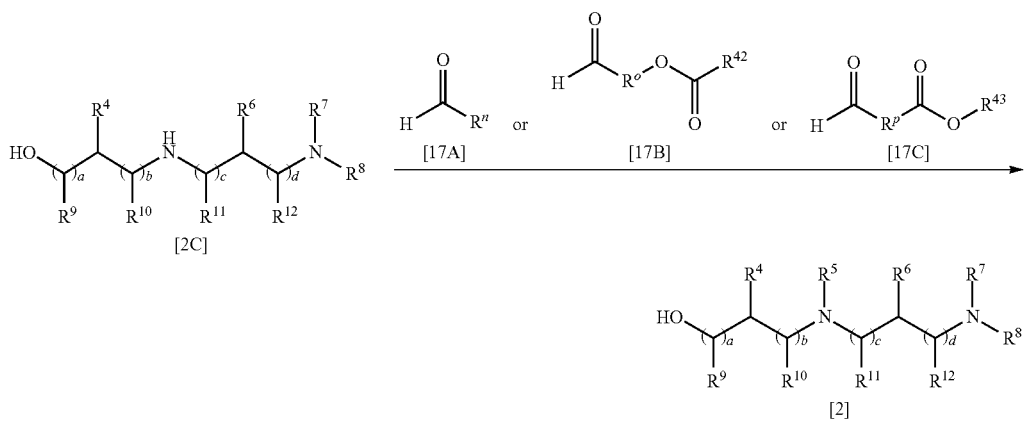

"In the formula, $R^n$, $R^o$, and $R^p$ each represent an alkyl group having 1 to 17 carbon atoms; and $R^4$, $R^5$, $R^6$, $R^7$, $R^8$, $R^9$, $R^{10}$, $R^{11}$, $R^{12}$, $R^{42}$, and $R^{43}$ have the same definitions as $R^4$, $R^5$, $R^6$, $R^7$, $R^8$, $R^9$, $R^{10}$, $R^{11}$, $R^{12}$, $R^{42}$, and $R^{43}$ described above."

(7-1)

As the compound represented by Formula [17A], for example, formaldehyde, acetaldehyde, propanal, butanal, pentanal, hexanal, heptanal, octanal, and the like are known.

The compound represented by Formula [2] can be manufactured by reacting the compound represented by Formula [2C] with the compound represented by Formula [17A] in the presence of a reducing agent, in the presence or absence of a reducing catalyst, or in the presence or absence of an acid.

The solvent used in this reaction is not particularly limited as long as the solvent does not affect the reaction. Examples of the solvent include alcohols, halogenated hydrocarbons, ethers, esters, amides, nitriles, sulfoxides, aromatic hydrocarbons, and water. These solvents may be used by being mixed together.

The amount of the solvent used is not particularly limited, but may be 1 to 500 times (v/w) the amount of the compound represented by Formula [2C].

Examples of the acid used in this reaction include an inorganic acid and an organic acid.

The amount of the acid used may be 0.01 to 10,000 times and preferably 0.05 to 100 times the molar amount of the compound represented by Formula [2C].

Examples of the reducing agent used in this reaction include sodium triacetoxyborohydride, sodium cyanoborohydride, 2-picolineborane, formic acid, hydrogen, and the like.

Examples of the reducing catalyst used in this reaction include palladium-carbon, palladium hydroxide-carbon, platinum-carbon, rhodium-carbon, ruthenium-carbon, and the like.

The amount of the used compound represented by Formula [17A] is not particularly limited, but may be 1 to 10 times (v/w) the amount of the compound represented by Formula [13].

This reaction may be carried out at −30° C. to 150° C. preferably at 0° C. to 100° C. for 5 minutes to 48 hours.

(7-2)

As the compound represented by Formula [17B], for example, 2-oxoethyloctanoate, 2-oxoethylnonanoate, and the like are known.

The compound represented by Formula [2] can be manufactured by reacting the compound represented by Formula [2C] with the compound represented by Formula [17B] in the presence of a reducing agent, in the presence or absence of a reducing catalyst, or in the presence or absence of an acid.

This reaction may be performed based on the manufacturing method (7-1).

(7-3)

As the compound represented by Formula [17C], for example, heptyl 3-oxopropanoate, octyl 3-oxopropanoate, and the like are known.

The compound represented by Formula [2] can be manufactured by reacting the compound represented by Formula [2C] with the compound represented by Formula [17C] in the presence of a reducing agent, in the presence or absence of a reducing catalyst, or in the presence or absence of an acid.

This reaction may be performed based on the manufacturing method (7-1).

In a case where the compounds used in the above manufacturing methods have isomers (for example, an optical isomer, a geometric isomer, a tautomer, and the like), these isomers can also be used.

Furthermore, in a case where the compounds are in the form of solvates, hydrates, and crystals of various shapes, these solvates, hydrates, and crystals of various shapes can also be used.

Among the compounds used in the aforementioned manufacturing methods, for example, for the compounds having an amino group, a hydroxyl group, or a carboxyl group, these groups can be protected in advance with general protecting groups, and the protecting groups can be eliminated by known methods after the reaction.

The compounds obtained by the aforementioned manufacturing methods can be induced into other compounds by being subjected to known reactions such as condensation, addition, oxidation, reduction, transition, substitution, halogenation, dehydration, and hydrolysis or subjected to these reactions that are appropriately combined.

<Lipid Particles>

In the present invention, lipid particles containing the compound or a salt thereof according to an embodiment of the present invention can be prepared. In preparing the lipid particles, in addition to the compound according to the embodiment of the present invention, it is possible to use at least one kind of lipid selected from the group consisting of a sterol, a neutral lipid, and a lipid having a nonionic hydrophilic polymer chain. The lipid particles can further contain a nucleic acid.

In the lipid particles according to the embodiment of the present invention, the amount of the compound according to the embodiment of the present invention mixed in with respect to the total mass of lipids is preferably 20 mol % to 80 mol %, more preferably 35 mol % to 70 mol %, and even more preferably 40 mol % to 65 mol %.

<Sterol>

The lipid particles according to the embodiment of the present invention preferably contain a sterol in an oil phase. In the present invention, in a case where the oil phase contains a sterol, the fluidity of the membrane can be reduced, and hence the lipid particle can be effectively stabilized.

The sterol is not particularly limited, and examples thereof include cholesterol, phytosterol (sitosterol, stigmasterol, fucosterol, spinasterol, brassicasterol), ergosterol, cholestanone, cholestenone, coprostanol, cholesteryl-2'-hydroxyethyl ether, cholesteryl-4'-hydroxybutyl ether, and the like. Among these, cholesterol is preferable.

In the present invention, the amount of the sterol mixed in with respect to the total mass of lipids is preferably 10 mol % to 60 mol %, more preferably 20 mol % to 55 mol %, and even more preferably 25 mol % to 50 mol %.

<Neutral Lipid>

The lipid particles according to the embodiment of the present invention preferably contain a neutral lipid. The neutral lipid is not particularly limited, and examples thereof include phosphatidylcholine, phosphatidylethanolamine, sphingomyelin, ceramide, and the like. Among these, phosphatidylcholine is preferable. The neutral lipid may be a single neutral lipid or a combination of a plurality of different neutral lipids.

The phosphatidylcholine is not particularly limited, and examples thereof include soybean lecithin (SPC), hydrogenated soybean lecithin (HSPC), egg yolk lecithin (EPC), hydrogenated egg yolk lecithin (HEPC), dimyristoylphosphatidylcholine (DMPC), dipalmitoylphosphatidylcholine (DPPC), distearoylphosphatidylcholine (DSPC), 1-palmitoyl-2-oleoylphosphatidylcholine (POPC), and the like. Among these, dipalmitoylphosphatidylcholine (DPPC) is preferable. Particularly, distearoylphosphatidylcholine (DSPC) is preferable.

The phosphatidylethanolamine is not particularly limited, and examples thereof include dimyristoylphosphatidylethanolamine (DMPE), dipalmitoylphosphatidylethanolamine (DPPE), distearoylphosphatidylethanolamine (DSPE), dioleoylphosphatidylethanolamine (DOPE), dilinoleoylphosphatidylethanolamine (DLoPE), diphytanoylphosphatidylethanolamine (D(Phy)PE), 1-palmitoyl-2-oleoylphosphatidylethanolamine (POPE), ditetradecylphosphatidylethanolamine, dihexadecylphosphatidylethanolamine, dioctadecylphosphatidylethanolamine, diphytanylphosphatidylethanolamine, and the like.

The sphingomyelin is not particularly limited, and examples thereof include egg yolk-derived sphingomyelin, milk-derived sphingomyelin, and the like.

The ceramide is not particularly limited, and examples thereof include egg yolk-derived ceramide, milk-derived ceramide, and the like.

In the lipid particles according to the embodiment of the present invention, the amount of the neutral lipid mixed in is preferably equal to or greater than 3 mol % and equal to or smaller than 55 mol % with respect to the total amount of the constituent lipid components.

<Lipid Having Nonionic Hydrophilic Polymer Chain>

The lipid particles according to the embodiment of the present invention may contain a lipid having a nonionic hydrophilic polymer chain in an oil phase. In the present invention, in a case where the lipid particles contain the lipid having a nonionic hydrophilic polymer chain in an oil phase, the dispersion of the lipid particles can be effectively stabilized.

The nonionic hydrophilic polymer is not particularly limited, and examples thereof include a nonionic vinyl-based polymer, a nonionic polyamino acid, a nonionic polyester, a nonionic polyether, a nonionic natural polymer, a nonionic modified natural polymer, and a block polymer or a graft copolymer having two or more kinds of these polymers as constitutional units.

Among these nonionic hydrophilic polymers, a nonionic polyether, a nonionic polyester, a nonionic polyamino acid, or a nonionic synthetic polypeptide is preferable, a nonionic polyether or a nonionic polyester is more preferable, a nonionic polyether or a nonionic monoalkoxy polyether is even more preferable, and polyethylene glycol (hereinafter, polyethylene glycol will be also called PEG) is particularly preferable.

The lipid having a nonionic hydrophilic polymer is not particularly limited, and examples thereof include PEG-modified phosphoethanolamine, a diacylglycerol PEG derivative, a dialkylglycerol PEG derivative, a cholesterol PEG derivative, a ceramide PEG derivative, and the like. Among these, diacylglycerol PEG is preferable.

The weight-average molecular weight of the PEG chain of the nonionic hydrophilic polymer derivative is preferably 500 to 5,000, and more preferably 750 to 3,000.

The nonionic hydrophilic polymer chain may be branched or may have a substituent such as a hydroxymethyl group.

In the lipid particles according to the embodiment of the present invention, the amount of the lipid having a nonionic hydrophilic polymer chain mixed in with respect to the total amount of lipids is preferably 0.25 mol % to 12 mol %, more preferably 0.5. mol % to 6 mol %, and even more preferably 1 mol % to 3 mol %.

<Nucleic Acid>

The lipid particles according to the embodiment of the present invention may contain a nucleic acid. Examples of the nucleic acid include a plasmid, single-stranded DNA, double-stranded DNA, small interfering RNA (siRNA), micro RNA (miRNA), mRNA, an antisense nucleic acid, ribozyme, and the like. The lipid particles may contain any of these. In addition, the lipid particles may contain a modified nucleic acid.

In the lipid particles according to the embodiment of the present invention, the amount of the nucleic acid mixed in with respect to the total amount of lipids is, for example, 0.010% to 50% by weight, preferably 0.10% to 30% by weight, and more preferably 0.5% to 15% by weight.

<Method for Manufacturing Lipid Particles>

The method for manufacturing the lipid particles according to an embodiment of the present invention will be described.

The method for manufacturing the lipid particles is not limited. For example, the lipid particles can be manufactured by a method in which all of the constituent components of the lipid particles or some of oil-soluble components of the lipid particles are dissolved in an organic solvent or the like such that an oil phase is formed, water-soluble components of the lipid particles are dissolved in water such that a water phase is formed, and the oil phase and the water phase are mixed together. A micromixer may be used for mixing, or an emulsifying machine such as a homogenizer, an ultrasonic emulsifying machine, or a high-pressure injection emulsifying machine may be used for emulsification.

Alternatively, the lipid particles can also be manufactured by a method in which a lipid-containing solution is subjected to evaporation to dryness using an evaporator under reduced pressure or subjected to spray drying using a spray drier such that a dried mixture containing a lipid is prepared, and the mixture is added to an aqueous solvent and further emulsified using the aforementioned emulsifying machine or the like.

One of the examples of the method for manufacturing the lipid particles containing a nucleic acid is a method including a step (a) of dissolving the constituent components of the lipid particles containing the compound according to an embodiment of the present invention in an organic solvent so as to obtain an oil phase;

a step (b) of mixing the oil phase obtained in the step (a) with a water phase containing a nucleic acid;

a step (c) of diluting the mixed solution containing the oil phase and the water phase obtained in step (b) so as to obtain a dispersion liquid of nucleic acid lipid particles; and a step (d) of removing the organic solvent from the dispersion liquid of the nucleic acid lipid particles obtained in the step (c).

In the step (a), the constituent components of the lipid particles containing the compound according to the embodiment of the present invention are dissolved in an organic solvent (an alcohol such as ethanol, an ester, or the like). The total lipid concentration is not particularly limited, but is generally 1 mmol/L to 100 mmol/L, preferably 5 mmol/L to 50 mmol/L, and more preferably 10 mmol/L to 30 mmol/L.

In the step (b), the water phase can be obtained by dissolving a nucleic acid (for example, siRNA, an antisense nucleic acid, or the like) in water or a buffer. If necessary, a component such as an antioxidant can be added. The mixing ratio (volume ratio) of water phase:oil phase is preferably 5:1 to 1:1 and more preferably 4:1 to 2:1.

In the step (b), the mixed solution can be diluted with water or a buffer (for example, phosphate buffered saline (PBS) or the like).

In the step (d), as the method of removing the organic solvent from the dispersion liquid of the nucleic acid lipid particles, a general method can be used without particular limitation. For example, by dialyzing the dispersion liquid with the phosphate buffered saline, the organic solvent can be removed.

If necessary, the lipid particles can be subjected to sizing. Although the sizing method is not particularly limited, an extruder or the like can be used to reduce the particle size.

<Lipid Particles>

In the present invention, lipid particles mean particles composed of a lipid, and include a composition having any structure selected from a lipid aggregate composed of aggregated lipids, a micelle, and a liposome. The structure of the lipid particles is not limited to these as long as the lipid particles are a composition containing a lipid. The liposome includes a liposome which has a lipid bilayer structure, contains an internal water phase, and has a single bilayer membrane, and a multiphase liposome which has multiple layers stacked together. The present invention may include any of these liposomes.

The form of the lipid particles can be checked by electron microscopy, structural analysis using X-rays, and the like. For example, by a method using Cryo transmission electron microscopy (CryoTEM method), it is possible to check, for example, whether a lipid particle such as a liposome has a structure composed of a bimolecular lipid membrane structure (lamella structure) and an inner water layer or a structure composed of an inner core with a high electron density and packed with constituent components including a lipid. The X-ray small angle scattering (SAXS) analysis also makes it possible to check whether or not a lipid particle has a bimolecular lipid membrane structure (lamella structure).

The particle size of the lipid particles according to the embodiment of the present invention is not particularly limited, but is preferably 10 to 1,000 nm, more preferably 30 to 500 nm, and even more preferably 50 to 250 nm. The particle size of the lipid particles can be measured by a general method (for example, a dynamic light scattering method, a laser diffraction method, or the like).

<Use of Lipid Particles>

For example, the lipid particles according to the embodiment of the present invention can be used to introduce a nucleic acid (for example, a gene) into a cell by introducing the lipid particles containing the nucleic acid into the cell. Furthermore, in a case where the lipid particles according to the embodiment of the present invention contain a nucleic acid for a pharmaceutical use, the lipid particles can be administered to a living body as a nucleic acid drug.

In a case where the lipid particles according to the embodiment of the present invention are used as a nucleic acid drug, the lipid particles according to the embodiment of the present invention can be administered alone to a living body or administered to a living body by being mixed with a pharmaceutically acceptable dosing medium (for example, physiological saline, a phosphate buffer, or the like).

The concentration of the lipid particles in the mixture with a pharmaceutically acceptable carrier is not particularly limited, and can be set to 0.05% by mass to 90% by mass in general. Furthermore, other pharmaceutically acceptable additives, for example, a pH adjusting buffer and an osmotic pressure adjusting agent, may be added to the nucleic acid drug containing the lipid particles according to the embodiment of the present invention.

The route of administration for administering the nucleic acid drug containing the lipid particles according to the embodiment of the present invention is not particularly limited. The nucleic acid drug can be administered by any method. Examples of the administration method include oral administration and parenteral administration (intra-articular administration, intravenous administration, intra-arterial administration, subcutaneous administration, intracutaneous administration, intravitreal administration, intraperitoneal administration, intramuscular administration, intravaginal administration, intravesical administration, intrathecal administration, pulmonary administration, rectal administration, colonic administration, buccal administration, nasal administration, intracisternal administration, inhalation, and the like). Among these, parenteral administration is preferable. As the method of administration, intravenous injection, subcutaneous injection, intracutaneous injection, or intramuscular injection is preferable. The nucleic acid drug containing the lipid particles according to the embodiment of the present invention can also be administered by being directly injected into the affected area.

The dosage form of the lipid particles according to the embodiment of the present invention is not particularly limited. For oral administration, the lipid particles according to the embodiment of the present invention can be used in the form of tablets, troches, capsules, pills, suspension, syrup, and the like by being combined with an appropriate excipient. In addition, additives such as an antioxidant, a buffer, a bacteriostat, an isotonic sterile injection, a suspending agent, a solubilizer, a thickener, a stabilizer, and a preservative can be appropriately incorporated into formulations suitable for parenteral administration.

<Nucleic Acid Delivery Carrier>

The lipid particles according to the embodiment of the present invention can retain a nucleic acid at a high encapsulation rate. Therefore, the lipid particles are extremely useful as a nucleic acid delivery carrier. According to the nucleic acid delivery carrier using the present invention, for example, by mixing the obtained lipid particles with a nucleic acid or the like and performing transfection in vitro or in vivo, the nucleic acid and the like can be introduced into cells. Furthermore, the nucleic acid delivery carrier using the present invention is also useful as a nucleic acid delivery carrier in nucleic acid drugs. That is, the lipid particles according to the embodiment of the present invention are useful as a composition for in vitro or in vivo (preferably in vivo) delivery of a nucleic acid.

Next, the present invention will be described based on examples, but the present invention is not limited thereto.

EXAMPLES

Unless otherwise specified, for the purification by column chromatography, an automatic purification device ISOLERA (Biotage) or a medium pressure liquid chromatograph YFLC W-prep 2XY (Yamazen Corporation) was used.

Unless otherwise specified, as a carrier for silica gel column chromatography, Chromatorex Q-Pack SI 50 (FUJI SILYSIA CHEMICAL LTD.) or HIGH FLASH COLUMN W001, W002, W003, W004, or W005 (Yamazen Corporation) was used.

As an NH silica gel, Chromatorex Q-Pack NH 60 (FUJI SILYSIA CHEMICAL LTD.) was used.

NMR spectra were measured using tetramethylsilane as an internal standard and using Bruker AV300 (manufactured by Bruker Corporation) or Bruker AV400 (manufactured by Bruker Corporation), and all δ scales are expressed as ppm.

MS spectra were measured using an ACQUITY SQD LC/MS System (manufactured by WATERS).

Synthesis of Compound

Example 1

(1)

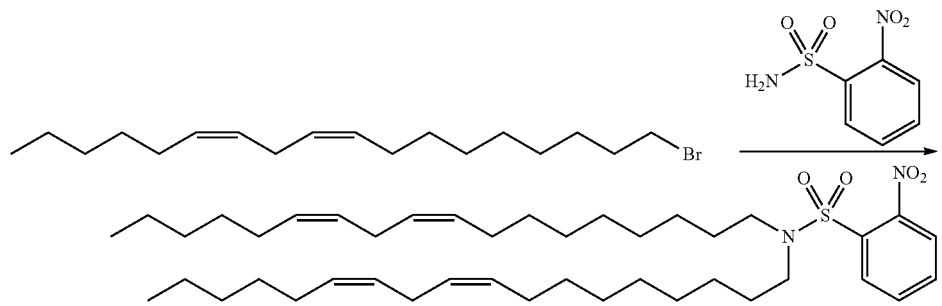

Potassium carbonate (70.4 g) and sodium iodide (2.54 g) were added to a N,N-dimethylformamide (830 mL) solution of (6Z,9Z)-18-bromooctadeca-6,9-diene (131 g) and 2-nitrobenzenesulfonamide (34.4 g), and the mixture was stirred at 80° C. for 5 hours. The reaction mixture was cooled to room temperature, and hexane (300 mL) and water (600 mL) were added thereto. The organic layer was separated, and then the obtained mixture was purified by silica gel column chromatography (ethyl acetate-hexane), thereby obtaining 2-nitro-N,N-di((9Z,12Z)-octadeca-9,12-dien-1-yl)benzenesulfonamide (96.7 g).

$^1$H-NMR (CDCl$_3$) δ: 8.03-7.99 (1H, m), 7.69-7.58 (3H, m), 5.43-5.28 (8H, m), 3.26 (4H, t, J=6.0 Hz), 2.77 (4H, t, J=6.0 Hz), 2.09-2.00 (8H, m), 1.56-1.45 (4H, m), 1.40-1.19 (32H, m), 0.89 (6H, t, J=6.0 Hz).

(2)

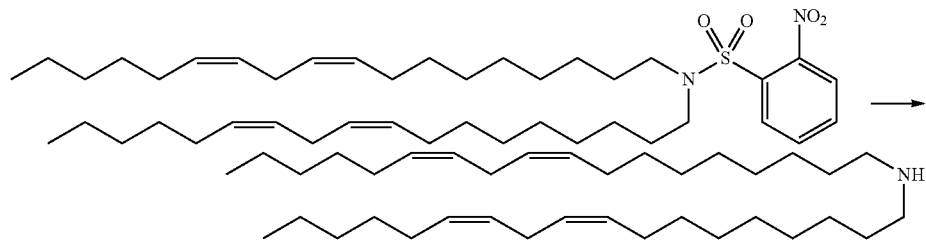

A 10.0 mol/L aqueous potassium hydroxide solution (47.5 mL) was added to a mixture of 2-nitro-N,N-di((9Z,12Z)-octadeca-9,12-dien-1-yl)benzenesulfonamide (96.7 g), dodecanethiol (54.9 mL), acetonitrile (400 mL), and tetrahydrofuran (400 mL), and the mixture was stirred at 40° C. for 2 hours. The reaction mixture was cooled to room temperature, hexane (400 mL), tert-butyl methyl ether (100 mL), and water (200 mL) were added thereto, the organic layer was separated and then dried over anhydrous magnesium sulfate, and the solvent was distilled away under reduced pressure. The obtained residue was purified by silica gel column chromatography (ethyl acetate-hexane), thereby obtaining (9Z,12Z)-di((9Z,12Z)-octadeca-9,12-dien-1-yl)amine (57.7 g).

$^1$H-NMR (CDCl$_3$) δ: 5.43-5.28 (8H, m), 2.77 (4H, t, J=6.0 Hz), 2.58 (4H, t, J=6.0 Hz), 2.09-1.99 (8H, m), 1.56-1.45 (4H, m), 1.40-1.19 (32H, m), 0.89 (6H, t, J=6.0 Hz).

MS m/z (M+H): 514.

(3)

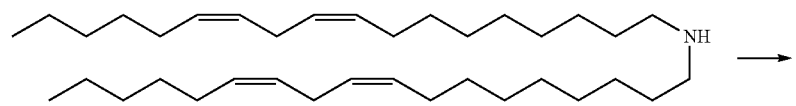

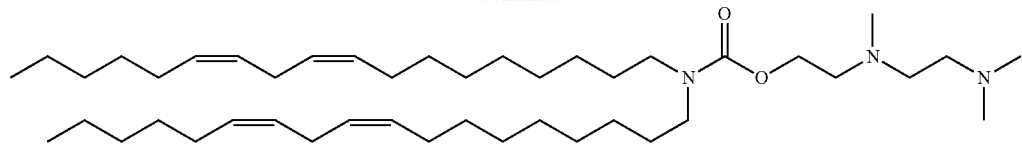

2-((2-(Dimethylamino)ethyl)(methyl)amino)ethan-1-ol (9.36 mL) was added to a tetrahydrofuran (150 mL) solution of 4-nitrophenyl chloroformate (11.7 g), and the mixture was stirred at room temperature for 1 hour. (9Z,12Z9-di((9Z,12Z)-octadeca-9,12-dien-1-yl)amine (15.0 g) and triethylamine (16.3 mL) were added to the reaction mixture, and the reaction mixture was stirred at 50° C. for 4 hours. The reaction mixture was cooled to room temperature, ethyl acetate (150 mL) and water (100 mL) were added thereto, the organic layer was separated and then dried over anhydrous magnesium sulfate, the solvent was distilled away under reduced pressure, and the obtained residue was purified by a silica gel column chromatography (methanol-chloroform). The obtained oily substance was purified by silica gel column chromatography (ethyl acetate-hexane, NH silica gel), thereby obtaining 2-((2-(dimethylamino)ethyl)(methyl)amino)ethyl di((9Z,12Z)-octadeca-9,12-dien-1-yl)carbamate (11.2 g).

$^1$H-NMR (CDCl$_3$) δ: 5.42-5.23 (8H, m), 4.17 (2H, t, J=6.0 Hz), 3.26-3.08 (4H, m), 2.77 (4H, t, J=6.0 Hz), 2.67 (2H, t, 6.0 Hz), 2.54 (2H, t, J=6.0 Hz), 2.39 (2H, t, J=6.0), 2.32 (3H, s), 2.24 (6H, s), 2.12-1.97 (8H, m), 1.57-1.43 (4H, m), 1.42-1.18 (32H, m), 0.89 (6H, t, J=6.0 Hz).

MS m/z (M+H): 687.

Example 2

(1)

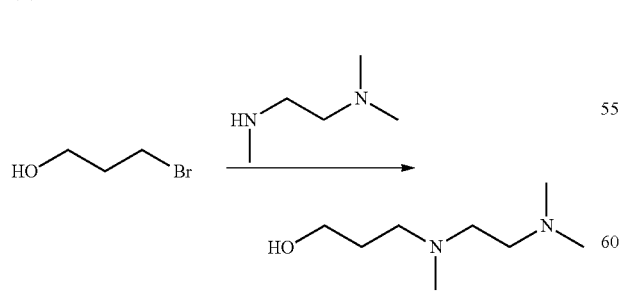

N,N,N'-trimethylethane-1,2-diamine (5 mL) was added to an ethanol (10 mL) solution of 3-bromopropan-1-ol (1.67 mL), and the mixture was stirred at 60° C. for 8 hours. The solvent of the reaction mixture was distilled away under reduced pressure, and the obtained residue was purified by silica gel column chromatography (ethyl acetate-hexane, NH silica gel), thereby obtaining 3-((2-(dimethylamino)ethyl)(methyl)amino)propan-1-ol (1.2 g).

MS m/z (M+H): 161.

(2)

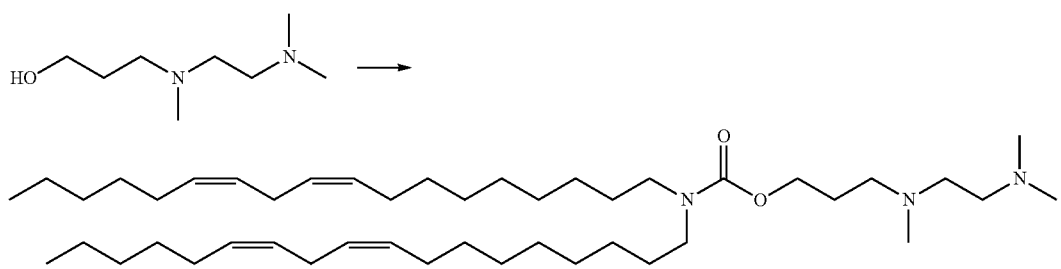

3-((2-(Dimethylamino)ethyl)(methyl)amino)propyl di((9Z,12Z)-octadeca-9,12-dien-1-yl)carbamate was obtained by the same method as that in (3) of Example 1, except that 3-((2-(dimethylamino)ethyl)(methyl)amino)propan-1-ol was used instead of 2-((2-(dimethylamino)ethyl)(methyl)amino)ethan-1-ol in (3) of Example 1.

$^1$H-NMR (CDCl$_3$) δ: 5.44-5.27 (8H, m), 4.09 (2H, t, J=6.0 Hz), 3.25-3.09 (4H, m), 2.77 (4H, t, J=6.0 Hz), 2.50-2.34 (6H, m), 2.25 (3H, s), 2.24 (6H, s), 2.10-1.99 (8H, m), 1.86-1.74 (2H, m), 1.58-1.43 (4H, m), 1.42-1.18 (32H, m), 0.89 (6H, t, J=6.0 Hz)

MS m/z (M+H): 701.

Example 3

(1)

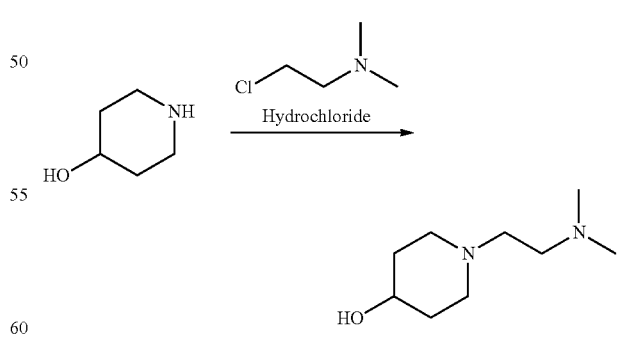

A 12.0 mol/L aqueous sodium hydroxide solution (5 mL) was added to an aqueous solution (5 mL) of piperidin-4-ol (2.0 g) and 2-chloro-N,N-dimethylethan-1-amine hydrochloride (5.69 g), and the mixture was stirred at room temperature for 9 hours. Dichloromethane and water were added to the reaction mixture, the organic layer was separated, and the aqueous layer was extracted using dichloromethane. The organic layer and the extract were combined and dried over anhydrous sodium sulfate, and the solvent was distilled away under reduced pressure. The obtained residue was purified by silica gel column chromatography (ethyl acetate-hexane, NH silica gel), thereby obtaining 1-(2-(dimethylamino)ethyl)piperidin-4-ol (1.3 g).

MS m/z (M+H): 173.

(2)

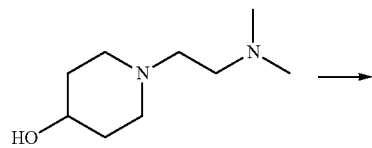

1-(2-(Dimethylamino)ethyl)piperidin-4-yl di((9Z,12Z)-octadeca-9,12-dien-1-yl)carbamate was obtained by the same method as that in (3) of Example 1, except that 1-(2-(dimethylamino)ethyl)piperidin-4-ol was used instead of 2-((2-(dimethylamino)ethyl)(methyl)amino)ethan-1-ol in (3) of Example 1.

¹H-NMR (CDCl₃) δ: 5.43-5.28 (8H, m), 4.75-4.66 (1H, m), 3.24-3.10 (4H, m), 2.77 (4H, t, J=6.0 Hz), 2.72-2.60 (2H, m), 2.50-2.39 (4H, m), 2.37-2.27 (2H, m), 2.24 (6H, s), 2.09-1.99 (8H, m), 1.97-1.85 (2H, m), 1.76-1.65 (2H, m), 1.66-1.58 (8H, m), 1.56-1.43 (4H, m), 1.41-1.19 (32H, m), 0.89 (6H, t, J=6.0 Hz).

MS m/z (M+H): 713.

Example 4

(1)

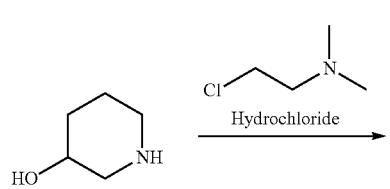

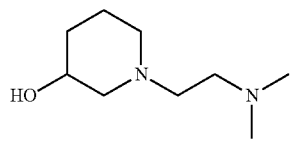

1-(2-(Dimethylamino)ethyl)piperidin-3-ol was obtained by the same method as that in (1) of Example 3, except that piperidin-3-ol was used instead of piperidin-4-ol in (1) of Example 3.

MS m/z (M+H): 173.

(2)

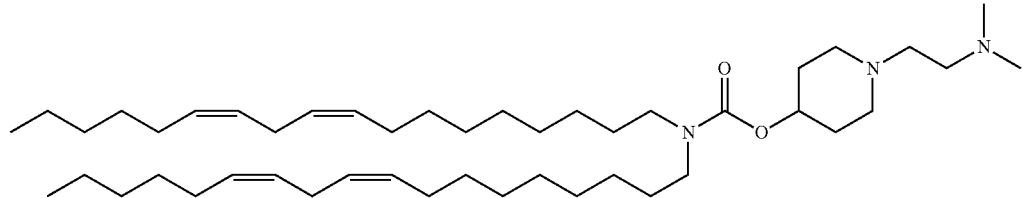

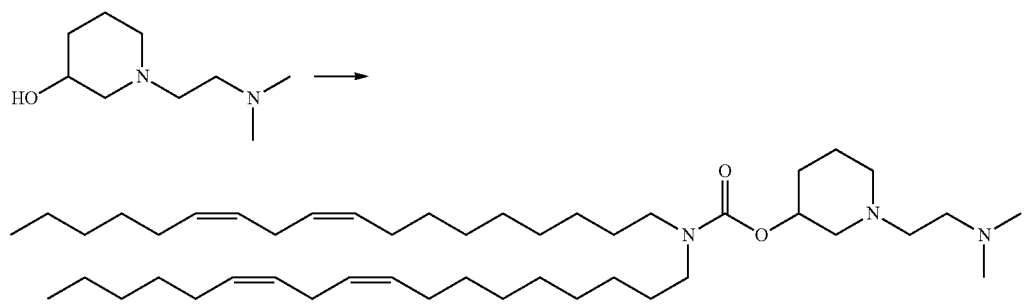

1-(2-(Dimethylamino)ethyl)piperidin-3-yl di((9Z,12Z)-octadeca-9,12-dien-1-yl)carbamate was obtained by the same method as that in (3) of Example 1, except that 1-(2-(dimethylamino)ethyl)piperidin-3-ol was used instead of 2-((2-(dimethylamino)ethyl)(methyl)amino)ethan-1-ol in (3) of Example 1.

¹H-NMR (CDCl₃) δ: 5.43-5.28 (8H, m), 4.78-4.68 (1H, m), 3.26-3.06 (4H, m), 2.94-2.87 (1H, m), 2.77 (4H, t, J=6.0 Hz), 2.70-2.61 (1H, m), 2.52-2.38 (4H, m), 2.24 (6H, s), 2.16-1.99 (10H, m), 1.97-1.87 (1H, m), 1.77-1.43 (7H, m), 1.41-1.19 (32H, m), 0.89 (6H, t, J=6.0 Hz).

MS m/z (M+H): 713.

Example 5

(1)

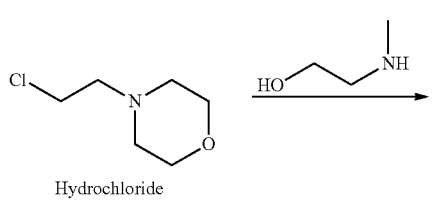

Hydrochloride 4-(2-Chloroethyl)morpholine hydrochloride (14.9 g) was added to an ethanol (60 mL) suspension of 2-(methylamino)ethan-1-ol (3.0 g) and potassium carbonate (22.1 g), and the mixture was stirred at 60° C. for 4 hours and stirred under reflux for 3 hours. The reaction mixture was cooled to room temperature, insoluble matters were then filtered off, and the solvent was distilled away under reduced pressure. The obtained residue was purified by silica gel column chromatography (ethyl acetate-hexane, NH silica gel), thereby obtaining 2-(methyl(2-morpholinoethyl)amino)ethan-1-ol (5.5 g).

MS m/z (M+H): 189.

(2)

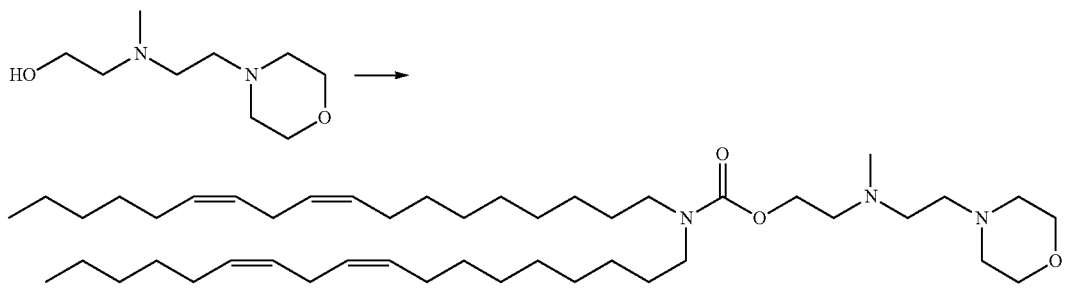

2-(Methyl(2-morpholinoethyl)amino)ethyl di((9Z,12Z)-octadeca-9,12-diene-1-yl)carbamate was obtained by the same method as that in (3) of Example 1, except that 2-(methyl(2-morpholinoethyl)amino)ethan-1-ol was used instead of 2-((2-(dimethylamino)ethyl)(methyl)amino)ethan-1-ol in (3) of Example 1.

$^1$H-NMR (CDCl$_3$) δ: 5.46-5.25 (8H, m), 4.16 (2H, t, J=6.0 Hz), 3.71 (4H, t, J=6.0 Hz), 3.25-3.09 (4H, m), 2.27 (4H, t, J=6.0 Hz), 2.67 (2H, t, J=6.0 Hz), 2.62-2.53 (2H, m), 2.52-2.42 (6H, m), 2.32 (3H, s), 2.11-1.97 (8H, m), 1.55-1.44 (4H, m), 1.42-1.17 (32H, m), 0.89 (6H, t, J=6.0 Hz).

MS m/z (M+H): 729.

Example 6

(1)

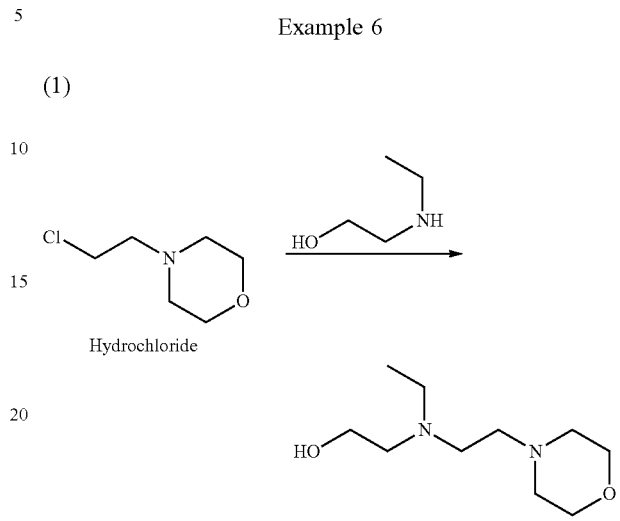

Hydrochloride 2-(Ethyl(2-morpholinoethyl)amino)ethan-1-ol was obtained by the same method as that in (1) of Example 5, except that 2-(ethylamino)ethan-1-ol was used instead of 2-(methylamino)ethan-1-ol in (1) of Example 5.

MS m/z (M+H): 203.

(2)

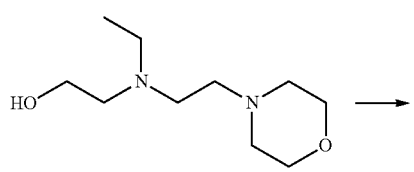

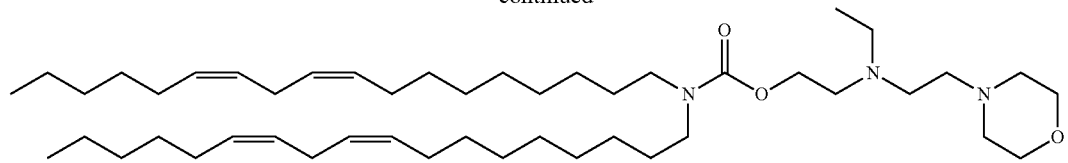

2-(Ethyl(2-morpholinoethyl)amino)ethyl di((9Z,12Z)-octadeca-9,12-dien-1-yl)carbamate was obtained by the same method as that In (3) of Example 1, except that 2-(ethyl(2-morpholinoethyl)amino)ethan-1-ol was used instead of 2-((2-(dimethylamino)ethyl)(methyl)amino)ethan-1-ol in (3) of Example 1.

$^1$H-NMR (CDCl$_3$) δ: 5.45-5.24 (8H, m), 4.12 (2H, t, J=6.0 Hz), 3.70 (4H, t, J=6.0 Hz), 3.27-3.06 (4H, m), 2.82-2.69 (6H, m), 2.69-2.54 (4H, m), 2.52-2.39 (6H, m), 2.12-1.97 (8H, m), 1.55-1.42 (4H, m), 1.41-1.17 (32H, m), 1.03 (3H, t, J=6.0 Hz), 0.89 (6H, t, J=6.0 Hz).

MS m/z (M+H): 743.

the same method as that in (3) of Example 1, except that 2-((2-(diethylamino)ethyl)(methyl)amino)ethan-1-ol was used instead of 2-((2-(dimethylamino)ethyl)(methyl)amino)ethan-1-ol in (3) of Example 1.

$^1$H-NMR (CDCl$_3$) δ: 5.45-5.26 (8H, m), 4.16 (2H, t, J=6.0 Hz), 3.25-3.09 (4H, m), 2.77 (4H, t, J=6.0 Hz), 2.67 (2H, t, J=6.0 Hz), 2.60-2.49 (8H, m), 2.32 (3H, s), 2.12-1.96 (8H, m), 1.56-1.44 (4H, m), 1.42-1.17 (32H, m), 1.02 (6H, t, J=6.0 Hz), 0.89 (6H, t, J=6.0 Hz).

MS m/z (M+H): 715.

Example 7

(1)

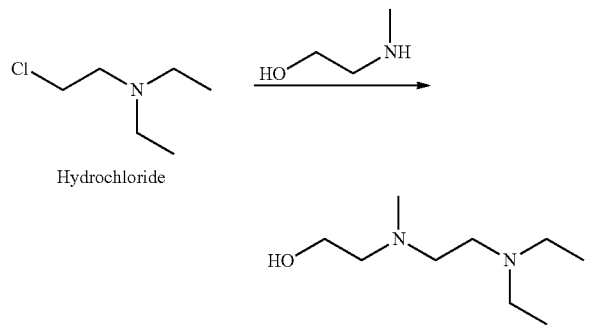

2-((2-(Diethylamino)ethyl)(methyl)amino)ethan-1-ol was obtained by the same method as that in (1) of Example 5, except that 2-chloro-N,N-diethylethan-1-amine hydrochloride was used instead of 4-(2-chloroethyl)morpholine hydrochloride in (1) of Example 5.

MS m/z (M+H): 175.

(2)

2-((2-(Diethylamino)ethyl)(methyl)amino)ethyl di((9Z,12Z)-octadeca-9,12-dien-1-yl)carbamate was obtained by

Example 8

(1)

2-((3-(Dimethylamino)propyl)(methyl)amino)ethan-1-ol was obtained by the same method as that in (1) of Example 2, except that in (1) of Example 2, 2-bromoethan-1-ol was used instead of 3-bromopropan-1-ol, and N,N,N'-trimethylpropane-1,3-diamine was used instead of N,N,N'-trimethylethane-1,2-diamine.

MS m/z (M+H): 161.

(2)

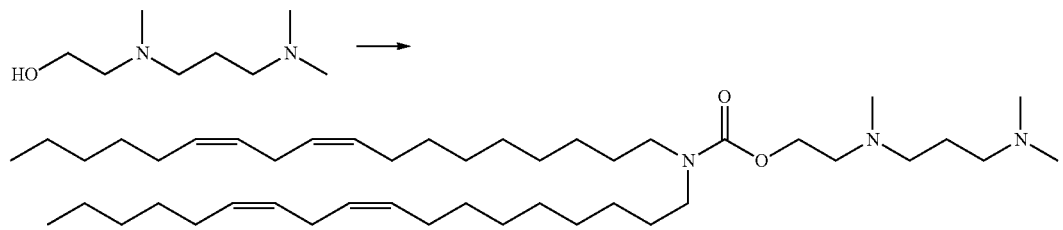

2-((3-(Dimethylamino)propyl)(methyl)amino)ethyl di((9Z,12Z)-octadeca-9,12-dien-1-yl)carbamate was obtained by the same method as that in (3) of Example 1, except that 2-((3-(dimethylamino)propyl)(methyl)amino)ethan-1-ol was used instead of 2-((2-(dimethylamino)ethyl)(methyl)amino)ethan-1-ol in (3) of Example 1.

$^1$H-NMR (CDCl$_3$) δ: 5.43-5.28 (8H, m), 4.16 (2H, t, J=6.0 Hz), 3.25-3.10 (4H, m), 2.77 (4H, t, J=6.0 Hz), 2.63 (2H, t, J=6.0 Hz), 2.42 (2H, t, J=6.0 Hz), 2.28 (3H, s), 2.27 (2H, t, J=6.0 Hz), 2.21 (6H, s), 2.04 (8H, q, J=6.0 Ha), 1.67-1.58 (2H, m), 1.56-1.43 (4H, m), 1.40-1.19 (32H, m), 0.89 (6H, t, J=6.0 Hz).

MS m/z (M+H): 701.

carbamate was obtained by the same method as that in (3) of Example 1, except that tert-butyl(2-((tert-butoxycarbonyl)amino)ethyl)(2-hydroxyethyl)carbamate was used instead of 2-((2-(dimethylamino)ethyl)(methyl)amino)ethan-1-ol in (3) of Example 1.

$^1$H-NMR (CDCl$_3$) δ: 5.44-5.27 (8H, m), 4.20-4.09 (1H, m), 3.51-3.10 (10H, m), 2.77 (4H, t, J=6.0 Hz), 2.10-1.99 (8H, m), 1.64-1.48 (4H, m), 1.41-1.23 (32H, m), 0.89 (6H, t, J=6.0 Hz).

(2)

Example 9

(1)

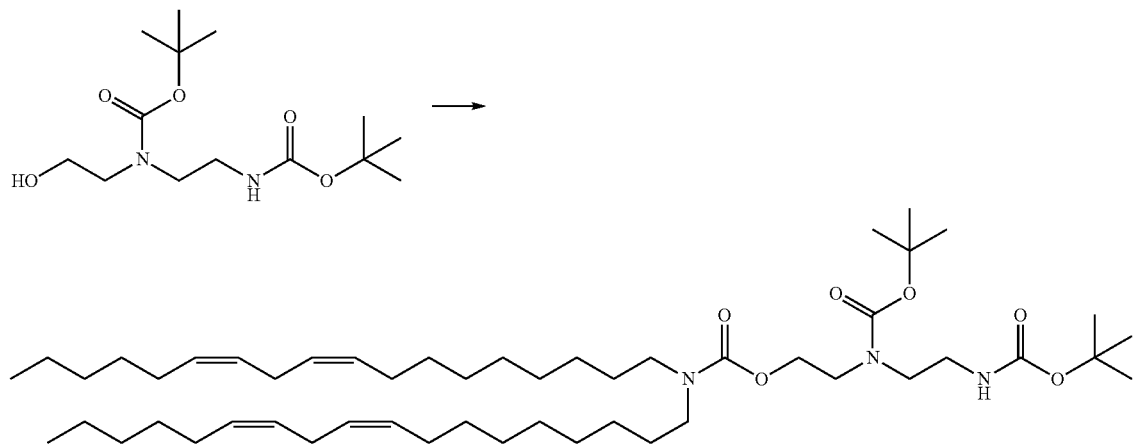

2-((tert-Butoxycarbonyl)(2-((tert-butoxycarbonyl)amino)ethyl)amino)ethyl di((9Z,12Z)-octadeca-9,12-dien-1-yl)

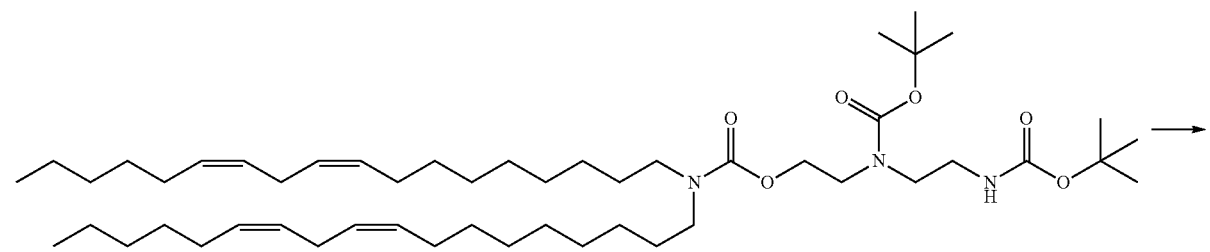

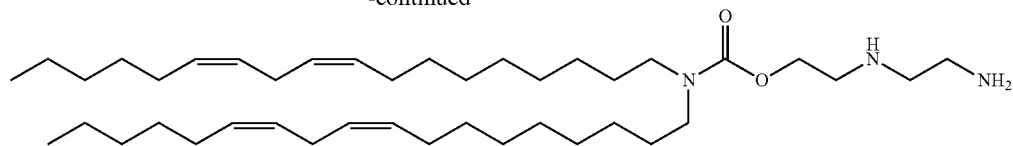

Trifluoroacetic acid (2 mL) was added to a mixture of 2-((tert-butoxycarbonyl)(2-((tert-butoxycarbonyl)amino)ethyl)amino)ethyl)di((9Z,12Z)-octadeca-9,12-dien-1-yl)carbamate (0.6 g), water (0.2 mL), and dichloromethane (0.5 mL), and the mixture was stirred at room temperature for 30 minutes. Toluene was added to the reaction mixture, and the solvent was distilled away under reduced pressure. The obtained residue was purified by silica gel column chromatography (methanol-chloroform, NH silica gel), thereby obtaining 2-((2-aminoethyl)amino)ethyl di((9Z,12Z)-octadeca-9,12-dien-1-yl)carbamate (0.3 g).

$^1$H-NMR (CDCl$_3$) δ: 5.43-5.28 (8H, m), 4.18 (2H, t, J=6.0 Hz), 3.24-3.11 (4H, m), 2.87 (2H, t, J=6.0 Hz), 2.80 (2H, t, J=6.0 Hz), 2.77 (4H, t, J=6.0 Hz), 2.70 (2H, t, J=6.0 Hz), 2.09-2.00 (8H, m), 1.59-1.44 (4H, m), 1.40-1.19 (32H, m), 0.89 (6H, t, J=6.0 Hz).

MS m/z (M+H): 645.

Example 10 used instead of (9Z,12Z9-di((9Z,12Z)-octadeca-9,12-dien-1-yl)amine in (3) of Example 1.

$^1$H-NMR (CDCl$_3$) δ: 4.17 (2H, t, J=6.0 Hz), 3.23-3.12 (4H, m), 2.67 (2H, t, J=6.0 Hz), 2.54 (2H, t, J=6.0 Hz), 2.39 (2H, t, J=6.0 Hz), 2.32 (3H, s), 2.24 (6H, s), 1.55-1.38 (4H, m), 1.35-1.18 (52H, m), 0.88 (6H, t, J=6.0 Hz).

MS m/z (M+H): 639.

Example 11

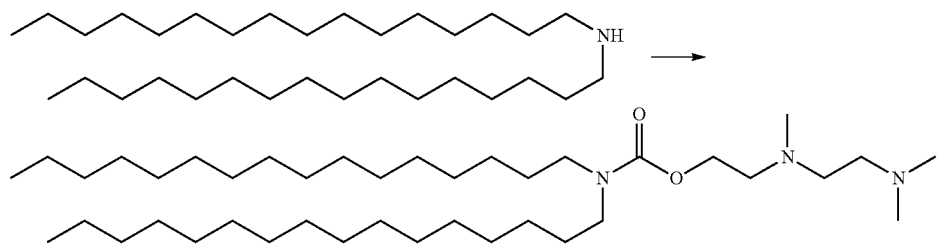

2-((2-(Dimethylamino)ethyl)(methyl)amino)ethyl dihexadecylcarbamate was obtained by the same method as that in (3) of Example 1, except that dihexadecylamine was

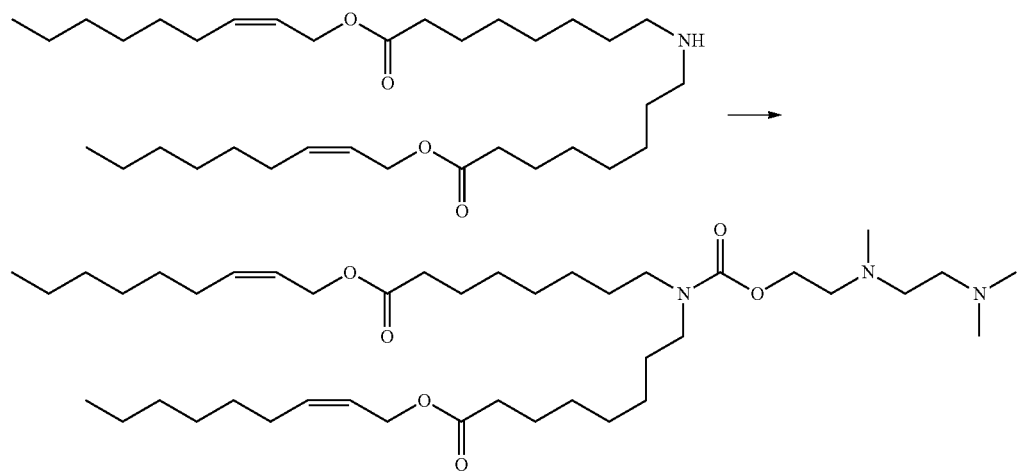

(Z)-non-2-en-1-yl 2,5-dimethyl-10-(8-(((Z)-non-2-en-1-yl)oxy)-8-oxooctyl)-9-oxo-8-oxa-2,5,10-triazaoctadecan- 18-oate was obtained by the same method as that in (3) of Example 1, except that di((Z)-non-2-en-1-yl)8,8'-azanedyl dioctanoate synthesized according to the method described in WO2016/081029A1 was used instead of (9Z,12Z9-di((9Z,12Z)-octadeca-9,12-dien-1-yl)amine in (3) of Example 1.

¹H-NMR (CDCl₃) δ: 5.70-5.46 (4H, m), 4.61 (4H, d, J=6.0 Hz), 4.16 (2H, t, J=6.0 Hz), 3.23-3.09 (4H, m), 2.66 (2H, t, J=6.0 Hz), 2.61-2.45 (2H, m), 2.42-2.25 (2H, m), 2.31 (3H, s), 2.23 (6H, s), 2.15-2.05 (4H, m), 1.65-1.56 (4H, m), 1.55-1.43 (4H, m), 1.39-1.20 (32H, m), 0.88 (6H, t, J=6.0 Hz).

MS m/z (M+H): 723.

Example 12

¹H-NMR (CDCl₃) δ: 5.83-5.70 (2H, m), 5.61-5.49 (2H, m), 4.50 (4H, d, J=6.0 Hz), 4.16 (2H, t, J=6.0 Hz), 3.24-3.09 (4H, m), 2.67 (2H, t, J=6.0 Hz), 2.54 (2H, t, J=6.0 Hz), 2.38 (2H, t, J=6.0 Hz), 2.31 (3H, s), 2.24 (6H, s), 2.09-2.00 (4H, m), 1.65-1.56 (4H, m), 1.55-1.44 (4H, m), 1.41-1.23 (32H, m), 0.88 (6H, t, J=6.0 Hz).

MS m/z (M+H): 723.

Example 13

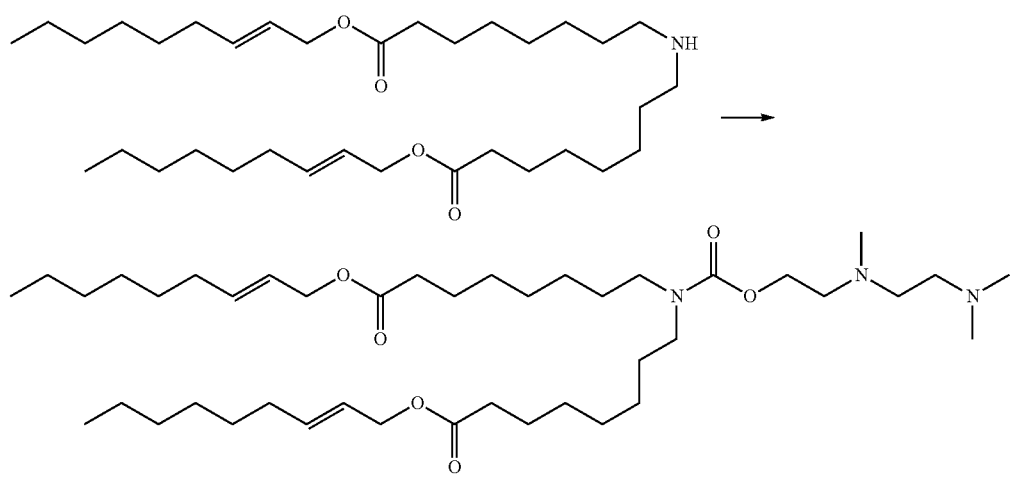

(E)-non-2-en-1-yl 2,5-dimethyl-10-(8-(((E)-non-2-en-1-yl)oxy)-8-oxooctyl)-9-oxo-8-oxa-2,5,10-triazaoctadecan-18-oate was obtained by the same method as that in (3) of

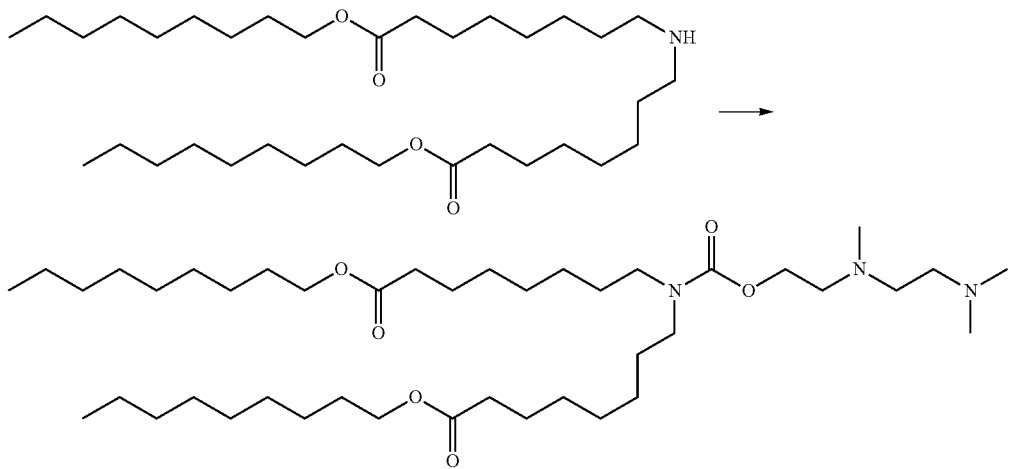

Example 1, except that di((E)-non-2-en-1-yl)8,8'-azanedyl dioctanoate synthesized according to the method described in WO2016/081029A1 was used instead of (9Z,12Z9-di((9Z,12Z)-octadeca-9,12-dien-1-yl)amine in (3) of Example 1.

Nonyl 2,5-dimethyl-10-(8-(nonyloxy)-8-oxooctyl)-9-oxo-8-oxa-2,5,10-triazaoctadecan-18-oate was obtained by the same method as that in (3) of Example 1, except that dinonyl 8,8'-azanedyl dioctanoate synthesized according to the method described in WO2016/081029A1 was used instead of (9Z,12Z9-di((9Z,12Z)-octadeca-9,12-dien-1-yl)amine in (3) of Example 1.

$^1$H-NMR (CDCl$_3$) δ: 4.20-4.01 (6H, m), 3.24-3.09 (4H, m), 2.71-2.51 (4H, m), 2.44-2.38 (2H, m), 2.31 (3H, s), 2.26 (6H, s), 1.79-1.43 (12H, m), 1.37-1.23 (40H, m), 0.88 (6H, t, J=6.0 Hz).

MS m/z (M+H): 727.

Example 14

(1)

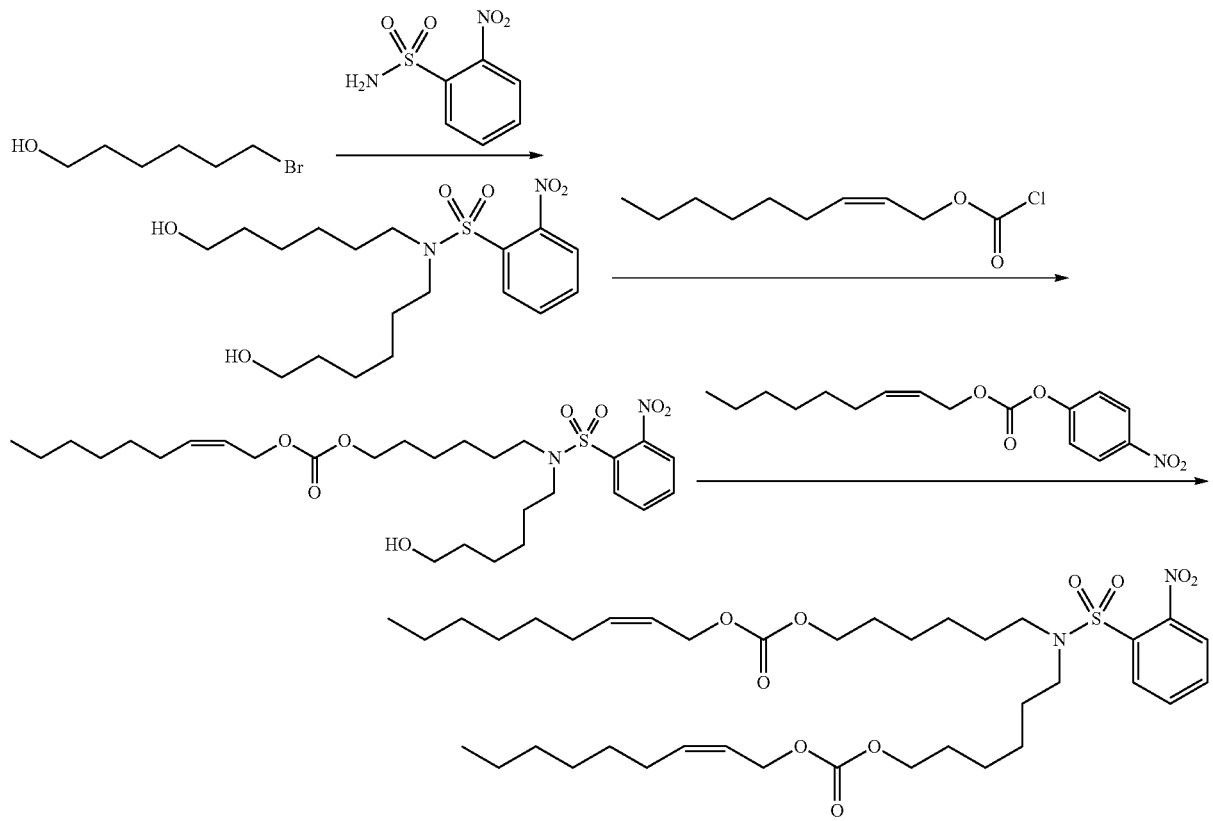

N,N-bis(6-hydroxyhexyl)-2-nitrobenzenesulfonamide was obtained by the same method as that in (1) of Example 1, except that 6-bromohexan-1-ol was used instead of (6Z,9Z)-18-bromooctadeca-6,9-diene in (1) of Example 1.

(Z)-non-2-en-1-yl carbonochloridate (3.15 g) was added to a mixture of the obtained N,N-bis(6-hydroxyhexyl)-2-nitrobenzenesulfonamide (2.13 g), triethylamine (0.58 mL), and tetrahydrofuran (5 mL), and the mixture was stirred at room temperature for 1 hour. Water and ethyl acetate were added to the reaction mixture, the organic layer was separated, washed with water, and then dried over anhydrous sodium sulfate, and the solvent was distilled away under reduced pressure, thereby obtaining (Z)-6-((N-(6-hydroxyhexyl)-2-nitrophenyl)sulfonamido)hexyl non-2-en-1-yl carbonate (1.67 g).

$^1$H-NMR (CDCl$_3$) δ: 8.04-7.97 (1H, m), 7.71-7.59 (3H, m), 5.72-5.51 (2H, m), 4.68 (2H, d, J=6.0 Hz), 4.12 (2H, t, J=6.0 Hz), 3.65-3.59 (2H, m), 3.30-3.24 (4H, m), 2.14-2.07 (2H, m), 1.66-1.48 (8H, m), 1.40-1.22 (16H, m), 0.88 (3H, t, J=6.0 Hz).

4-Dimethylaminopyridine (0.37 g) was added to a mixture of the obtained (Z)-6-((N-(6-hydroxyhexyl)-2-nitrophenyl)sulfonamido)hexyl non-2-en-1-yl carbonate (1.67 g), (Z)-4-nitrophenyl non-2-en-1-yl carbonate (1.84 g), triethylamine (1.7 mL), and tetrahydrofuran (17 mL), and the mixture was stirred at 50° C. for 6 hours. The reaction mixture was cooled to room temperature, and then the solvent was distilled away under reduced pressure. The obtained residue was purified by silica gel column chromatography (ethyl acetate-hexane), thereby obtaining (((2-nitrophenyl)sulfonyl)azanediyl)bis(hexane-6,1-diyl)di((Z)-non-2-en-1-yl)bis(carbonate) (1.96 g).

$^1$H-NMR (CDCl$_3$) δ: 8.04-7.97 (1H, m), 7.71-7.59 (3H, m), 5.72-5.51 (4H, m), 4.68 (4H, d, J=6.0 Hz), 4.12 (4H, t, J=6.0 Hz), 3.27 (4H, t, J=6.0 Hz), 2.14-2.07 (4H, m), 1.66-1.48 (8H, m), 1.40-1.22 (24H, m), 0.88 (6H, t, J=6.0 Hz).

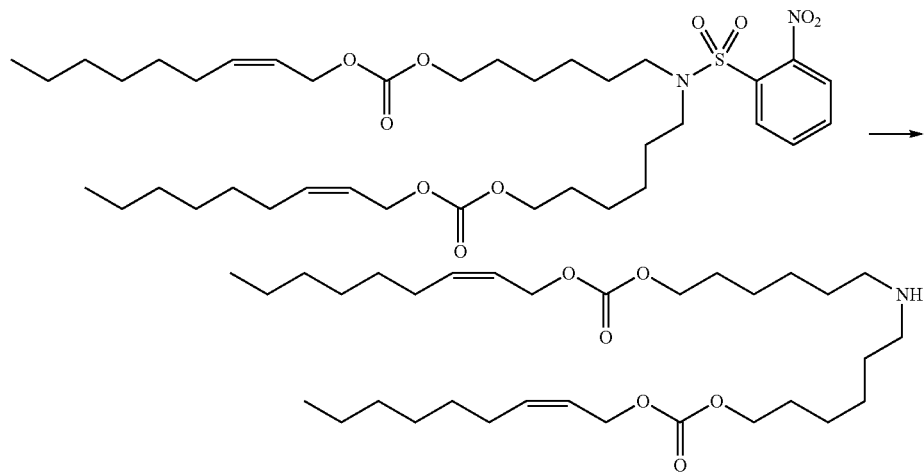

Cesium carbonate (2.51 g) was added to a mixture of (((2-nitrophenyl)sulfonyl)azanedyl)bis(hexane-6,1-diyl)di((Z)-non-2-en-1-yl)bis(carbonate) (1.01 g), dodecane-1-thiol (1.05 mL), and acetonitrile (10 mL), and the mixture was stirred at 50° C. for 10 hours. The reaction mixture was cooled to room temperature, water and ethyl acetate were added thereto, the organic layer was separated and dried over anhydrous sodium sulfate, and then the solvent was distilled away under reduced pressure. The obtained residue was purified by silica gel column chromatography (ethyl acetate-hexane), thereby obtaining azanedylbis(hexane-6,1-diyl)di((Z)-non-2-en-1-yl)bis(carbonate) (1.59 g).

$^1$H-NMR (CDCl$_3$) δ: 5.73-5.50 (4H, m), 4.68 (4H, d, J=6.0 Hz), 4.12 (4H, t, J=6.0 Hz), 2.61 (4H, t, J=6.0 Hz), 2.15-2.05 (4H, m), 1.73-1.46 (8H, m), 1.42-1.24 (24H, m), 0.88 (6H, t, J=6.0 Hz).

(3)

1, except that azanedylbis(hexane-6,1-diyl)di((Z)-non-2-en-1-yl)bis(carbonate) was used instead of (9Z,12Z9-di((9Z,12Z)-octadeca-9,12-dien-1-yl)amine in (3) of Example 1.

$^1$H-NMR (CDCl$_3$) δ:5.73-5.50 (4H, m), 4.67 (4H, d, J=6.0 Hz), 4.20-4.08 (6H, m), 3.24-3.10 (4H, m), 2.66 (2H, d, J=6.0 Hz), 2.53 (2H, t, J=6.0 Hz), 2.38 (2H, t, J=6.0 Hz), 2.31 (3H, s), 2.24 (6H, s), 2.15-2.06 (4H, m), 1.72-1.45 (8H, m), 1.42-1.23 (24H, m), 0.88 (6H, t, J=6.0 Hz).

MS m/z (M+H): 727.

Example 15

(1)

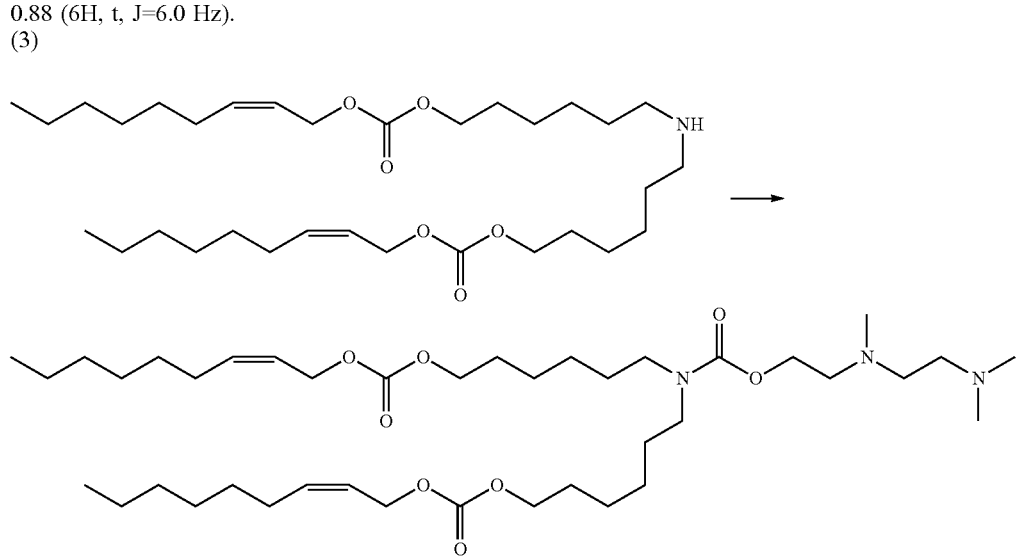

2-((2-(Dimethylamino)ethyl)(methyl)amino)ethyl bis(6-(((((Z)-non-2-en-1-yl)oxy)carbonyl)oxy)hexyl)carbamate was obtained by the same method as that in (3) of Example

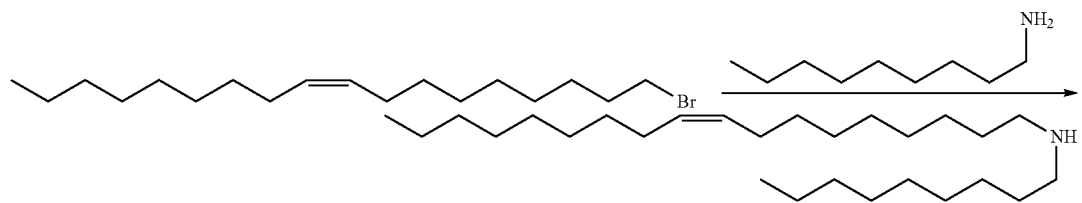

(Z)-1-bromooctadec-9-ene (4.53 g) was added to a N,N-dimethylformamide (20 mL) suspension of nonan-1-amine (1.95 g) and potassium carbonate (1.87 g), and the mixture was stirred at 80° C. for 9 hours. The reaction mixture was cooled to room temperature, and water (40 mL) and hexane (40 mL) were added thereto. The organic layer was separated, the solvent was then distilled away under reduced pressure, and the obtained residue was purified by silica gel column chromatography (ethyl acetate-hexane), thereby obtaining (Z)—N-nonyloctadec-9-en-1-amine (1.72 g).

MS m/z (M+H): 394.

(2)

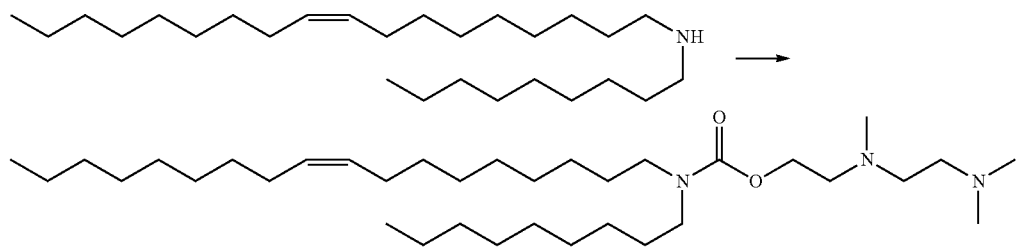

2-((2-(Dimethylamino)ethyl)(methyl)amino)ethyl(Z)-nonyl(octadec-9-en-1-yl)carbamate was obtained by the same method as that in (3) of Example 1, except that (Z)—N-nonyloctadec-9-en-1-amine was used instead of (9Z,12Z9-di((9Z,12Z)-octadeca-9,12-dien-1-yl)amine in (3) of Example 1.

$^1$H-NMR (CDCl$_3$) δ: 5.41-5.29 (2H, m), 4.17 (2H, t, J=6.0 Hz), 3.24-3.11 (4H, m), 2.68 (2H, t, J=6.0 Hz), 2.54 (2H, t, J=6.0 Hz), 2.38 (2H, t, J=6.0 Hz), 2.32 (3H, s), 2.24 (6H, s), 2.08-1.93 (4H, m), 1.56-1.43 (4H, m), 1.38-1.18 (34H, m), 0.89 (6H, t, J=6.0 Hz).

MS m/z (M+H): 567.

Example 16

(1)

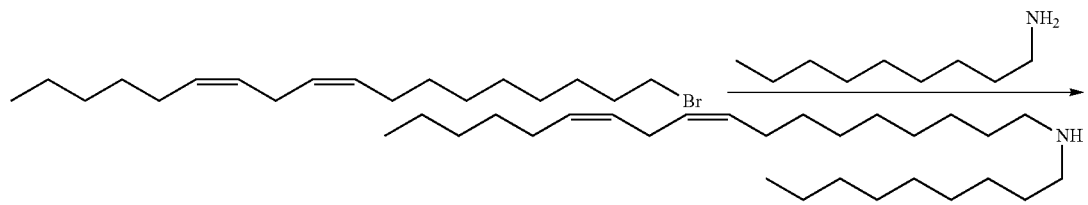

(9Z,12Z)—N-nonyloctadeca-9,12-dien-1-amine was obtained by the same method as that in (1) of Example 15, except that (6Z,9Z)-18-bromooctadeca-6,9-diene was used instead of (Z)-1-bromooctadec-9-ene in (1) of Example 15.

MS m/z (M+H): 392.

(2)

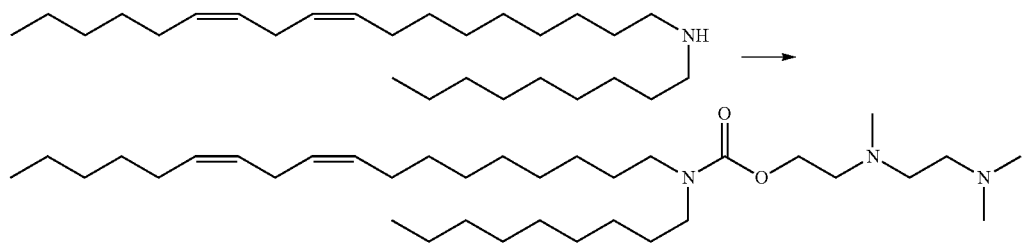

2-((2-(Dimethylamino)ethyl)(methyl)amino)ethyl nonyl((9Z,12Z)-octadeca-9,12-dien-1-yl)carbamate was obtained by the same method as that in (3) of Example 1, except that (9Z,12Z)—N-nonyloctadeca-9,12-dien-1-amine was used instead of (9Z,12Z9-di((9Z,12Z)-octadeca-9,12-dien-1-yl)amine in (3) of Example 1.

$^1$H-NMR (CDCl$_3$) δ: 5.43-5.29 (4H, m), 4.17 (2H, t, J=6.0 Hz), 3.25-3.11 (4H, m), 2.77 (2H, t, J=6.0 Hz), 2.68 (2H, t, J=6.0 Hz), 2.54 (2H, t, J=6.0 Hz), 2.38 (2H, t, J=6.0 Hz), 2.32 (3H, s), 2.24 (6H, s), 2.10-1.99 (4H, m), 1.56-1.43 (4H, m), 1.41-1.19 (28H, m), 0.92-0.85 (6H, m).

MS m/z (M+H): 565.

Example 17

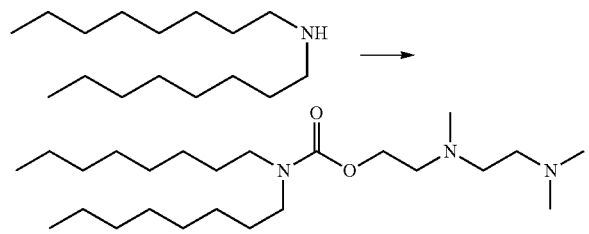

2-((2-(Dimethylamino)ethyl)(methyl)amino)ethyl dioctylcarbamate was obtained by the same method as that in (3) of Example 1, except that dioctylamine was used instead of (9Z,12Z9-di((9Z,12Z)-octadeca-9,12-dien-1-yl)amine in (3) of Example 1.

$^1$H-NMR (CDCl$_3$) δ: 4.17 (2H, t, J=6.0 Hz), 3.24-3.12 (4H, m), 2.68 (2H, t, J=6.0 Hz), 2.54 (2H, t, J=6.0 Hz), 2.39 (2H, t, J=6.0 Hz), 2.32 (3H, s), 2.24 (6H, s), 1.55-1.43 (4H, m), 1.34-1.19 (20H, m), 0.88 (6H, t, J=6.0 Hz).

MS m/z (M+H): 414.

Example 18

2-((2-(Dimethylamino)ethyl)(methyl)amino)ethyl dinonylcarbamate was obtained by the same method as that in (3) of Example 1, except that dinonylamine was used instead of (9Z,12Z9-di((9Z,12Z)-octadeca-9,12-dien-1-yl)amine in (3) of Example 1.

$^1$H-NMR (CDCl$_3$) δ: 4.17 (2H, t, J=6.0 Hz), 3.24-3.12 (4H, m), 2.68 (2H, t, J=6.0 Hz), 2.54 (2H, t, J=6.0 Hz), 2.39 (2H, t, J=6.0 Hz), 2.32 (3H, s), 2.24 (6H, s), 1.55-1.43 (4H, m), 1.34-1.19 (24H, m), 0.88 (6H, t, J=6.0 Hz).

MS m/z (M+H): 442.

Example 19

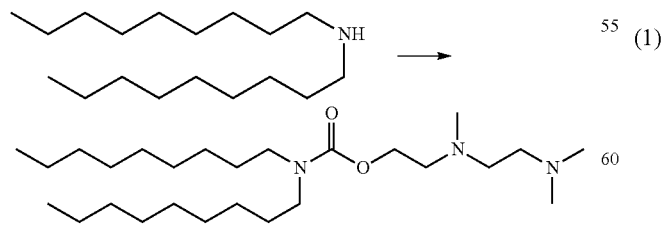

2-((2-(Dimethylamino)ethyl)(methyl)amino)ethyl didecylcarbamate was obtained by the same method as that in (3) of Example 1, except that didecylamine was used instead of (9Z,12Z9-di((9Z,12Z)-octadeca-9,12-dien-1-yl)amine in (3) of Example 1.

$^1$H-NMR (CDCl$_3$) δ: 4.17 (2H, t, J=6.0 Hz), 3.23-3.12 (4H, m), 2.67 (2H, t, J=6.0 Hz), 2.54 (2H, t, J=6.0 Hz), 2.39 (2H, t, J=6.0 Hz), 2.32 (3H, s), 2.24 (6H, s), 1.55-1.38 (4H, m), 1.35-1.18 (28H, m), 0.88 (6H, t, J=6.0 Hz).

MS m/z (M+H): 470.

Example 20

(1)

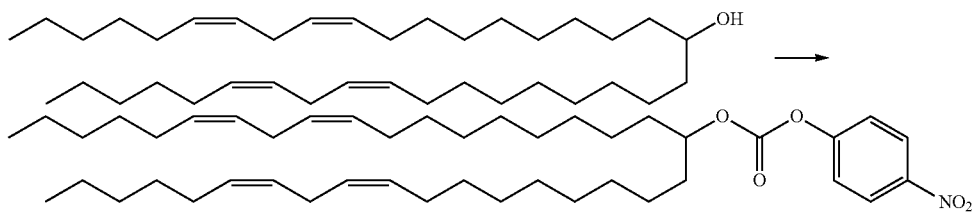

4-Nitrophenyl chloroformate (3.8 g) was added a mixture of (6Z,9Z,28Z,31Z)-heptatriaconta-6,9,28,31-tetraen-19-ol (5.0 g) synthesized according to the method described in WO2010/054401A1, triethylamine (4.0 mL), and tetrahydrofuran (25 mL), and the mixture was stirred at room temperature for 6 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining (6Z,9Z,28Z,31Z)-heptatriaconta-6,9,28,31-tetraen-19-yl(4-nitrophenyl)carbonate (6.25 g).

$^1$H-NMR (CDCl$_3$) δ: 8.31-8.24 (2H, m), 7.42-7.35 (2H, m), 5.44-5.27 (8H, m), 4.87-4.76 (1H, m), 2.77 (4H, t, J=6.0 Hz), 2.11-1.99 (8H, m), 1.74-1.57 (4H, m), 1.44-1.21 (36H, m), 0.89 (6H, t, J=6.0 Hz).

(2)

sulfate, and the solvent was distilled away under reduced pressure. The obtained residue was purified by silica gel column chromatography (ethyl acetate-hexane), thereby obtaining 2-((2-(dimethylamino)ethyl)(methyl)amino)ethyl ((6Z,9Z,28Z,31Z)-heptatriaconta-6,9,28,31-tetraen-19-yl)carbonate (0.36 g).

$^1$H-NMR (CDCl$_3$) δ: 5.44-5.27 (8H, m), 4.73-4.62 (1H, m), 4.22 (2H, t, J=6.0 Hz), 2.77 (4H, t, J=6.0 Hz), 2.71 (2H, t, J=6.0 Hz), 2.58-2.50 (2H, m), 2.43-2.35 (2H, m), 2.32 (3H, s), 2.24 (6H, s), 2.11-1.97 (8H, m), 1.63-1.48 (4H, m), 1.42-1.19 (36H, m), 0.89 (6H, t, J=6.0 Hz).

MS m/z (M+H): 702.

Example 21

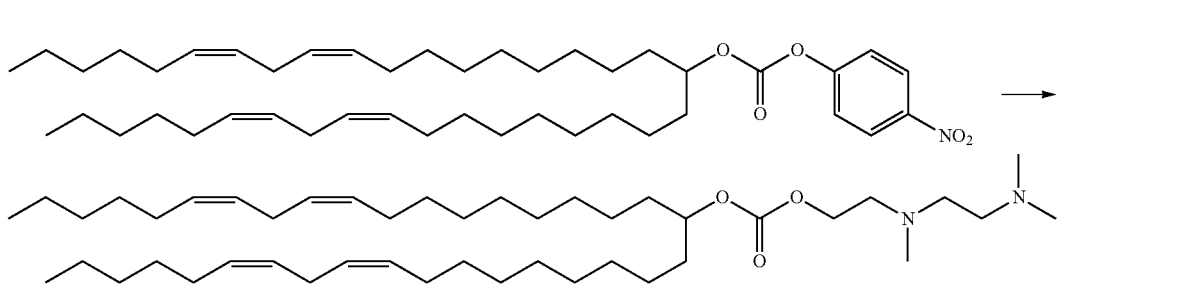

4-Dimethylaminopyridine (0.23 g) was added to a mixture of (6Z,9Z,28Z,31Z)-heptatriaconta-6,9,28,31-tetraen-19-yl(4-nitrophenyl)carbonate (0.89 g), 2-((2-(dimethylamino)ethyl)(methyl)amino)ethan-1-ol (0.30 mL), triethylamine (0.27 mL), and tetrahydrofuran (5 mL), and the mixture was stirred at 60° C. for 6 hours. The reaction mixture was cooled to room temperature, water and ethyl

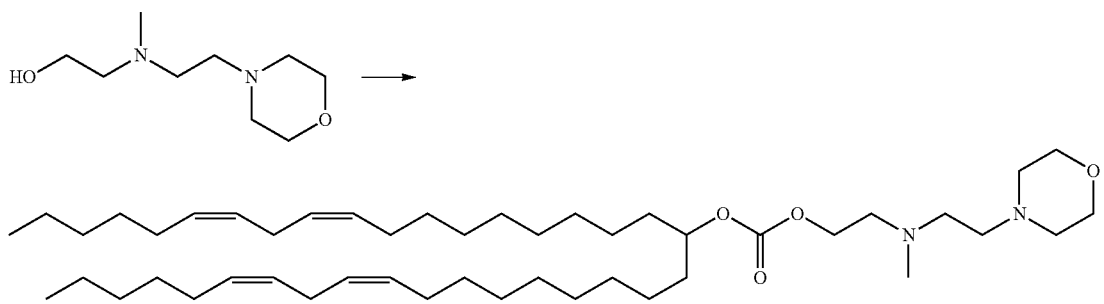

acetate were added thereto, the organic layer was separated, washed with water, and then dried over anhydrous sodium 2-(Methyl(2-morpholinoethyl)amino)ethyl((6Z,9Z,28Z, 31Z)-heptatriaconta-6,9,28,31-tetraen-19-yl)carbonate was obtained by the same method as that in (2) of Example 20, except that 2-(methyl(2-morpholinoethyl)amino)ethan-1-ol synthesized in (1) of Example 5 was used instead of 2-((2-(dimethylamino)ethyl)(methyl)amino)ethan-1-ol in (2) of Example 20.

¹H-NMR (CDCl₃) δ: 5.46-5.25 (8H, m), 4.73-4.61 (1H, m), 4.21 (2H, t, J=6.0 Hz), 3.71 (4H, t, J=6.0 Hz), 2.77 (4H, t, J=6.0 Hz), 2.71 (2H, t, J=6.0 Hz), 2.62-2.54 (2H, m), 2.51-2.43 (6H, m), 2.32 (3H, s), 2.13-1.98 (8H, m), 1.65-1.46 (4H, m), 1.43-1.20 (36H, m), 0.89 (6H, t, J=6.0 Hz).

MS m/z (M+H): 744.

¹H-NMR (CDCl₃) δ: 5.44-5.27 (8H, m), 4.72-4.61 (1H, m), 4.21 (2H, t, J=6.0 Hz), 2.77 (4H, t, J=6.0), 2.70 (2H, t, J=6.0 Hz), 2.59-2.49 (8H, m), 2.31 (3H, s), 2.14-1.94 (8H, m), 1.64-1.47 (4H, m), 1.43-1.19 (36H, m), 1.02 (6H, t, J=6.0 Hz), 0.89 (6H, t, J=6.0 Hz).

MS m/z (M+H): 730.

Example 22

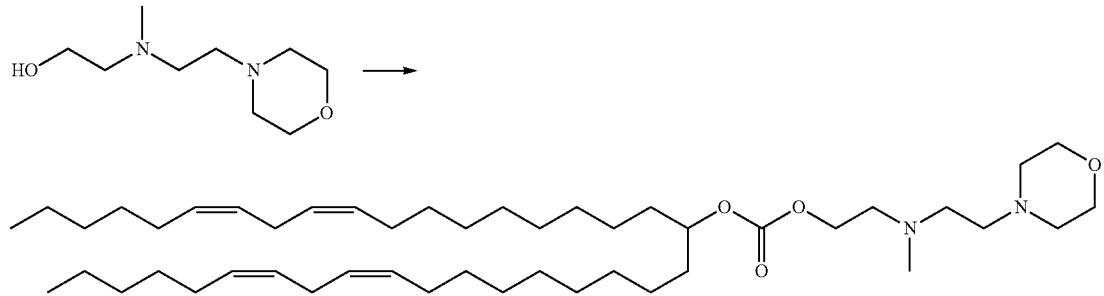

2-(Ethyl(2-morpholinoethyl)amino)ethyl((6Z,9Z,28Z,31Z)-heptatriaconta-6,9,28,31-tetraen-19-yl)carbonate was obtained by the same method as that in (2) of Example 20, except that 2-(ethyl(2-morpholinoethyl)amino)ethan-1-ol synthesized in (1) of Example 6 was used instead of 2-((2-(dimethylamino)ethyl)(methyl)amino)ethan-1-ol in (2) of Example 20.

¹H-NMR (CDCl₃) δ: 5.45-5.26 (8H, m), 4.74-4.60 (1H, m), 4.17 (2H, t, J=6.0 Hz), 3.71 (4H, t, J=6.0 Hz), 2.84-2.72 (6H, m), 2.70-2.54 (4H, m), 2.52-2.39 (6H, m), 2.12-1.94 (8H, m), 1.66-1.47 (4H, m), 1.44-1.18 (36H, m), 1.03 (3H, t, J=6.0 Hz), 0.89 (6H, t, J=6.0 Hz).

MS m/z (M+H): 758.

Example 23

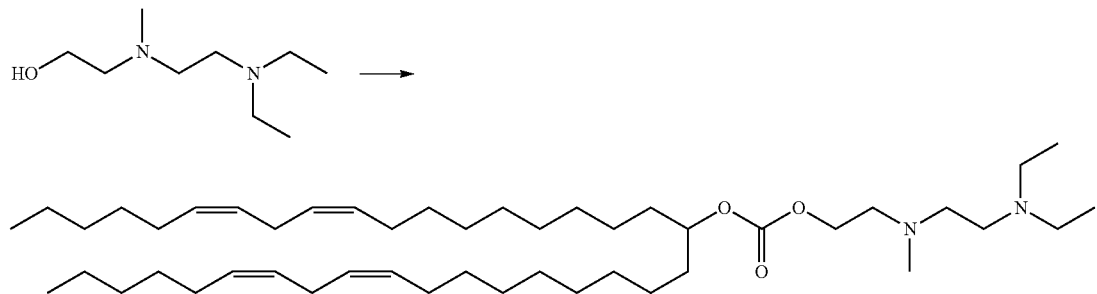

2-((2-(Diethylamino)ethyl)(methyl)amino)ethyl((6Z,9Z,28Z,31Z)-heptatriaconta-6,9,28,31-tetraen-19-yl)carbonate was obtained by the same method as that in (2) of Example 20, except that 2-((2-(diethylamino)ethyl)(methyl)amino)ethan-1-ol synthesized in (1) of Example 7 was used instead of 2-((2-(dimethylamino)ethyl)(methyl)amino)ethan-1-ol in (2) of Example 20.

Example 24

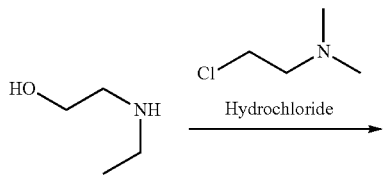

(1)

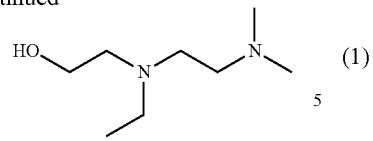

2-((2-(Dimethylamino)ethyl)(ethyl)amino)ethan-1-ol was obtained by the same method as that in (1) of Example 5, except that in (1) of Example 5, 2-chloro-N,N-dimethylethan-1-amine hydrochloride was used instead of 4-(2-chloroethyl)morpholine hydrochloride, and 2-(ethylamino)ethan-1-ol was used instead of 2-(methylamino)ethan-1-ol.

MS m/z (M+H): 161.

(2)

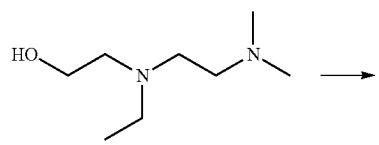

2-((2-(Dimethylamino)ethyl)(ethyl)amino)ethyl((6Z,9Z,28Z,31Z)-heptatriaconta-6,9,28,31-tetraen-19-yl)carbonate was obtained by the same method as that in (2) of Example 20, except that 2-((2-(dimethylamino)ethyl)(ethyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.26 (8H, m), 4.73-4.61 (1H, m), 4.18 (2H, t, J=6.0 Hz), 2.83-2.71 (6H, m), 2.67-2.55 (4H, m), 2.42-2.33 (2H, m), 2.24 (6H, s), 2.12-1.98 (8H, m), 1.64-1.50 (4H, m), 1.45-1.19 (36H, m), 1.03 (3H, t, J=6.0 Hz), 0.89 (6H, t, J=6.0 Hz).

MS m/z (M+H): 716.

Example 25

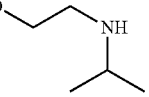 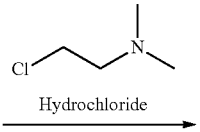

-continued

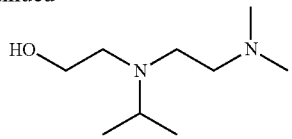

2-((2-(Dimethylamino)ethyl)(isopropyl)amino)ethan-1-ol was obtained by the same method as that in (1) of Example 5, except that in (1) of Example 5, 2-chloro-N,N-dimethylethan-1-amine hydrochloride was used instead of 4-(2-chloroethyl)morpholine hydrochloride, and 2-(isopropylamino)ethan-1-ol was used instead of 2-(methylamino)ethan-1-ol.

MS m/z (M+H): 175.

(2)

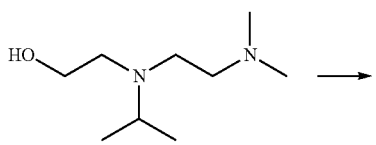

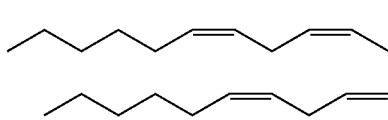

2-((2-(Dimethylamino)ethyl)(isopropyl)amino)ethyl((6Z,9Z,28Z,31Z)-heptatriaconta-6,9,28,31-tetraen-19-yl)carbonate was obtained by the same method as that in (2) of Example 20, except that 2-((2-(dimethylamino)ethyl)(isopropyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.46-5.26 (8H, m), 4.73-4.61 (1H, m), 4.10 (2H, t, J=6.0 Hz), 2.98-2.85 (1H, m), 2.77 (4H, t, J=6.0 Hz), 2.69 (2H, t, J=6.0 Hz), 2.60-2.52 (2H, m), 2.37-2.29 (2H, m), 2.24 (6H, s), 2.10-1.99 (8H, m), 1.58-1.49 (4H, m), 1.45-1.20 (36H, m), 0.99 (6H, d, J=6.0 Hz), 0.89 (6H, t, J=6.0 Hz).

MS m/z (M+H): 730.

Example 26

(1)

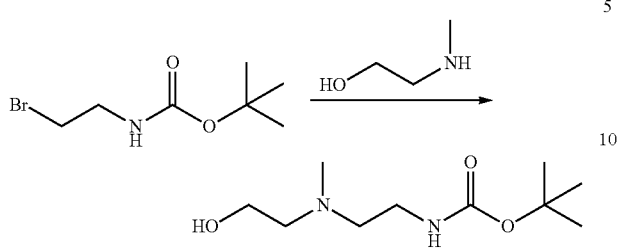

tert-Butyl(2-((2-hydroxyethyl)(methyl)amino)ethyl)carbamate was obtained by the same method as that in (1) of Example 5, except that tert-butyl(2-bromoethyl)carbamate was used instead of 4-(2-chloroethyl)morpholine hydrochloride in (1) of Example 5.

MS m/z (M+H): 219.

(2)

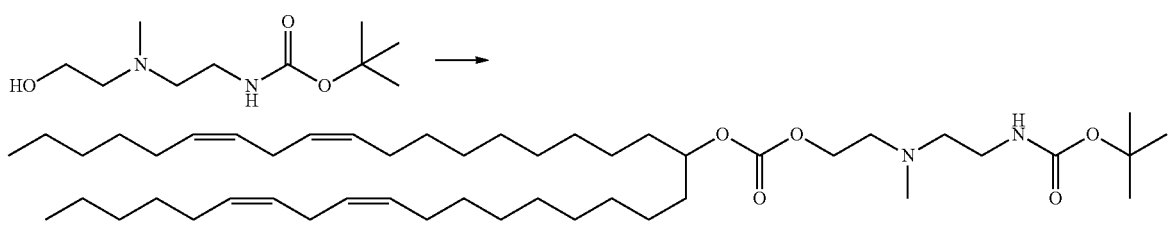

tert-Butyl(2-((2-(((((6Z,9Z,28Z,31Z)-heptatriaconta-6,9,28,31-tetraen-19-yl)oxy)ethyl)(methyl)amino)ethyl)carbamate was obtained by the same method as that in (2) of Example 20, except that tert-butyl(2-((2-hydroxyethyl)(methyl)amino)ethyl)carbamate was used instead of 2-((2-(dimethylamino)ethyl)(methyl)amino)ethan-1-ol in (2) of Example 20.

$^1$H-NMR (CDCl$_3$) δ: 5.45-5.26 (8H, m), 5.04 (1H, bs), 4.76-4.62 (1H, m), 4.20 (2H, t, J=6.0 Hz), 3.25-3.12 (2H, m), 2.77 (4H, t, J=6.0 Hz), 2.68 (2H, t, J=6.0 Hz), 2.52 (2H, t, J=6.0 Hz), 2.28 (3H, s), 2.12-1.96 (8H, m), 1.62-1.50 (4H, m), 1.45 (9H, s), 1.62-1.50 (36H, m), 0.89 (6H, t, J=6.0 Hz).

MS m/z (M+H): 774.

(3)

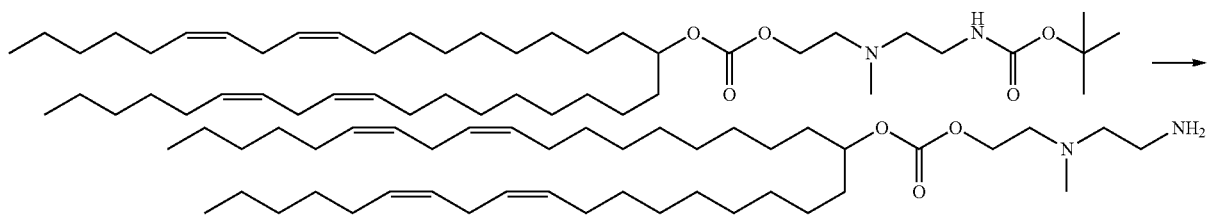

2-((2-(Aminoethyl)(methyl)amino)ethyl((6Z,9Z,28Z,31Z)-heptatriaconta-6,9,28,31-tetraen-19-yl)carbonate was obtained by the same method as that in (2) of Example 9, except that tert-butyl (2-((2-(((((6Z,9Z,28Z,31Z)-heptatriaconta-6,9,28,31-tetraen-19-yl)oxy)ethyl)(methyl)amino) ethyl)carbamate synthesized in (2) of Example 26 was used instead of 2-((tert-butoxycarbonyl)(2-((tert-butoxycarbonyl)amino)ethyl)amino)ethyl)di((9Z,12Z)-octadeca-9,12-dien-1-yl)carbamate in (2) of Example 9.

$^1$H-NMR (CDCl$_3$) δ: 5.45-5.26 (8H, m), 4.73-4.61 (1H, m), 4.22 (2H, t, J=6.0 Hz), 2.82-2.72 (6H, m), 2.68 (2H, t, J=6.0 Hz), 2.47 (2H, t, J=6.0 Hz), 2.29 (3H, s), 2.11-1.98 (8H, m), 1.62-1.44 (4H, m), 1.42-1.19 (36H, m), 0.89 (6H, t, J=6.0 Hz).

MS m/z (M+H): 674.

Example 27

(1)

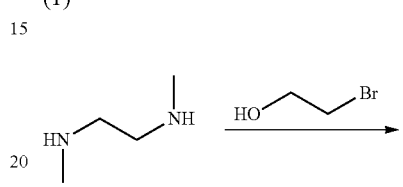

-continued

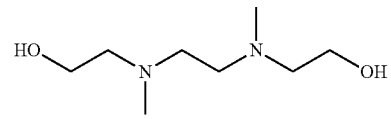

2-Bromoethan-1-ol (14.2 g) was added to an ethanol (50 mL) suspension of N,N'-dimethylethane-1,2-diamine (5.0 g) and potassium carbonate (17.2 g), and the mixture was stirred at 60° C. for 5 hours. The reaction mixture was cooled to room temperature, the insoluble matters were filtered off, and then the solvent was distilled away under reduced pressure, thereby obtaining 2,2'-(ethane-1,2-diylbis (methylazanediyl))bis(ethan-1-ol) (10.2 g).

MS m/z (M+H): 177.

(2)

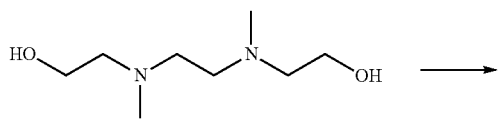

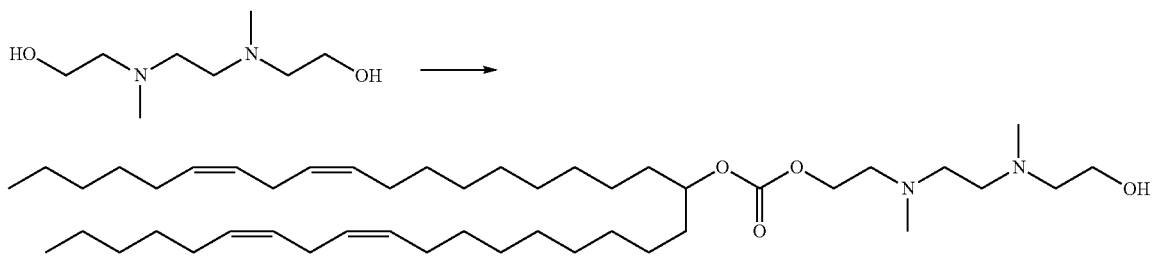

(6Z,9Z,28Z,31Z)-heptatriaconta-6,9,28,31-tetraen-19-yl (2-((2-((2-hydroxyethyl)(methyl)amino)ethyl)(methyl)amino)ethyl)carbonate was obtained by the same method as that in (2) of Example 20, except that 2,2'-(ethane-1,2-diylbis(methylazanediyl))bis(ethan-1-ol) was used instead of 2-((2-(dimethylamino)ethyl)(methyl)amino)ethan-1-ol in (2) of Example 20.

$^1$H-NMR (CDCl$_3$) δ: 5.44-5.27 (8H, m), 4.73-4.61 (1H, m), 4.23 (2H, t, J=6.0 Hz), 3.56 (2H, t, J=6.0 Hz), 2.82-2.67 (6H, m), 2.58-2.52 (6H, m), 2.31 (6H, s), 2.11-1.99 (8H, m), 1.63-1.46 (4H, m), 1.42-1.20 (36H, m), 0.89 (6H, t, J=6.0 Hz).

MS m/z (M+H): 732.

-continued

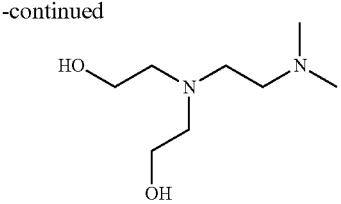

2,2'-((2-(Dimethylamino)ethyl)azanediyl)bis(ethan-1-ol) was obtained by the same method as that in (1) of Example 5, except that in (1) of Example 5, 2,2'-azanedylbis(ethan-1-ol) was used instead of 2-(methylamino)ethan-1-ol, and 2-chloro-N,N-dimethylethan-1-amine hydrochloride was used instead of 4-(2-chloroethyl)morpholine hydrochloride.

MS m/z (M+H): 177.

(2)

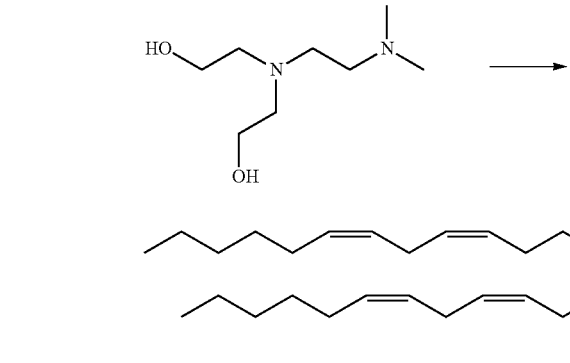

Example 28

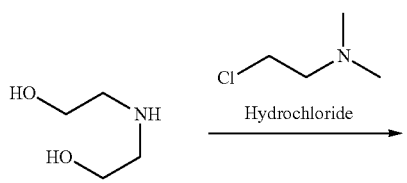

2-((2-(Dimethylamino)ethyl)(2-hydroxyethyl)amino)ethyl)((6Z,9Z,28Z,31Z)-heptatriaconta-6,9,28,31-tetraen-19-yl)carbonate was obtained by the same method as that in (2) of Example 20, except that 2,2'-((2-(dimethylamino)ethyl)azanediyl)bis(ethan-1-ol) was used instead of 2-((2-(dimethylamino)ethyl)(methyl)amino)ethan-1-ol in (2) of Example 20.

$^1$H-NMR (CDCl$_3$) δ: 5.45-5.25 (8H, m), 4.73-4.62 (1H, m), 4.21 (2H, t, J=6.0 Hz), 3.53 (2H, t, J=6.0 Hz), 2.89 (2H, t, J=6.0 Hz), 2.77 (4H, t, J=6.0 Hz), 2.73-2.64 (4H, m), 2.37 (2H, t, J=6.0 Hz), 2.23 (6H, s), 2.10-1.98 (8H, m), 1.65-1.46 (4H, m), 1.43-1.18 (36H, m), 0.89 (6H, t, J=6.0 Hz).

MS m/z (M+H): 732.

Example 29

(1)

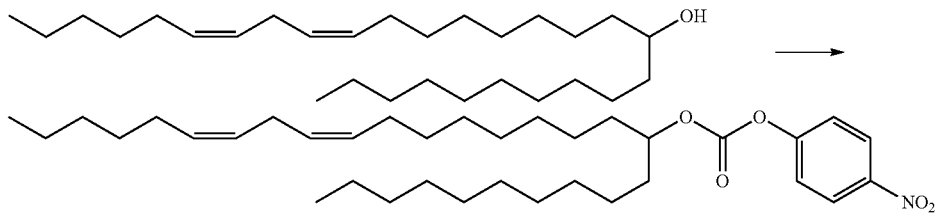

4-Nitrophenyl chloroformate (1.0 g) was added to a mixture of ((19Z,22Z)-octacosa-19,22-dien-11-ol (1.0 g) synthesized according to the method described in WO2015/005253A1, triethylamine (1.0 mL), and tetrahydrofuran (5.0 mL), and the mixture was stirred at room temperature for 2 hours. Water and ethyl acetate were added to the reaction mixture, the organic layer was separated and dried over anhydrous sodium sulfate, and then the solvent was distilled away under reduced pressure. The obtained residue was purified by silica gel column chromatography (ethyl acetate-hexane), thereby obtaining 4-nitrophenyl((19Z,22Z)-octacosa-19,22-dien-11-yl)carbonate (2.0 g).

$^1$H-NMR (CDCl$_3$) δ: 8.28 (2H, d, J=9.0 Hz), 7.38 (2H, d, J=9.0 Hz), 5.43-5.28 (4H, m), 4.87-4.77 (1H, m), 2.77 (2H, t, J=6.0 Hz), 2.10-1.99 (4H, m), 1.76-1.60 (4H, m), 1.43-1.20 (32H, m), 0.92-0.83 (6H, m).

(2)

2-((2-(Dimethylamino)ethyl)(methyl)amino)ethyl((19Z,22Z)-octacosa-19,22-dien-11-yl)carbonate was obtained by the same method as that in (2) of Example 20, except that 4-nitrophenyl((19Z,22Z)-octacosa-19,22-dien-11-yl)carbonate was used instead of (6Z,9Z,28Z,31Z)-heptatriaconta-6,9,28,31-tetraen-19-yl(4-nitrophenyl)carbonate in (2) of Example 20.

$^1$H-NMR (CDCl$_3$) δ: 5.44-5.26 (4H, m), 4.73-4.62 (1H, m), 4.22 (2H, t, J=6.0 Hz), 2.77 (2H, t, J=6.0 Hz), 2.71 (2H, t, J=6.0 Hz), 2.54 (2H, t, J=6.0 Hz), 2.39 (2H, t, J=6.0 Hz), 2.31 (3H, s), 2.24 (6H, s), 2.11-1.97 (4H, m), 1.65-1.45 (4H, m), 1.42-1.19 (32H, m), 0.93-0.84 (6H, m).

MS m/z (M+H): 580.

Reference Example 1

The following compounds were prepared.

According to the method described in WO2010/054401, (6Z,9Z,28Z,31Z)-heptatriaconta-6,9,28,31-tetraen-19-yl-4-(dimethylamino)butanoate was obtained.

$^1$H-NMR (CDCl$_3$) δ: 5.44-5.27 (8H, m), 4.91-4.81 (1H, m), 2.77 (4H, t, J=6.0 Hz), 2.35-2.24 (4H, m), 2.22 (6H, s), 2.09-1.98 (8H, m), 1.84-1.73 (2H, m), 1.56-1.43 (4H, m), 1.40-1.21 (36H, m), 0.89 (6H, t, J=6.0 Hz).

Reference Example 2

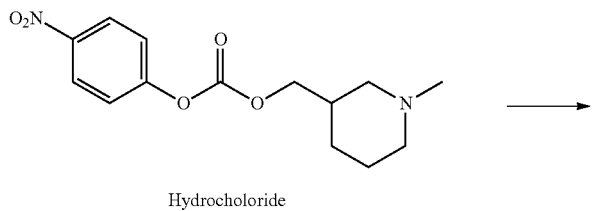

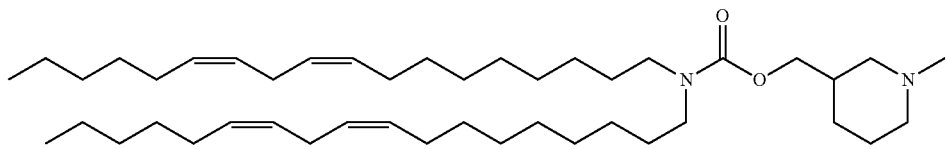

(1-Methylpiperidin-3-yl)methyl di((9Z,12Z)-octadeca-9,12-dien-1-yl)carbamate was obtained by the same method as that in (3) of Example 1, except that (1-methylpiperidin-3-yl)methyl(4-nitrophenyl)carbonate hydrochloride synthesized according to the method described in WO2014/007398A1 was used instead of 2-((2-(dimethylamino)ethyl)(methyl)amino)ethan-1-ol in (3) of Example 1.

$^1$H-NMR (CDCl$_3$) δ: 5.43-5.29 (8H, m), 3.98 (1H, dd, J=7.8 Hz, 3.9 Hz), 3.86 (1H, dd, J=7.8 Hz, 5.7 Hz), 3.24-3.10 (4H, m), 2.90-2.83 (1H, m), 2.82-2.70 (5H, m), 2.26 (3H, s), 2.09-1.80 (10H, m), 1.75-1.44 (7H, m), 1.41-1.19 (32H, m), 0.89 (6H, t, J=6.0 Hz).

Comparative Example 3

2-(Dimethylamino)ethyl((6Z,9Z,28Z,31Z)-heptatriaconta-6,9,28,31-tetraen-19-yl)carbonate was obtained by the same method as that in (2) of Example 20, except that 2-(dimethylamino)ethan-1-ol was used instead of 2-((2-(dimethylamino)ethyl)(methyl)amino)ethan-1-ol in (2) of Example 20. $^1$H-NMR (CDCl$_3$) δ: 5.43-5.27 (8H, m), 4.73-4.61 (1H, m), 4.21 (2H, t, J=6.0 Hz), 2.77 (4H, t, J=6.0 Hz), 2.59 (2H, t, J=6.0 Hz), 2.28 (6H, s), 2.10-1.99 (8H, m), 1.66-1.47 (4H, m), 1.43-1.21 (36H, m), 0.89 (6H, t, J=6.0 Hz).

Comparative Example 5

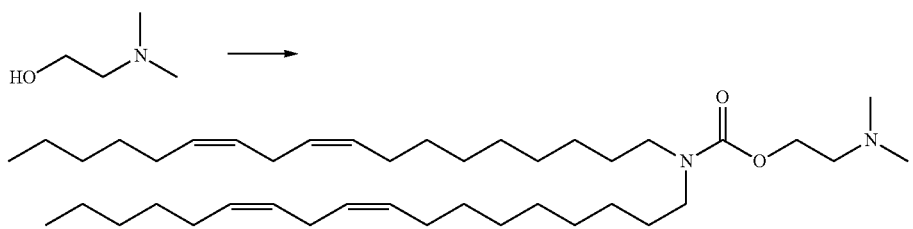

2-(Dimethylamino)ethyl)di((9Z,12Z)-octadeca-9,12-dien-1-yl)carbamate was obtained by the same method as that in (3) of Example 1, except that 2-(dimethylamino)ethan-1-ol was used instead of 2-((2-(dimethylamino)ethyl)(methyl)amino)ethan-1-ol in (3) of Example 1.

$^1$H-NMR (CDCl$_3$) δ: 5.44-5.27 (8H, m), 4.17 (2H, t, J=6.0 Hz), 3.25-3.12 (4H, m), 2.77 (4H, t, J=6.0 Hz), 2.56 (2H, t, J=6.0 Hz), 2.28 (6H, s), 2.11-1.99 (8H, m), 1.57-1.43 (4H, m), 1.42-1.19 (32H, m), 0.89 (6H, t, J=6.0 Hz).

Comparative Example 4

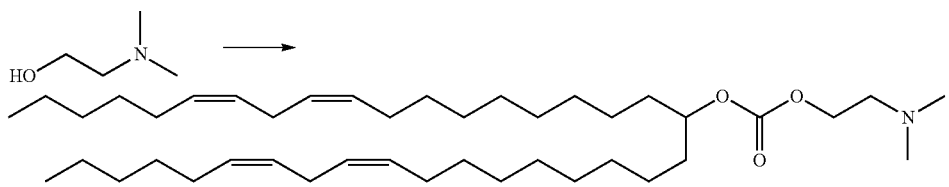

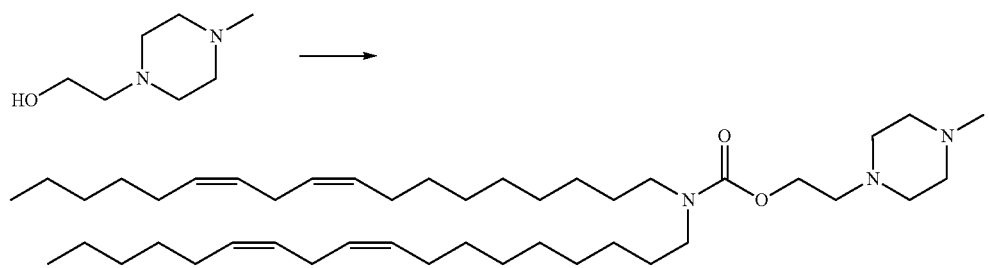

2-(4-Methylpiperazin-1-yl)ethyl di((9Z,12Z)-octadeca-9,12-dien-1-yl)carbamate was obtained by the same method as that in (2) of Example 20, except that 2-(4-methylpiperazin-1-yl)ethan-1-ol was used instead of 2-((2-(dimethylamino)ethyl)(methyl)amino)ethan-1-ol in (2) of Example 20.

$^1$H-NMR (CDCl$_3$) δ: 5.43-5.28 (8H, m), 4.19 (2H, t, J=6.0 Hz), 3.24-3.09 (4H, m), 2.77 (4H, t, J=6.0 Hz), 2.64 (2H, t, J=6.0 Hz), 2.63-2.33 (8H, m), 2.28 (3H, s), 2.09-2.00 (8H, m), 1.57-1.43 (4H, m), 1.41-1.19 (32H, m), 0.89 (6H, t, J=6.0 Hz).

Comparative Example 6

(1)

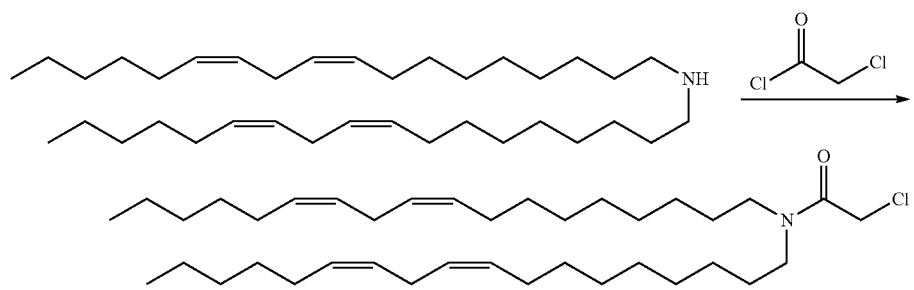

Chloroacetyl chloride (0.09 mL) was added to a mixture of (9Z,12Z9-di((9Z,12Z)-octadeca-9,12-dien-1-yl)amine (400 mg) synthesized in (2) of Example 1, pyridine (0.09 mL), and dichloromethane (2 mL), and the mixture was stirred at room temperature for 3 hours. Water, ethyl acetate, and hexane were added to the reaction mixture, the organic layer was separated and dried over anhydrous sodium sulfate, and then the solvent was distilled away under reduced pressure. The obtained residue was purified by silica gel column chromatography (ethyl acetate-hexane), thereby obtaining 2-chloro-N,N-di((9Z,12Z)-octadeca-9,12-dien-1-yl)acetamide (553 mg).

$^1$H-NMR (CDCl$_3$) δ: 5.43-5.29 (8H, m), 4.05 (2H, s), 3.32-3.23 (4H, m), 2.77 (4H, t, J=6.0 Hz), 2.09-2.01 (8H, m), 1.64-1.48 (4H, m), 1.41-1.23 (32H, m), 0.89 (6H, t, J=6.0 Hz).

(2)

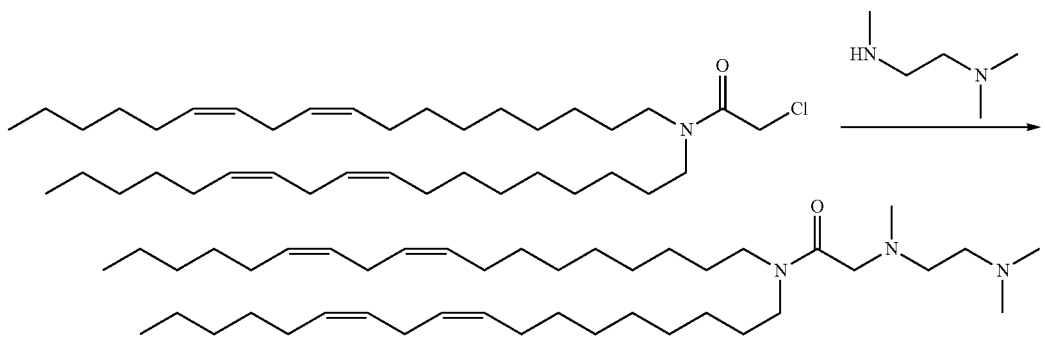

Potassium carbonate (160 mg) was added to a mixture of 2-chloro-N,N-di((9Z,12Z)-octadeca-9,12-dien-1-yl)acetamide (553 mg), N,N,N'-trimethylethane-1,2-diamine (119 mg), acetonitrile (2 mL), and tetrahydrofuran (1 mL), and the mixture was stirred at room temperature for 20 minutes.

Water and ethyl acetate were added to the reaction mixture, the organic layer was separated and dried over anhydrous sodium sulfate, then the solvent was distilled away under reduced pressure, and the obtained residue was purified by silica gel column chromatography (methanol-ethyl acetate). The obtained oily substance was purified by silica gel column chromatography (ethyl acetate-hexane, NH silica gel), thereby obtaining 2-((2-(dimethylamino)ethyl) (methyl)amino)-N,N-di((9Z,12Z)-octadeca-9,12-dien-1-yl) acetamide (251 mg).

$^1$H-NMR (CDCl$_3$) δ: 5.43-5.28 (8H, m), 3.35-3.22 (4H, m), 3.23 (2H, s), 2.77 (4H, t, J=6.0 Hz), 2.59 (2H, t, J=6.0 Hz), 2.41 (2H, t, J=6.0 Hz), 2.33 (3H, s), 2.23 (6H, s), 2.09-2.00 (8H, m), 1.58-1.46 (4H, m), 1.41-1.22 (32H, m), 0.89 (6H, t, J=6.0 Hz).

Comparative Example 7

(1)

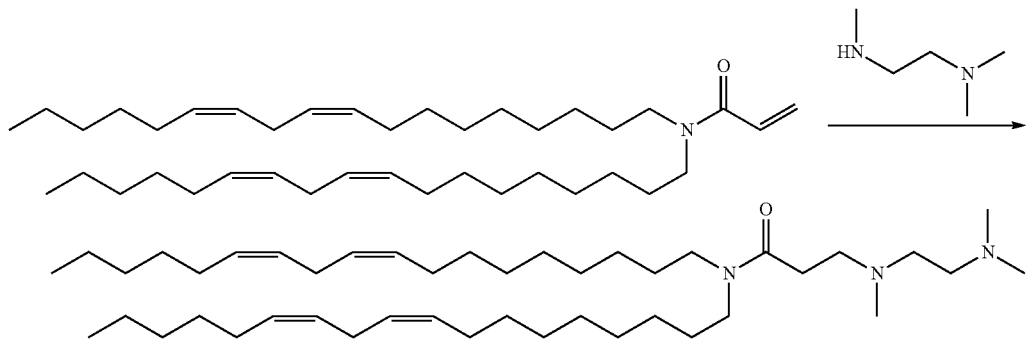

Acrylic acid chloride (0.16 mL) was added to a mixture of (9Z,12Z9-di((9Z,12Z)-octadeca-9,12-dien-1-yl)amine (500 mg) synthesized in (2) of Example 1, triethylamine (0.27 mL), and dichloromethane (2.5 mL), and the mixture was stirred at room temperature for 30 minutes. Water and ethyl acetate were added to the reaction mixture, the organic layer was separated and dried over anhydrous sodium sulfate, and then the solvent was distilled away under reduced pressure. The obtained residue was purified by silica gel column chromatography (ethyl acetate-hexane), thereby obtaining N,N-di((9Z,12Z)-octadeca-9,12-dien-1-yl)acrylamide (580 mg).

$^1$H-NMR (CDCl$_3$) δ: 6.55 (1H, dd, J=16.8 Hz, 10.5 Hz), 6.33 (dd, J=16.8 Hz, 2.4 Hz), 5.65 (1H, dd, J=10.5 Hz, 2.4 Hz), 5.45-5.27 (8H, m), 3.40-3.23 (4H, m), 2.77 (4H, J=6.0 Hz), 2.10-1.99 (8H, m), 1.64-1.48 (4H, m), 1.41-1.23 (32H, m), 0.89 (6H, t, J=6.0 Hz).

(2)

N,N,N'-trimethylethane-1,2-diamine (108 mg) was added to a mixture of N,N-di((9Z,12Z)-octadeca-9,12-dien-1-yl) acrylamide (580 mg), tetrahydrofuran (1.0 mL), and ethanol (0.5 mL), and the mixture was stirred at 65° C. for 7 hours. The solvent of the reaction mixture was distilled away under reduced pressure, and the obtained residue was purified by silica gel column chromatography (methanol-chloroform). The obtained oily substance was purified by silica gel column chromatography (ethyl acetate-hexane, NH silica gel), thereby obtaining 3-((2-(dimethylamino)ethyl) (methyl)amino)-N,N-di((9Z,12Z)-octadeca-9,12-dien-1-yl) propanamide (302 mg).

$^1$H-NMR (CDCl$_3$) δ: 5.43-5.29 (8H, m), 3.31-3.17 (4H, m), 2.80-2.72 (6H, m), 2.53-2.46 (4H, m), 2.43-2.38 (2H, m), 2.27 (3H, s), 2.23 (6H, s), 2.09-2.01 (8H, m), 1.59-1.44 (4H, m), 1.40-1.21 (32H, m), 0.89 (6H, t, J=6.0 Hz).

Example 30

(1)

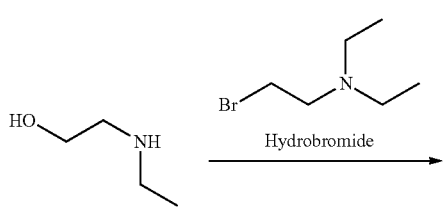

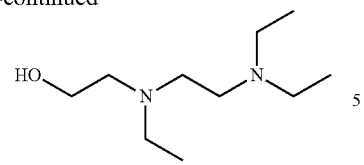

Potassium carbonate (18.6 g) was added to a mixture of 2-(ethylamino)ethan-1-ol (4.0 g), 2-bromo-N,N-diethyl-ethan-1-amine hydrobromide (17.6 g), and ethanol (80 mL), and the mixture was stirred and heated under reflux for 7 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2-((2-(diethylamino)ethyl)(ethyl)amino)ethan-1-ol (6.5 g) as a light yellow oily substance.

MS m/z (M+H): 189.

(2)

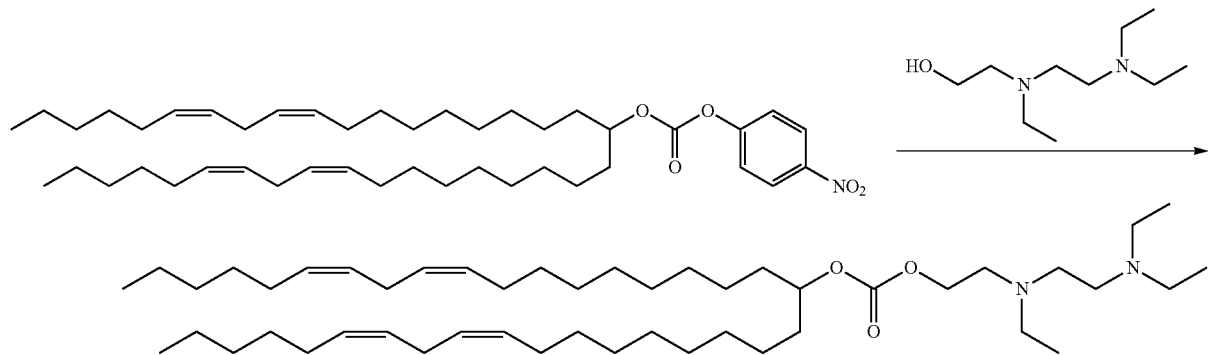

2-((2-(Diethylamino)ethyl)(ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(diethylamino)ethyl)(ethyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.26 (8H, m), 4.72-4.60 (1H, m), 4.17 (2H, t, J=6.6 Hz), 2.83-2.69 (6H, m), 2.65-2.46 (10H, m), 2.13-1.96 (8H, m), 1.65-1.47 (4H, m), 1.43-1.20 (36H, m), 1.09-0.98 (9H, m), 0.89 (6H, t, J=6.6 Hz).

MS m/z (M+H): 744.

Example 31

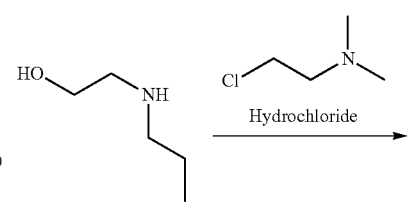

Potassium carbonate (8.0 g) was added to a mixture of 2-(propylamino)ethan-1-ol (2.0 g), 2-chloro-N,N-dimethyl-ethan-1-amine hydrochloride (4.2 g), and ethanol (40 mL), and the mixture was stirred and heated under reflux for 9 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2-((2-(dimethylamino)ethyl)(propyl)amino)ethan-1-ol(0.87 g) as a yellow oily substance.

MS m/z (M+H): 175.

(2)

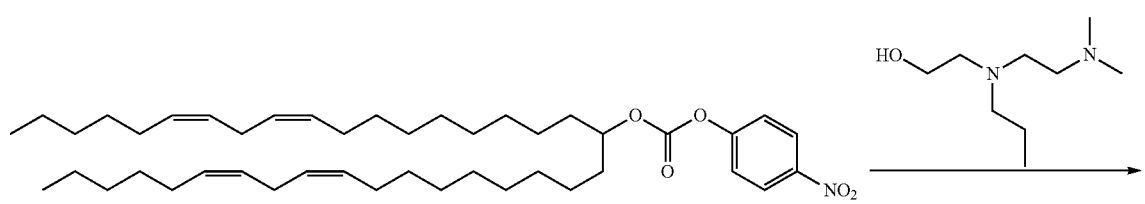

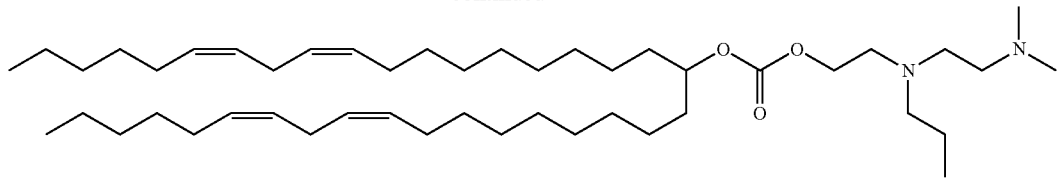

2-((2-(Dimethylamino)ethyl)(propyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(dimethylamino)ethyl)(propyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.26 (8H, m), 4.73-4.61 (1H, m), 4.17 (2H, t, J=6.0 Hz), 2.85-2.70 (6H, m), 2.66-2.56 (2H, m), 2.51-2.41 (2H, m), 2.41-2.32 (2H, m), 2.24 (6H, s), 2.12-1.95 (8H, m), 1.66-1.18 (42H, m), 0.96-0.81 (9H, m).

MS m/z (M+H): 730.

-continued

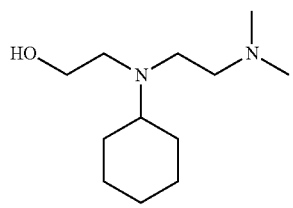

2-(Cyclohexyl(2-(dimethylamino)ethyl)amino)ethan-1-ol as a yellow oily substance was obtained by the same method as that in (1) of Example 31, except that 2-(cyclohexylamino)ethan-1-ol was used instead of 2-(propylamino)ethan-1-ol in (1) of Example 31.

MS m/z (M+H): 215.

(2)

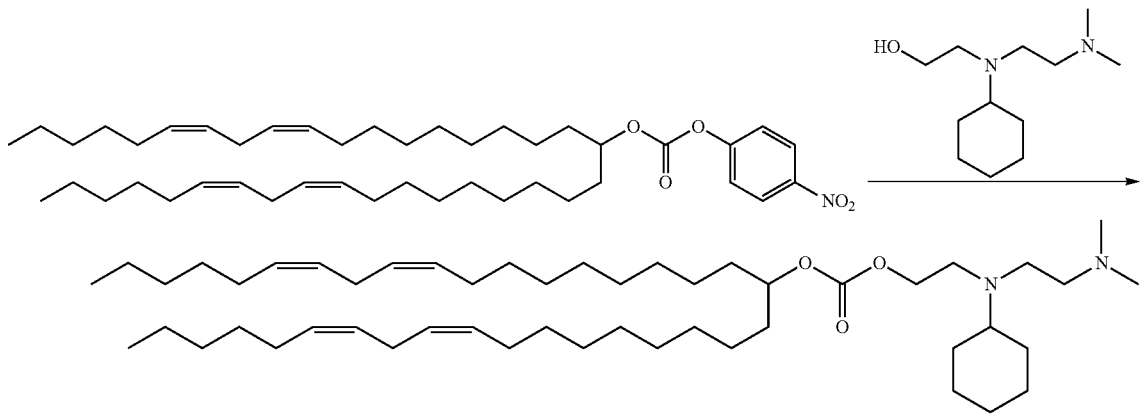

Example 32

(1)

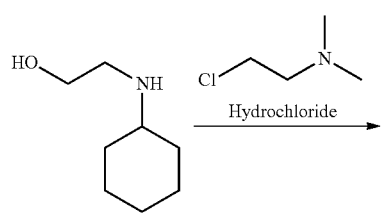

2-(Cyclohexyl(2-(dimethylamino)ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-(cyclohexyl(2-(dimethylamino)ethyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.25 (8H, m), 4.74-4.59 (1H, m), 4.08 (2H, t, J=6.6 Hz), 2.85-2.70 (6H, m), 2.68-2.57 (2H, m), 2.48-2.37 (1H, m), 2.37-2.29 (2H, m), 2.24 (6H, s), 2.13-1.94 (8H, m), 1.85-1.69 (4H, m), 1.66-1.49 (4H, m), 1.46-1.09 (42H, m), 0.89 (6H, t, J=6.6 Hz).

MS m/z (M+H): 770.

Example 33

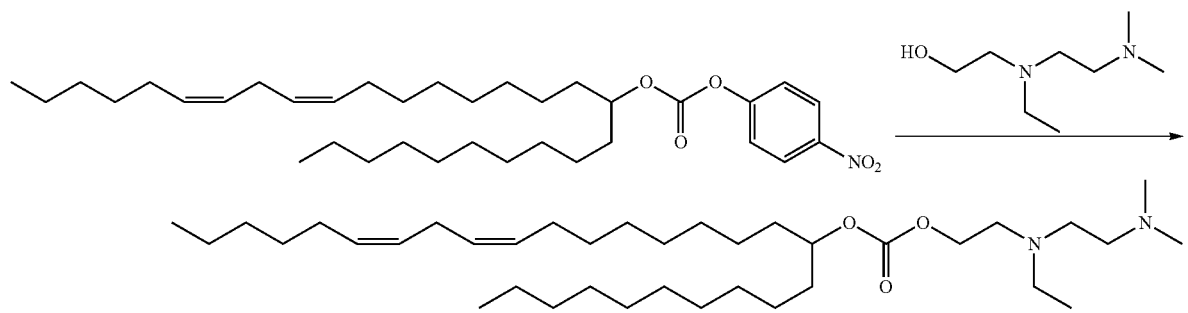

2-((2-(Dimethylamino)ethyl)(ethyl)amino)ethyl((19Z,22Z)-octacosa-19,22-dien-11-yl)carbonate as a colorless oily substance was obtained by the same method as that in (2) of Example 29, except that 2-((2-(dimethylamino)ethyl)(ethyl)amino)ethan-1-ol was used instead of 2-((2-(dimethylamino)ethyl)(methyl)amino)ethan-1-ol in (2) of Example 29.

$^1$H-NMR (CDCl$_3$) δ:5.45-5.27 (4H, m), 4.73-4.62 (1H, m), 4.18 (2H, t, J=4.8 Hz), 2.83-2.71 (4H, m), 2.67-2.55 (4H, m), 2.42-2.34 (2H, m), 2.24 (6H, s), 2.12-1.97 (4H, m), 1.67-1.47 (4H, m), 1.43-1.19 (32H, m), 1.03 (3H, t, J=5.4 Hz), 0.95-0.82 (6H, m).

MS m/z (M+H): 594.

Example 34

N,N'-dicyclohexylcarbodiimide (9.0 g) was added to a mixture of propane-1,2,3-triol (2.0 g), oleic acid (12.3 g), 4-dimethylaminopyridine (5.3 g), and tetrahydrofuran (100 mL), and the mixture was stirred at room temperature for 12 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 2-hydroxypropane-1,3-diyl-dioleate (2.5 g) as a colorless oily substance.

$^1$H-NMR (CDCl$_3$) δ: 5.41-5.28 (4H, m), 4.22-4.04 (5H, m), 2.35 (4H, t, J=7.2 Hz), 2.05-1.97 (8H, m), 1.68-1.56 (4H, m), 1.40-1.23 (40H, m), 0.88 (6H, t, J=7.5 Hz).

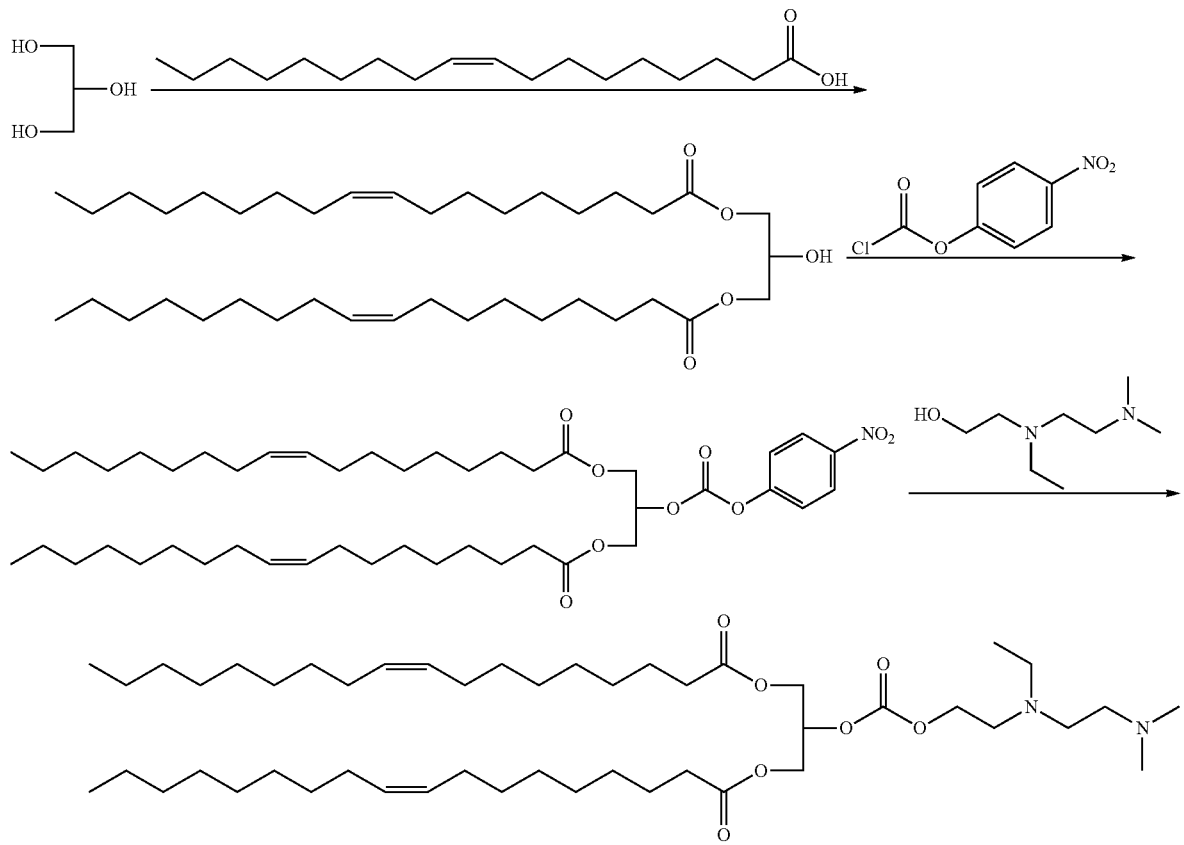

4-Nitrophenyl chloroformate (246 mg) was added to a mixture of 2-hydroxypropane-1,3-diyldioleate (500 mg), triethylamine (0.34 mL), and tetrahydrofuran (5 mL), and the mixture was stirred at room temperature for 5 hours. 2-((2-(Diethylamino)ethyl)(ethyl)amino)ethan-1-ol (0.26 g), triethylamine (0.23 mL), and 4-dimethylaminopyridine (0.20 g) were added to the reaction mixture, and the reaction mixture was stirred at 70° C. for 5 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 2-(((2-((2-(dimethylamino)ethyl)(ethyl)amino)ethoxy)carbonyl)oxy)propane-1,3-diyl-dioleate (74 mg) as a colorless oily substance.

$^1$H-NMR (CDCl$_3$) δ: 5.42-5.27 (4H, m), 5.13-5.04 (1H, m), 4.38-4.27 (2H, m), 4.25-4.10 (4H, m), 2.83-2.73 (2H, m), 2.67-2.54 (4H, m), 2.43-2.29 (6H, m), 2.24 (6H, s), 2.08-1.93 (8H, m), 1.68-1.46 (4H, m), 1.40-1.18 (40H, m), 1.03 (3H, t, J=5.1 Hz), 0.88 (6H, t, J=5.4 Hz).

MS m/z (M+H): 808.

Example 35

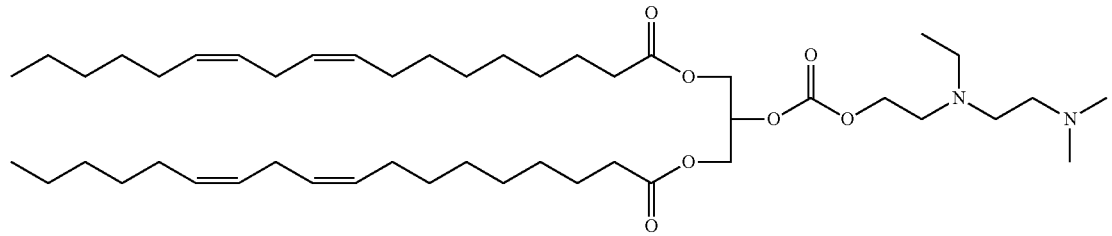 [SMILES: CCCCC/C=C\C/C=C\CCCCCCCC(=O)OCC(COC(=O)CCCCCCC/C=C\C/C=C\CCCCC)OC(=O)OCCN(CC)CCN(C)C]

2-(((2-((2-(Dimethylamino)ethyl)(ethyl)amino)ethoxy) carbonyl)oxy)propane-1,3-diyl(9Z,9'Z,12Z,12'Z)-bis(octa-deca-9,12-dienoate) as a colorless oily substance was obtained by the same method as that in Example 34, except that (9Z,12Z)-octadeca-9,12-dienoic acid was used instead of oleic acid used in Example 34.

$^1$H-NMR (CDCl$_3$) δ: 5.44-5.28 (8H, m), 5.13-5.03 (1H, m), 4.38-4.29 (2H, m), 4.25-4.13 (4H, m), 2.83-2.72 (6H, m), 2.66-2.55 (4H, m), 2.42-2.28 (6H, m), 2.24 (6H, s), 2.13-1.95 (8H, m), 1.68-1.50 (4H, m), 1.42-1.23 (28H, m), 1.03 (3H, t, J=5.4 Hz), 0.89 (6H, t, J=5.4 Hz).

MS m/z (M+H): 804.

Example 36

(1)

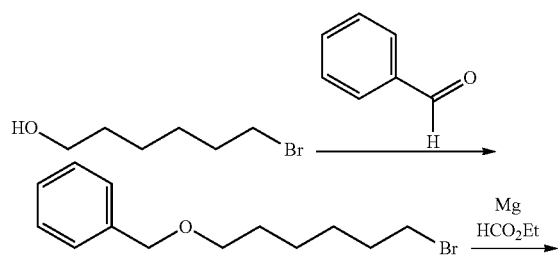

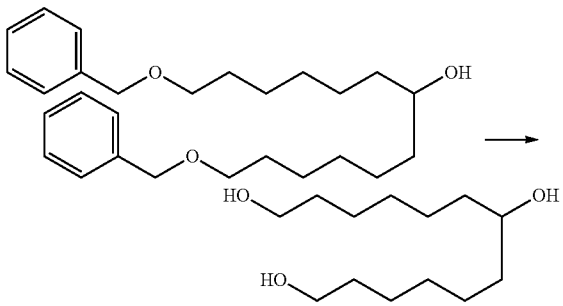

A boron trifluoride-diethyl ether complex (46.2 mL) was added to a mixture of benzaldehyde (30.0 g), 6-bromohexan-1-ol (56.1 g), triethylsilane (67.5 mL), and toluene (300 mL) under ice cooling, and the mixture was stirred at the same temperature for 40 minutes. Water was added to the reaction mixture, the organic layer was separated and washed with a saturated aqueous sodium hydrogen carbonate solution, and the solvent was distilled away under reduced pressure. The obtained residue was purified by silica gel column chromatography (ethyl acetate-hexane), thereby obtaining (((6-bromohexyl)oxy)methyl)benzene (73.5 g) as a colorless oily substance.

$^1$H-NMR (CDCl$_3$) δ: 7.38-7.23 (5H, m), 4.50 (2H, s), 3.47 (2H, t, J=6.6 Hz), 3.40 (2H, t, J=6.6 Hz), 1.92-1.81 (2H, m), 1.68-1.58 (2H, m), 1.52-1.35 (4H, m).

A mixture of (((6-bromohexyl)oxy)methyl)benzene (66.7 g) and tetrahydrofuran (200 mL) was added dropwise to a mixture of magnesium (7.5 g) and tetrahydrofuran (40 mL), and the mixture was stirred at room temperature for 1 hour. A mixture of ethyl formate (8.3 g) and tetrahydrofuran (100 mL) was added to the reaction mixture under ice cooling, and the reaction mixture was stirred at the same temperature for 1 hour. The reaction mixture was poured into a 10% aqueous sulfuric acid solution (330 mL) under ice cooling, hexane (300 mL) was added thereto, the organic layer was separated and dried over anhydrous magnesium sulfate, and then the solvent was distilled away under reduced pressure. Tetrahydrofuran (200 mL), ethanol (100 mL), and a 10 mol/L aqueous potassium hydroxide solution were added to the obtained residue, and the mixture was stirred at 40° C. for 1 hour. Hexane (200 mL) and water (100 mL) were added to the reaction mixture, the organic layer was separated and then dried over anhydrous magnesium sulfate, and the solvent was distilled away under reduced pressure. The obtained residue was purified by silica gel column chromatography (ethyl acetate-hexane), thereby obtaining 1,13-bis(benzyloxy)tridecan-7-ol (25.3 g) as a colorless oily substance.

$^1$H-NMR (CDCl$_3$) δ: 7.36-7.24 (10H, m), 4.50 (4H, s), 3.61-3.54 (1H, m), 3.46 (4H, t, J=6.6 Hz), 1.68-1.56 (4H, m), 1.48-1.26 (16H, m).

A mixture of 1,13-bis(benzyloxy)tridecan-7-ol (24.0 g), 10% palladium hydroxide-carbon (10.0 g), and methanol (240 mL) was stirred at 50° C. for 3 hours in a hydrogen atmosphere. The reaction mixture was cooled to room temperature, the insoluble matters were filtered off using celite, and then the solvent was distilled away under reduced pressure. Ethyl acetate (40 mL) was added to the obtained residue, and solids was collected by filtration, washed with ethyl acetate, and then dried under reduced pressure, thereby obtaining tridecane-1,7,13-triol (11.7 g) as white solids.

$^1$H-NMR (CDCl$_3$) δ: 3.70-3.55 (5H, m), 1.64-1.24 (20H, m).

(2)

g), triethylamine (0.22 mL), and 4-dimethylaminopyridine (0.19 g) were added to the reaction mixture, and the reaction mixture was stirred at 70° C. for 4 hours. Water and ethyl acetate were added to the reaction mixture, the organic layer was separated and washed with a saturated aqueous sodium chloride solution, and then the solvent was distilled away under reduced pressure. The obtained residue was purified by silica gel column chromatography (methanol-ethyl acetate) and silica gel column chromatography (ethyl acetate-hexane, NH silica gel), thereby obtaining 7-(((2-((2-(dimethylamino)ethyl)(ethyl)amino)ethoxy)carbonyl)oxy) tridecane-1,13-diyldioleate (138 mg) as a colorless oily substance.

$^1$H-NMR (CDCl$_3$) δ:5.41-5.26 (4H, m), 4.72-4.63 (1H, m), 4.18 (2H, t, J=6.4 Hz), 4.04 (4H, t. J=6.8 Hz). 2.77 (2H, t. J=6.8 Hz). 2.66-2.56 (4H, m). 2.43-2.34 (2H, m), 2.34-

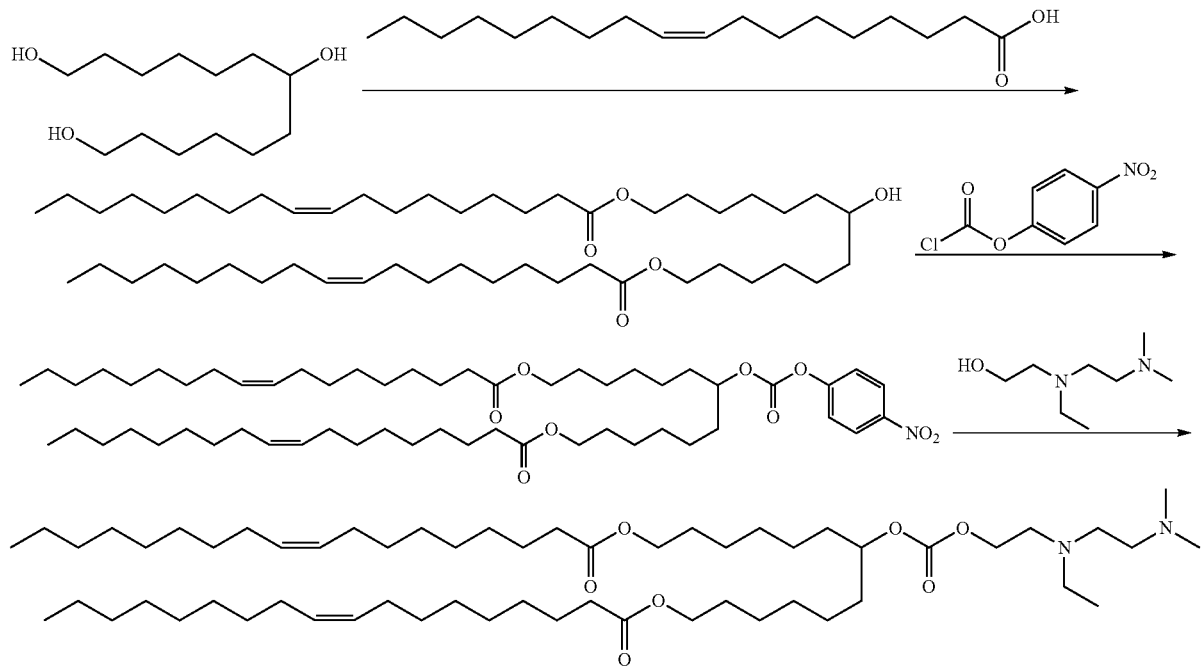

1-Ethyl-3-(3-dimethylaminopropyl)carbodiimide hydrochloride (10.3 g) was added to a mixture of tridecane-1,7,13-triol (5.0 g), oleic acid (13.4 g), triethylamine (18.2 mL), 4-dimethylaminopyridine (0.26 g), and N,N-dimethylformamide (25 mL), and the mixture was stirred at room temperature for 15 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 7-hydroxytridecane-1,3-diyldioleate (3.6 g) as a colorless oily substance.

$^1$H-NMR (CDCl$_3$) δ:5.41-5.28 (4H, m), 4.06 (4H, t, J=6.6 Hz), 3.63-3.53 (1H, m), 2.29 (4H, t, J=7.2 Hz), 2.06-1.96 (8H, m), 1.68-1.20 (64H, m), 0.88 (6H, t, J=7.2 Hz).

4-Nitrophenyl chloroformate (161 mg) was added to a mixture of 7-hydroxytridecane-1,3-diyldioleate (400 mg), triethylamine (0.22 mL), and tetrahydrofuran (4 mL), and the mixture was stirred at room temperature for 5 hours. 2-((2-(Dimethylamino)ethyl)(ethyl)amino)ethan-1-ol (0.26

2.25 (4H, m), 2.24 (6H, s), 2.09-1.94 (8H, m), 1.70-1.47 (12H, m), 1.44-1.19 (52H, m), 1.03 (3H, t, J=7.2), 0.88 (6H, t, J=6.8 Hz).

MS m/z (M+H): 948.

Example 37

(1)

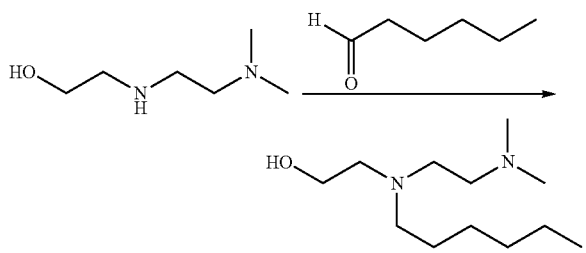

Sodium triacetoxyborohydride (1.8 g) was added to a mixture of 2-((2-(dimethylamino)ethyl)amino)ethan-1-ol (250 mg), hexanal (0.35 mL), acetic acid (0.16 mL), and tetrahydrofuran (2.5 mL), and the mixture was stirred at room temperature for 2 hours. Methanol was added to the reaction mixture under ice cooling, and the reaction mixture was purified by silica gel column chromatography (ethyl acetate-hexane, NH silica gel), thereby obtaining 2-((2-(dimethylamino)ethyl)(hexyl)amino)ethane-1-ol (400 mg) as a colorless oily substance.

MS m/z (M+H): 217.

(2)

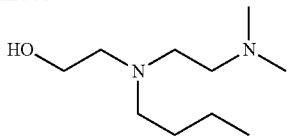

2-(Butyl(2-(dimethylamino)ethyl)amino)ethan-1-ol as a yellow oily substance was obtained by the same method as

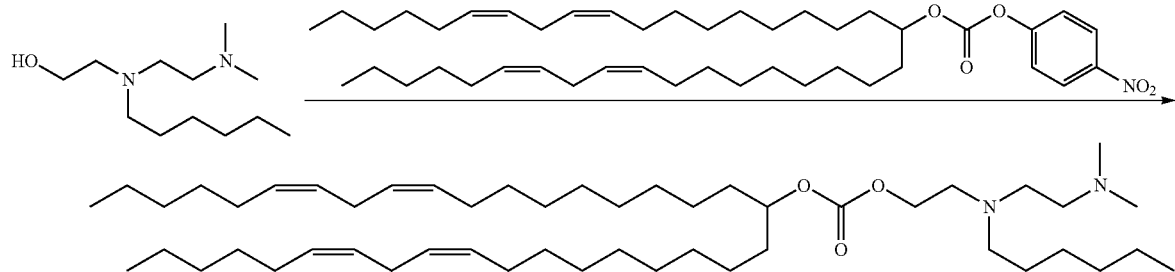

2-((2-(Dimethylamino)ethyl)(hexyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(dimethylamino)ethyl)(hexyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.27 (8H, m), 4.72-4.62 (1H, m), 4.17 (2H, t, J=6.4 Hz), 2.84-2.71 (6H, m), 2.65-2.57 (2H, m), 2.53-2.54 (2H, m), 2.41-2.32 (2H, m), 2.23 (6H, s), 2.12-1.97 (8H, m), 1.68-1.49 (4H, m), 1.48-1.20 (44H, m), 0.97-0.83 (9H, m).

MS m/z (M+H): 772.

Example 38

(1)

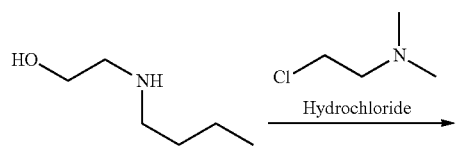

that in (1) of Example 31, except that 2-(butylamino)ethan-1-ol was used instead of 2-(propylamino)ethan-1-ol in (1) of Example 31.

MS m/z (M+H): 189.

(2)

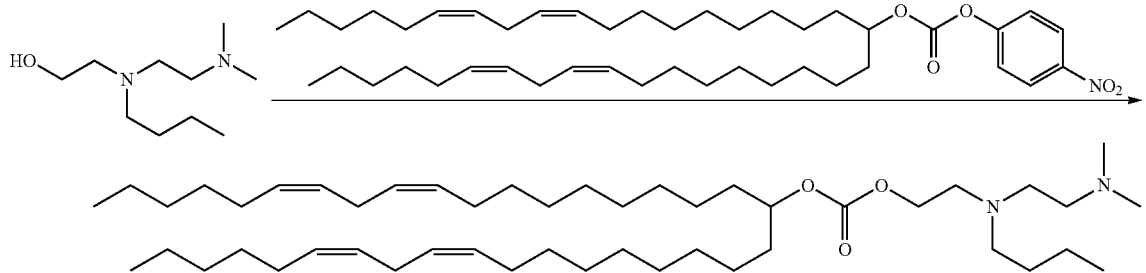

2-(Butyl(2-(dimethylamino)ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-(butyl(2-(dimethylamino)ethyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.44-5.26 (8H, m), 4.72-4.61 (1H, m), 4.17 (2H, t, J=6.4 Hz), 2.84-2.71 (6H, m), 2.67-2.57 (2H, m), 2.54-2.44 (2H, m), 2.42-2.33 (2H, m), 2.23 (6H, s), 2.12-1.96 (8H, m), 1.67-1.48 (4H, m), 1.48-1.19 (40H, m), 0.97-0.84 (9H, m).

MS m/z (M+H): 744.

Example 39

(1)

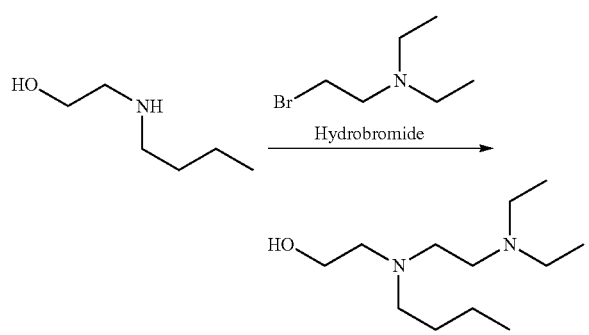

2-(Butyl(2-(diethylamino)ethyl)amino)ethan-1-ol as a light yellow oily substance was obtained by the same method as that in (1) of Example 30, except that 2-(butylamino)ethan-1-ol was used instead of 2-(ethylamino)ethan-1-ol in (1) of Example 30.

MS m/z (M+H): 217.

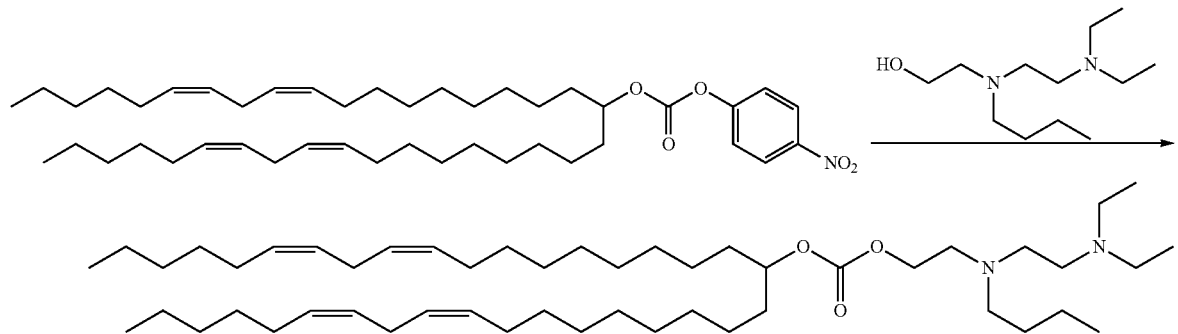

2-(Butyl(2-(diethylamino)ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-(butyl(2-(diethylamino)ethyl)amino)ethan-1-ol was used instead of 2-((2-(dimethylamino)ethyl)(methyl)amino)ethan-1-ol in (2) of Example 20.

¹H-NMR (CDCl₃) δ: 5.43-5.28 (8H, m), 4.71-4.62 (1H, m), 4.16 (2H, t, J=6.4 Hz), 2.83-2.70 (6H, m), 2.65-2.43 (10H, m), 2.11-1.96 (8H, m), 1.65-1.49 (4H, m), 1.46-1.19 (40H, m), 1.02 (6H, t, J=7.2 Hz), 0.96-0.83 (9H, m).

MS m/z (M+H): 772.

Example 40

(1)

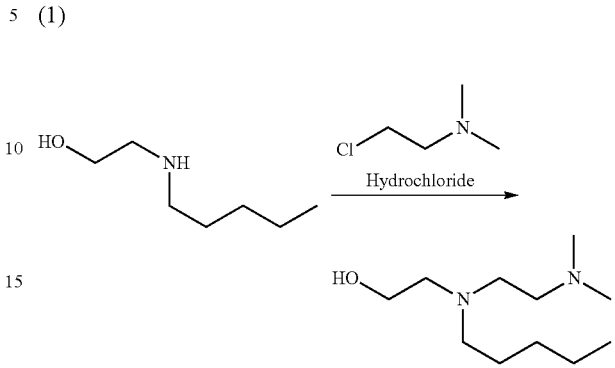

2-((2-(Dimethylamino)ethyl)(pentyl)amino)ethan-1-ol as a brown oily substance was obtained by the same method as that in (1) of Example 31, except that 2-(pentylamino)ethan-1-ol was used instead of 2-(propylamino)ethan-1-ol in (1) of Example 31.

MS m/z (M+H): 203.

(2)

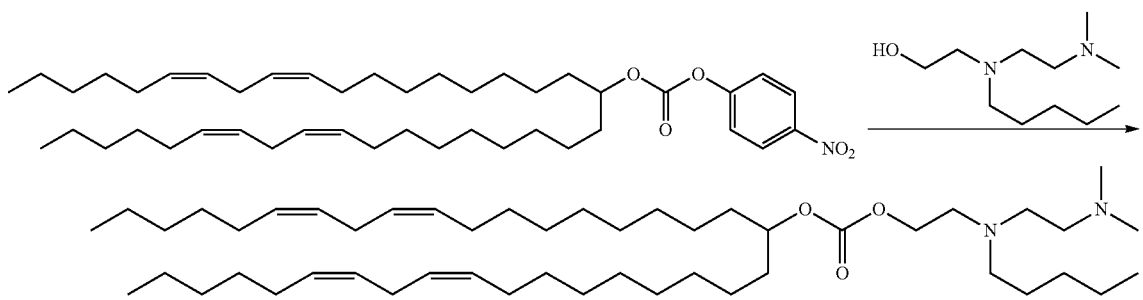

2-((2-(Dimethylamino)ethyl)(pentyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(dimethylamino)ethyl)(pentyl)amino)ethan-1-ol was used instead of 2-((2-(dimethylamino)ethyl)(methyl)amino)ethan-1-ol in (2) of Example 20.

¹H-NMR (CDCl₃) δ: 5.43-5.26 (8H, m), 4.72-4.61 (1H, m), 4.17 (2H, t, J=6.0 Hz), 2.83-2.70 (6H, m), 2.65-2.57 (2H, m), 2.53-2.43 (2H, m), 2.41-2.32 (2H, m), 2.23 (6H, s), 2.11-1.97 (8H, m), 1.65-1.49 (4H, m), 1.48-1.19 (42H, m), 0.95-0.83 (9H, m).

MS m/z (M+H): 758.

Example 41

(1)

obtained residue was purified by silica gel column chromatography (ethyl acetate-hexane), thereby obtaining 7-hydroxytridecane-1,3-diyldioleate (3.6 g) as a colorless oily substance.

¹H-NMR (CDCl₃) δ: 5.41-5.28 (4H, m), 4.06 (4H, t, J=6.6 Hz), 3.63-3.53 (1H, m), 2.29 (4H, t, J=7.2 Hz), 2.06-1.96 (8H, m), 1.68-1.20 (64H, m), 0.88 (6H, t, J=7.2 Hz).

4-Nitrophenyl chloroformate (1.4 g) was added to a mixture of 7-hydroxytridecane-1,3-diyldioleate (3.6 g), triethylamine (2.0 mL), and tetrahydrofuran (36 mL), and the mixture was stirred at room temperature for 1 hour. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby

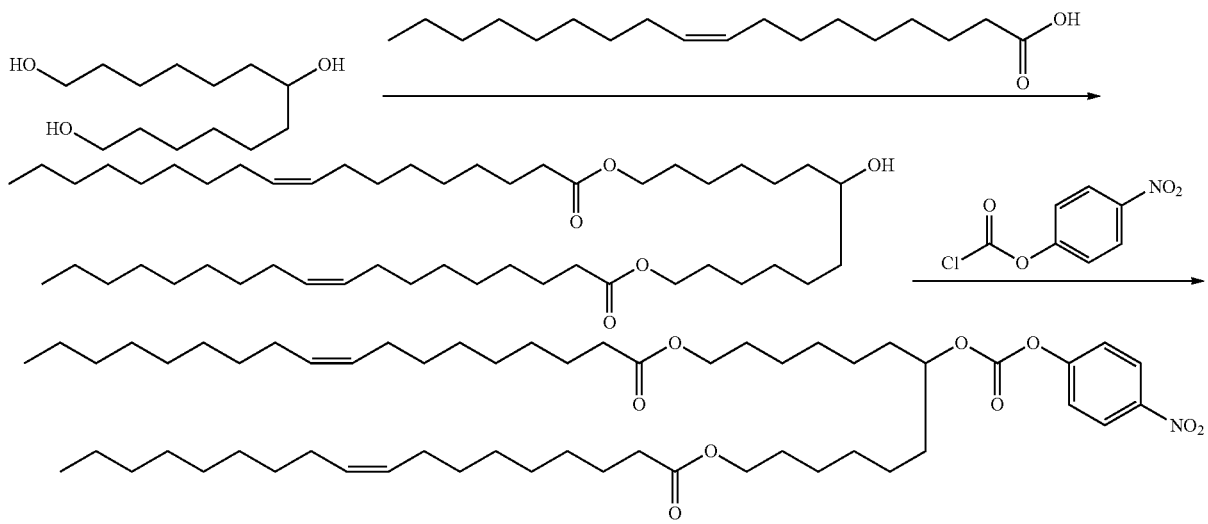

1-Ethyl-3-(3-dimethylaminopropyl)carbodiimide hydrochloride (10.3 g) was added to a mixture of tridecane-1,7,13-triol (5.0 g), oleic acid (13.4 g), triethylamine (18.2 mL), 4-dimethylaminopyridine (0.26 g), and N,N-dimethylformamide (25 mL), and the mixture was stirred at room temperature for 15 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtaining 7-(((4-nitrophenoxy)carbonyl)oxy)tridecane-1,13-diyldioleate (4.1 g) as a light yellow oily substance.

¹H-NMR (CDCl₃) δ: 8.28 (2H, dd, J=7.2H, 2.1 Hz), 7.39 (2H, dd, J=7.2 Hz, 2.1 Hz), 5.40-5.28 (4H, m), 4.86-4.76 (1H, m), 4.06 (4H, t, J=6.6 Hz), 2.29 (4H, t, J=7.2 Hz), 2.05-1.96 (8H, m), 1.74-1.56 (12H, m), 1.42-1.21 (52H, m), 0.88 (6H, t, J=7.2 Hz).

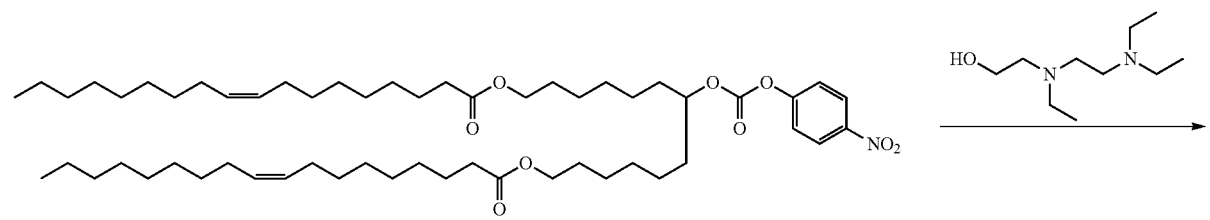

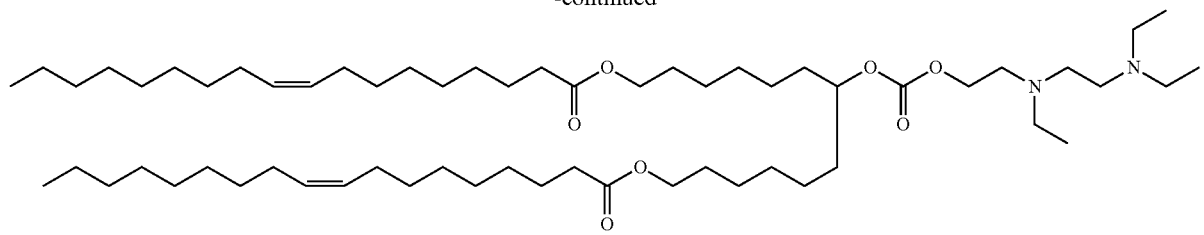

4-Dimethylaminopyridine (0.79 g) was added to a mixture of 7-(((4-nitrophenoxy)carbonyl)oxy)tridecane-1,13-diyldioleate (2.0 g), 2-((2-(diethylamino)ethyl)(ethyl)amino)ethan-1-ol (1.2 g), triethylamine (0.91 mL), and tetrahydrofuran (20 mL), and the mixture was stirred and heated under reflux for 8 hours. The reaction mixture was cooled to room temperature, water and ethyl acetate were added thereto, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 7-(((2-((2-(diethylamino)ethyl)(ethyl)amino)ethoxy)carbonyl)oxy)tridecane-1,13-diyldioleate (1.7 g) as a colorless oily substance.

$^1$H-NMR (CDCl$_3$) δ: 5.39-5.27 (4H, m), 4.71-4.62 (1H, m), 4.17 (2H, t, J=6.4 Hz), 4.04 (4H, t, J=6.8 Hz), 2.76 (2H, t, J=6.0 Hz), 2.66-2.46 (10H, m), 2.29 (4H, t, J=7.6 Hz), 2.08-1.94 (8H, m), 1.69-1.48 (12H, m), 1.41-1.19 (52H, m), 1.07-0.97 (9H, m), 0.88 (6H, t, J=7.2 Hz).

MS m/z (M+H): 976.

Example 42

(1)

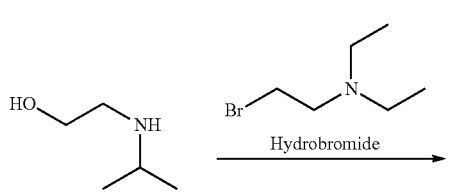

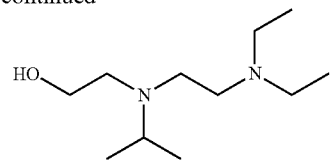

Potassium carbonate (8.0 g) was added to a mixture of 2-(isopropylamino)ethan-1-ol (2.0 g), 2-bromo-N,N-diethylethan-1-amine hydrobromide (7.6 g), and ethanol (20 mL), and the mixture was stirred and heated under reflux for 7 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2-((2-(diethylamino)ethyl)(isopropyl)amino)ethan-1-ol (3.5 g) as a light yellow oily substance.

MS m/z (M+H): 203.

(2)

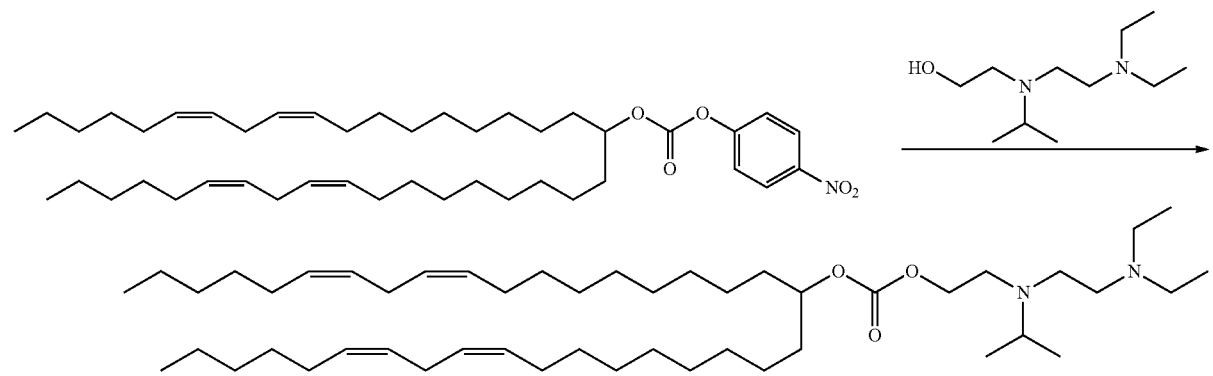

2-((2-(Diethylamino)ethyl)(isopropyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(diethylamino)ethyl)(isopropyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.27 (8H, m), 4.72-4.61 (1H, m), 4.10 (2H, t, J=6.8 Hz), 2.96-2.85 (1H, m), 2.83-2.74 (4H, m), 2.68 (2H, t, J=6.8 Hz), 2.60-2.41 (8H, m), 2.12-1.96 (8H, m), 1.65-1.48 (4H, m), 1.45-1.19 (36H, m), 1.10-0.95 (12H, m), 0.89 (6H, t, J=6.8 Hz).

MS m/z (M+H): 758.

Example 43

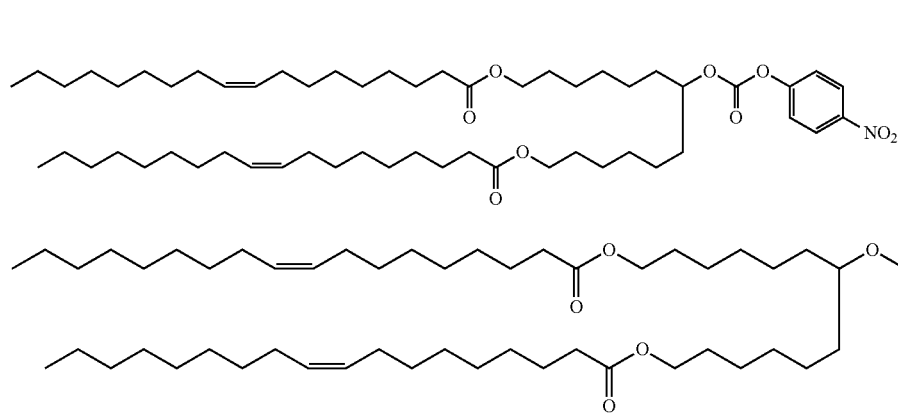

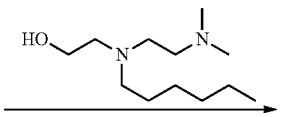

7-(((2-((2-(Dimethylamino)ethyl)(hexyl)amino)ethoxy)carbonyl)oxy)tridecane-1,13-diyldioleate) as a colorless oily substance was obtained by the same method as that in (2) of Example 41, except that 2-((2-(dimethylamino)ethyl)(hexyl)amino)ethan-1-ol was used instead of 2-((2-(diethylamino)ethyl)(ethyl)amino)ethan-1-ol in (2) of Example 41.

$^{1}$H-NMR (CDCl$_{3}$) δ: 5.42-5.26 (4H, m), 4.73-4.60 (1H, m), 4.17 (2H, t, J=5.7 Hz), 4.04 (4H, t, J=6.6 Hz), 2.76 (2H, t, J=6.6 Hz), 2.67-2.56 (2H, m), 2.55-2.44 (2H, m), 2.42-2.34 (2H, m), 2.29 (4H, t, J=7.5 Hz), 2.23 (6H, s), 2.10-1.93 (8H, m), 1.69-1.49 (12H, m), 1.48-1.19 (60H, m), 0.95-0.81 (9H, m).

MS m/z (M+H): 1004.

Example 44

(1)

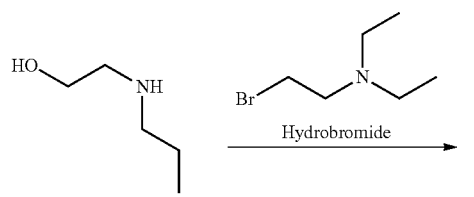

-continued

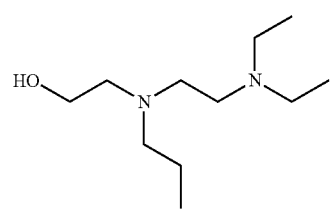

2-((2-(Diethylamino)ethyl)(propyl)amino)ethan-1-ol as a light yellow oily substance was obtained by the same method as that in (1) of Example 30, except that 2-(propylamino)ethan-1-ol was used instead of 2-(ethylamino)ethan-1-ol in (1) of Example 30.

MS m/z (M+H): 203.

(2)

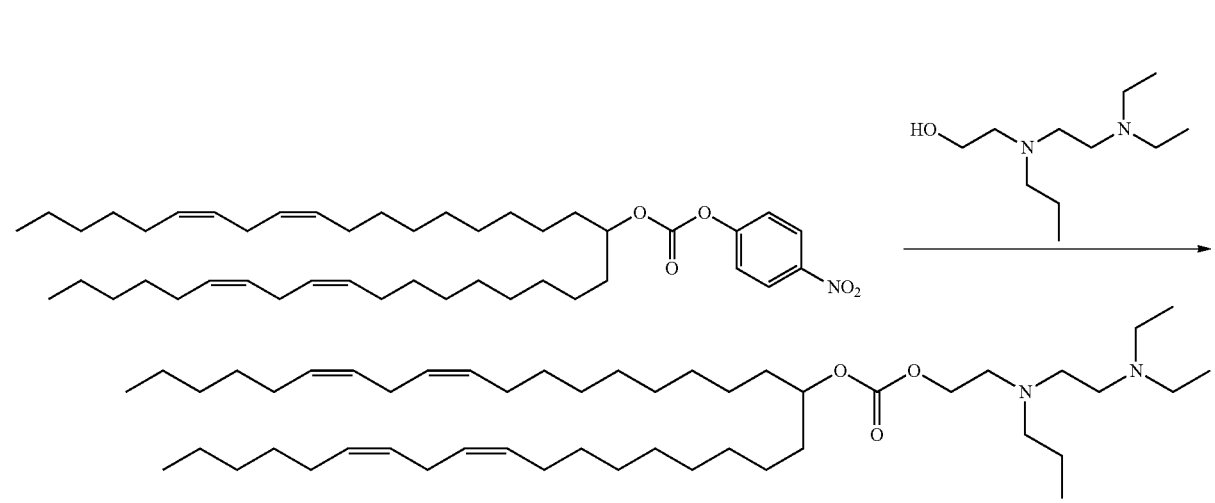

2-((2-(Diethylamino)ethyl)(propyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(diethylamino)ethyl)(propyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.46-5.24 (8H, m), 4.73-4.61 (1H, m), 4.16 (2H, t, J=6.6 Hz), 2.83-2.70 (6H, m), 2.65-2.41 (10H, m), 2.11-1.96 (8H, m), 1.64-1.51 (4H, m), 1.49-1.21 (38H, m), 1.02 (6H, t, J=7.2 Hz), 0.95-0.81 (9H, m).

MS m/z (M+H): 758.

Example 45

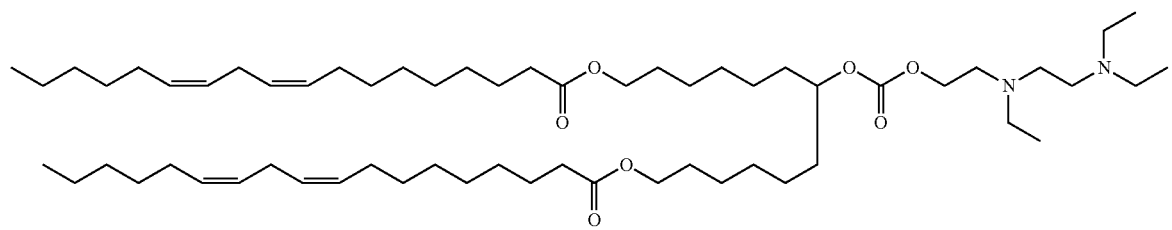 [SMILES: CCCCC/C=C\C/C=C\CCCCCCCC(=O)OCCCCCCC(CCCCCCOC(=O)CCCCCCC/C=C\C/C=C\CCCCC)OC(=O)OCCN(CC)CCN(CC)CC]

7-(((2-((2-(Diethylamino)ethyl)(ethyl)amino)ethoxy)carbonyl)oxy)tridecane-1,13-diyl(9Z,9'Z,12Z,12'Z)-bis(octadeca-9,12-dienoate) as a colorless oily substance was obtained by the same method as that in (1) and (2) of Example 41, except that (9Z,12Z)-octadeca-9,12-dienoic acid was used instead of oleic acid in (1) and (2) of Example 41.

$^1$H-NMR (CDCl$_3$) δ: 5.46-5.24 (8H, m), 4.73-4.61 (1H, m), 4.17 (2H, t, J=6.6 Hz), 4.04 (4H, t, J=6.6 Hz), 2.83-2.71 (6H, m), 2.66-2.47 (10H, m), 2.29 (4H, t, J=8.1 Hz), 2.13-1.96 (8H, m), 1.69-1.50 (12H, m), 1.44-1.21 (40H, m), 1.08-0.97 (9H, m), 0.89 (6H, t, J=6.6 Hz).

MS m/z (M+H): 972.

Example 46

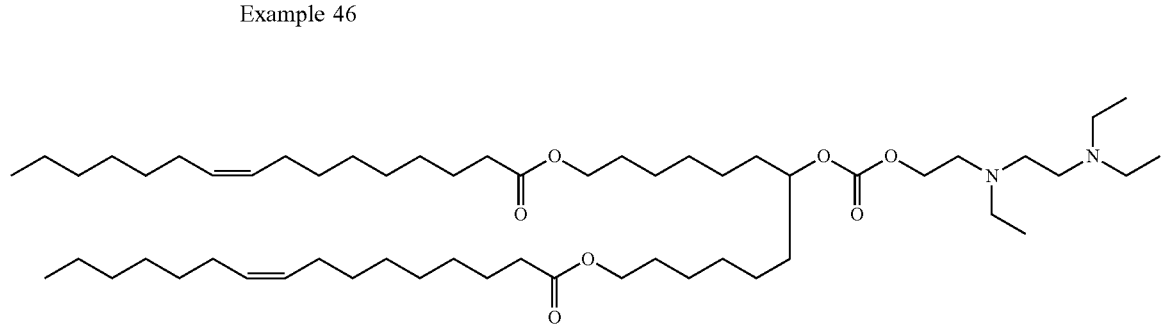

7-(((2-((2-(Diethylamino)ethyl)(ethyl)amino)ethoxy)carbonyl)oxy)tridecane-1,13-diyl(9Z,9'Z)-bis(hexadec-9-enoate) as a colorless oily substance was obtained by the same method as that in (1) and (2) of Example 41, except that (Z)-hexadec-9-enoic acid was used instead of oleic acid in (1) and (2) of Example 41.

$^1$H-NMR (CDCl$_3$) δ: 5.40-5.27 (4H, m), 4.73-4.61 (1H, m), 4.17 (2H, t, J=6.6 Hz), 4.04 (4H, t, J=6.6 Hz), 2.76 (2H, t, J=6.6 Hz), 2.66-2.45 (10H, m), 2.29 (4H, t, J=7.2 Hz), 2.09-1.93 (8H, m), 1.70-1.48 (12H, m), 1.43-1.20 (44H, m), 1.11-0.97 (9H, m), 0.88 (6H, t, J=6.6 Hz).

MS m/z (M+H): 920.

Example 47

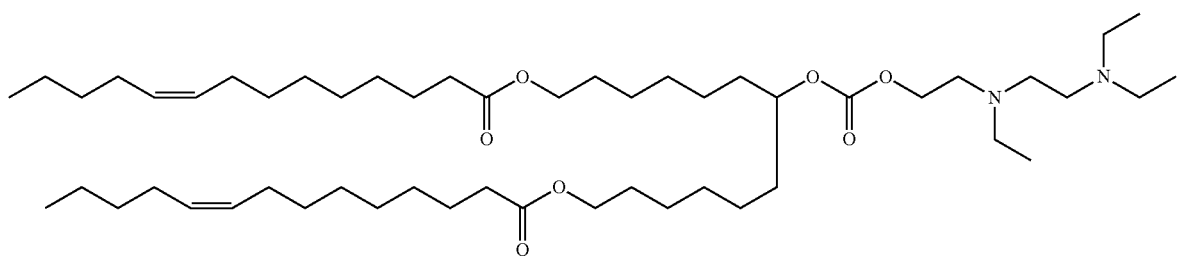 [SMILES: CCCC/C=C\CCCCCCCC(=O)OCCCCCCC(CCCCCCOC(=O)CCCCCCC/C=C\CCCC)OC(=O)OCCN(CC)CCN(CC)CC]

Example 48

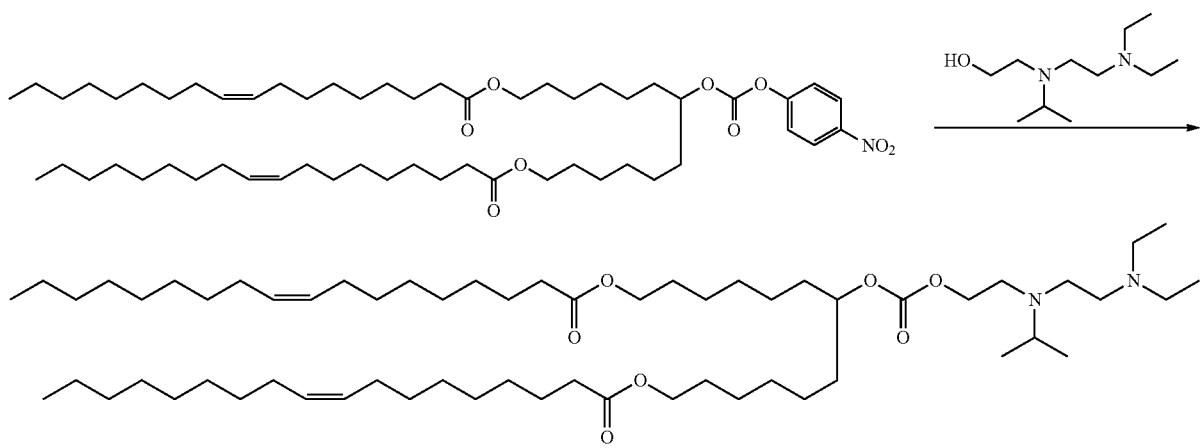

7-(((2-((2-(Diethylamino)ethyl)(ethyl)amino)ethoxy)carbonyl)oxy)tridecane-1,13-diyl(9Z,9'Z)-bis(tetradec-9-enoate) as a colorless oily substance was obtained by the same method as that in (1) and (2) of Example 41, except that (Z)-tetradec-9-enoic acid was used instead of oleic acid in (1) and (2) of Example 41.

$^1$H-NMR (CDCl$_3$) δ: 5.44-5.24 (4H, m), 4.73-4.61 (1H, m), 4.17 (2H, t, J=6.0 Hz), 4.04 (4H, t, J=6.6 Hz), 2.76 (2H, t, J=6.6 Hz), 2.67-2.46 (10H, m), 2.29 (4H, t, J=7.8 Hz), 2.11-1.92 (8H, m), 1.71-1.47 (12H, m), 1.45-1.21 (36H, m), 1.09-0.96 (9H, m), 0.95-0.83 (6H, m).

MS m/z (M+H): 864.

Example 49

(1)

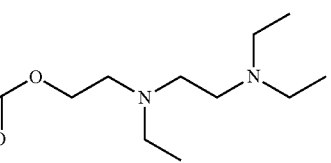

7-(((2-((2-(Diethylamino)ethyl)(isopropyl)amino)ethoxy)carbonyl)oxy)tridecane-1,13-diyldioleate as a colorless oily substance was obtained by the same method as that in (1) and (2) of Example 41, except that 2-((2-(diethylamino)ethyl)(isopropyl)amino)ethan-1-ol was used instead of 2-((2-(diethylamino)ethyl)(ethyl)amino)ethan-1-ol in (1) and (2) of Example 41.

$^1$H-NMR (CDCl$_3$) δ: 5.41-5.27 (4H, m), 4.72-4.61 (1H, m), 4.17-3.99 (6H, m), 2.95-2.86 (1H, m), 2.68 (2H, t, J=6.4 Hz), 2.60-2.42 (8H, m), 2.28 (4H, t, J=8.0 Hz), 2.08-1.93 (8H, m), 1.69-1.48 (12H, m), 1.43-1.20 (52H, m), 1.09-0.95 (12H, m), 0.88 (6H, t, J=6.8 Hz).

MS m/z (M+H): 990.

-continued

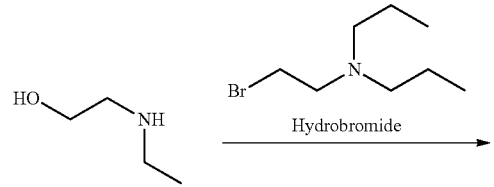

2-((2-(Dipropylamino)ethyl)(ethyl)amino)ethan-1-ol as a colorless oily substance was obtained by the same method as that in (1) of Example 30, except that N-(2-bromoethyl)-N-propylpropan-1-amine hydrobromide was used instead of 2-bromo-N,N-diethylethan-1-amine hydrobromide in (1) of Example 30.

MS m/z (M+H): 217.

(2)

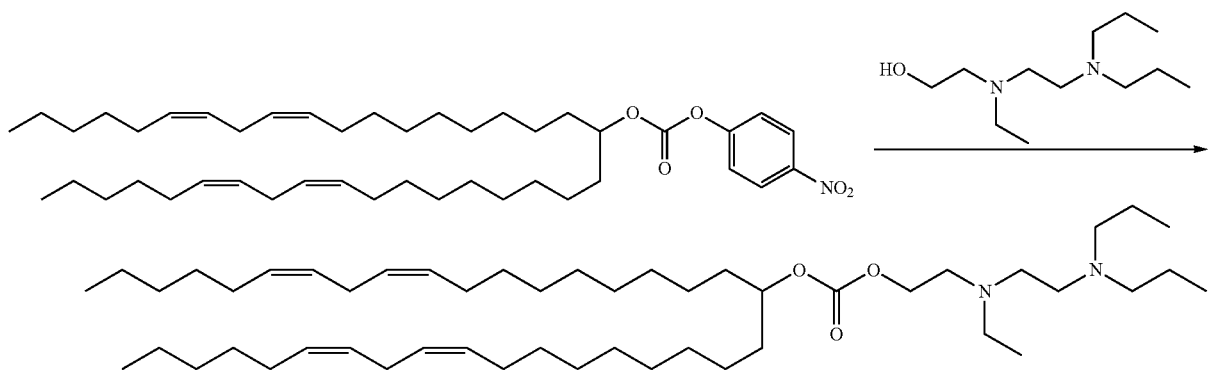

2-((2-(Dipropylamino)ethyl)(ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(dipropylamino)ethyl)(ethyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.26 (8H, m), 4.74-4.61 (1H, m), 4.17 (2H, t, J=6.0 Hz), 2.84-2.70 (6H, m), 2.65-2.46 (6H, m), 2.43-2.31 (4H, m), 2.13-1.97 (8H, m), 1.66-1.52 (4H, m), 1.50-1.21 (40H, m), 1.03 (3H, t, J=6.6 Hz), 0.95-0.80 (12H, m).

MS m/z (M+H): 772.

Example 50

(1)

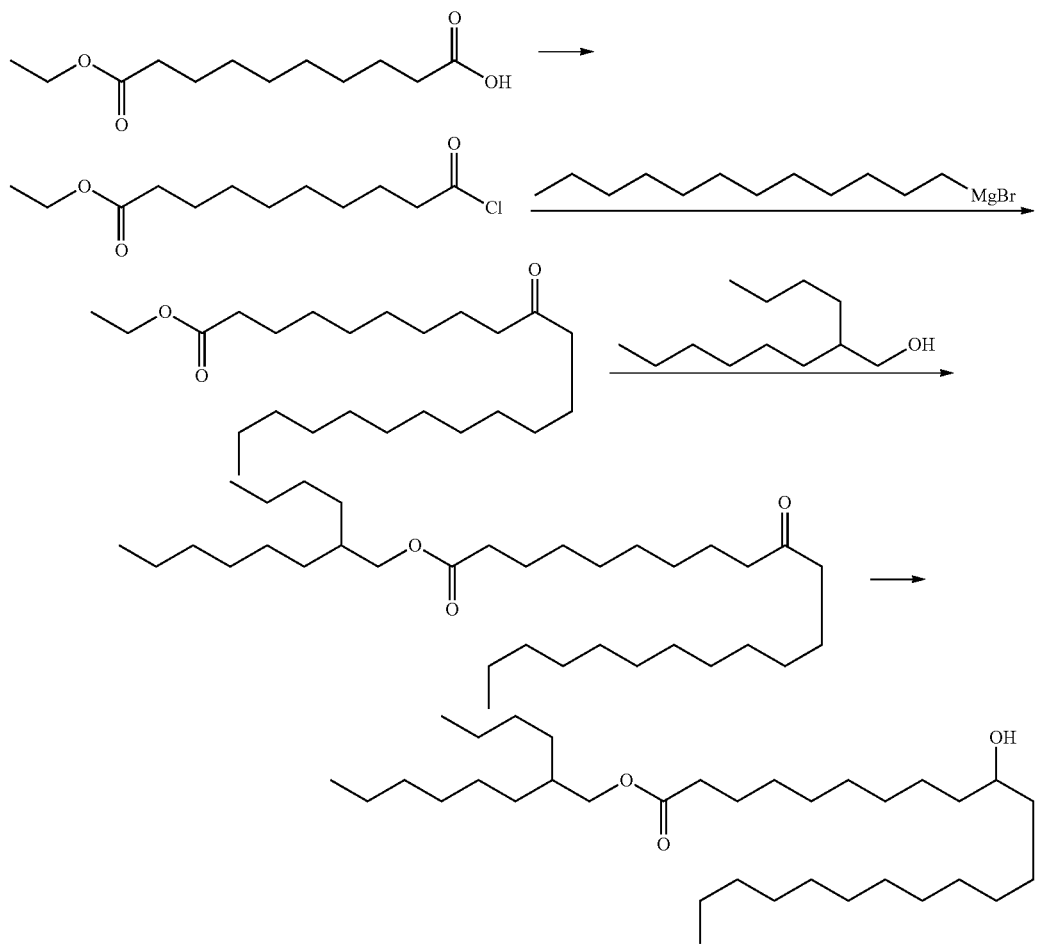

A mixture of 10-ethoxy-10-oxodecanoic acid (22.0 g), thionyl chloride (22.0 mL), and N,N-dimethylformamide (0.1 mL) was stirred and heated under reflux for 1 hour and 30 minutes. The solvent was distilled away under reduced pressure, thereby obtaining ethyl 10-chloro-10-oxodecanoate in the form of a light yellow oily substance as a crude product.

A 1.0 mol/L dodecyl magnesium bromide-diethyl ether solution (190 mL) was added dropwise to a tetrahydrofuran (284 mL) suspension of zinc (II) chloride (13.0 g) at −78° C., and the mixture was heated to 0° C. and then stirred at the same temperature for 30 minutes. Tetrakis(triphenylphosphine)palladium(0) (2.8 g) and ethyl 10-chloro-10-oxodecanoate were added to the reaction mixture, and the reaction mixture was stirred at 0° C. for 1 hour. A 1.0 mol/L aqueous hydrochloric acid solution (50 mL) and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining ethyl 10-oxodocosanoate (13.2 g) as a brown oily substance.

Tetraisopropyl orthotitanate (1.7 g) was added to a mixture of ethyl 10-oxodocosanoate (22.0 g) and 2-butyloctan-1-ol (31.9 g), and the mixture was stirred at 110° C. for 17 hours. Water and ethyl acetate were added to the reaction mixture, the organic layer was separated and dried over anhydrous sodium sulfate, and then the solvent was distilled away under reduced pressure. The obtained residue was purified by silica gel column chromatography (ethyl acetate-hexane), thereby obtaining 2-butyloctyl 10-oxodocosanoate (11.7 g) as light yellow solids.

Sodium borohydride (4.2 g) was added to a mixture of 2-butyloctyl 10-oxodocosanoate (11.7 g), methanol (47 mL), and tetrahydrofuran (47 mL) under ice cooling, and the mixture was stirred at room temperature for 1 hour. The reaction mixture was poured into a mixture of ice and water, a 1.0 mol/L aqueous hydrochloric acid solution (22 mL) was added thereto, the organic layer was separated and dried over anhydrous sodium sulfate, and then the solvent was distilled away under reduced pressure. The obtained residue was purified by silica gel column chromatography (ethyl acetate-hexane), thereby obtaining 2-butyloctyl 10-hydroxydocosanoate (7.8 g) as white solids.

$^1$H-NMR (CDCl$_3$) δ: 3.96-3.98 (2H, d), 3.58 (1H, s), 2.27-2.31 (2H, t), 1.60-1.63 (2H, t), 1.38-1.43 (6H, d), 1.26-1.29 (46H, m), 0.86-0.89 (9H, m).

(2)

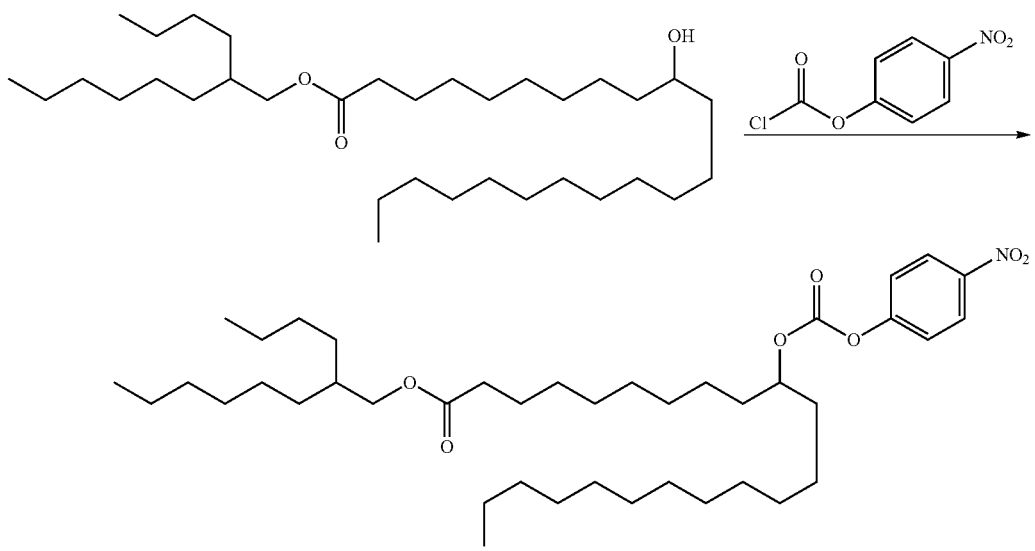

4-Nitrophenyl chloroformate (408 mg) was added to a mixture of 2-butyloctyl 10-hydroxydocosanoate (500 mg), triethylamine (0.43 mL), and tetrahydrofuran (5 mL), and the mixture was stirred at room temperature for 3 hours. Water and ethyl acetate were added to the reaction mixture, the organic layer was separated, washed with a saturated aqueous sodium chloride solution, and then dried over sodium sulfate, and the solvent was distilled away under reduced pressure. The obtained residue was purified by silica gel column chromatography (ethyl acetate-hexane), thereby obtaining 2-butyloctyl 10-(((4-nitrophenoxy)carbonyl)oxy) docosanoate (750 mg) as a colorless oily substance.

$^1$H-NMR (CDCl$_3$) δ: 8.28 (2H, dd, J=7.2H, 2.1 Hz), 7.39 (2H, dd, J=7.2 Hz, 2.1 Hz), 4.86-4.77 (1H, m), 3.97 (2H, d, J=6.0 Hz), 2.30 (2H, t, J=7.2 Hz), 1.74-1.55 (7H, m), 1.40-1.21 (46H, m), 0.92-0.85 (9H, m).

(3)

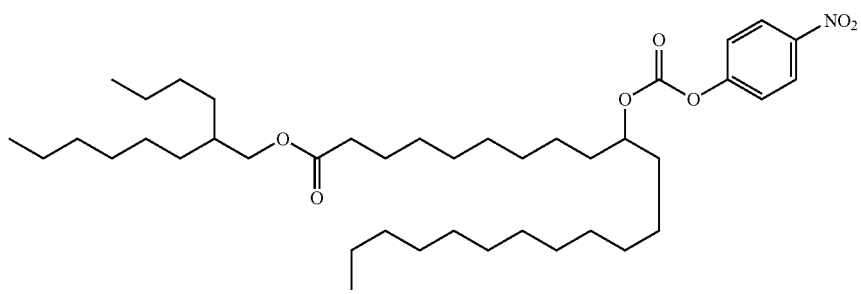
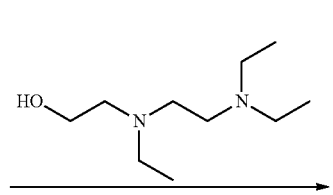
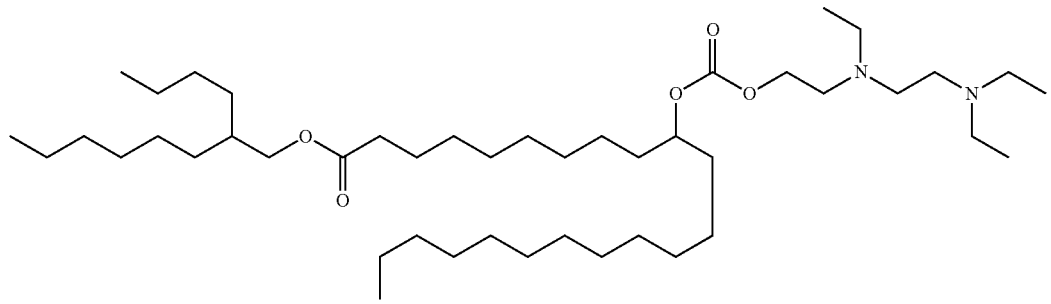

2-Butyloctyl 12-dodecyl-3,6-diethyl-10-oxo-9,11-dioxa-3,6-diazahenicosan-21-oate as a colorless oily substance was obtained by the same method as that in (2) of Example 41, except that 2-butyloctyl 10-(((4-nitrophenoxy)carbonyl)oxy)docosanoate was used instead of 7-(((4-nitrophenoxy)carbonyl)oxy)tridecane-1,13-diyldioleate in (2) of Example 41.

$^{1}$H-NMR (CDCl$_3$) δ: 4.73-4.61 (1H, m), 4.17 (2H, t, J=6.6 Hz), 3.97 (2H, d, J=6.0 Hz), 2.76 (2H, t, J=6.6 Hz), 2.67-2.46 (10H, m), 2.29 (2H, t, J=7.8 Hz), 1.67-1.48 (7H, m), 1.39-1.18 (46H, m), 1.10-0.98 (9H, m), 0.96-0.82 (9H, m).

MS m/z (M+H): 740.

Example 51

(1)

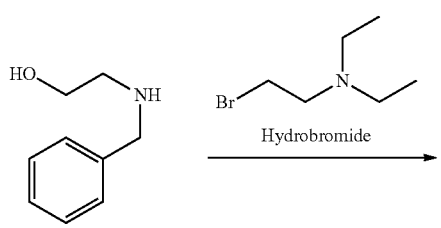

-continued

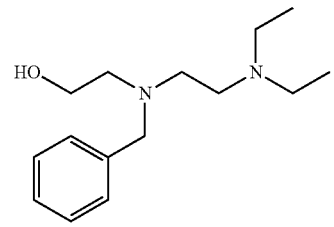

2-(Benzyl(2-(diethylamino)ethyl)amino)ethan-1-ol as a light yellow oily substance was obtained by the same method as that in (1) of Example 30, except that 2-(benzylamino)ethan-1-ol was used instead of 2-(ethylamino)ethan-1-ol in (1) of Example 30.

MS m/z (M+H): 251.

(2)

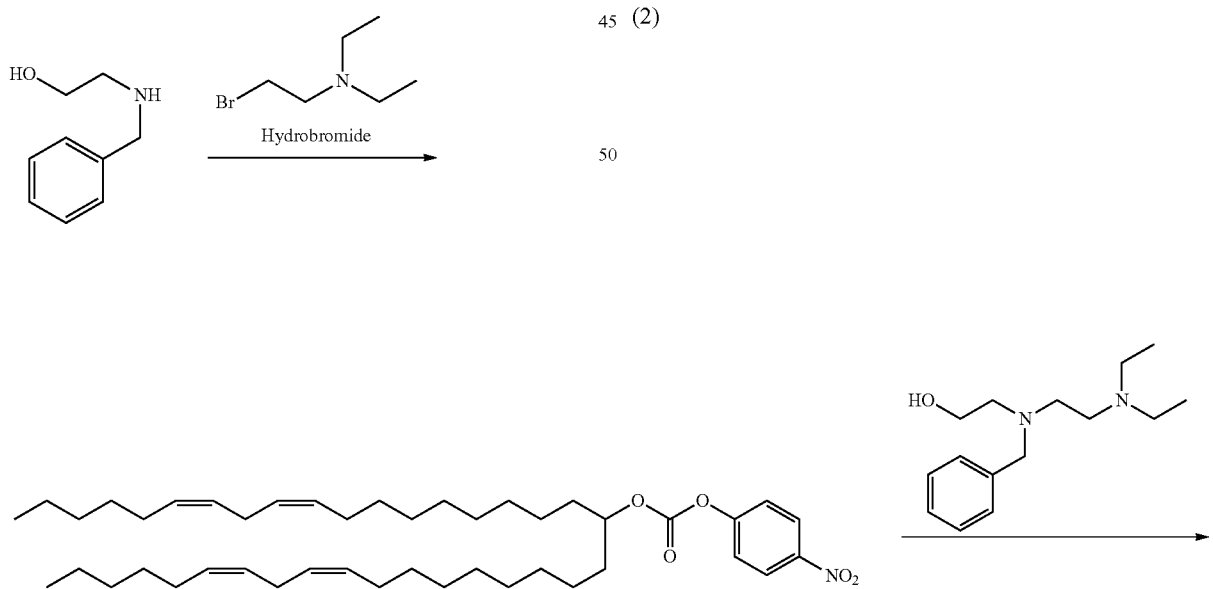

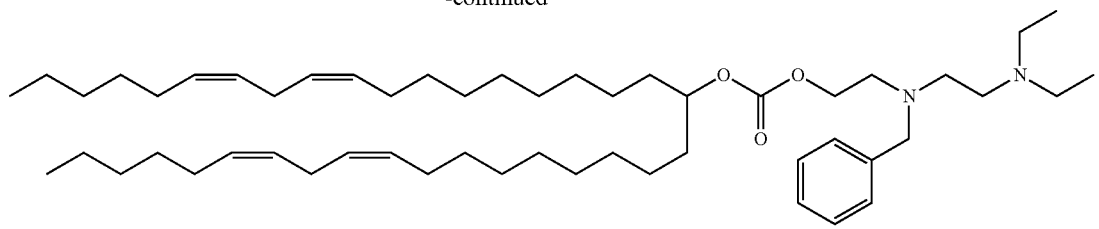

2-(Benzyl(2-(diethylamino)ethyl)amino)ethyl((6Z,9Z, 28Z,31Z)-heptatriaconta-6,9,28,31-tetraen-19-yl)carbonate as a colorless oily substance was obtained by the same method as that in (2) of Example 20, except that 2-(benzyl (2-(diethylamino)ethyl)amino)ethan-1-ol was used instead of 2-((2-(dimethylamino)ethyl)(methyl)amino)ethan-1-ol in (2) of Example 20.

$^1$H-NMR (CDCl$_3$) δ: 7.36-7.19 (5H, m), 5.46-5.27 (8H, m), 4.72-4.61 (1H, m), 4.18 (2H, t, J=6.0 Hz), 3.68 (2H, s), 2.84-2.73 (6H, m), 2.69-2.42 (8H, m), 2.13-1.97 (8H, m), 1.65-1.49 (4H, m), 1.42-1.19 (36H, m), 0.98 (6H, t, J=7.2 Hz), 0.89 (6H, t, J=6.6 Hz).

MS m/z (M+H): 806.

Example 52

(1)

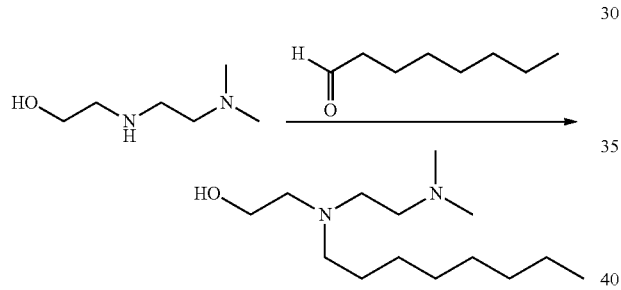

2-((2-Dimethylamino)ethyl)(octyl)amino)ethan-1-ol as a colorless oily substance was obtained by the same method as that in (1) of Example 37, except that octanal was used instead of hexanal in (1) of Example 37.

MS m/z (M+H): 245.

(2)

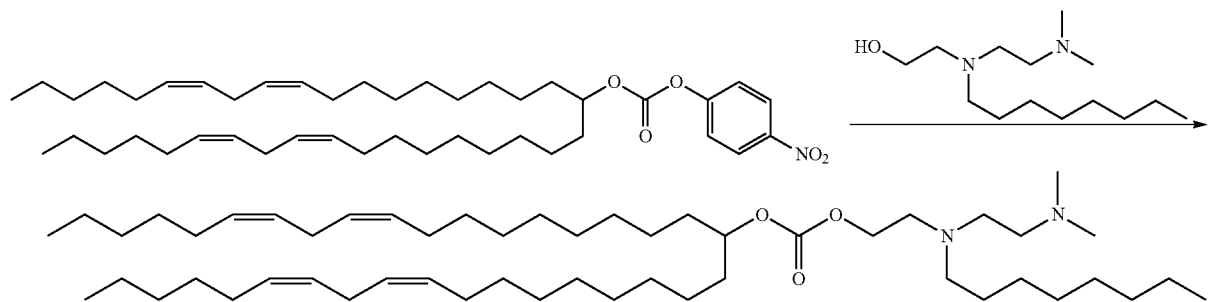

2-((2-(Dimethylamino)ethyl)(octyl)amino)ethyl((6Z,9Z, 28Z,31Z)-heptatriaconta-6,9,28,31-tetraen-19-yl)carbonate as a colorless oily substance was obtained by the same method as that in (2) of Example 20, except that 2-((2-dimethylamino)ethyl)(octyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.24 (8H, m), 4.73-4.62 (1H, m), 4.17 (2H, t, J=6.0 Hz), 2.84-2.71 (6H, m), 2.67-2.56 (2H, m), 2.53-2.43 (2H, m), 2.43-2.31 (2H, m), 2.23 (6H, s), 2.12-1.96 (8H, m), 1.66-1.51 (4H, m), 1.47-1.19 (48H, m), 0.96-0.80 (9H, m).

MS m/z (M+H): 800.

Example 53

(1)

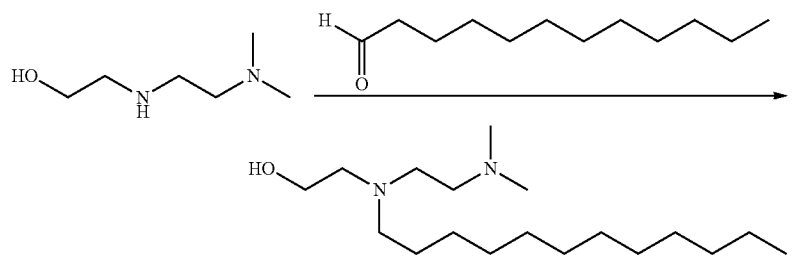

2-((2-(Dimethylamino)ethyl)(dodecyl)amino)ethan-1-ol as a colorless oily substance was obtained by the same method as that in (1) of Example 37, except that dodecanal was used instead of hexanal in (1) of Example 37.
MS m/z (M+H): 301.

(2)

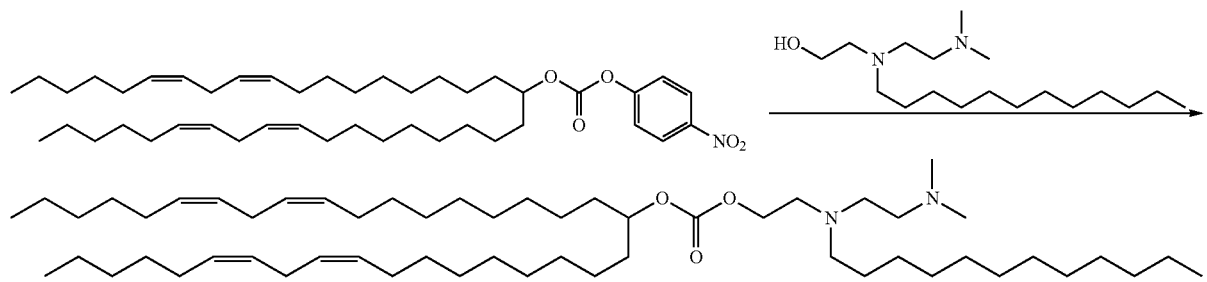

2-((2-(Dimethylamino)ethyl)(dodecyl)amino)ethyl)((6Z,9Z,28Z,31Z)-heptatriaconta-6,9,28,31-tetraen-19-yl)carbonate as a colorless oily substance was obtained by the same method as that in (2) of Example 20, except that 2-((2-(dimethylamino)ethyl)(dodecyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.46-5.25 (8H, m), 4.72-4.61 (1H, m), 4.17 (2H, t, J=6.6 Hz), 2.85-2.70 (6H, m), 2.66-2.57 (2H, m), 2.54-2.43 (2H, m), 2.42-2.32 (2H, m), 2.23 (6H, s), 2.11-1.97 (8H, m), 1.66-1.50 (4H, m), 1.47-1.17 (56H, m), 0.97-0.81 (9H, m).
MS m/z (M+H): 856.

Example 54

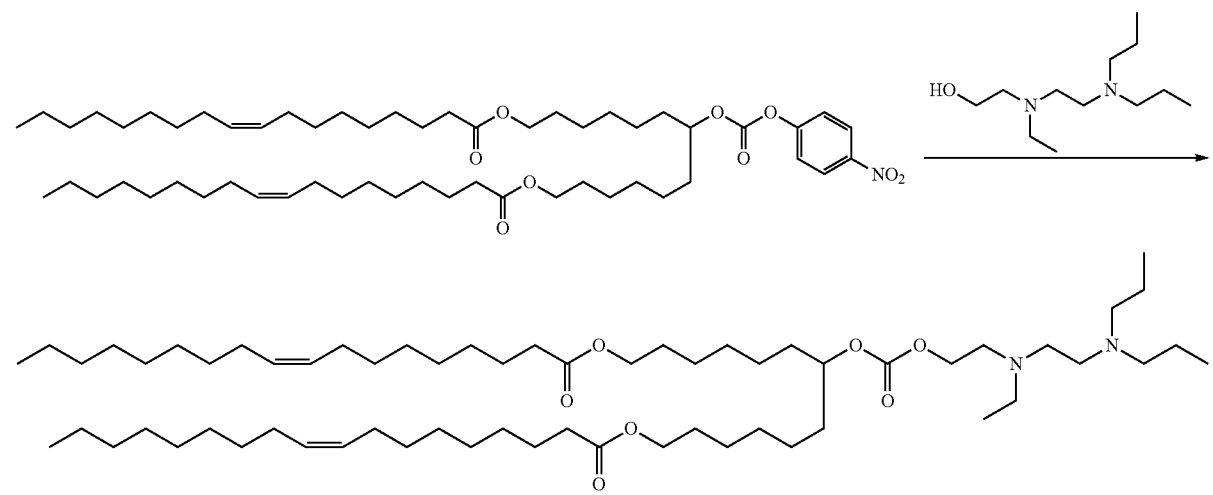

7-(((2-((2-(Dipropylamino)ethyl)(ethyl)amino)ethoxy)carbonyl)oxy)tridecane-1,13-diyldioleate as a colorless oily substance was obtained by the same method as that in (2) of Example 41, except that 2-((2-(dipropylamino)ethyl)(ethyl)amino)ethan-1-ol was used instead of 2-((2-(diethylamino)ethyl)(ethyl)amino)ethan-1-ol in (2) of Example 41.

$^1$H-NMR (CDCl$_3$) δ: 5.41-5.26 (4H, m), 4.73-4.60 (1H, m), 4.17 (2H, t, J=6.0 Hz), 4.04 (4H, t, J=6.6 Hz), 2.75 (2H, t, J=6.6 Hz), 2.65-2.46 (6H, m), 2.43-2.34 (4H, m), 2.28 (4H, t, J=7.2 Hz), 2.10-1.95 (8H, m), 1.69-1.51 (12H, m), 1.50-1.19 (56H, m), 1.03 (3H, t, J=7.5 Hz), 0.94-0.81 (12H, m).

MS m/z (M+H): 1004.

Example 55 substance was obtained by the same method as that in (2) of Example 41, except that 2-(benzyl(2-(diethylamino)ethyl)amino)ethan-1-ol was used instead of 2-((2-(diethylamino)ethyl)(ethyl)amino)ethan-1-ol in (2) of Example 41.

$^1$H-NMR (CDCl$_3$) δ: 7.36-7.17 (5H, m), 5.42-5.27 (4H, m), 4.71-4.61 (1H, m), 4.19 (2H, t, J=6.6 Hz), 4.04 (4H, t, J=7.2 Hz), 3.68 (2H, s), 2.79 (2H, t, J=6.0 Hz), 2.67-2.42 (8H, m), 2.28 (4H, t, J=8.1 Hz), 2.08-1.93 (8H, m), 1.69-1.49 (12H, m), 1.42-1.20 (52H, m), 0.97 (6H, t, J=7.2 Hz), 0.88 (6H, t, J=6.6 Hz).

MS m/z (M+H): 1038.

Example 56

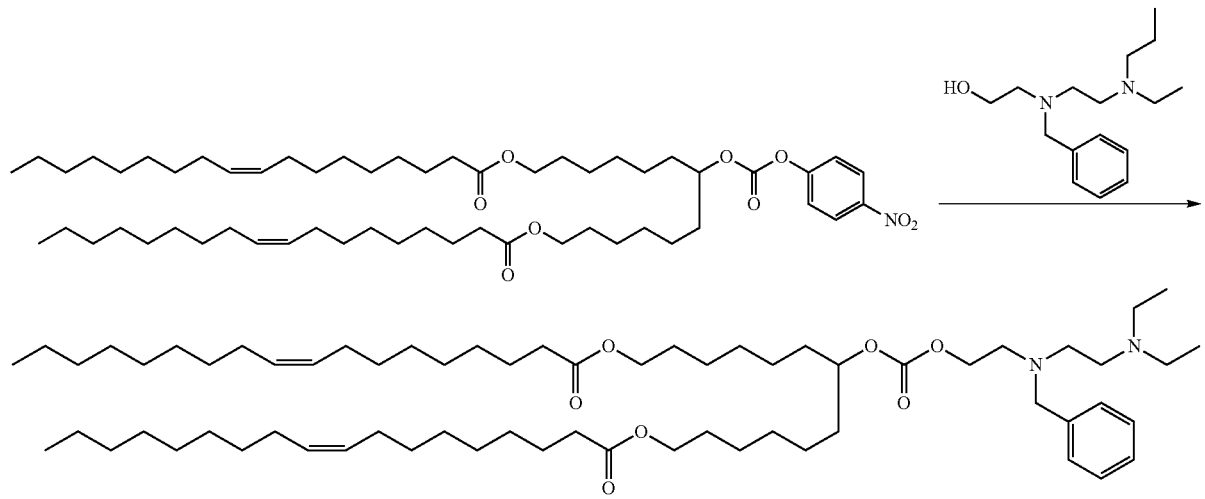

7-(((2-(Benzyl(2-(diethylamino)ethyl)amino)ethoxy)carbonyl)oxy)tridecane-1,13-diyldioleate as a colorless oily

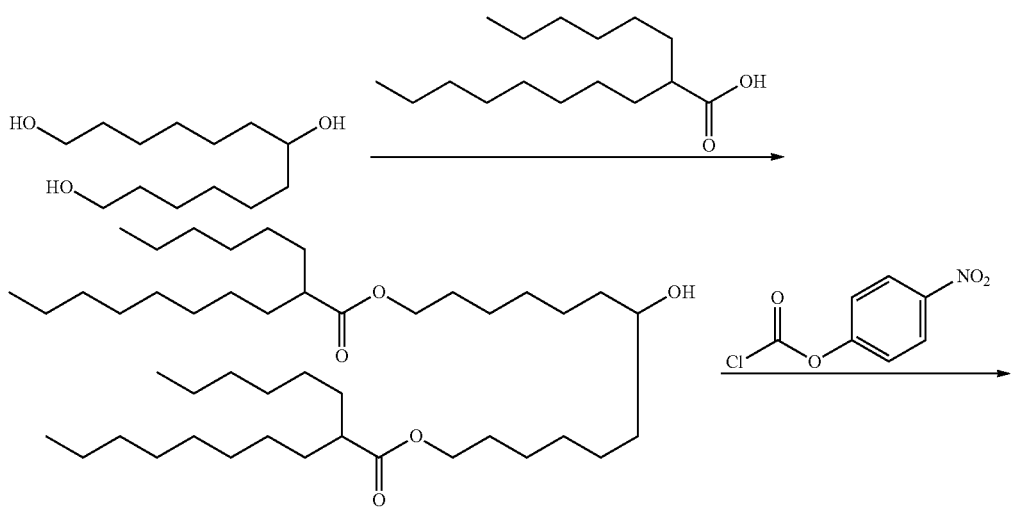

-continued

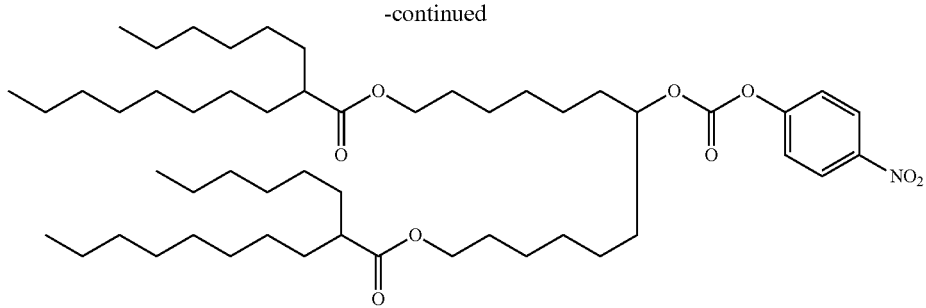

7-(((4-Nitrophenoxy)carbonyl)oxy)tridecane-1,13-diyl-bis(2-hexyldecanoate) as a colorless oily substance was obtained by the same method as that in (1) of Example 41, except that 2-hexyl decanoate was used instead of oleic acid in (1) of Example 41.

$^1$H-NMR (CDCl$_3$) δ: 8.28 (2H, dd, J=7.2H, 2.1 Hz), 7.39 (2H, dd, J=7.2 Hz, 2.1 Hz), 4.86-4.76 (1H, m), 4.07 (4H, t, J=6.6 Hz), 2.36-2.25 (2H, m), 1.72-1.20 (68H, m), 0.87 (12H, t, J=6.0 Hz).

(2)

used instead of 7-(((4-nitrophenoxy)carbonyl)oxy)tride-cane-1,13-diyldioleate in (2) of Example 41.

$^1$H-NMR (CDCl$_3$) δ: 4.73-4.61 (1H, m), 4.17 (2H, t, J=6.6 Hz), 4.05 (4H, t, J=6.6 Hz), 2.76 (2H, t, J=6.6 Hz), 2.67-2.46 (10H, m), 2.36-2.23 (2H, m), 1.68-1.16 (68H, m), 1.09-0.97 (9H, m), 0.94-0.81 (12H, m).

MS m/z (M+H): 924.

Example 57

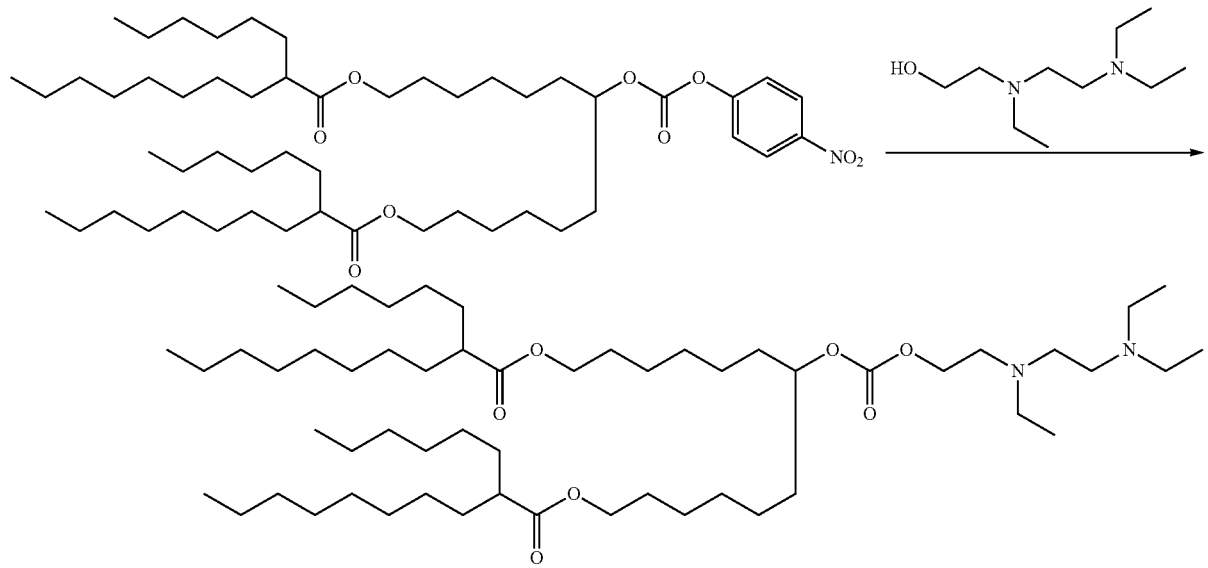

7-(((2-((2-(Diethylamino)ethyl)(ethyl)amino)ethoxy)carbonyl)oxy)tridecane-1,13-diylbis(2-hexyldecanoate) as a colorless oily substance was obtained by the same method as that in (2) of Example 41, except that 7-(((4-nitrophenoxy)carbonyl)oxy)tridecane-1,13-diylbis(2-hexyldecanoate) was

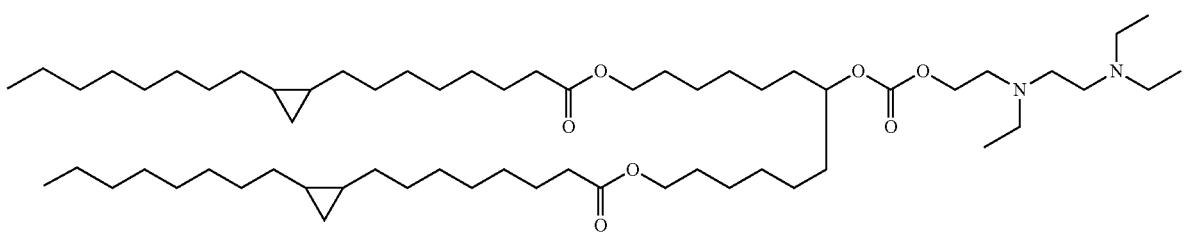 [SMILES: CCCCCCCCC1CC1CCCCCCCC(=O)OCCCCCCC(CCCCCCOC(=O)CCCCCCCC1CC1CCCCCCCC)OC(=O)OCCN(CC)CCN(CC)CC]

7-(((2-((2-(Diethylamino)ethyl)(ethyl)amino)ethoxy)carbonyl)oxy)tridecane-1,13-diylbis(8-(2-octylcyclopropyl)octanoate)) as a colorless oily substance was obtained by the same method as that in (1) and (2) of Example 41, except that 8-(2-octylcyclopropyl)octanoate synthesized according to the method described in European Journal of Medicinal Chemistry, 2016, 109, p 134-145 was used instead of oleic acid in (1) and (2) of Example 41.

$^1$H-NMR (CDCl$_3$) δ: 4.72-4.62 (1H, m), 4.18 (2H, t, J=6.6 Hz), 4.05 (4H, t, J=6.6 Hz), 2.76 (2H, t, J=6.6 Hz), 2.66-2.47 (10H, m), 2.29 (4H, t, J=8.1 Hz), 1.69-1.48 (12H, m), 1.45-1.08 (60H, m), 1.08-0.97 (9H, m), 0.88 (6H, t, J=7.2 Hz), 0.71-0.51 (6H, m), −0.29-0.38 (2H, m).

MS m/z (M+H): 1004.

Example 58

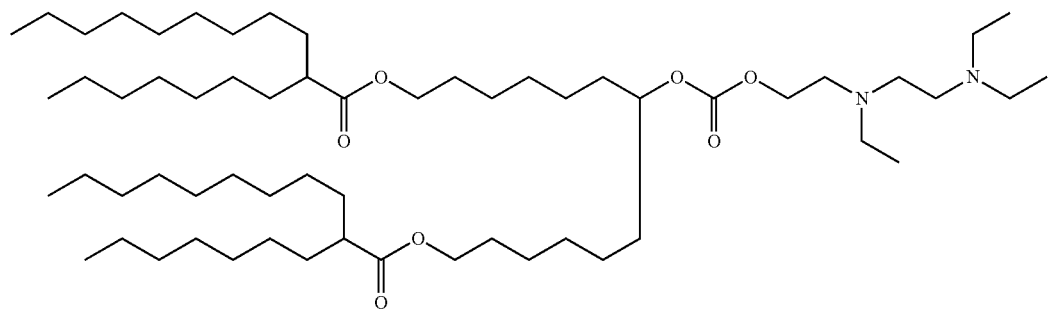 [SMILES: CCCCCCCCCC(CCCCCCC)C(=O)OCCCCCCC(CCCCCCOC(=O)C(CCCCCCC)CCCCCCCCC)OC(=O)OCCN(CC)CCN(CC)CC]

7-(((2-((2-(Diethylamino)ethyl)(ethyl)amino)ethoxy)carbonyl)oxy)tridecane-1,13-diylbis(2-heptylundecanoate) as a colorless oily substance was obtained by the same method as that in (1) and (2) of Example 41, except that 2-heptyl undecaonate was used instead of oleic acid in (1) and (2) of Example 41.

$^1$H-NMR (CDCl$_3$) δ: 4.72-4.62 (1H, m), 4.17 (2H, t, J=6.6 Hz), 4.05 (4H, t, J=6.6 Hz), 2.76 (2H, t, J=5.7 Hz), 2.65-2.47 (10H, m), 2.36-2.24 (2H, m), 1.69-1.17 (76H, m), 1.08-0.98 (9H, m), 0.88 (12H, t, J=7.5 Hz).

MS m/z (M+H): 980.

Example 59

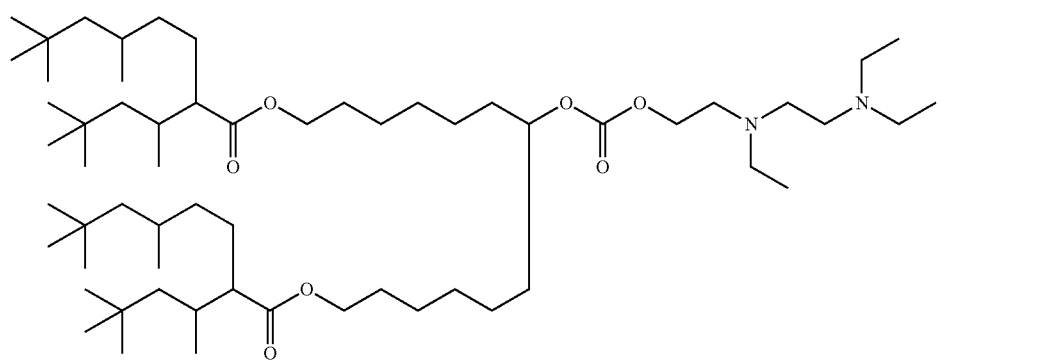 [SMILES: CCN(CC)CCN(CC)CCOC(=O)OC(CCCCCCOC(=O)C(CCC(C)CC(C)(C)C)C(C)CC(C)(C)C)CCCCCCOC(=O)C(CCC(C)CC(C)(C)C)C(C)CC(C)(C)C]

7-(((2-((2-(Diethylamino)ethyl)(ethyl)amino)ethoxy)carbonyl)oxy)tridecane-1,13-diylbis(2-(4,4-dimethylpentan-2-yl)-5,7,7-trimethyloctanoate) as a colorless oily substance was obtained by the same method as that in (1) and (2) of Example 41, except that 2-(4,4-dimethylpentan-2-yl)-5,7,7-trimethyloctanoate was used instead of oleic acid in (1) and (2) of Example 41.

$^1$H-NMR (CDCl$_3$) δ: 4.73-4.62 (1H, m), 4.17 (2H, t, J=6.6 Hz), 4.11-3.95 (4H, m), 2.76 (2H, t, J=6.0 Hz), 2.65-2.46 (10H, m), 2.19-2.06 (2H, m), 1.86-1.13 (40H, m), 1.10-0.79 (57H, m).

MS m/z (M+H): 980.

Example 60

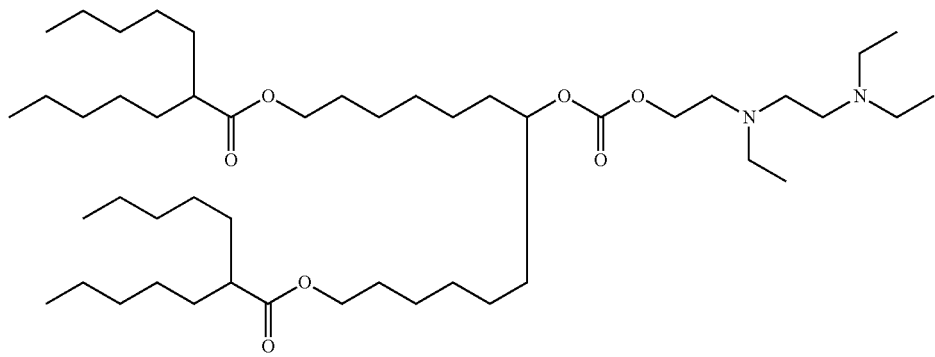 [SMILES: CCCCCC(CCCCC)C(=O)OCCCCCCC(CCCCCCOC(=O)C(CCCCC)CCCCC)OC(=O)OCCN(CC)CCN(CC)CC]

7-(((2-((2-(Diethylamino)ethyl)(ethyl)amino)ethoxy)carbonyl)oxy)tridecane-1,13-diylbis(2-pentylheptanoate) as a colorless oily substance was obtained by the same method as that in (1) and (2) of Example 41, except that 2-pentyl heptanoate was used instead of oleic acid in (1) and (2) of Example 41.

$^1$H-NMR (CDCl$_3$) δ: 4.73-4.61 (1H, m), 4.17 (2H, t, J=6.6 Hz), 4.05 (4H, t, J=6.6 Hz), 2.76 (2H, t, J=6.0 Hz), 2.65-2.47 (10H, m), 2.37-2.25 (2H, m), 1.69-1.19 (52H, m), 1.07-0.98 (9H, m), 0.87 (12H, t, J=6.6 Hz).

MS m/z (M+H): 812.

Example 61 stance was obtained by the same method as that in (3) of Example 50, except that 2-((2-(diethylamino)ethyl)(isopropyl)amino)ethan-1-ol was used instead of 2-((2-(diethylamino)ethyl)(ethyl)amino)ethan-1-ol in (3) of Example 50.

$^1$H-NMR (CDCl$_3$) δ: 4.73-4.60 (1H, m), 4.10 (2H, t, J=6.6 Hz), 3.97 (2H, d, J=6.0 Hz), 2.97-2.85 (1H, m), 2.68 (2H, t, J=7.2 Hz), 2.60-2.41 (8H, m), 2.29 (2H, t, J=7.8 Hz), 1.66-1.48 (7H, m), 1.40-1.20 (46H, m), 1.07-0.95 (12H, m), 0.94-0.81 (9H, m).

MS m/z (M+H): 754.

Example 62

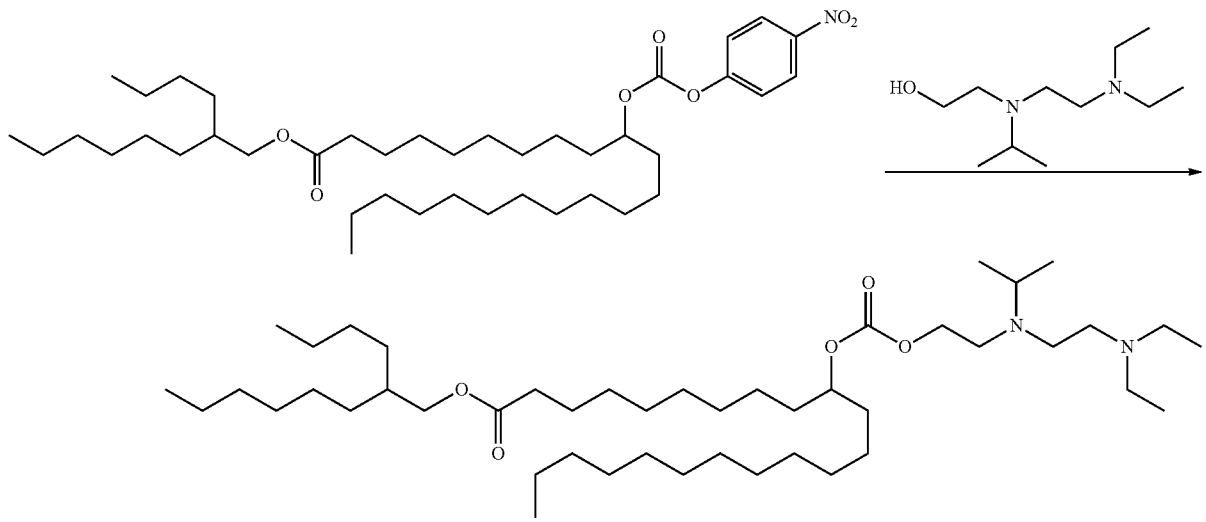

2-Butyloctyl 12-dodecyl-3-ethyl-6-isopropyl-10-oxo-9,11-dioxa-3,6-diazahenicosan-21-oate as a colorless oily sub-

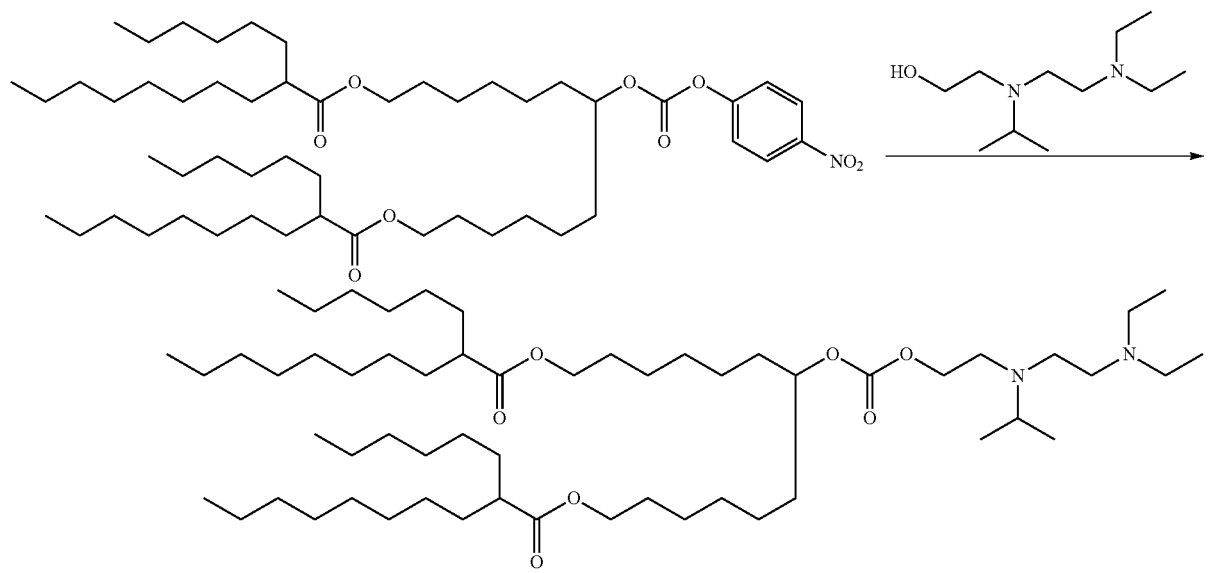

7-(((2-((2-(Diethylamino)ethyl)(isopropyl)amino)ethoxy)carbonyl)oxy)tridecane-1,13-diylbis(2-hexyldecanoate) as a colorless oily substance was obtained by the same method as that in (2) of Example 56, except that 2-((2-(diethylamino)ethyl)(isopropyl)amino)ethan-1-ol was used instead of 2-((2-(diethylamino)ethyl)(ethyl)amino)ethan-1-ol in (2) of Example 56.

$^1$H-NMR (CDCl$_3$) δ: 4.73-4.61 (1H, m), 4.15-3.99 (6H, m), 2.97-2.84 (1H, m), 2.68 (2H, t, J=6.6 Hz), 2.60-2.41 (8H, m), 2.37-2.23 (2H, m), 1.69-1.16 (68H, m), 1.10-0.95 (12H, m), 0.87 (12H, t, J=6.6 Hz).

MS m/z (M+H): 938.

Example 63

(1)

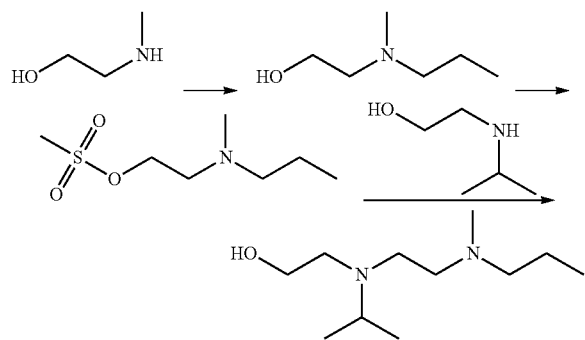

A mixture of 2-(methylamino)ethan-1-ol (3 g), potassium carbonate (6.6 g), 1-bromopropane (5.6 mL), and acetonitrile (30 mL) was stirred at 60° C. for 9 hours and 30 minutes. A saturated aqueous sodium hydrogen carbonate solution was added to the reaction mixture, and extraction was performed using chloroform. The organic layer was washed with saturated saline and dried over anhydrous sodium sulfate. The solvent was distilled away under reduced pressure, thereby obtaining 2-(methyl(propyl)amino)ethan-1-ol (4.3 g) as a colorless oily substance.

MS m/z (M+H): 118.

Methanesulfonic anhydride (1.9 g) was added dropwise to a mixture of 2-(methyl(propyl)amino)ethan-1-ol (1.2 g) and acetonitrile (10 mL) under ice cooling, and the mixture was stirred at 0° C. for 30 minutes and then stirred at room temperature for 30 minutes. 2-(Isopropylamino)ethan-1-ol (2.0 g) and N,N-diisopropylethylamine (2.0 mL) were added to the reaction mixture, and the reaction mixture was stirred at 70° C. for 25 hours and 30 minutes. The reaction mixture was cooled to room temperature, potassium carbonate and water were then added thereto, and extraction was performed using ethyl acetate. The organic layer was washed with saturated saline and dried over anhydrous sodium sulfate. The solvent was distilled away under reduced pressure, and the obtained residue was purified by silica gel column chromatography (methanol-chloroform), thereby obtaining 2-(isopropyl(2-(methyl(propyl)amino)ethyl)amino)ethan-1-ol (0.3 g) as a yellow oily substance.

MS m/z (M+H): 203.

(2)

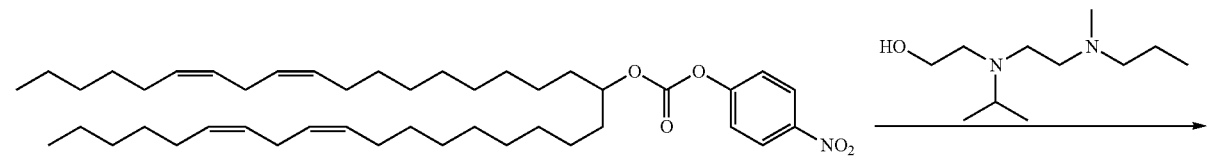

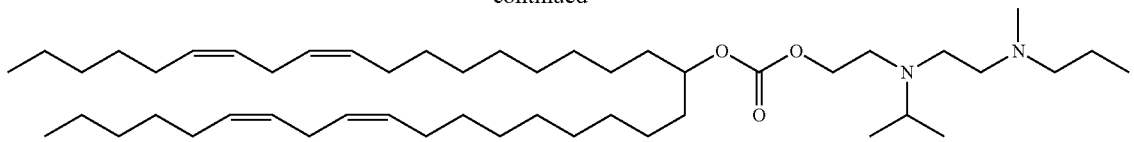

(6Z, 9Z, 28Z, 31Z)-heptatriaconta-6,9,28,31-tetraen-19-yl(2-(isopropyl(2-(methyl(propyl)amino)ethyl)amino)ethyl) carbonate as a colorless oily substance was obtained by the same method as that in (2) of Example 20, except that 2-(isopropyl(2-(methyl(propyl)amino)ethyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.45-5.26 (8H, m), 4.73-4.62 (1H, m), 4.09 (2H, t, J=6.6 Hz), 2.97-2.86 (1H, m), 2.77 (4H, t, J=6.0 Hz), 2.69 (2H, t, J=7.2 Hz), 2.62-2.51 (2H, m), 2.44-2.35 (2H, m), 2.35-2.27 (2H, m), 2.23 (3H, s), 2.11-1.96 (8H, m), 1.66-1.20 (42H, m), 0.98 (6H, d, J=6.6 Hz), 0.94-0.82 (9H, m).

MS m/z (M+H): 758.

Example 64

(1)

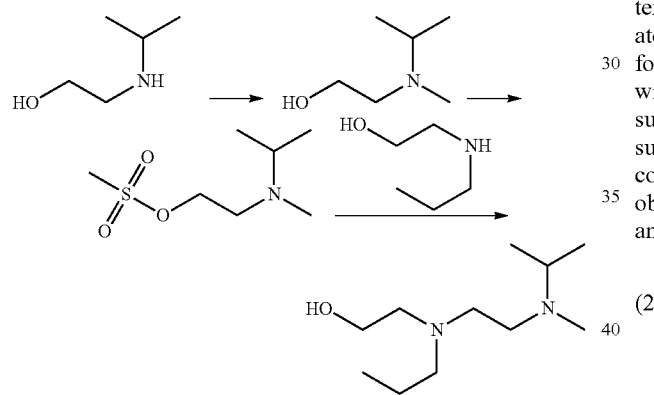

Methyl iodide (1.9 mL) was added dropwise to a dichloromethane (30 mL) solution of 2-(isopropylamino)ethan-1-ol (3 g) under ice cooling. The mixture was stirred at the same temperature for 1 hour and 15 minutes and then stirred at room temperature for 6 hours and 50 minutes. Potassium carbonate and water were added to the reaction mixture, and extraction was performed using chloroform. The organic layer was washed with saturated saline and dried over anhydrous sodium sulfate. The solvent was distilled away under reduced pressure, and the obtained residue was purified by silica gel column chromatography (methanol-chloroform, NH silica gel), thereby obtaining 2-(isopropyl(methyl)amino)ethan-1-ol (2.2 g) as a colorless oily substance.

MS m/z (M+H): 118.

Methanesulfonic anhydride (2.6 g) was added to a mixture of 2-(isopropyl(methyl)amino)ethan-1-ol (1.5 g), N,N-diisopropylethylamine (2.5 mL), and acetonitrile (15 mL) under ice cooling, and the mixture was stirred at room temperature for 4 hours and 50 minutes. 2-(Propylamino)ethan-1-ol (4.3 mL) was added to the reaction mixture, and the reaction mixture was stirred at 70° C. for 23 hours and 30 minutes. The reaction mixture was cooled to room temperature, a saturated aqueous sodium hydrogen carbonate solution was added thereto, and extraction was performed using ethyl acetate. The organic layer was washed with saturated saline and dried over anhydrous sodium sulfate. The solvent was distilled away under reduced pressure, and the obtained residue was purified by silica gel column chromatography (methanol-chloroform), thereby obtaining 2-((2-(isopropyl(methyl)amino)ethyl)(propyl)amino)ethan-1-ol (0.7 g) as a yellow oily substance.

MS m/z (M+H): 203.

(2)

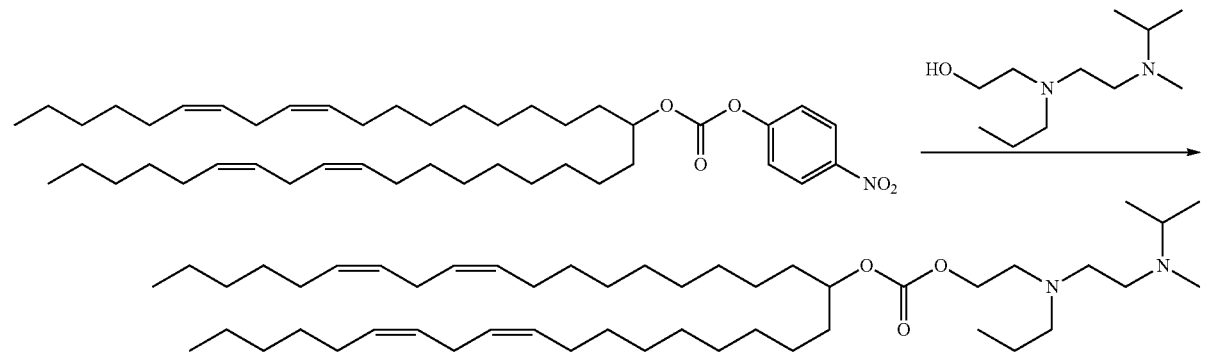

(6Z, 9Z, 28Z, 31Z)-heptatriaconta-6, 9, 28, 31-tetraen-19-yl(2-((2-isopropyl(methyl)amino)ethyl)(propyl)amino)ethyl)carbonate as a colorless oily substance was obtained by the same method as that in (2) of Example 20, except that 2-((2-(isopropyl(methyl)amino)ethyl)(propyl)amino)ethan-1-ol was used instead of 2-((2-(dimethylamino)ethyl)(methyl)amino)ethan-1-ol in (2) of Example 20.

$^1$H-NMR (CDCl$_3$) δ: 5.46-5.26 (8H, m), 4.74-4.60 (1H, m), 4.17 (2H, t, J=6.6 Hz), 2.87-2.70 (7H, m), 2.65-2.54 (2H, m), 2.51-2.40 (4H, m), 2.21 (3H, s), 2.12-1.95 (8H, m), 1.64-1.20 (42H, m), 1.00 (6H, d, J=6.6 Hz), 0.94-0.81 (9H, m).

MS m/z (M+H): 758.

Example 65

(1)

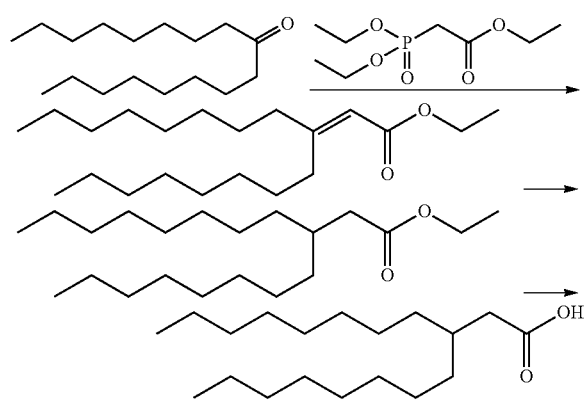

Ethyl 2-(diethoxyphosphoryl)acetate (9.4 mL) was added dropwise to a tetrahydrofuran (60 mL) suspension of 60% wt sodium hydride (1.7 g) under ice cooling, and the mixture was stirred at the same temperature for 30 minutes. Heptadecan-9-one (1.5 g) was added to the reaction mixture, and the reaction mixture was stirred and heated under reflux for 16 hours. The reaction mixture was cooled to room temperature and poured into ice water, and then ethyl acetate was added thereto. The organic layer was separated and washed with a saturated aqueous sodium chloride solution, then the solvent was distilled away under reduced pressure, and the obtained residue was purified by silica gel column chromatography (ethyl acetate-hexane), thereby obtaining ethyl 3-octyl undec-2-enoate (1.2 g) as a colorless oily substance.

$^1$H-NMR (CDCl$_3$) δ: 5.61 (1H, s), 4.14 (2H, q, J=6.6 Hz), 2.58 (2H, t, J=7.2 Hz), 2.12 (2H, t, J=7.2 Hz), 1.50-1.20 (27H, m), 0.91-0.85 (6H, m).

Ammonium formate (1.4 g) was added to a mixture of ethyl 3-octyl undec-2-enoate (1.2 g), 10% palladium-carbon (0.35 g), and methanol (24 mL), and the mixture was stirred and heated under reflux for 4 hours. The reaction mixture was cooled to room temperature, the insoluble matters were filtered off using celite, and then the solvent was distilled away under reduced pressure. The obtained residue was purified by silica gel column chromatography (ethyl acetate-hexane), thereby obtaining ethyl 3-octylundecanoate (1.1 g) as a colorless oily substance.

$^1$H-NMR (CDCl$_3$) δ: 4.12 (2H, q, J=7.2 Hz), 2.21 (2H, d, J=6.6 Hz), 2.05-2.04 (1H, m), 1.34-1.20 (31H, m), 0.88 (6H, t, J=6.6 Hz).

A 5 mol/L aqueous sodium hydroxide solution (5 mL) was added to a mixture of ethyl 3-octylundecanoate (1.1 g) and ethanol (10 mL), and the mixture was stirred at 80° C. for 5 hours. The reaction mixture was cooled to room temperature, a 1 mol/L aqueous hydrochloric acid solution was added until the reaction mixture became acidic, and then ethyl acetate was added thereto. The organic layer was separated and washed with a saturated aqueous sodium chloride solution, the solvent was then distilled away under reduced pressure, and the obtained residue was purified by silica gel column chromatography (ethyl acetate-hexane), thereby obtaining 3-octyl undecanoate (1.1 g) as a colorless oily substance.

$^1$H-NMR (CDCl$_3$) δ: 2.28 (2H, d, J=6.6 Hz), 1.90-1.79 (1H, m), 1.35-1.19 (28H, m), 0.88 (6H, t, J=6.6 Hz).

(2)

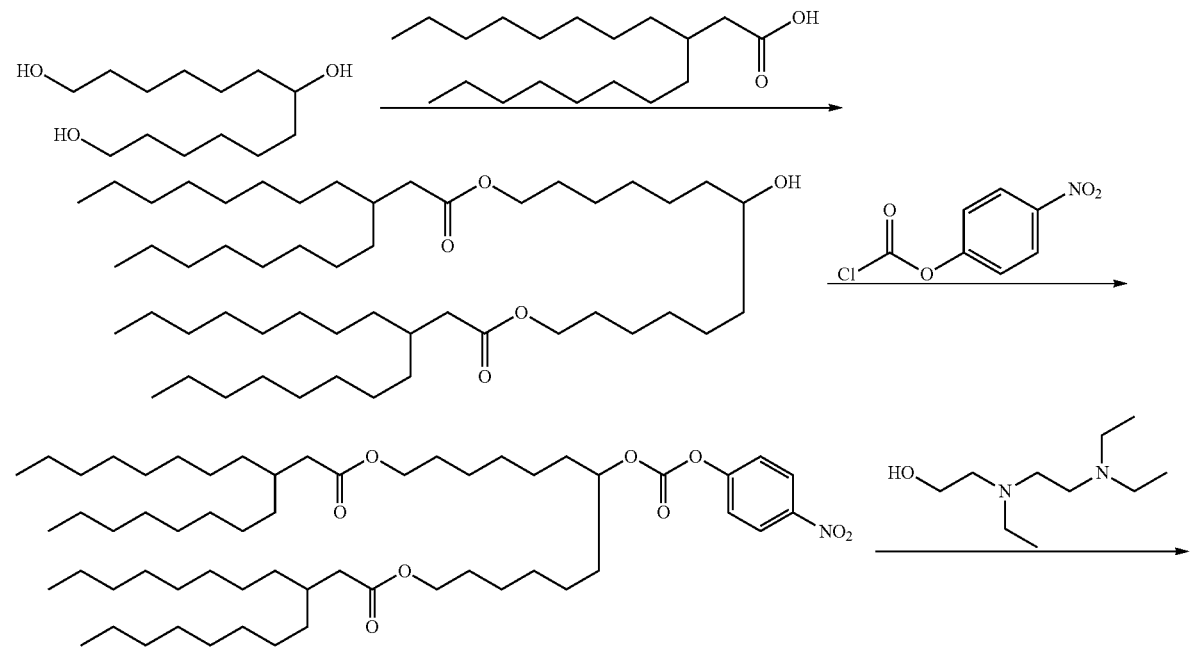

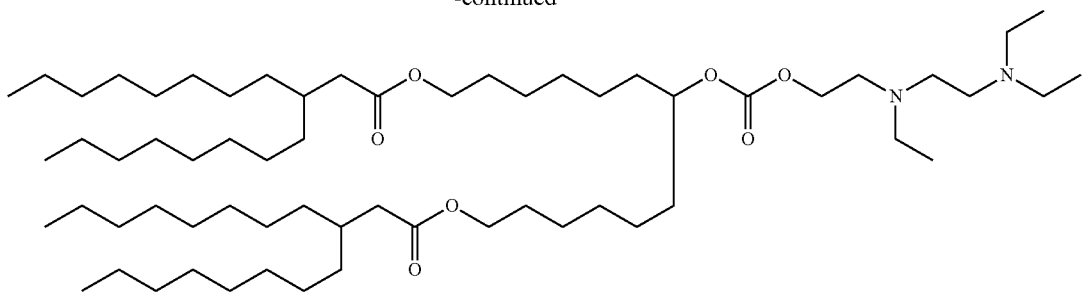

7-(((2-((2-(Diethylamino)ethyl)(ethyl)amino)ethoxy)carbonyl)oxy)tridecane-1,13-diylbis(3-octylundecanoate) as a colorless oily substance was obtained by the same method as that in (1) and (2) of Example 41, except that 3-octyl undecanoate was used instead of oleic acid in (1) and (2) of Example 41.

$^1$H-NMR (CDCl$_3$) δ:4.74-4.62 (1H, m), 4.17 (2H, t, J=6.6 Hz), 4.04 (4H, t, J=6.6 Hz), 2.76 (2H, t, J=6.6 Hz), 2.66-2.47 (10H, m), 2.22 (4H, d, J=6.6 Hz), 1.90-1.76 (2H, m), 1.70-1.17 (76H, m), 1.10-0.97 (9H, m), 0.88 (12H, t, J=6.6 Hz).

MS m/z (M+H): 1008

Example 66

2-Butyloctyl 12-decyl-3,6-diethyl-10-oxo-9,11-dioxa-3,6-diazatricosan-23-oate as a colorless oily substance was obtained by the same method as that in (1), (2), and (3) of Example 50, except that in (1), (2), and (3) of Example 50, 12-ethoxy-12-oxododecanoic acid was used instead of 10-ethoxy-10-oxodecanoic acid, and a 1.0 mol/L decyl magnesium bromide-diethyl ether solution was used instead of a 1.0 mol/L dodecyl magnesium bromide-diethyl ether solution.

$^1$H-NMR (CDCl$_3$) δ:4.73-4.61 (1H, m), 4.17 (2H, t, J=6.6 Hz), 3.97 (2H, d, J=5.7 Hz), 2.76 (2H, t, J=6.6 Hz), 2.66-2.46 (10H, m), 2.30 (2H, t, J=7.2 Hz), 1.70-1.47 (7H, m), 1.41-1.20 (46H, m), 1.11-0.98 (9H, m), 0.95-0.82 (9H, m).

MS m/z (M+H): 740.

Example 67

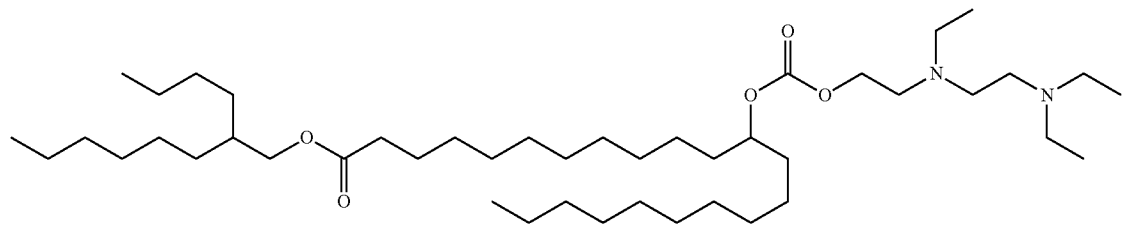 [SMILES: CCCCCCCCCCC(CCCCCCCCCCC(=O)OCC(CCCC)CCCCCC)OC(=O)OCCN(CC)CCN(CC)CC]

7-(((2-((2-(Diethylamino)ethyl)(ethyl)amino)ethoxy)carbonyl)oxy)tridecane-1,13-diylbis(3-hexylnonanoate) as a colorless oily substance was obtained by the same method as that in (1) and (2) of Example 65, except that tridecan-7-one was used instead of heptadecan-9-one in (1) and (2) of Example 65.

¹H-NMR (CDCl₃) δ: 4.73-4.62 (1H, m), 4.17 (2H, t, J=6.6 Hz), 4.04 (4H, t, J=6.6 Hz), 2.76 (2H, t, J=6.6 Hz), 2.67-2.45 (10H, m), 2.22 (4H, d, J=6.6 Hz), 1.89-1.77 (2H, m), 1.67-1.17 (60H, m), 1.08-0.98 (9H, m), 0.88 (12H, t, J=6.6 Hz).
MS m/z (M+H): 896.

Example 68

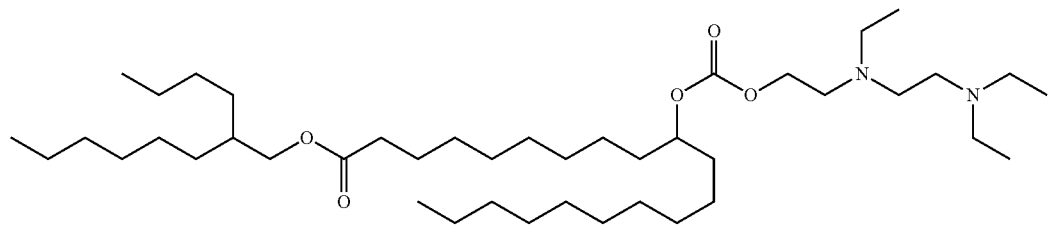 [SMILES: CCCCCCCCCCC(CCCCCCCCC(=O)OCC(CCCC)CCCCCC)OC(=O)OCCN(CC)CCN(CC)CC]

2-Butyloctyl 12-decyl-3,6-diethyl-10-oxo-9,11-dioxa-3,6-diazahenicosan-21-oate as a colorless oily substance was obtained by the same method as that in (1), (2), and (3) of Example 50, except that a 1.0 mol/L decyl magnesium bromide-diethyl ether solution was used instead of a 1.0 mol/L dodecyl magnesium bromide-diethyl ether solution in (1), (2), and (3) of Example 50.

¹H-NMR (CDCl₃) δ: 4.73-4.60 (1H, m), 4.17 (2H, t, J=6.6 Hz), 3.97 (2H, d, J=5.4 Hz), 2.76 (2H, t, J=6.0 Hz), 2.67-2.46 (10H, m), 2.29 (2H, t, J=7.8 Hz), 1.68-1.50 (7H, m), 1.39-1.20 (42H, m), 1.07-0.98 (9H, m), 0.94-0.83 (9H, m).
MS m/z (M+H): 712.

Example 69

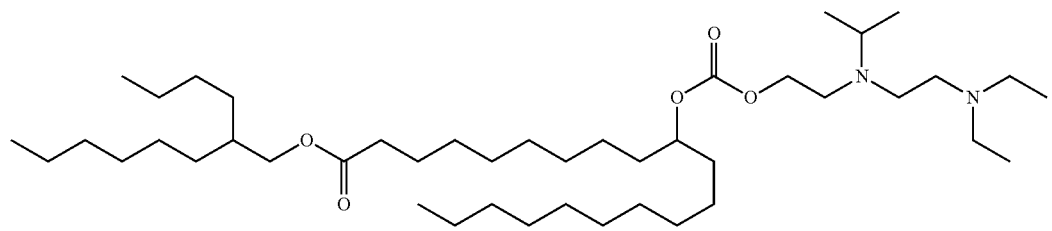 [SMILES: CCCCCCCCCCC(CCCCCCCCC(=O)OCC(CCCC)CCCCCC)OC(=O)OCCN(CCN(CC)CC)C(C)C]

2-Butyloctyl 12-decyl-3-ethyl-6-isopropyl-10-oxo-9,11-dioxa-3,6-diazahenicosan-21-oate as a colorless oily substance was obtained by the same method as that in Example 68, except that 2-((2-(diethylamino)ethyl)(isopropyl)amino)ethan-1-ol was used instead of 2-((2-(diethylamino)ethyl)(ethyl)amino)ethan-1-ol in Example 68.

¹H-NMR (CDCl₃) δ: 4.73-4.61 (1H, m), 4.10 (2H, t, J=6.6 Hz), 3.97 (2H, d, J=6.0 Hz), 2.99-2.83 (1H, m), 2.68 (2H, t, J=6.6 Hz), 2.62-2.41 (8H, m), 2.29 (2H, t, J=7.2 Hz), 1.69-1.47 (7H, m), 1.40-1.19 (42H, m), 1.10-0.96 (12H, m), 0.94-0.83 (9H, m).
MS m/z (M+H): 726.

Example 70

(1)

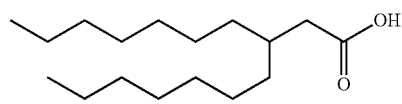 [SMILES: CCCCCCCC(CCCCCCC)CC(=O)O]

3-Heptyldecanoate as a colorless oily substance was obtained by the same method as that in (1) of Example 65, except that pentadecan-8-one was used instead of heptadecane-9-one in (1) of Example 65.

¹H-NMR (CDCl₃) δ: 2.28 (2H, d, J=6.6 Hz), 1.90-1.79 (1H, m), 1.35-1.19 (24H, m), 0.88 (6H, t, J=6.6 Hz).

(2)

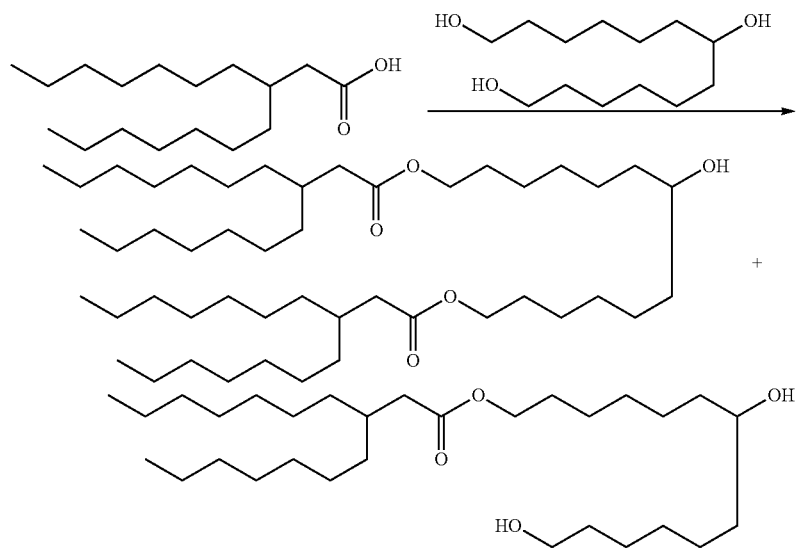

1-Ethyl-3-(3-dimethylaminopropyl)carbodiimide hydrochloride (1.07 g) was added to a mixture of 3-heptyldecanoate (974 mg), tridecane-1,7,13-triol (2.49 g), triethylamine (3.5 mL), 4-dimethylaminopyridine (51 mg), and dichloromethane (20 mL), and the mixture was stirred at room temperature for 4 days. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 7-hydroxytridecane-1,13-diylbis(3-heptyldecanoate) (1.03 g) as a colorless oily substance and 7,13-dihydroxytridecyl 3-heptyldecanoate (1.03 g) as a colorless oily substance.

7-Hydroxytridecane-1,13-diylbis(3-heptyldecanoate)
¹H-NMR (CDCl₃) δ: 4.05 (4H, t, J=6.6 Hz), 3.61-3.54 (1H, m), 2.22 (4H, d, J=7.2 Hz), 1.88-1.20 (70H, m), 0.88 (12H, t, J=6.6 Hz).

7,13-Dihydroxytridecyl 3-heptyldecanoate ¹H-NMR (CDCl₃) δ: 4.05 (2H, t, J=6.6 Hz), 3.68-3.55 (3H, m), 2.22 (2H, d, J=6.6 Hz), 1.88-1.77 (1H, m), 1.68-1.20 (44H, m), 0.88 (6H, t, J=6.6 Hz).

(3)

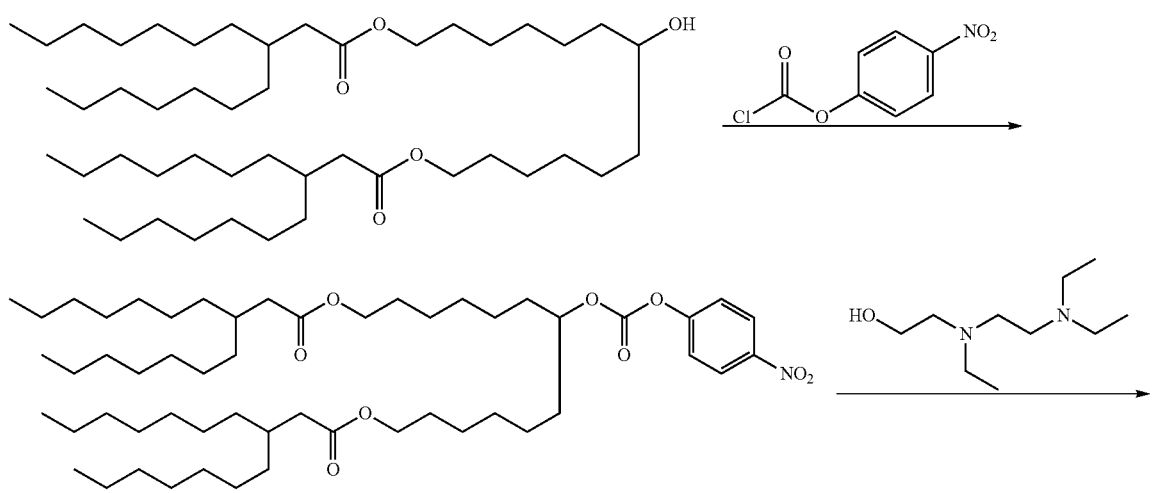

-continued

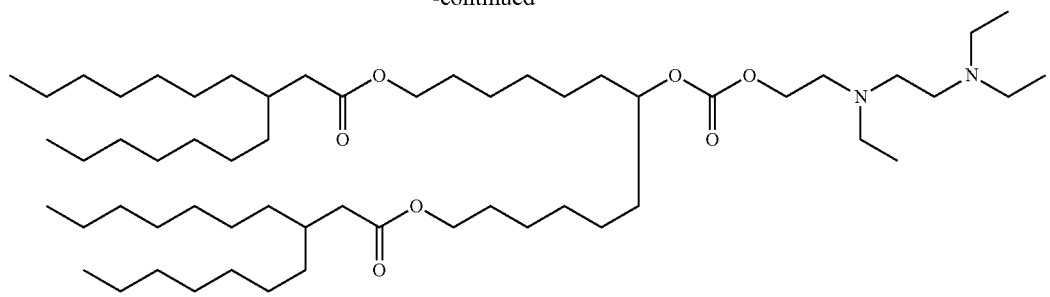

7-(((2-((2-(diethylamino)ethyl)(ethyl)amino)ethoxy)carbonyl)oxy)tridecane-1,13-diylbis(3-heptyldecanoate) as a colorless oily substance was obtained by the same method as that in (1) and (2) of Example 20, except that in (1) and (2) of Example 20, 7-hydroxytridecane-1,13-diylbis(3-heptyldecanoate) was used instead of (6Z,9Z,28Z,31Z)-heptatriaconta-6,9,28,31-tetraen-19-ol, and 2-((2-(diethylamino)ethyl)(ethyl)amino)ethan-1-ol was used instead of 2-((2-(dimethylamino)ethyl)(methyl)amino)ethan-1-ol.

$^1$H-NMR (CDCl$_3$) δ: 4.73-4.61 (1H, m), 4.17 (2H, t, J=6.6 Hz), 4.04 (4H, t, J=7.2 Hz), 2.76 (2H, t, J=6.0 Hz), 2.66-2.46 (10H, m), 2.22 (4H, d, J=7.2 Hz), 1.91-1.76 (2H, m), 1.67-1.15 (68H, m), 1.08-0.97 (9H, m), 0.88 (12H, t, J=6.6 Hz).

MS m/z (M+H): 952.

Example 71

(1)

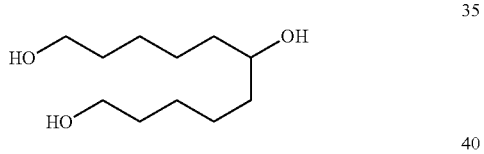

Undecane-1,6,11-triol as white solids was obtained by the same method as that in (1) of Example 36, except that 5-bromopentan-1-ol was used instead of 6-bromohexan-1-ol in (1) of Example 36.

$^1$H-NMR (CDCl$_3$) δ: 3.70-3.55 (5H, m), 1.64-1.24 (16H, m).

(2)

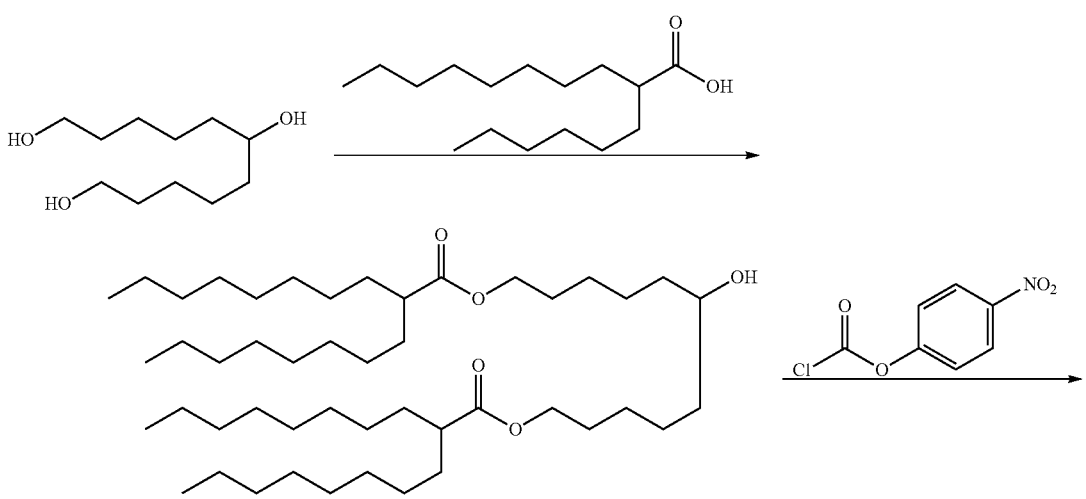

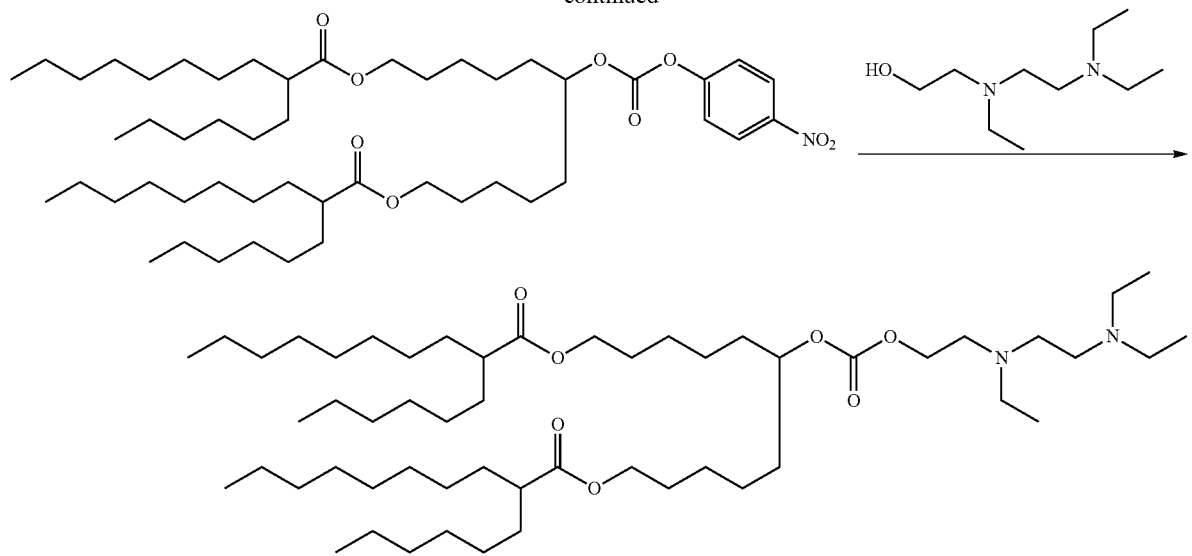
6-(((2-((2-(Diethylamino)ethyl)(ethyl)amino)ethoxy)carbonyl)oxy)undecane-1,11-diylbis(2-hexyldecanoate) as a colorless oily substance was obtained by the same method as that in (1) and (2) of Example 56, except that undecane-1,6,11-triol was used instead of tridecane-1,7,13-triol in (1) and (2) of Example 56.
$^1$H-NMR (CDCl$_3$) δ: 4.72-4.63 (1H, m), 4.17 (2H, t, J=6.6 Hz), 4.05 (4H, t, J=6.6 Hz), 2.76 (2H, t, J=6.6 Hz), 2.66-2.47 (10H, m), 2.37-2.23 (2H, m), 1.71-1.18 (64H, m), 1.10-0.98 (9H, m), 0.88 (12H, t, J=7.2 Hz).
MS m/z (M+H): 896.
Example 72
(1)
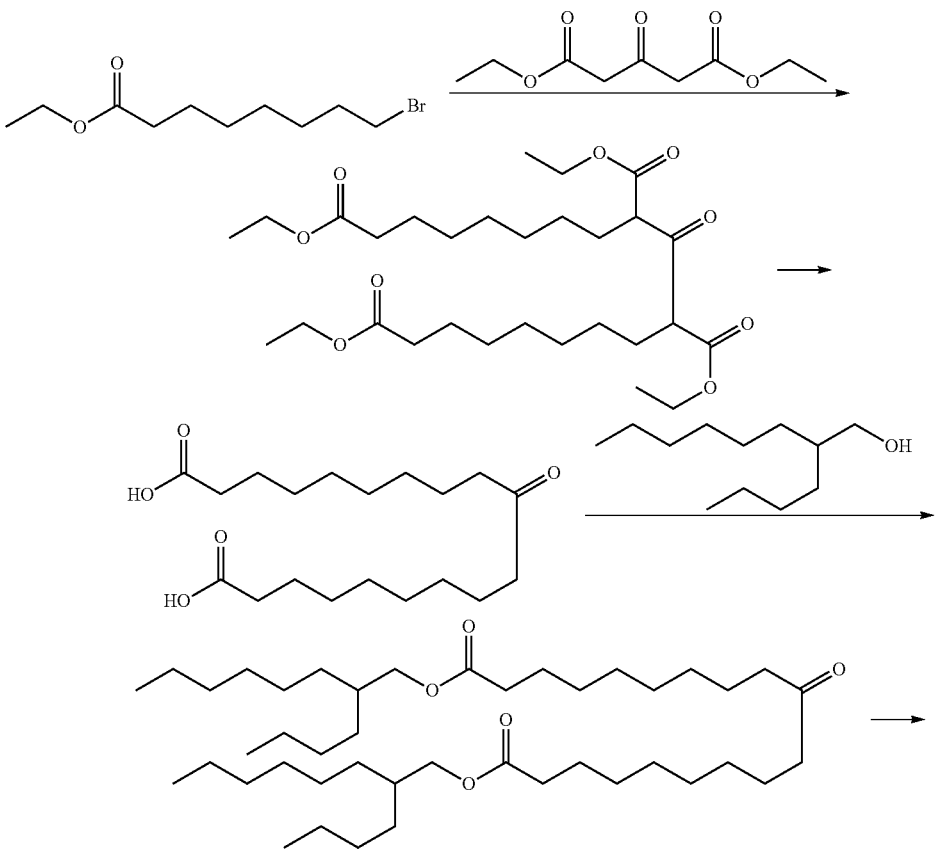

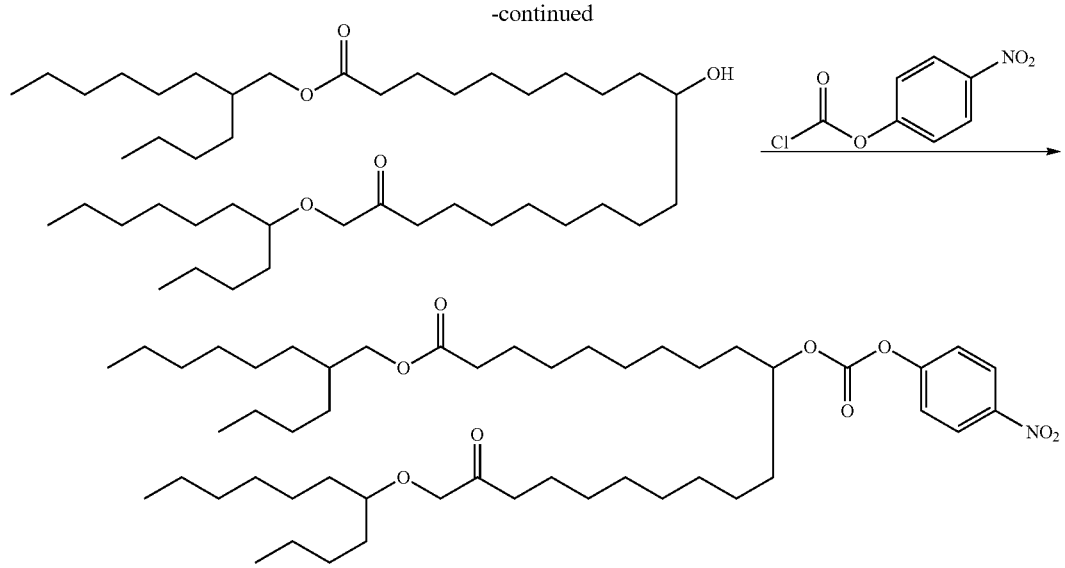

A mixture of diethyl 3-oxopentanedioate (4.0 g) and a 20% sodium ethoxide-ethanol solution (6.7 g) was stirred at 80° C. for 20 minutes, ethyl 8-bromooctanoate (5.0 g) was then added thereto, and the mixture was stirred for 4 hours. A 20% sodium ethoxide-ethanol solution (6.7 g) was added to the reaction mixture, the reaction mixture was stirred for 5 minutes, ethyl 8-bromooctanoate (5.0 g) was then added thereto, and the mixture was stirred for 3 hours. The reaction mixture was cooled to room temperature, hexane and a 20% aqueous ammonium chloride solution (10 mL) were then added thereto, the organic layer was separated, and the solvent was distilled away under reduced pressure, thereby obtaining tetraethyl 9-oxoheptadecane-1,8,10,17-tetracarboxylate (10.3 g) as a crude product.

A mixture of the obtained tetraethyl 9-oxoheptadecane-1,8,10,17-tetracarboxylate (2.5 g), acetic acid (4.0 mL), and a 30% aqueous hydrochloric acid solution (8.0 mL) was stirred at 115° C. for 6 hours. The reaction mixture was cooled to room temperature, the solvent was then distilled away under reduced pressure, and water and acetone were added to the residue. Solids were collected by filtration, washed with water and acetone, and then dried under reduced pressure, thereby obtaining 10-oxononane decanedioic acid (0.6 g) as white solids.

$^1$H-NMR (DMSO-$d_6$) δ: 2.38 (4H, t, J=7.2 Hz), 2.18 (4H, t, J=7.2 Hz), 1.54-1.38 (8H, m), 1.31-1.18 (16H, m).

1-Ethyl-3-(3-dimethylaminopropyl)carbodiimide hydrochloride (853 mg) was added to a mixture of 10-oxononane decanedioic acid (610 mg), 2-butyloctan-1-ol (663 mg), triethylamine (1.25 mL), 4-dimethylaminopyridine (217 mg), and dichloromethane (6 mL), and the mixture was stirred at room temperature for 2 days. A 10% aqueous potassium hydrogen sulfate solution (12 mL), hexane (6 mL), and ethyl acetate (6 mL) were added to the reaction mixture, the organic layer was separated and then dried over anhydrous sodium sulfate, and the solvent was distilled away under reduced pressure. The obtained residue was purified by silica gel column chromatography (ethyl acetate-hexane), thereby obtaining bis(2-butyloctyl)10-oxononane decanedioate (612 mg) as a colorless oily substance.

$^1$H-NMR (CDCl$_3$) δ: 3.97 (4H, d, J=6.0 Hz), 2.38 (4H, t, J=7.2 Hz), 2.30 (4H, t, J=7.2 Hz), 1.66-1.49 (10H, m), 1.36-1.23 (48H, m), 0.92-0.83 (12H, m).

Sodium borohydride (35 mg) was added to a mixture of bis(2-butyloctyl)10-oxononane decanedioate (612 mg) and methanol (6 mL) under ice cooling, and the mixture was stirred at the same temperature for 1 hour. A 10% aqueous potassium hydrogen sulfate solution (6 mL) and hexane (6 mL) were added to the reaction mixture under ice cooling, the organic layer was separated and dried over anhydrous sodium sulfate, and the solvent was distilled away under reduced pressure. The obtained residue was purified by silica gel column chromatography (ethyl acetate-hexane), thereby obtaining bis(2-butyloctyl)10-hydroxynonadecanedioate (369 mg) as a colorless oily substance.

$^1$H-NMR (CDCl$_3$) δ: 3.97 (4H, d, J=6.0 Hz), 3.62-3.52 (1H, m), 2.30 (4H, t, J=7.2 Hz), 1.66-1.53 (10H, m), 1.45-1.20 (52H, m), 0.92-0.83 (12H, m).

4-Nitrophenyl chloroformate (218 mg) was added to a mixture of bis(2-butyloctyl)10-hydroxynonadecanedioate (369 mg), triethylamine (0.30 mL), and tetrahydrofuran (2 mL), and the mixture was stirred at room temperature for 17 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining bis(2-butyloctyl)10-(((4-nitrophenoxy)carbonyl)oxy)nonadecanedioate (436 mg) as a colorless oily substance.

$^1$H-NMR (CDCl$_3$) δ: 8.28 (2H, dd, J=7.2 Hz, 1.8 Hz), 7.38 (2H, dd, J=7.2 Hz, 1.8 Hz), 4.86-4.74 (1H, m), 3.97 (4H, d, J=6.0 Hz), 2.30 (4H, t, J=7.2 Hz), 1.66-1.53 (10H, m), 1.45-1.20 (52H, m), 0.92-0.83 (12H, m).

(2)

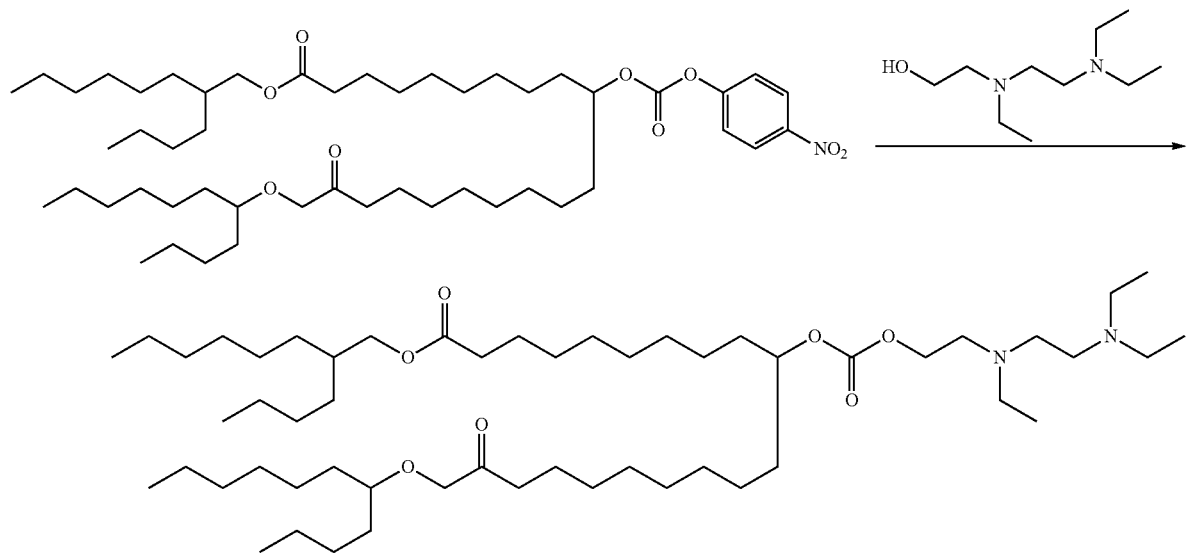

Bis(2-butyloctyl)10-(((2-((2-(diethylamino)ethyl)(ethyl)amino)ethoxy)carbonyl)oxy)nonadecanedioate as a colorless oily substance was obtained by the same method as that in (2) of Example 41, except that bis(2-butyloctyl)10-(((4-nitrophenoxy)carbonyl)oxy)nonadecanedioate was used instead of 7-(((4-nitrophenoxy)carbonyl)oxy)tridecane-1,13-diyldioleate in (2) of Example 41.

$^1$H-NMR (CDCl$_3$) δ: 4.71-4.62 (1H, m), 4.17 (2H, t, J=6.6 Hz), 3.96 (4H, d, J=6.0 Hz), 2.76 (2H, t, J=6.6 Hz), 2.64-2.48 (10H, m), 2.29 (4H, t, J=7.2 Hz), 1.66-1.50 (10H, m), 1.36-1.20 (52H, m), 1.03 (3H, t, J=7.2 Hz), 1.02 (6H, t, J=7.2 Hz), 0.93-0.84 (12H, m).

MS m/z (M+H): 896.

Example 73

(1)

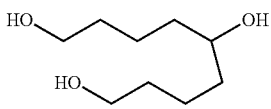

Nonane-1,5,9-triol as white solids was obtained by the same method as that in (1) of Example 36, except that 4-bromobutan-1-ol was used instead of 6-bromohexan-1-ol in (1) of Example 36.

$^1$H-NMR (CDCl$_3$) δ: 3.70-3.55 (5H, m), 1.64-1.24 (12H, m).

(2)

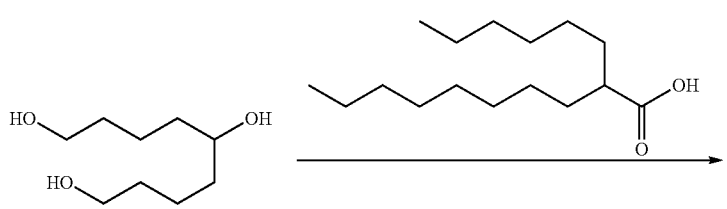

-continued

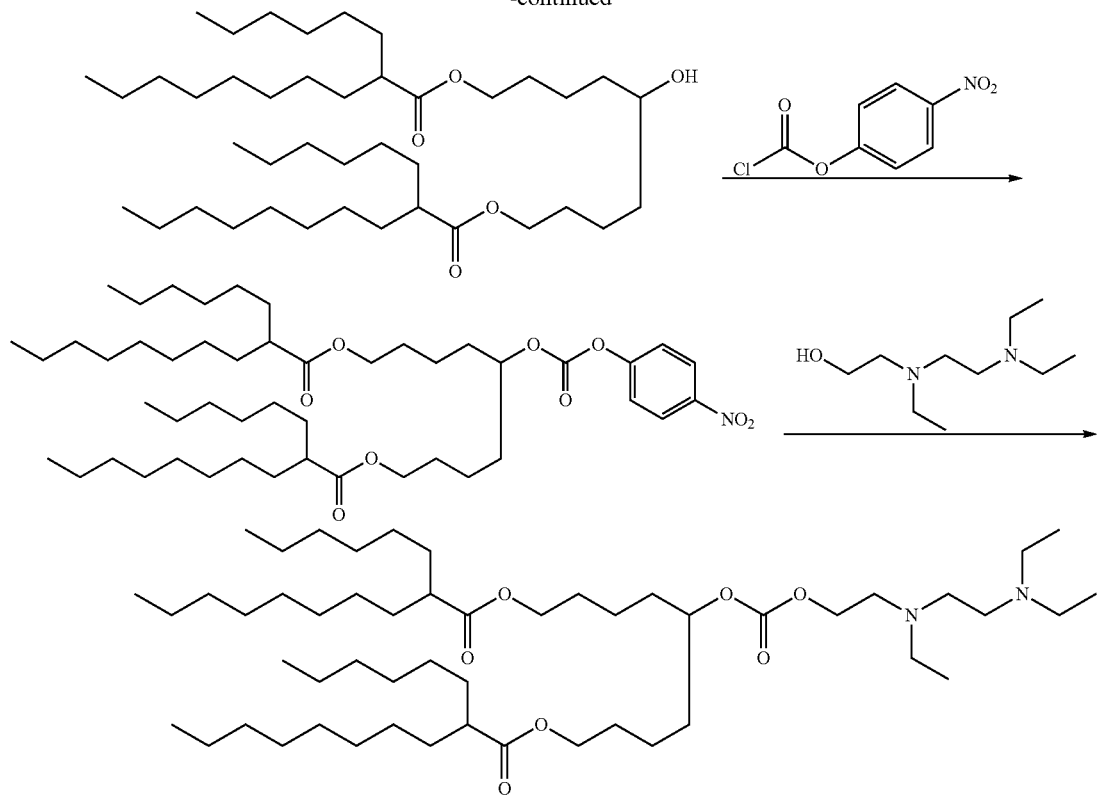

5-(((2-((2-(Diethylamino)ethyl)(ethyl)amino)ethoxy)carbonyl)oxy)nonane-1,9-diylbis(2-hexyldecanoate) as a colorless oily substance was obtained by the same method as that in (1) and (2) of Example 56, except that nonane-1,5,9-triol was used instead of tridecane-1,7,13-triol in (1) and (2) of Example 56.

$^1$H-NMR (CDCl$_3$) δ: 4.74-4.63 (1H, m), 4.17 (2H, t, J=5.7 Hz), 4.05 (4H, t, J=6.6 Hz), 2.76 (2H, t, J=6.6 Hz), 2.66-2.48 (10H, m), 2.36-2.24 (2H, m), 1.70-1.16 (60H, m), 1.09-0.98 (9H, m), 0.88 (12H, t, J=6.6 Hz).

MS m/z (M+H): 868.

Example 74

(1)

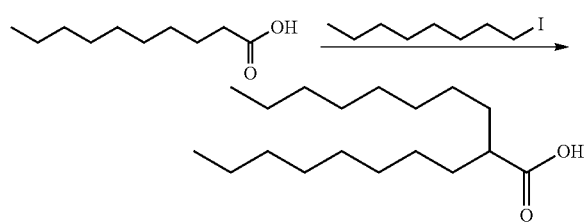

Decanoic acid (3.0 g) was added dropwise to a tetrahydrofuran (30 mL) suspension of 60% wt sodium hydride under ice cooling, and the mixture was stirred at the same temperature for 30 minutes. A 1.5 mol/L lithium diisopropylamide-tetrahydrofuran-heptane-ethyl benzene solution (13.9 mL) was added to the reaction mixture at the same temperature, and the reaction mixture was stirred at room temperature for 30 minutes. Then, 1-iodooctane (3.8 mL) was added dropwise thereto, and the reaction mixture was stirred at 45° C. for 6 hours.

The reaction mixture was poured into a mixture of a 1 mol/L aqueous hydrochloric acid solution and ethyl acetate under ice cooling, the organic layer was then separated, washed with a saturated aqueous sodium chloride solution, and dried over anhydrous magnesium sulfate, and then the solvent was distilled away under reduced pressure. The obtained residue was purified by silica gel column chromatography (ethyl acetate-hexane), thereby obtaining 2-octyl decanoate (2.62 g) as a yellow oily substance.

$^1$H-NMR (CDCl$_3$) δ: 2.43-2.30 (1H, m), 1.72-1.20 (28H, m), 0.88 (6H, t, J=6.6 Hz).

(2)

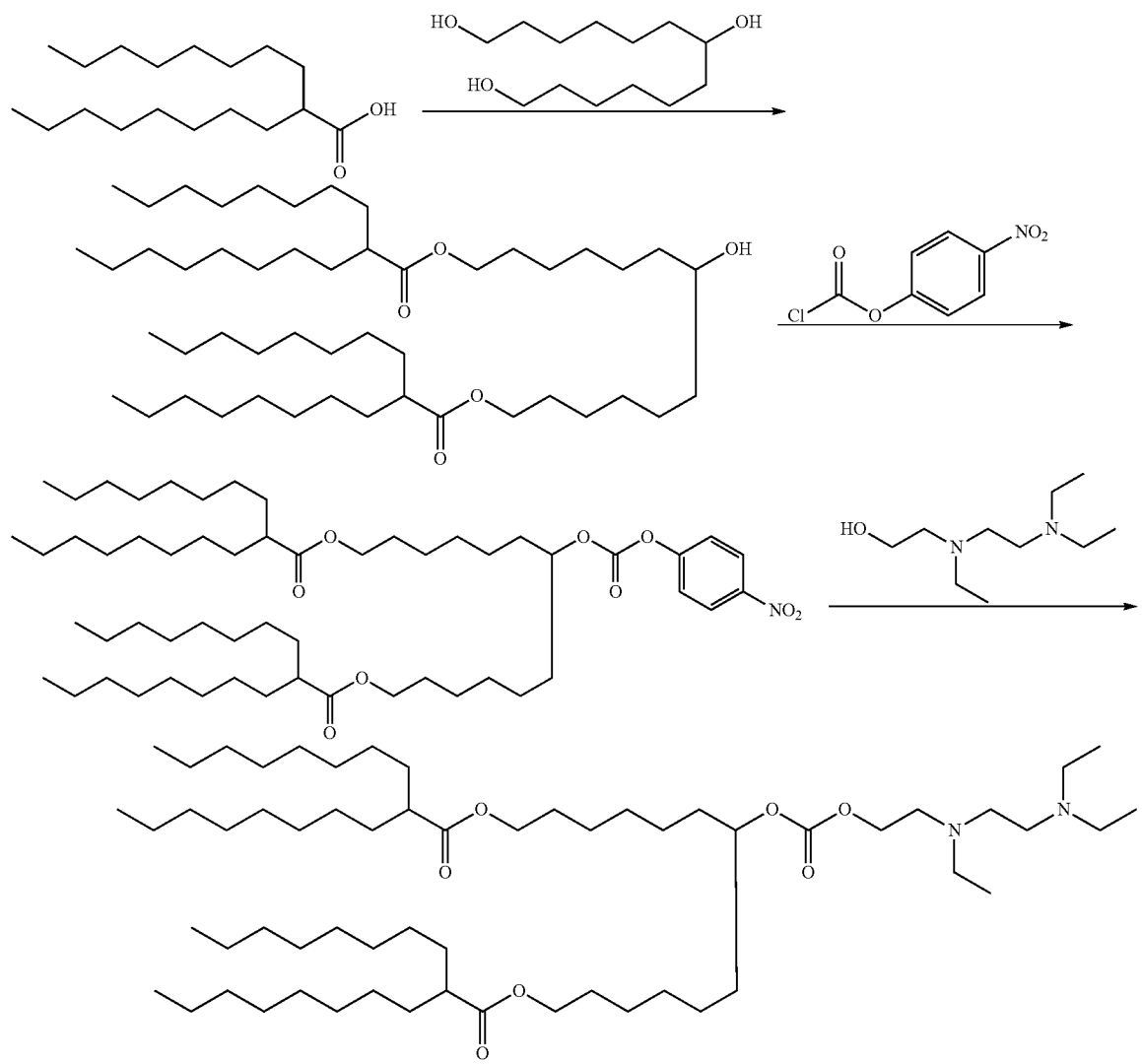
7-(((2-((2-(Diethylamino)ethyl)(ethyl)amino)ethoxy)carbonyl)oxy)tridecane-1,13-diylbis(2-octyldecanoate) as a colorless oily substance was obtained by the same method as that in (1) and (2) of Example 41, except that 2-octyl decanoate was used instead of oleic acid in (1) and (2) of Example 41.
$^1$H-NMR (CDCl$_3$) δ: 4.73-4.60 (1H, m), 4.17 (2H, t, J=6.6 Hz), 4.05 (4H, t, J=6.6 Hz), 2.76 (2H, t, J=6.0 Hz), 2.66-2.47 (10H, m), 2.37-2.24 (2H, m), 1.70-1.16 (76H, m), 1.11-0.98 (9H, m), 0.88 (12H, t, J=6.6 Hz).
MS m/z (M+H): 980.
Example 75
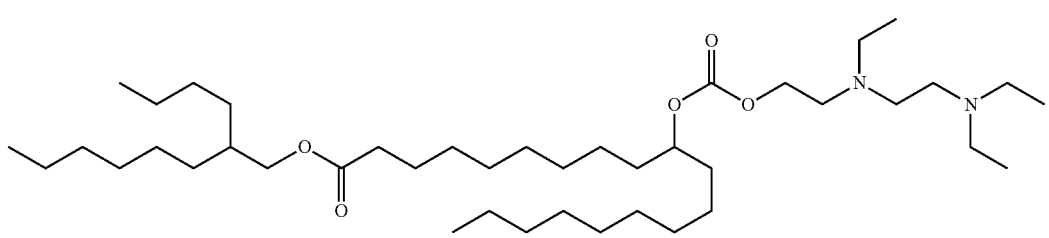 [SMILES: CCCCCCCCCC(CCCCCCCCC(=O)OCC(CCCC)CCCCCC)OC(=O)OCCN(CC)CCN(CC)CC]

2-Butyloctyl 3,6-diethyl-12-nonyl-10-oxo-9,11-dioxa-3,6-diazahenicosan-21-oate as a colorless oily substance was obtained by the same method as that in Example 50, except that a 1.0 mol/L nonyl magnesium bromide-diethyl ether solution was used instead of a 1.0 mol/L dodecyl magnesium bromide-diethyl ether solution in Example 50.

$^1$H-NMR (CDCl$_3$) δ: 4.73-4.60 (1H, m), 4.18 (2H, t, J=6.6 Hz), 3.97 (2H, d, J=5.7 Hz), 2.76 (2H, t, J=6.6 Hz), 2.66-2.47 (10H, m), 2.30 (2H, t, J=7.8 Hz), 1.69-1.47 (7H, m), 1.41-1.19 (40H, m), 1.09-0.97 (9H, m), 0.94-0.83 (9H, m).

MS m/z (M+H): 698.

Example 76

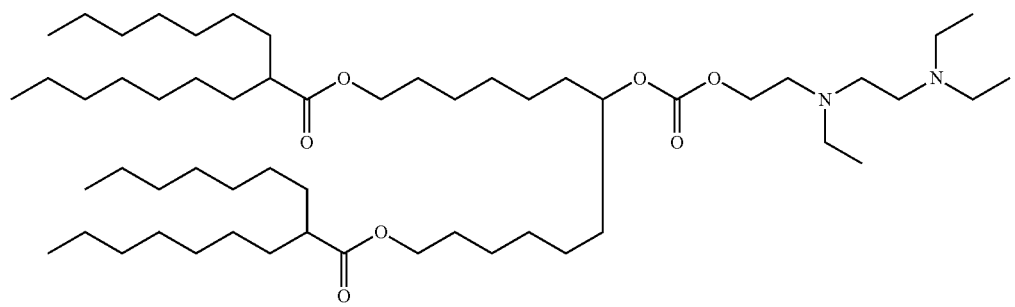 [SMILES: CCCCCCCC(CCCCCCC)C(=O)OCCCCCCC(CCCCCCOC(=O)C(CCCCCCC)CCCCCCC)OC(=O)OCCN(CC)CCN(CC)CC]

7-(((2-((2-(Diethylamino)ethyl)(ethyl)amino)ethoxy)carbonyl)oxy)tridecane-1,13-diylbis(2-heptylnonanoate) as a colorless oily substance was obtained by the same method as that in (1) and (2) of Example 74, except that in (1) and (2) of Example 74, nonanoic acid was used instead of decanoic acid, and 1-iodoheptane was used instead of 1-iodooctane.

$^1$H-NMR (CDCl$_3$) δ: 4.73-4.61 (1H, m), 4.18 (2H, t, J=6.6 Hz), 4.05 (4H, t, J=6.6 Hz), 2.76 (2H, t, J=6.6 Hz), 2.66-2.48 (10H, m), 2.37-2.23 (2H, m), 1.68-1.16 (68H, m), 1.08-0.97 (9H, m), 0.87 (12H, t, J=6.6 Hz).

MS m/z (M+H): 924.

Example 77

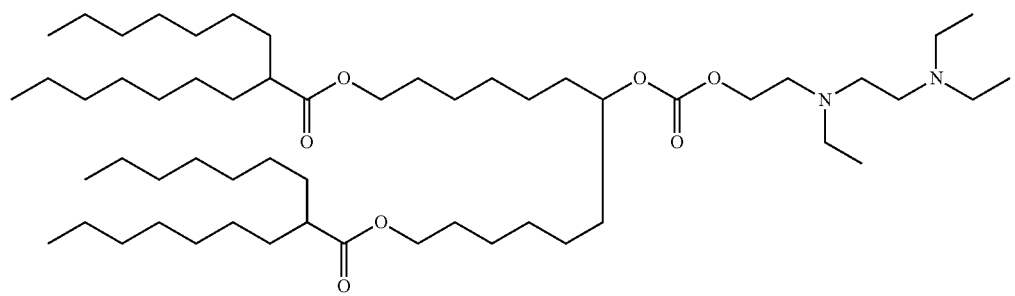 [SMILES: CCCCCCCC(CCCCCCC)C(=O)OCCCCCCC(CCCCCCOC(=O)C(CCCCCCC)CCCCCCC)OC(=O)OCCN(CC)CCN(CC)CC]

7-(((2-((2-(Diethylamino)ethyl)(ethyl)amino)ethoxy)carbonyl)oxy)tridecane-1,13-diylbis(2-hexyloctanoate) as a colorless oily substance was obtained by the same method as that in (1) and (2) of Example 74, except that in (1) and (2) of Example 74, octanoic acid was used instead of decanoic acid, and 1-iodohexane was used instead of 1-iodooctane.

$^1$H-NMR (CDCl$_3$) δ: 4.73-4.60 (1H, m), 4.17 (2H, t, J=6.6 Hz), 4.05 (4H, t, J=6.6 Hz), 2.76 (2H, t, J=6.6 Hz), 2.67-2.45 (10H, m), 2.37-2.24 (2H, m), 1.72-1.15 (60H, m), 1.12-0.96 (9H, m), 0.87 (12H, t, J=6.6 Hz).

MS m/z (M+H): 868.

Example 78

(1)

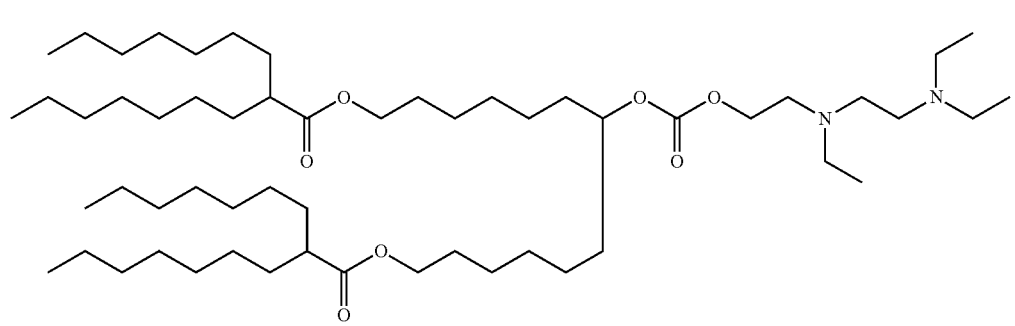

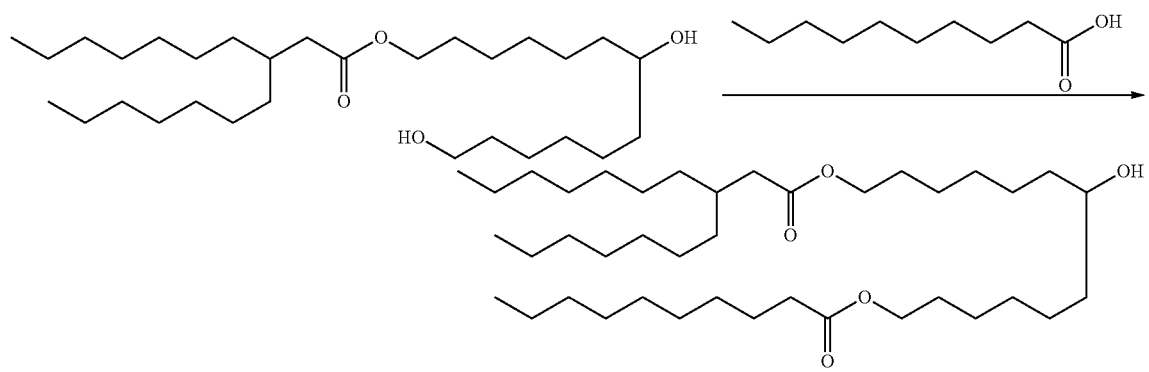

1-Ethyl-3-(3-dimethylaminopropyl)carbodiimide hydrochloride (126 mg) was added to a mixture of 7,13-dihy-  (2)

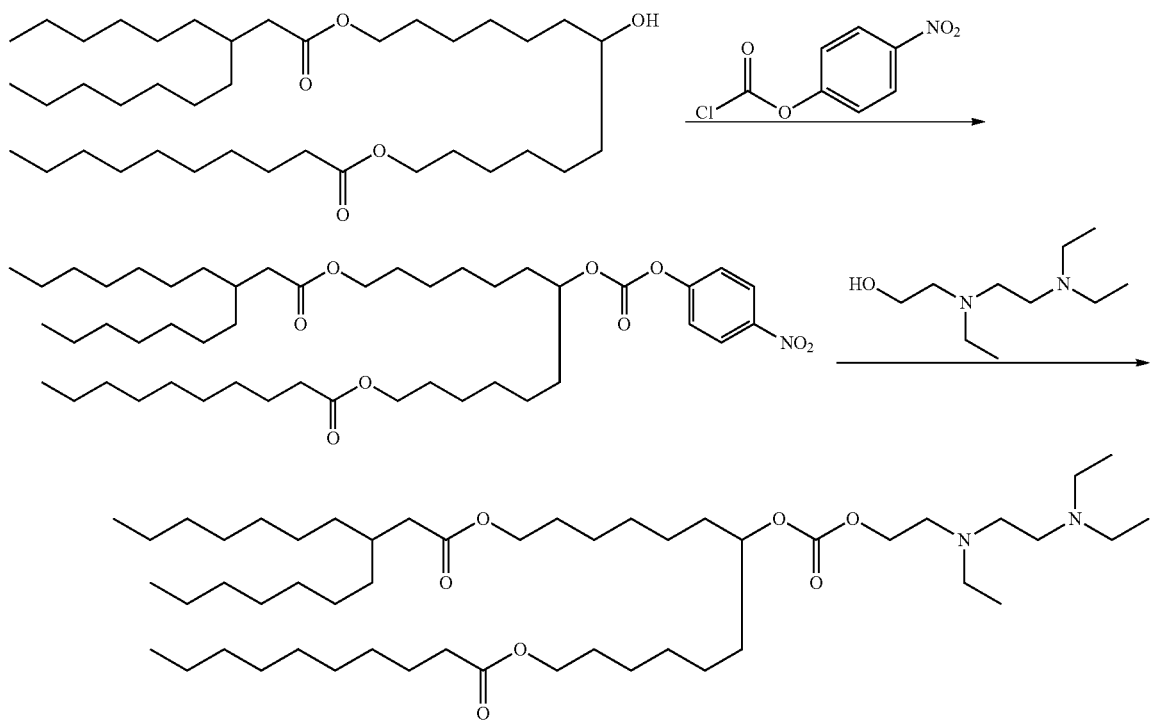

droxytridecyl 3-heptyldecanoate (500 mg) synthesized in (1) and (2) of Example 70, decanoic acid (195 mg), triethylamine (0.43 mL), 4-dimethylaminopyridine (38 mg), and dichloromethane (10 mL), and the mixture was stirred at room temperature for 18 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 13-(decanoyloxy)-7-hydroxytridecyl 3-heptyldecanoate (469 mg) as a colorless oily substance.

$^1$H-NMR (CDCl$_3$) δ: 4.06 (4H, t, J=6.6 Hz), 3.63-3.53 (1H, m), 2.29 (2H, t, J=7.2 Hz), 2.22 (2H, d, J=7.2 Hz), 1.88-1.78 (1H, m), 1.68-1.20 (60H, m), 0.88 (9H, t, J=6.6 Hz).

12-(6-(Decanoyloxy)hexyl)-3,6-diethyl-10-oxo-9,11-dioxa-3,6-diazooctadecan-18-yl 3-heptyldecanoate as a colorless oily substance was obtained by the same method as that in (1) and (2) of Example 20, except that in (1) and (2) of Example 20, 13-(decanoyloxy)-7-hydroxytridecyl-3-heptyldecanoate was used instead of (6Z,9Z,28Z,31Z)-heptatriaconta-6,9,28,31-tetraen-19-ol, and 2-((2-(diethylamino)ethyl)(ethyl)amino)ethan-1-ol was used instead of 2-((2-(dimethylamino)ethyl)(methyl)amino)ethan-1-ol.

$^1$H-NMR (CDCl$_3$) δ: 4.72-4.61 (1H, m), 4.17 (2H, t, J=6.0 Hz), 4.04 (4H, t, J=6.6 Hz), 2.76 (2H, t, J=6.6 Hz), 2.67-2.45 (10H, m), 2.29 (2H, t, J=8.1 Hz), 2.22 (2H, d, J=7.2 Hz), 1.87-1.78 (1H, m), 1.70-1.18 (58H, m), 1.11-0.97 (9H, m), 0.93-0.82 (9H, m).

MS m/z (M+H): 854.

Example 79

(1)

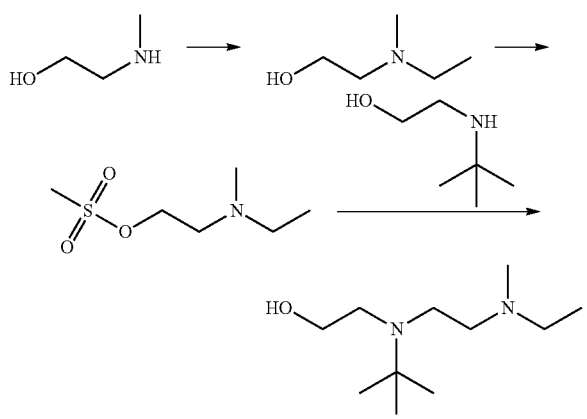

Ethyl iodide (3.4 mL) was added dropwise to an acetonitrile solution (30 mL) of 2-(methylamino)ethan-1-ol (3.0 g) under ice cooling, and the mixture was stirred at the same temperature for 1 hour and 45 minutes and then stirred at 60° C. for 3 hours and 10 minutes. Potassium carbonate and water were added to the reaction mixture, and extraction was performed using chloroform. The organic layer was washed with saturated saline and dried over anhydrous sodium sulfate. The solvent was distilled away under reduced pressure, thereby obtaining 2-(ethyl(methyl)amino)ethan-1-ol (3.4 g) as a colorless oily substance.

MS m/z (M+H): 104.

A tetrahydrofuran solution (20 mL) of methanesulfonic anhydride (7.6 g) was added dropwise to a mixture of 2-(ethyl(methyl)amino)ethan-1-ol (3.0 g), 4-dimethylaminopyridine (0.36 g), N,N-diisopropylethylamine (9.9 mL), and tetrahydrofuran (60 mL) under ice cooling. The mixture was stirred at 0° C. for 15 minutes and then stirred at room temperature for 3 hours and 45 minutes. 2-(tert-Butylamino)ethan-1-ol (6.0 g), sodium iodide (0.45 g), and water (1 mL) were added to the reaction mixture, and the reaction mixture was stirred at 75° C. for 30 hours. The reaction mixture was cooled to room temperature, the solvent was distilled away under reduced pressure, water and a 2 mol/L aqueous sodium hydroxide solution were then added thereto, and extraction was performed using ethyl acetate. The organic layer was washed with saturated saline and dried over anhydrous sodium sulfate. The solvent was distilled away under reduced pressure, and the obtained residue was purified by silica gel column chromatography (ethyl acetate-hexane, NH silica gel), thereby obtaining 2-(tert-butyl(2-(ethyl(methyl)amino)ethyl)amino)ethan-1-ol (0.15 g) as a yellow oily substance.

MS m/z (M+H): 203.

(2)

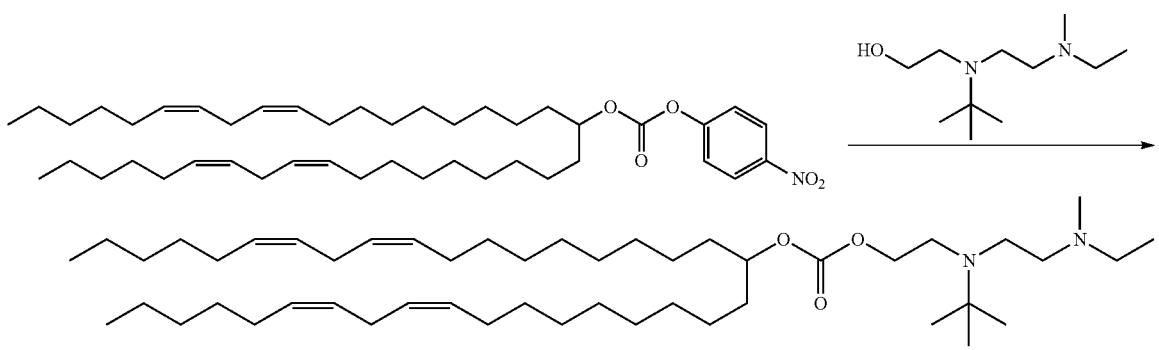

2-(tert-Butyl(2-(ethyl(methyl)amino)ethyl)amino)ethyl ((6Z,9Z,28Z,31Z)-heptatriaconta-6,9,28,31-tetraen-19-yl) carbonate as a colorless oily substance was obtained by the same method as that in (2) of Example 20, except that 2-(tert-butyl(2-(ethyl(methyl)amino)ethyl)amino)ethan-1-ol was used instead of 2-((2-(dimethylamino)ethyl)(methyl)amino)ethan-1-ol in (2) of Example 20.

¹H-NMR (CDCl₃) δ: 5.44-5.25 (8H, m), 4.73-4.62 (1H, m), 4.06 (2H, t, J=7.5 Hz), 2.84-2.73 (6H, m), 2.72-2.59 (2H, m), 2.50-2.34 (4H, m), 2.25 (3H, s), 2.11-1.97 (8H, m), 1.65-1.48 (4H, m), 1.43-1.19 (36H, m), 1.12-1.01 (12H, m), 0.89 (6H, t, J=6.6 Hz).

MS m/z (M+H): 758.

Example 80

(1)

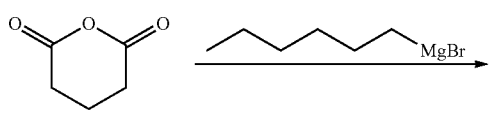

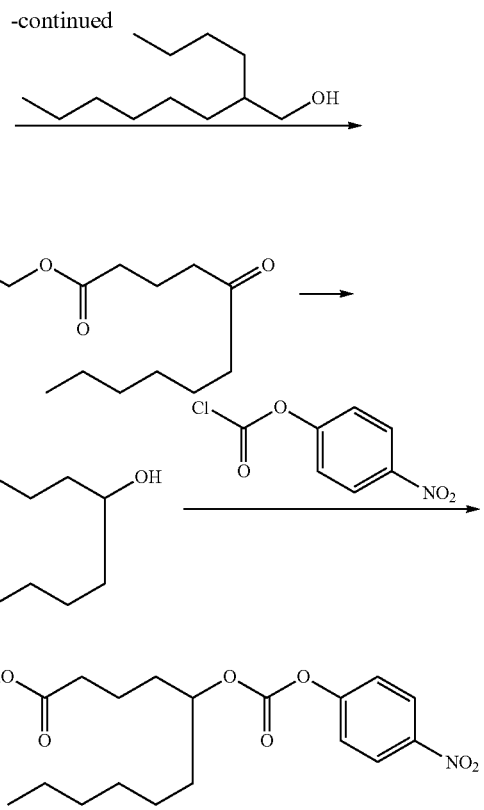

A 1 mol/L hexyl magnesium bromide-tetrahydrofuran solution (200 mL) was added dropwise to a tetrahydrofuran (273 mL) solution of glutaric anhydride (27.3 g) under ice cooling, and the mixture was stirred at the same temperature for 1 hour. A 2 mol/L aqueous hydrochloric acid solution (240 mL) was added to the reaction mixture under ice cooling, ethyl acetate (270 mL) was then added thereto, the organic layer was separated, washed with water and a saturated aqueous sodium chloride solution, and dried over anhydrous magnesium sulfate, and then the solvent was distilled away under reduced pressure. The obtained residue was purified by silica gel column chromatography (ethyl acetate-hexane), hexane (10 mL) was then added thereto, and solids were collected by filtration, washed with hexane, and then dried under reduced pressure, thereby obtaining 5-oxoundecanoic acid (16.0 g) as white solids.

$^1$H-NMR (CDCl$_3$) δ: 2.50 (2H, t, J=7.2 Hz), 2.40 (4H, t, J=7.2 Hz), 2.02-1.80 (2H, m), 1.63-1.48 (2H, m), 1.37-1.20 (6H, m), 0.88 (3H, t, J=6.6 Hz).

1-Ethyl-3-(3-dimethylaminopropyl)carbodiimide hydrochloride (5.8 g) was added to a mixture of 5-oxoundecanoic acid (4.0 g), 2-butyloctan-1-ol (3.7 g), triethylamine (8.4 mL), 4-dimethylaminopyridine (1.22 g), and dichloromethane (40 mL), and the mixture was stirred at 40° C. for 3 hours. Water and ethyl acetate were added to the reaction mixture, the organic layer was separated, washed with water, and then dried over anhydrous magnesium sulfate, and the solvent was distilled away under reduced pressure. The obtained residue was purified by silica gel column chromatography (ethyl acetate-hexane), thereby obtaining 2-butyloctyl 5-oxoundecanoate (7.3 g) as a colorless oily substance.

$^1$H-NMR (CDCl$_3$) δ: 3.97 (2H, d, J=5.1 Hz), 2.47 (2H, t, J=7.2 Hz), 2.39 (2H, t, J=7.2 Hz), 2.33 (2H, t, J=7.2 Hz), 1.95-1.83 (2H, m), 1.66-1.49 (3H, m), 1.36-1.20 (22H, m), 0.92-0.82 (9H, m).

Sodium borohydride (1.1 g) was added to a mixture of 2-butyloctyl 5-oxoundecanoate (7.3 g), tetrahydrofuran (35 mL), and methanol (35 mL) under ice cooling, and the mixture was stirred at the same temperature for 30 minutes. A 2.0 mol/L aqueous hydrochloric acid solution (35 mL) and hexane (35 mL) were added to the reaction mixture under ice cooling, the organic layer was separated, then washed with a saturated aqueous sodium chloride solution, and dried over anhydrous sodium sulfate, and then the solvent was distilled away under reduced pressure. The obtained residue was purified by silica gel column chromatography (ethyl acetate-hexane), thereby obtaining 2-butyloctyl 5-hydroxyundecanoate (6.3 g) as a colorless oily substance.

$^1$H-NMR (CDCl$_3$) δ: 3.97 (2H, d, J=5.7 Hz), 3.65-3.53 (1H, m), 2.35 (2H, t, J=7.2 Hz), 1.87-1.20 (32H, m), 0.92-0.84 (9H, m).

4-Nitrophenyl chloroformate (1.71 g) was added to a mixture of 2-butyloctyl 5-hydroxyundecanoate (1.62 g), triethylamine (2.38 mL), and tetrahydrofuran (16 mL), and the mixture was stirred at room temperature for 4 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining 2-butyloctyl 5-(((4-nitrophenoxy)carbonyl)oxy)undecanoate (1.99 g) as a colorless oily substance.

¹H-NMR (CDCl₃) δ: 8.28 (2H, d, J=9.3 Hz), 7.39 (2H, d, J=9.3 Hz), 4.88-4.77 (1H, m), 3.99 (2H, d, J=6.0 Hz), 2.41-2.31 (2H, m), 1.80-1.48 (7H, m), 1.44-1.20 (24H, m), 0.92-0.83 (9H, m).

(2)

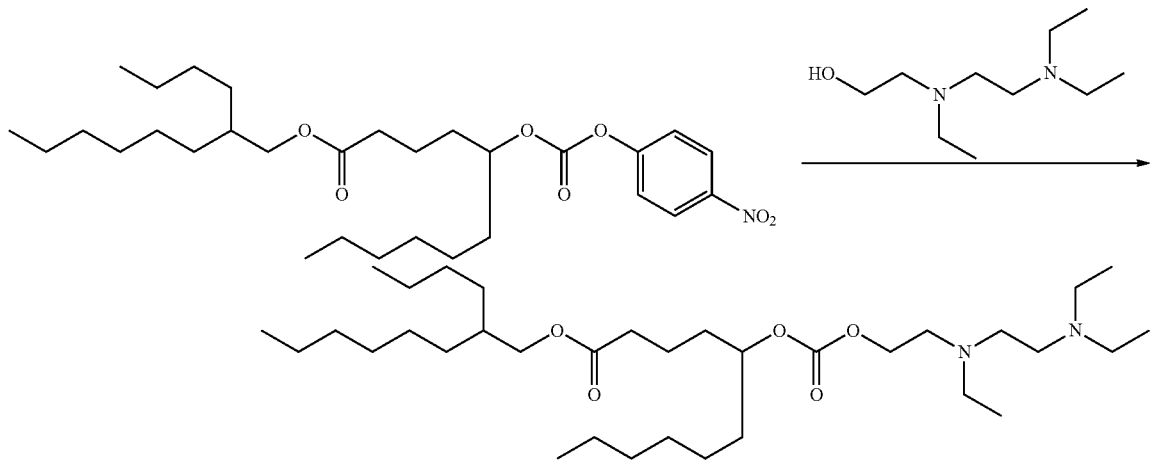

4-Dimethylaminopyridine (342 mg) was added to a mixture of 2-butyloctyl 5-(((4-nitrophenoxy)carbonyl)oxy)undecanoate (500 mg), 2-((2-(diethylamino)ethyl)(ethyl)amino)ethan-1-ol (527 mg), triethylamine (0.787 mL), and tetrahydrofuran (2.5 mL), and the mixture was stirred at 60° C. for 10 hours. The reaction mixture was cooled to room temperature, water and ethyl acetate were added thereto, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane,

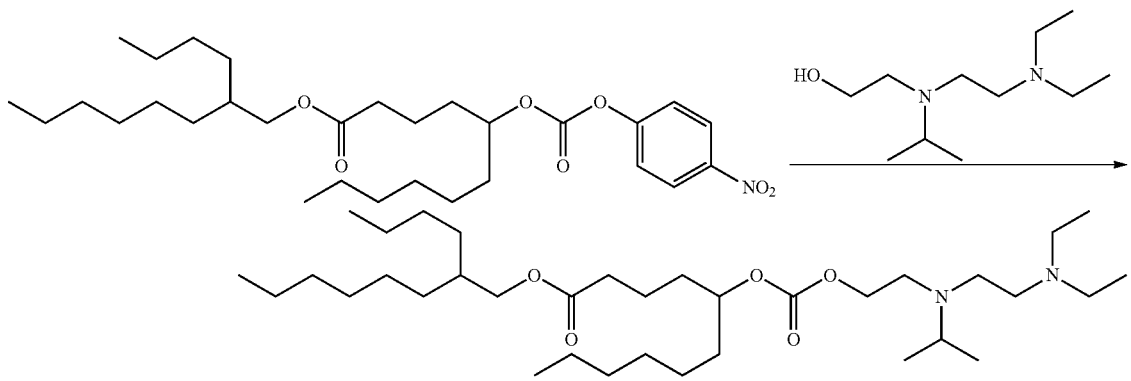

NH silica gel), thereby obtaining 2-butyloctyl 3,6-diethyl-12-hexyl-10-oxo-9,11-dioxa-3,6-diazahexadecan-16-oate (356 mg) as a colorless oily substance.

¹H-NMR (CDCl₃) δ: 4.73-4.64 (1H, m), 4.22-4.12 (2H, m), 3.97 (2H, d, J=5.1 Hz), 2.76 (2H, t, J=6.6 Hz), 2.64-2.49 (10H, m), 2.32 (2H, t, J=6.6 Hz), 1.73-1.50 (7H, m), 1.36-1.20 (24H, m), 1.06-0.99 (9H, m), 0.92-0.84 (9H, m).

MS m/z (M+H): 586.

Example 81

2-Butyloctyl 3-ethyl-12-hexyl-6-isopropyl-10-oxo-9,11-dioxa-3,6-diazahexadecan-16-oate as a colorless oily substance was obtained by the same method as that in (2) of Example 80, except that 2-((2-(diethylamino)ethyl)(isopropyl)amino)ethan-1-ol was used instead of 2-((2-(diethylamino)ethyl)(ethyl)amino)ethan-1-ol in (2) of Example 80.

¹H-NMR (CDCl₃) δ: 4.73-4.64 (1H, m), 4.15-4.04 (2H, m), 3.97 (2H, d, J=5.4 Hz), 2.97-2.83 (1H, m), 2.68 (2H, t, 6.6 Hz), 2.58-2.43 (8H, m), 2.32 (2H, t, J=6.6 Hz), 1.73-1.50 (7H, m), 1.36-1.20 (24H, m), 1.06-0.96 (12H, m), 0.92-0.84 (9H, m).
MS m/z (M+H): 600.

Example 82

(1)

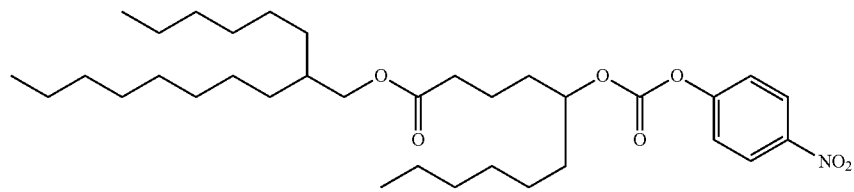 [SMILES: CCCCCCCCC(CCCCCC)COC(=O)CCCC(CCCCCC)OC(=O)Oc1ccc([N+](=O)[O-])cc1]

2-Hexyldecyl 5-(((4-nitrophenoxy)carbonyl)oxy)undecanoate as a colorless oily substance was obtained by the same method as that in (1) of Example 80, except that 2-hexyldecan-1-ol was used instead of 2-butyloctan-1-ol in (1) of Example 80.
$^1$H-NMR (CDCl$_3$) δ: 8.27 (2H, dd, J=6.6 Hz, 1.8 Hz), 7.38 (2H, dd, J=6.6 Hz, 1.8 Hz), 4.88-4.78 (1H, m), 3.98 (2H, d, J=6.0 Hz), 2.41-2.30 (2H, m), 1.79-1.53 (7H, m), 1.42-1.20 (32H, m), 0.92-0.83 (9H, m).

(2)

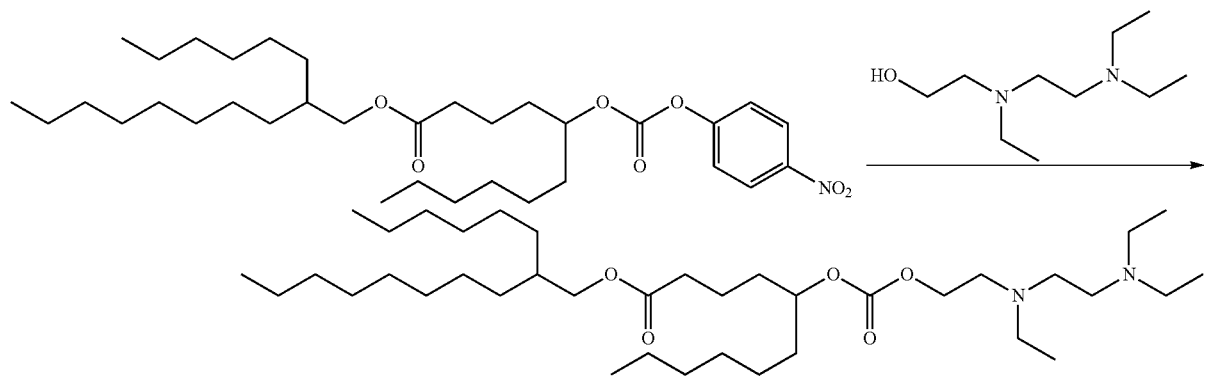

2-Hexyldecyl 3,6-diethyl-12-hexyl-10-oxo-9,11-dioxa-3,6-diazahexadecan-16-oate as a colorless oily substance was obtained by the same method as that in (2) of Example 80, except that 2-hexyldecyl 5-(((4-nitrophenoxy)carbonyl)oxy)undecanoate was used instead of 2-butyloctyl 5-(((4-nitrophenoxy)carbonyl)oxy)undecanoate in (2) of Example 80.
$^1$H-NMR (CDCl$_3$) δ: 4.73-4.64 (1H, in), 4.23-4.12 (2H, in), 3.97 (2H, d, J=5.7 Hz), 2.76 (2H, t, J=6.6 Hz), 2.64-2.48 (10H, in), 2.32 (2H, t, J=6.6 Hz), 1.75-1.50 (7H, in), 1.36-1.20 (32H, in), 1.06-0.99 (9H, in), 0.92-0.84 (9H, in).
MS m/z (M+H): 642.

Example 83

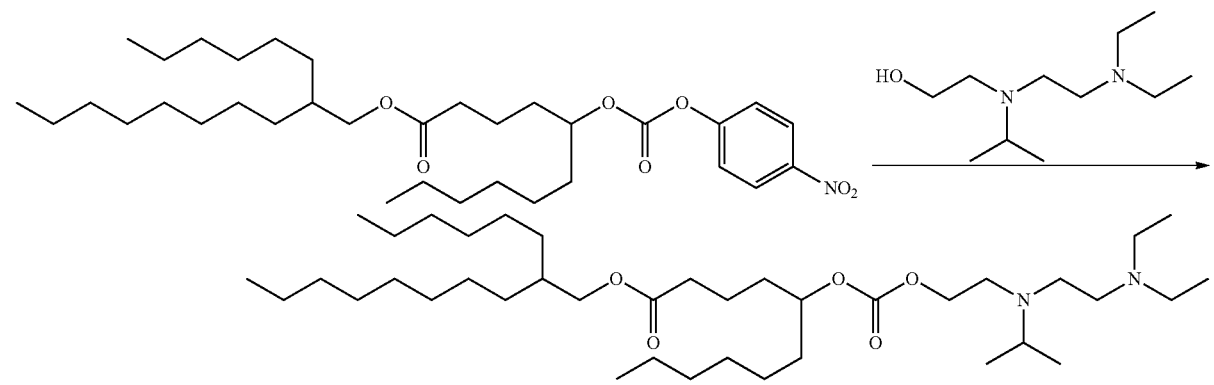

2-Hexyldecyl 3-ethyl-12-hexyl-6-isopropyl-10-oxo-9,11-dioxa-3,6-diazahexadecan-16-oate as a colorless oily substance was obtained by the same method as that in (2) of Example 82, except that 2-((2-(diethylamino)ethyl)(isopropyl)amino)ethan-1-ol was used instead of 2-((2-(diethylamino)ethyl)(ethyl)amino)ethan-1-ol in (2) of Example 82.

$^1$H-NMR (CDCl$_3$) δ: 4.73-4.64 (1H, in), 4.17-4.03 (2H, in), 3.97 (2H, d, J=6.0 Hz), 2.97-2.84 (1H, in), 2.68 (2H, t, J=6.6 Hz), 2.57-2.42 (8H, in), 2.32 (2H, t, J=6.6 Hz), 1.73-1.50 (7H, m), 1.38-1.19 (32H, m), 1.06-0.96 (12H, m), 0.92-0.84 (9H, m).

MS m/z (M+H): 656.

Example 84

(1)

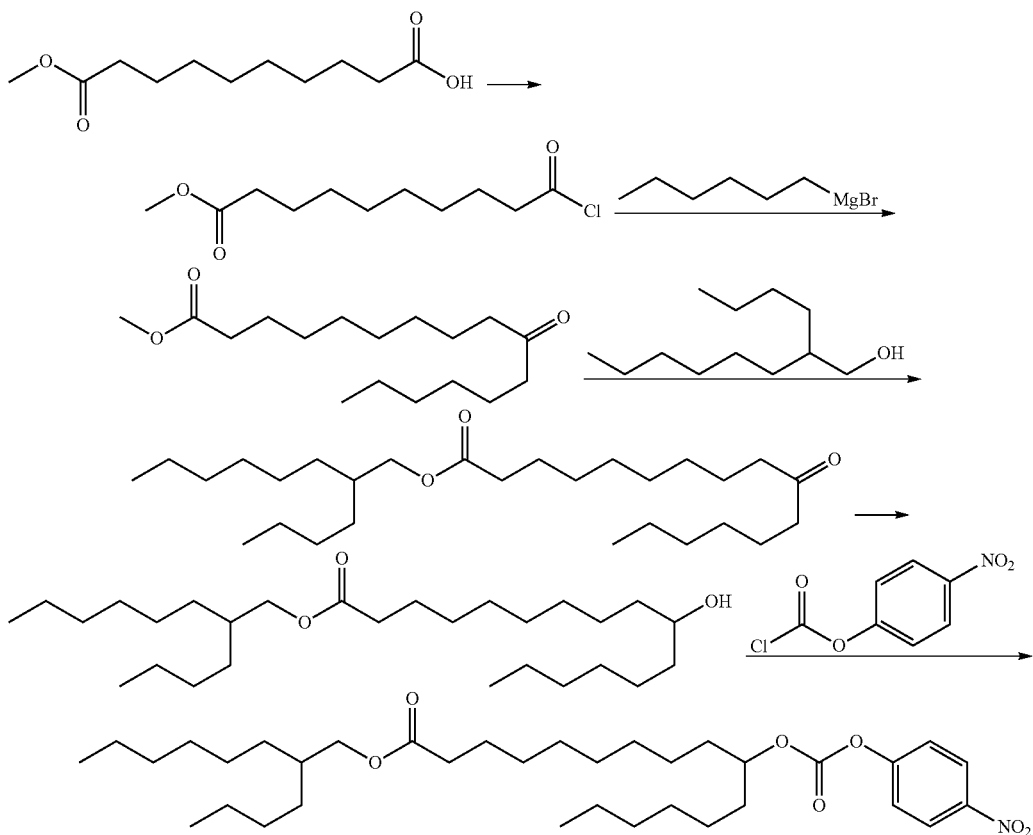

A mixture of 10-methoxy-10-oxodecanoic acid (47.6 g), thionyl chloride (47.6 mL), and N,N-dimethylformamide (0.1 mL) was stirred and heated under reflux for 1 hour. The solvent was distilled away under reduced pressure, thereby obtaining methyl 10-chloro-10-oxodecanoate (59.7 g) as a brown oily substance.

$^1$H-NMR (CDCl$_3$) δ: 3.67 (3H, s), 2.88 (2H, t, J=7.2 Hz), 2.30 (2H, t, J=7.2 Hz), 1.75-1.57 (4H, m), 1.38-1.25 (8H, m).

A 1.0 mol/L hexyl magnesium bromide-diethyl ether solution (440 mL) was added dropwise to a tetrahydrofuran (500 mL) suspension of zinc (II) chloride (30.0 g) at −78° C., and the mixture was heated to 0° and then stirred at the same temperature for 30 minutes. Tetrakis(triphenylphosphine)palladium(0) (6.4 g) was added to the reaction mixture under ice cooling, methyl 10-chloro-10-oxodecanoate (59.7 g) was then added dropwise thereto at the same temperature, and the reaction mixture was stirred at the same temperature for 1 hour. A 1.0 mol/L aqueous hydrochloric acid solution (200 mL) and ethyl acetate (600 mL) were added to the reaction mixture, the organic layer was separated, washed with a saturated aqueous sodium chloride solution (560 mL), and then dried over anhydrous sodium sulfate, and the solvent was distilled away under reduced pressure. The obtained residue was purified by silica gel column chromatography (ethyl acetate-hexane), thereby obtaining methyl 10-oxohexadecanoate (50.6 g) as white solids.

$^1$H-NMR (CDCl$_3$) δ: 3.67 (3H, s), 2.38 (4H, t, J=7.2 Hz), 2.30 (2H, t, 7.2 Hz), 1.65-1.49 (6H, m), 1.35-1.20 (14H, m), 0.88 (3H, t, J=7.2 Hz).

Tetraisopropyl orthotitanate (1.5 g) was added to a mixture of methyl 10-oxohexadecanoate (15.0 g) and 2-butyloctan-1-ol (14.7 g), and the mixture was stirred at 110° C. for 1 hour. Water (1 mL) was added to the reaction mixture, and the reaction mixture was stirred at room temperature for 15 minutes and then purified by silica gel column chromatography (ethyl acetate-hexane), thereby obtaining 2-butyloctyl 10-oxohexadecanoate (21.6 g) as a colorless oily substance.

$^1$H-NMR (CDCl$_3$) δ: 3.97 (2H, d, J=5.6 Hz), 2.38 (4H, t, J=7.6 Hz), 2.29 (2H, t, J=7.6 Hz), 1.65-1.50 (7H, m), 1.35-1.20 (30H, m), 0.92-0.83 (9H, m).

Sodium borohydride (2.8 g) was added to a mixture of 2-butyloctyl 10-oxohexadecanoate (21.6 g), methanol (86 mL), and tetrahydrofuran (86 mL) under ice cooling, and the mixture was stirred at the same temperature for 30 minutes. The reaction mixture was poured into a mixture of ice (80 g) and water (80 g), a 1.0 mol/L aqueous hydrochloric acid solution (110 mL) and ethyl acetate (200 mL) were added thereto, the organic layer was separated, then washed with a saturated aqueous sodium chloride solution (200 mL), and dried over anhydrous sodium sulfate, and then the solvent was distilled away under reduced pressure. The obtained residue was purified by silica gel column chromatography (ethyl acetate-hexane), thereby obtaining 2-butyloctyl 10-hydroxyhexadecanoate (18.0 g) as a colorless oily substance.

$^1$H-NMR (CDCl$_3$) δ: 3.97 (2H, d, J=6.0 Hz), 3.61-3.54 (1H, m), 2.30 (2H, t, J=7.6 Hz), 1.65-1.56 (3H, m), 1.48-1.22 (38H, m), 0.92-0.83 (9H, m).

4-Nitrophenyl chloroformate (1.03 g) was added to a mixture of 2-butyloctyl 10-hydroxyhexadecanoate (1.50 g), triethylamine (1.43 mL), and tetrahydrofuran (15 mL), and the mixture was stirred at room temperature for 4 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining 2-butyloctyl 10-(((4-nitrophenoxy)carbonyl)oxy)hexadecanoate (2.07 g) as a colorless oily substance.

$^1$H-NMR (CDCl$_3$) δ: 8.28 (2H, dd, J=7.2 Hz, 2.1 Hz), 7.39 (2H, dd, J=7.2 Hz, 2.1 Hz), 4.86-4.76 (1H, m), 3.97 (2H, d, J=5.7 Hz), 2.30 (2H, t, J=7.2 Hz), 1.74-1.20 (41H, m), 0.92-0.85 (9H, m).

(2)

4-Dimethylaminopyridine (183 mg) was added to a mixture of 2-butyloctyl 10-(((4-nitrophenoxy)carbonyl)oxy)hexadecanoate (300 mg), 2-((2-(diethylamino)ethyl)(isopropyl)amino)ethan-1-ol (304 mg), triethylamine (0.211 mL), and tetrahydrofuran (6 mL), and the mixture was stirred at 80° C. for 8 hours. The reaction mixture was cooled to room temperature, water and ethyl acetate were added thereto, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 2-butyloctyl 3-ethyl-12-hexyl-6-isopropyl-10-oxo-9,11-dioxa-3,6-diazahenicosan-21-oate (296 mg) as a colorless oily substance.

$^1$H-NMR (CDCl$_3$) δ: 4.73-4.61 (1H, m), 4.10 (2H, t, J=6.6 Hz), 3.97 (2H, d, J=6.0 Hz), 2.97-2.85 (1H, m), 2.68 (2H, t, J=7.2 Hz), 2.63-2.40 (8H, m), 2.29 (2H, t, J=7.2 Hz), 1.68-1.47 (7H, m), 1.40-1.19 (34H, m), 1.10-0.96 (12H, m), 0.95-0.79 (9H, m).

MS m/z (M+H): 670.

Example 85

(1)

Potassium carbonate (7.9 g) was added to a mixture of 2,2'-azanediylbis(ethan-1-ol) (2.0 g), 2-bromo-N,N-diethylethan-1-amine hydrobromide (7.4 g), and ethanol (40 mL), and the mixture was stirred and heated under reflux for 8 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2,2'-((2-(diethylamino)ethyl)azanediyl)bis(ethan-1-ol) (2.3 g) as a light yellow oily substance.

MS m/z (M+H): 205.

(2)

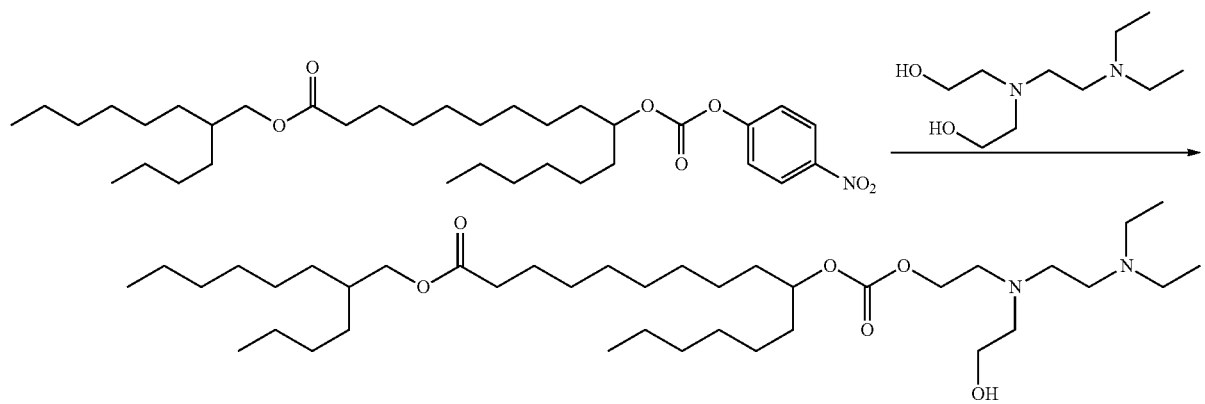

2-Butyloctyl 3-ethyl-12-hexyl-6-(2-hydroxyethyl)-10-oxo-9,11-dioxa-3,6-diazahenicosan-21-oate as a colorless oily substance was obtained by the same method as that in (2) of Example 84, except that 2,2'-((2-(diethylamino)ethyl)azanediyl)bis(ethan-1-ol) was used instead of 2-((2-(diethylamino)ethyl)(isopropyl)amino)ethan-1-ol in (2) of Example 84.

$^1$H-NMR (CDCl$_3$) δ: 4.75-4.61 (1H, m), 4.21 (2H, t, J=6.6 Hz), 3.97 (2H, d, J=5.7 Hz), 3.55 (2H, t, J=5.1 Hz), 2.89 (2H, t, J=6.6 Hz), 2.76-2.65 (4H, m), 2.64-2.41 (6H, m), 2.30 (2H, t, J=8.1 Hz), 1.72-1.45 (7H, m), 1.40-1.20 (34H, m), 1.13-0.98 (6H, m), 0.96-0.81 (9H, m).

MS m/z (M+H): 672.

Example 86 gel column chromatography (ethyl acetate-hexane, NH silica gel), thereby obtaining 2-butyloctyl 6-(2-(dodecanoyloxy)ethyl)-3-ethyl-12-hexyl-10-oxo-9,11-dioxa-3,6-diazahenicosan-21-oate (177 mg) as a colorless oily substance.

$^1$H-NMR (CDCl$_3$) δ: 4.72-4.60 (1H, m), 4.21-4.08 (4H, m), 3.97 (2H, d, J=6.0 Hz), 2.88-2.75 (4H, m), 2.73-2.43 (8H, m), 2.29 (4H, t, J=7.5 Hz), 1.70-1.46 (9H, m), 1.39-1.18 (50H, m), 1.12-0.97 (6H, m), 0.95-0.81 (12H, m).

MS m/z (M+H): 854.

Example 87

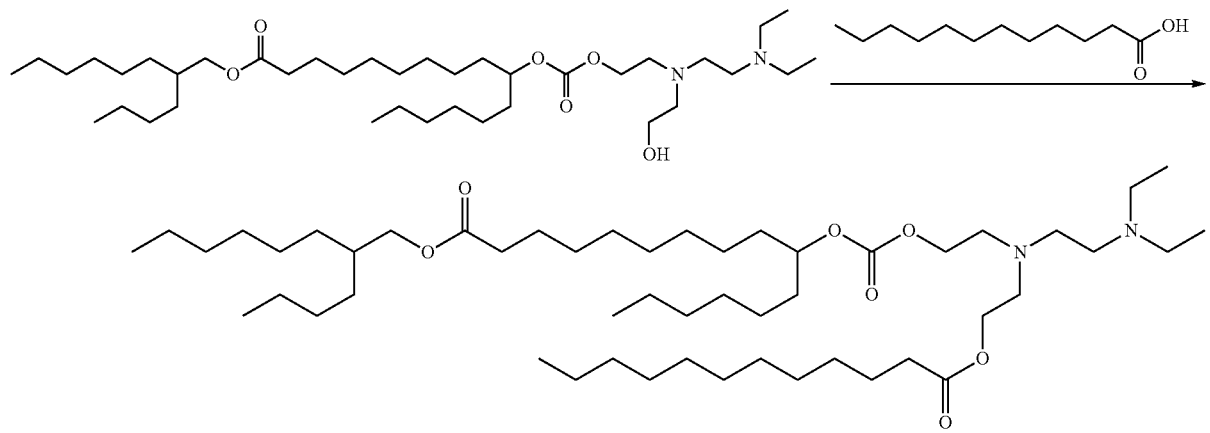

1-Ethyl-3-(3-dimethylaminopropyl)carbodiimide hydrochloride (142 mg) was added to a mixture of 2-butyloctyl 3-ethyl-12-hexyl-6-(2-hydroxyethyl)-10-oxo-9,11-dioxa-3,6-diazahenicosan-21-oate (250 mg) synthesized in (2) of Example 85, dodecanoic acid (112 mg), triethylamine (0.31 mL), 4-dimethylaminopyridine (136 mg), and dichloromethane (5 mL), and the mixture was stirred at room temperature for 6 hours. Water and ethyl acetate were added to the reaction mixture, the organic layer was separated, washed with water, and then dried over anhydrous magnesium sulfate, and the solvent was distilled away under reduced pressure. The obtained residue was purified by silica gel column chromatography (methanol-ethyl acetate) and silica

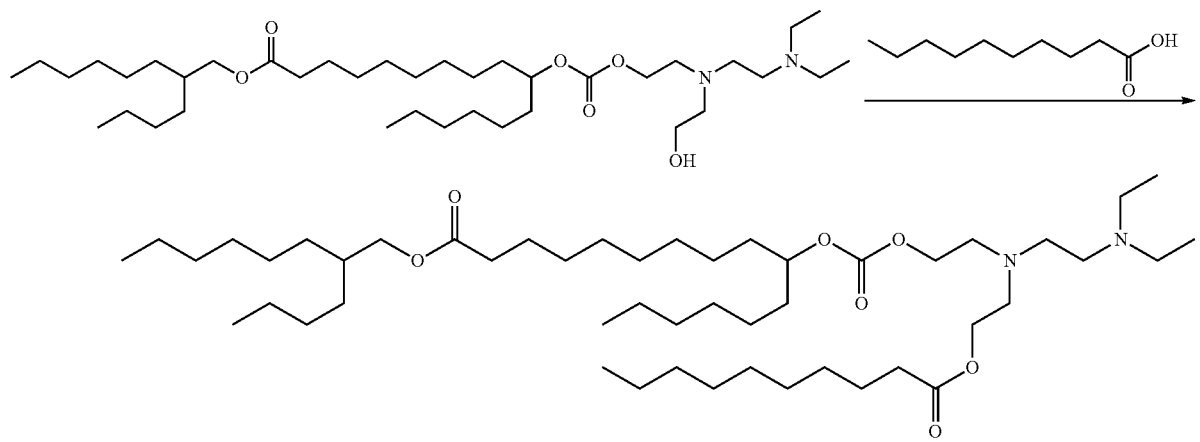

2-Butyloctyl 6-(2-(decanoyloxy)ethyl)-3-ethyl-12-hexyl-10-oxo-9,11-dioxa-3,6-diazahenicosan-21-oate as a colorless oily substance was obtained by the same method as that in Example 86, except that decanoic acid was used instead of dodecanoic acid in Example 86.

$^1$H-NMR (CDCl$_3$) δ: 4.72-4.61 (1H, m), 4.22-4.07 (4H, m), 3.97 (2H, d, J=6.0 Hz), 2.89-2.77 (4H, m), 2.74-2.43 (8H, m), 2.30 (4H, t, J=8.1 Hz), 1.68-1.46 (9H, m), 1.40-1.18 (46H, m), 1.13-0.97 (6H, m), 0.95-0.80 (12H, m).

MS m/z (M+H): 826.

Example 88 in Example 86, except that octanoic acid was used instead of dodecanoic acid in Example 86.

$^1$H-NMR (CDCl$_3$) δ: 4.71-4.62 (1H, m), 4.20-4.08 (4H, m), 3.97 (2H, d, J=5.6 Hz), 2.89-2.77 (4H, m), 2.73-2.42 (8H, m), 2.29 (4H, t, J=7.6 Hz), 1.68-1.48 (9H, m), 1.39-1.18 (42H, m), 1.10-0.98 (6H, m), 0.94-0.81 (12H, m).

MS m/z (M+H): 798.

Example 89

(1)

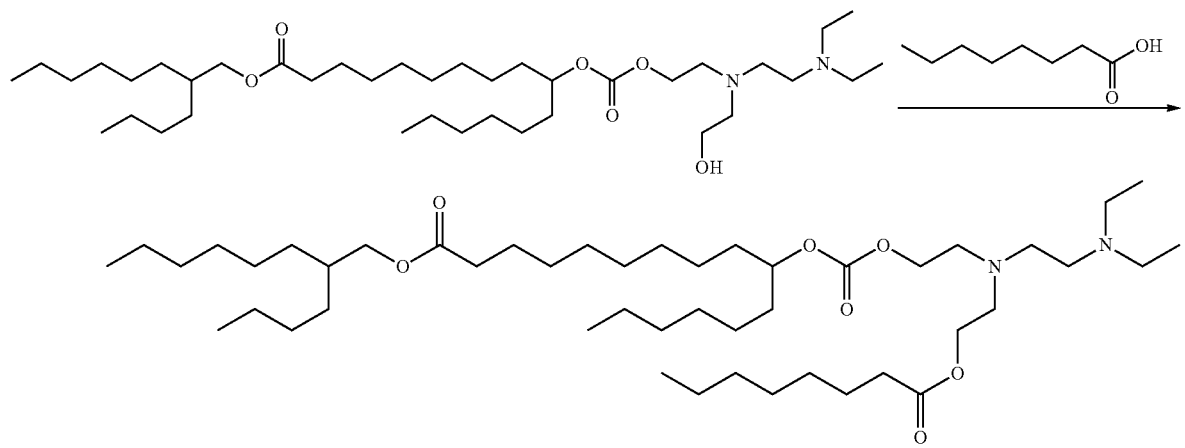

2-Butyloctyl 3-ethyl-12-hexyl-6-(2-(octanoyloxy)ethyl)-10-oxo-9,11-dioxa-3,6-diazahenicosan-21-oate as a colorless oily substance was obtained by the same method as that

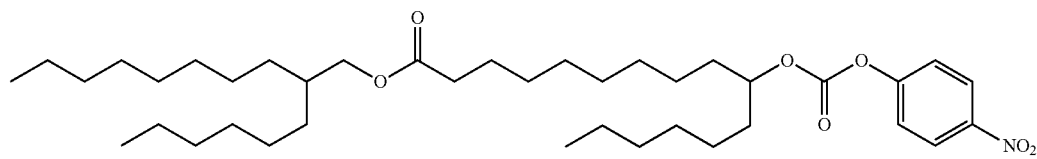 [SMILES: CCCCCCCCC(CCCCCC)COC(=O)CCCCCCCCC(CCCCCC)OC(=O)Oc1ccc([N+](=O)[O-])cc1]

2-Hexyldecyl 10-(((4-nitrophenoxy)carbonyl)oxy)hexadecanoate as a colorless oily substance was obtained by the same method as that in (1) of Example 84, except that 2-hexyldecan-1-ol was used instead of 2-butyloctan-1-ol in (1) of Example 84.

$^{1}$H-NMR (CDCl$_{3}$) δ: 8.28 (2H, dd, J=7.2 Hz, 2.4 Hz), 7.39 (2H, dd, J=7.2 Hz, 2.4 Hz), 4.85-4.77 (1H, m), 3.97 (2H, d, J=5.6 Hz), 2.30 (2H, t, J=7.6 Hz), 1.72-1.20 (49H, m), 0.92-0.85 (9H, m).

(2)

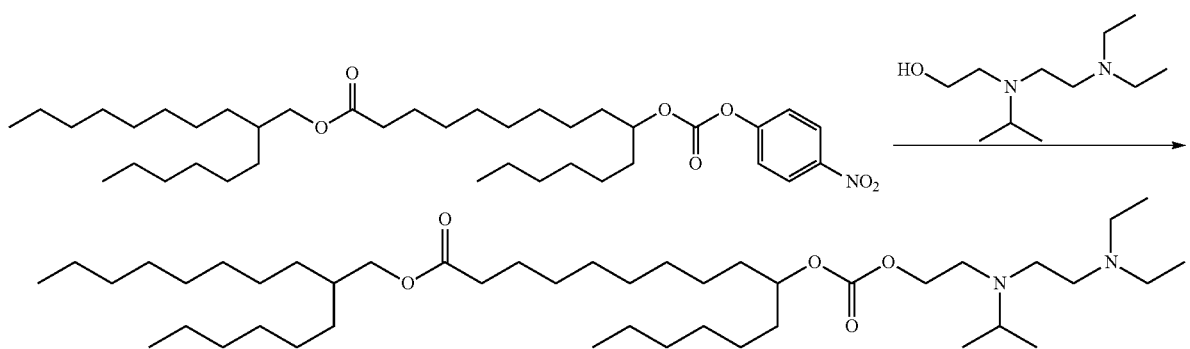

2-Hexyldecyl 3-ethyl-12-hexyl-6-isopropyl-10-oxo-9,11-dioxa-3,6-diazahenicosan-21-oate as a colorless oily substance was obtained by the same method as that in (2) of Example 84, except that 2-hexyldecyl 10-((((4-nitrophenoxy)carbonyl)oxy)hexadecanoate was used instead of 2-butyloctyl 10-(((4-nitrophenoxy)carbonyl)oxy)hexadecanoate in (2) of Example 84.

$^{1}$H-NMR (CDCl$_{3}$) δ: 4.72-4.61 (1H, m), 4.10 (2H, t, J=6.6 Hz), 3.97 (2H, d, J=5.7 Hz), 2.97-2.87 (1H, m), 2.68 (2H, t, J=6.6 Hz), 2.62-2.40 (8H, m), 2.29 (2H, t, J=7.2 Hz), 1.69-1.49 (7H, m), 1.40-1.19 (42H, m), 1.12-0.95 (12H, m), 0.93-0.82 (9H, m).

MS m/z (M+H): 726.

Example 90

(1)

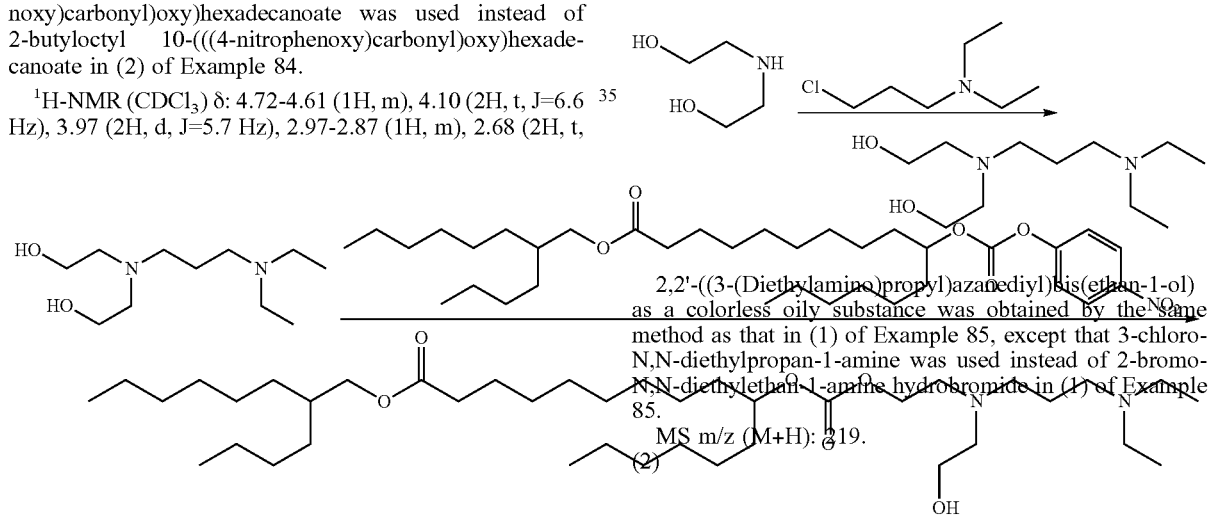

2,2'-((3-(Diethylamino)propyl)azanediyl)bis(ethan-1-ol) as a colorless oily substance was obtained by the same method as that in (1) of Example 85, except that 3-chloro-N,N-diethylpropan-1-amine was used instead of 2-bromo-N,N-diethylethan-1-amine hydrobromide in (1) of Example 85.

MS m/z (M+H): 219.

(2)

2-Butyloctyl 3-ethyl-13-hexyl-7-(2-hydroxyethyl)-11-oxo-10,12-dioxa-3,7-diazadocosan-22-oate as a colorless oily substance was obtained by the same method as that in (2) of Example 85, except that 2,2'-((3-(diethylamino)propyl)azanediyl)bis(ethan-1-ol) was used instead of 2,2'-((2-(diethylamino)ethyl)azanediyl)bis(ethan-1-ol) in (2) of Example 85.

$^{1}$H-NMR (CDCl$_{3}$) δ: 4.73-4.61 (1H, m), 4.17 (2H, t, J=6.0 Hz), 3.97 (2H, d, J=6.0 Hz), 3.58 (2H, t, J=5.4 Hz), 2.76 (2H, t, J=5.7 Hz), 2.67-2.40 (10H, m), 2.30 (2H, t, J=8.1 Hz), 1.76-1.46 (9H, m), 1.38-1.19 (34H, m), 1.12-0.98 (6H, m), 0.94-0.82 (9H, m).

MS m/z (M+H): 686.

Example 91

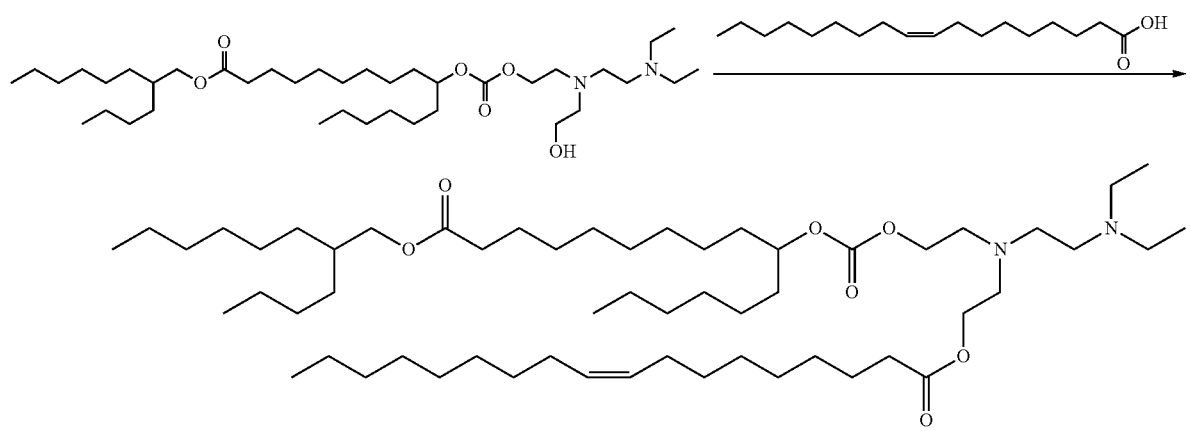

2-Butyloctyl 3-ethyl-12-hexyl-6-(2-(oleoyloxy)ethyl)-10-oxo-9,11-dioxa-3,6-diazahenicosan-21-oate as a colorless oily substance was obtained by the same method as that in Example 86, except that oleic acid was used instead of dodecanoic acid in Example 86.

$^1$H-NMR (CDCl$_3$) δ: 5.38-5.28 (2H, m), 4.72-4.63 (1H, m), 4.21-4.06 (4H, m), 3.97 (2H, d, J=6.0 Hz), 2.90-2.76 (4H, m), 2.74-2.44 (8H, m), 2.29 (4H, t, J=7.8 Hz), 2.07-1.93 (4H, m), 1.68-1.45 (9H, m), 1.38-1.17 (54H, m), 1.11-0.96 (6H, m), 0.94-0.81 (12H, m).

MS m/z (M+H): 936.

stance was obtained by the same method as that in (1) and (2) of Examples 84, except that 8-methoxy-8-oxooctanoic acid was used instead of 10-methoxy-10-oxodecanoic acid in (1) and (2) of Example 84.

$^1$H-NMR (CDCl$_3$) δ: 4.72-4.59 (1H, m), 4.17-4.04 (2H, m), 3.97 (2H, d, J=5.4 Hz), 2.97-2.84 (1H, m), 2.69 (2H, t, J=6.6 Hz), 2.64-2.42 (8H, m), 2.29 (2H, t, J=7.2 Hz), 1.68-1.46 (7H, m), 1.40-1.18 (30H, m), 1.14-0.94 (12H, m), 0.93-0.82 (9H, m).

MS m/z (M+H): 642.

Example 93

Example 92

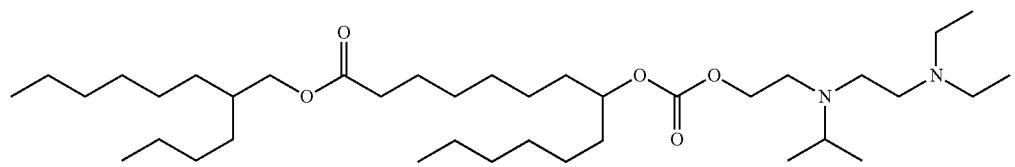 [SMILES: CCCCCCC(CCCC)COC(=O)CCCCCCC(CCCCCC)OC(=O)OCCN(CCN(CC)CC)C(C)C]

2-Butyloctyl 3-ethyl-12-hexyl-6-isopropyl-10-oxo-9,11-dioxa-3,6-diazanonadecan-19-oate as a colorless oily sub-

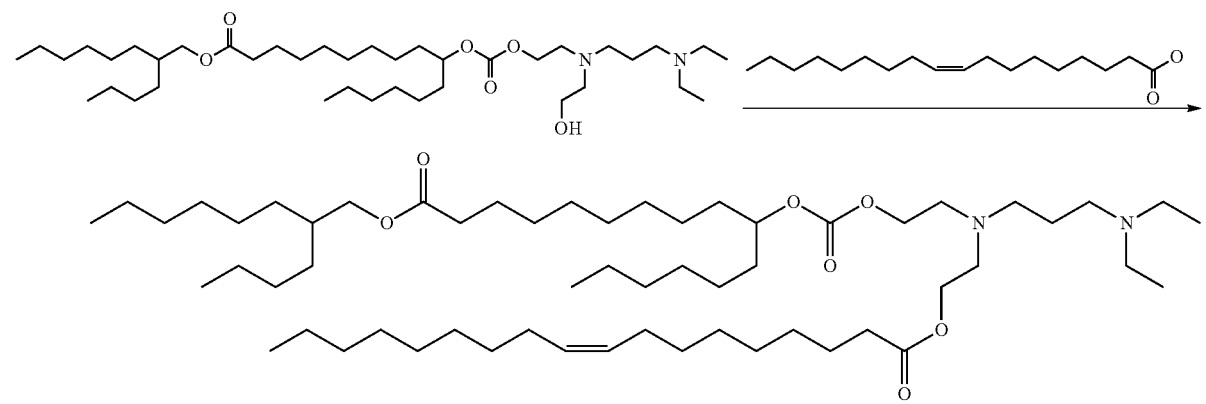

2-Butyloctyl 3-ethyl-13-hexyl-7-(2-(oleoyloxy)ethyl)-11-oxo-10,12-dioxa-3,7-diazadocosan-22-oate as a colorless oily substance was obtained by the same method as that in Example 86, except that in Example 86, 2-butyloctyl 3-ethyl-13-hexyl-7-(2-hydroxyethyl)-11-oxo-10,12-dioxa-3,7-diazadocosan-22-oate was used instead of 2-butyloctyl 3-ethyl-12-hexyl-6-(2-hydroxyethyl)-10-oxo-9,11-dioxa-3,6-diazahenicosan-21-oate, and oleic acid was used instead of dodecanoic acid.

$^1$H-NMR (CDCl$_3$) δ: 5.42-5.27 (2H, m), 4.72-4.59 (1H, m), 4.21-4.07 (4H, m), 3.97 (2H, d, J=6.0 Hz), 2.86-2.71 (4H, m), 2.65-2.35 (8H, m), 2.29 (4H, t, J=7.2H), 2.07-1.94 (4H, m), 1.70-1.48 (11H, m), 1.41-1.19 (54H, m), 1.11-0.97 (6H, m), 0.96-0.82 (12H, m).

MS m/z (M+H): 950.

Example 94

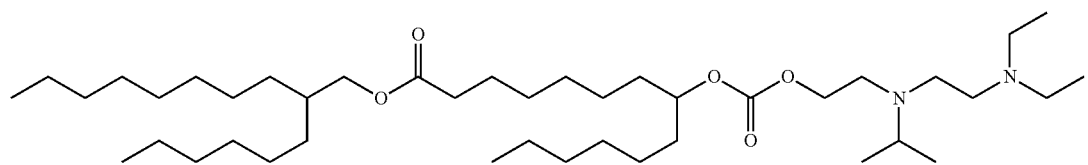 [SMILES: CCCCCCCCC(CCCCCC)COC(=O)CCCCCCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazanonadecan-19-oate as a colorless oily substance was obtained by the same method as that in Example 92, except that 2-hexyldecan-1-ol was used instead of 2-butyloctan-1-ol in Example 92.

$^1$H-NMR (CDCl$_3$) δ: 4.71-4.62 (1H, m), 4.16-4.04 (2H, m), 3.96 (2H, d, J=6.0 Hz), 2.97-2.85 (1H, m), 2.68 (2H, t, J=6.6 Hz), 2.64-2.41 (8H, m), 2.29 (2H, t, J=7.5 Hz), 1.70-1.47 (7H, m), 1.41-1.19 (38H, m), 1.11-0.95 (12H, m), 0.93-0.83 (9H, m).

MS m/z (M+H): 698.

Example 95

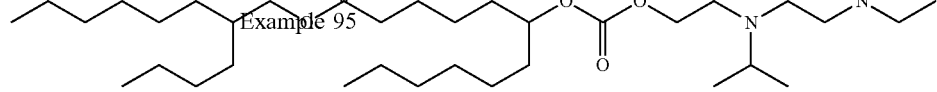

2-Butyloctyl 3-ethyl-12-hexyl-6-isopropyl-10-oxo-9,11-dioxa-3,6-diazaheptadecan-17-oate as a colorless oily substance was obtained by the same method as that in (1) and (2) of Examples 84, except that 6-methoxy-6-oxohexanoic acid was used instead of 10-methoxy-10-oxodecanoic acid in (1) and (2) of Example 84.

$^1$H-NMR (CDCl$_3$) δ: 4.73-4.61 (1H, m), 4.16-4.04 (2H, m), 3.96 (2H, d, J=5.7 Hz), 2.97-2.85 (1H, m), 2.68 (2H, t, J=6.6 Hz), 2.63-2.42 (8H, m), 2.30 (2H, t, J=8.1 Hz), 1.69-1.49 (7H, m), 1.44-1.20 (26H, m), 1.12-0.95 (12H, m), 0.94-0.82 (9H, m).

MS m/z (M+H): 614.

Example 96

2-Hexyldecyl 3-ethyl-12-hexyl-6-isopropyl-10-oxo-9,11-dioxa-3,6-diazaheptadecan-17-oate as a colorless oily substance was obtained by the same method as that in Example 95, except that 2-hexyldecan-1-ol was used instead of 2-butyloctan-1-ol in Example 95.

$^1$H-NMR (CDCl$_3$) δ: 4.73-4.62 (1H, m), 4.17-4.04 (2H, m), 3.96 (2H, d, J=5.7 Hz), 2.98-2.83 (1H, m), 2.68 (2H, t, J=6.6 Hz), 2.62-2.41 (8H, m), 2.30 (2H, t, J=7.8 Hz), 1.69-1.49 (7H, m), 1.42-1.18 (34H, m), 1.12-0.96 (12H, m), 0.93-0.81 (9H, m).

MS m/z (M+H): 670.

Example 97

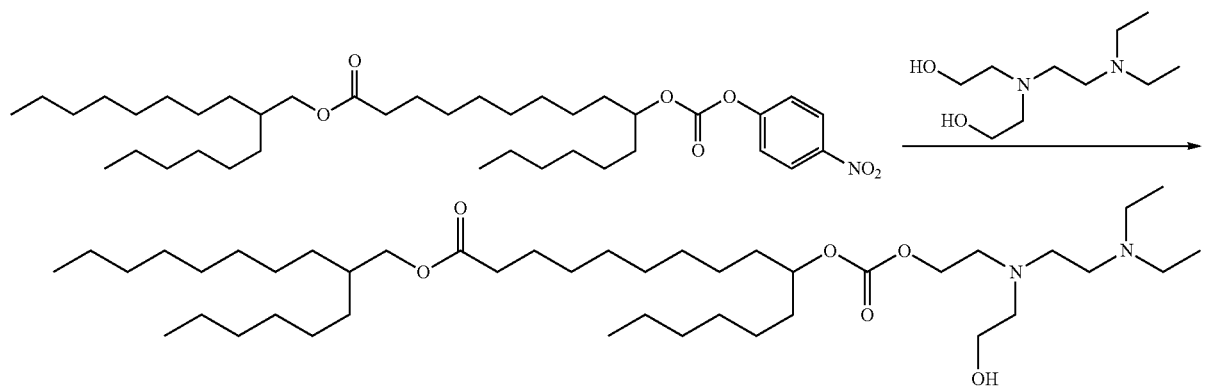

2-Hexyldecyl 3-ethyl-12-hexyl-6-(2-hydroxyethyl)-10-oxo-9,11-dioxa-3,6-diazahenicosan-21-oate as a colorless oily substance was obtained by the same method as that in Example 85, except that 2-hexyldecyl 10-((((4-nitrophenoxy)carbonyl)oxy)hexadecanoate was used instead of 2-butyloctyl 10-(((4-nitrophenoxy)carbonyl)oxy)hexadecanoate in Example 85.

$^1$H-NMR (CDCl$_3$) δ: 4.73-4.61 (1H, m), 4.20 (2H, t, J=6.6 Hz), 3.96 (2H, d, J=5.4 Hz), 3.54 (2H, t, J=5.4 Hz), 2.89 (2H, t, J=6.0 Hz), 2.76-2.63 (4H, m), 2.62-2.42 (6H, m), 2.29 (2H, t, J=7.5 Hz), 1.72-1.46 (7H, m), 1.39-1.18 (42H, m), 1.04 (6H, t, J=7.2 Hz), 0.94-0.80 (9H, m).
MS m/z (M+H): 728.

colorless oily substance was obtained by the same method as that in Example 86, except that in Example 86, 2-hexyldecyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and decanoic acid was used instead of dodecanoic acid.

$^1$H-NMR (CDCl$_3$) δ: 4.72-4.63 (1H, m), 4.22-4.08 (4H, m), 3.96 (2H, d, J=5.4 Hz), 2.88-2.76 (4H, m), 2.75-2.43 (8H, m), 2.29 (4H, t, J=7.2 Hz), 1.68-1.50 (9H, m), 1.39-1.16 (54H, m), 1.03 (6H, t, J=6.6 Hz), 0.95-0.82 (12H, m).
MS m/z (M+H): 882.

Example 98

Example 99

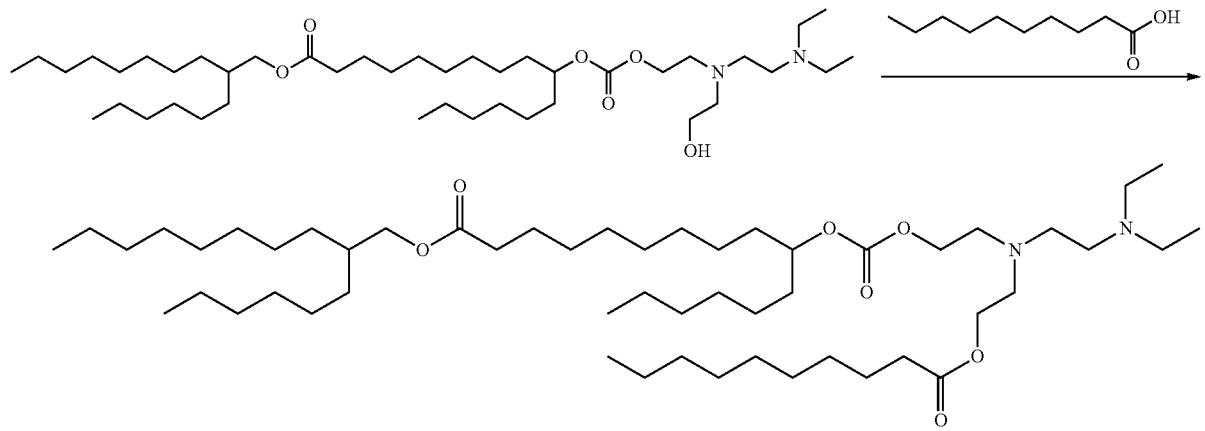

2-Hexyldecyl 6-(2-(decanoyloxy)ethyl)-3-ethyl-12-hexyl-10-oxo-9,11-dioxa-3,6-diazahenicosan-21-oate as a

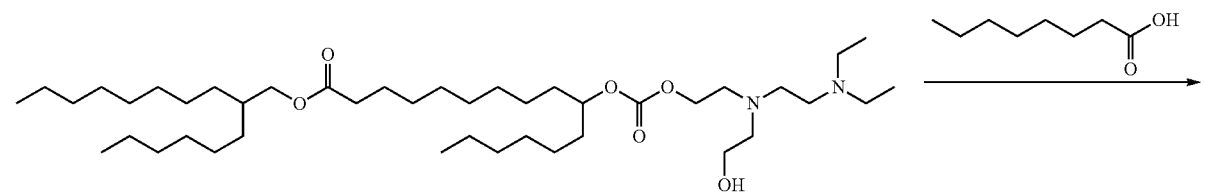

-continued

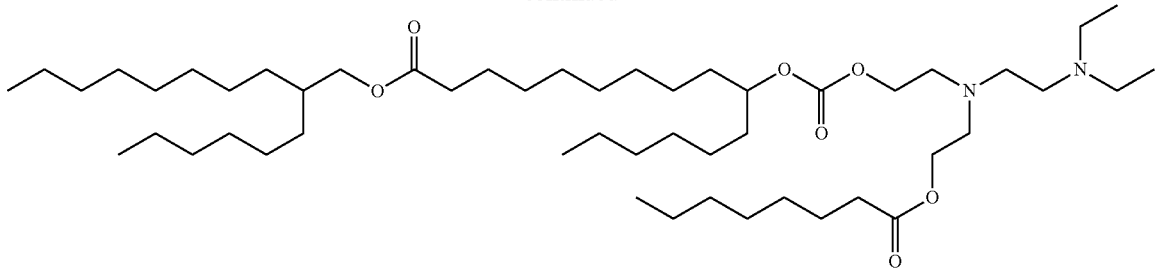

2-Hexyldecyl 3-ethyl-12-hexyl-6-(2-(octanoyloxy)ethyl)-10-oxo-9,11-dioxa-3,6-diazahenicosan-21-oate as a colorless oily substance was obtained by the same method as that in Example 98, except that octanoic acid was used instead of decanoic acid in Example 98.

$^1$H-NMR (CDCl$_3$) δ: 4.72-4.61 (1H, m), 4.21-4.07 (4H, m), 3.96 (2H, d, J=5.1 Hz), 2.90-2.76 (4H, m), 2.76-2.42 (8H, m), 2.29 (4H, t, J=7.8 Hz), 1.68-1.47 (9H, m), 1.39-1.19 (50H, m), 1.12-0.96 (6H, m), 0.95-0.82 (12H, m).

MS m/z (M+H): 854.

colorless oily substance was obtained by the same method as that in Example 98, except that hexanoic acid was used instead of decanoic acid in Example 98.

$^1$H-NMR (CDCl$_3$) δ: 4.72-4.61 (1H, m), 4.21-4.07 (4H, m), 3.96 (2H, d, J=5.7 Hz), 2.90-2.77 (4H, m), 2.73-2.41 (8H, m), 2.29 (4H, t, J=7.2 Hz), 1.70-1.46 (9H, m), 1.42-1.18 (46H, m), 1.13-0.97 (6H, m), 0.95-0.81 (12H, m).

MS m/z (M+H): 826.

Example 100

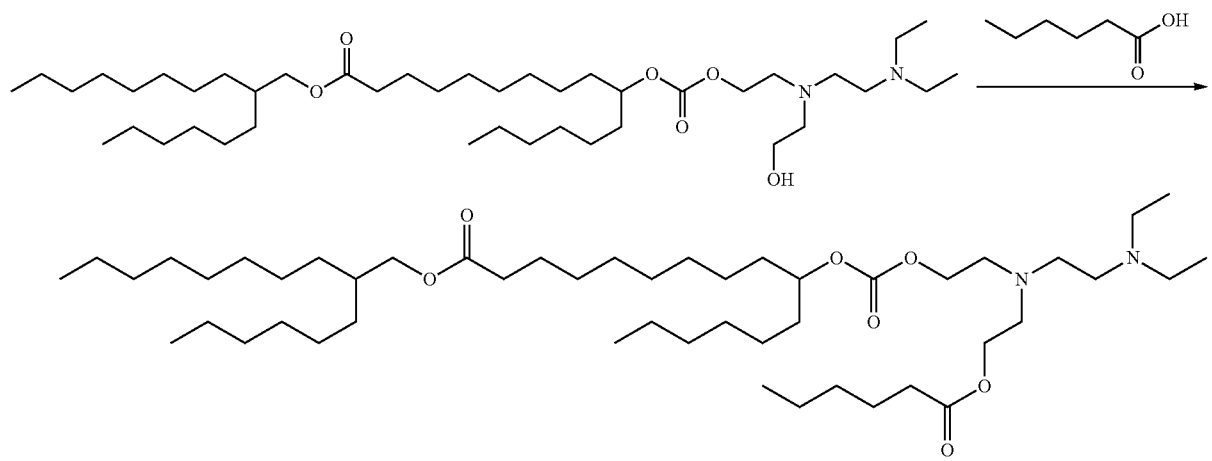

2-Hexyldecyl 3-ethyl-6-(2-(hexanoyloxy)ethyl)-12-hexyl-10-oxo-9,11-dioxa-3,6-diazahenicosan-21-oate as a Example 101

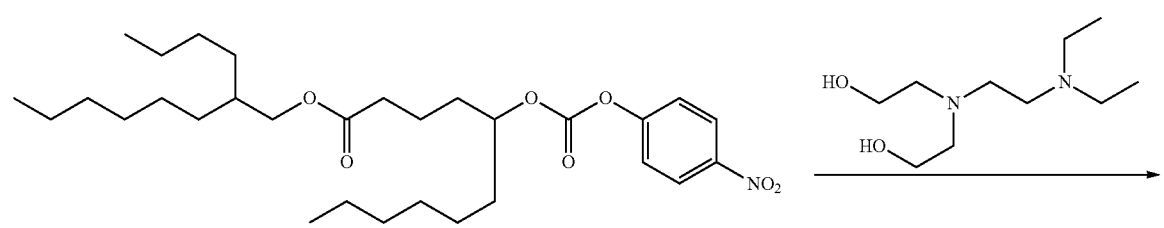

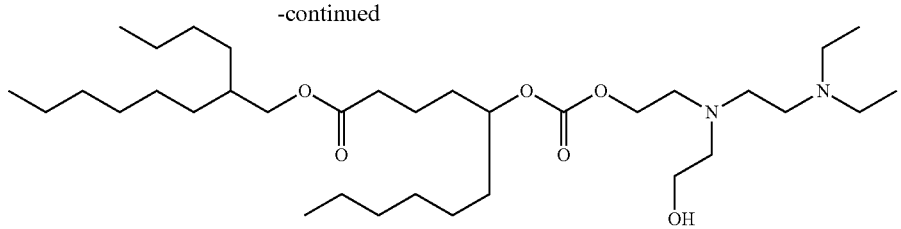

2-Butyloctyl 3-ethyl-12-hexyl-6-(2-hydroxyethyl)-10-oxo-9,11-dioxa-3,6-diazahexadecan-16-oate as a colorless oily substance was obtained by the same method as that in (2) of Example 80, except that 2,2'-((2-(diethylamino)ethyl)azanediyl)bis(ethan-1-ol) was used instead of 2-((2-(diethylamino)ethyl)(ethyl)amino)ethan-1-ol in (2) of Example 80.

¹H-NMR (CDCl₃) δ: 4.75-4.64 (1H, m), 4.25-4.15 (2H, m), 3.97 (2H, d, J=6.0 Hz), 3.54 (2H, t, J=5.4 Hz), 2.89 (2H, t, J=6.6 Hz), 2.75-2.63 (4H, m), 2.60-2.42 (6H, m), 2.33 (2H, t, J=6.6 Hz), 1.73-1.50 (7H, m), 1.39-1.20 (24H, m), 1.03 (6H, t, J=7.2 Hz), 0.95-0.81 (9H, m).

MS m/z (M+H): 602.

oily substance was obtained by the same method as that in (2) of Example 85, except that 2-hexyldecyl 5-(((4-nitrophenoxy)carbonyl)oxy)undecanoate was used instead of 2-butyloctyl 10-(((4-nitrophenoxy)carbonyl)oxy)hexadecanoate in (2) of Example 85.

¹H-NMR (CDCl₃) δ: 4.75-4.63 (1H, m) 4.25-4.14 (2H, m), 3.97 (2H, d, J=6.0 Hz), 3.54 (2H, t, J=4.8 Hz), 2.89 (2H, t, J=6.0 Hz), 2.76-2.63 (4H, m), 2.60-2.43 (6H, m), 2.33 (2H, t, J=7.5 Hz), 1.73-1.48 (7H, m), 1.40-1.17 (32H, m), 1.03 (6H, t, J=7.2 Hz), 0.96-0.78 (9H, m).

MS m/z (M+H): 658.

Example 102

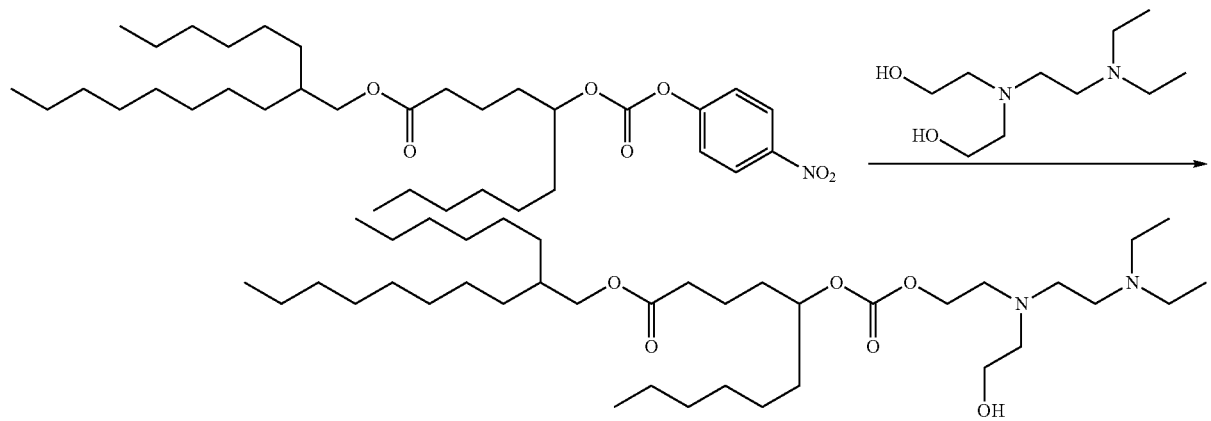

2-Hexyldecyl 3-ethyl-12-hexyl-6-(2-hydroxyethyl)-10-oxo-9,11-dioxa-3,6-diazahexadecan-16-oate as a colorless Example 103

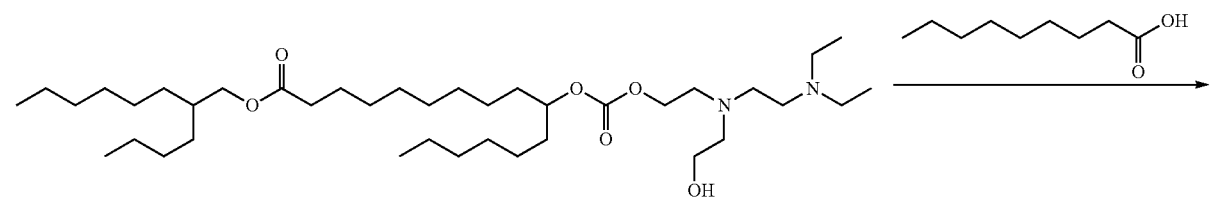

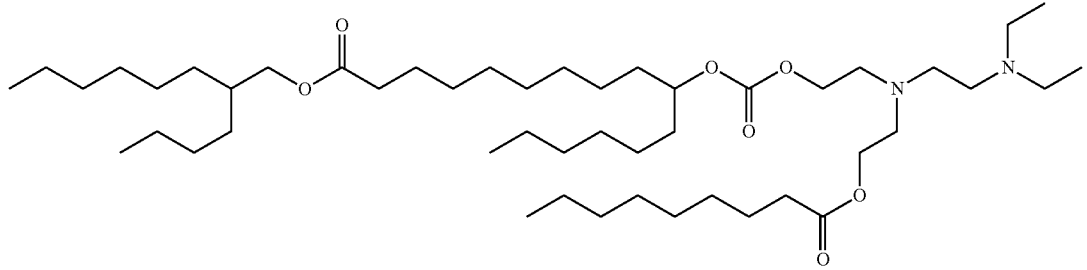

2-Butyloctyl 3-ethyl-12-hexyl-6-(2-(nonanoyloxy)ethyl)-10-oxo-9,11-dioxa-3,6-diazahenicosan-21-oate as a colorless oily substance was obtained by the same method as that in Example 86, except that nonanoic acid was used instead of dodecanoic acid in Example 86.

$^1$H-NMR (CDCl$_3$) δ: 4.72-4.61 (1H, m), 4.21-4.09 (4H, m), 3.97 (2H, d, J=6.0 Hz), 2.88-2.47 (4H, m), 2.72-2.62 (2H, m), 2.58-2.46 (6H, m), 2.29 (4H, t, J=7.8 Hz), 1.69-1.50 (9H, m), 1.40-1.19 (44H, m), 1.01 (6H, t, J=7.2 Hz), 0.95-0.82 (12H, m).

MS m/z (M+H): 812.

Example 104 that in Example 86, except that heptanoic acid was used instead of dodecanoic acid in Example 86.

$^1$H-NMR (CDCl$_3$) δ: 4.72-4.60 (1H, m), 4.20-4.06 (4H, m), 3.97 (2H, d, J=5.1 Hz), 2.89-2.76 (4H, m), 2.71-2.62 (2H, m), 2.58-2.46 (6H, m), 2.30 (4H, t, J=8.1 Hz), 1.68-1.47 (9H, m), 1.39-1.19 (40H, m), 1.02 (6H, t, J=6.6 Hz), 0.95-0.83 (12H, m).

MS m/z (M+H): 784.

Example 105

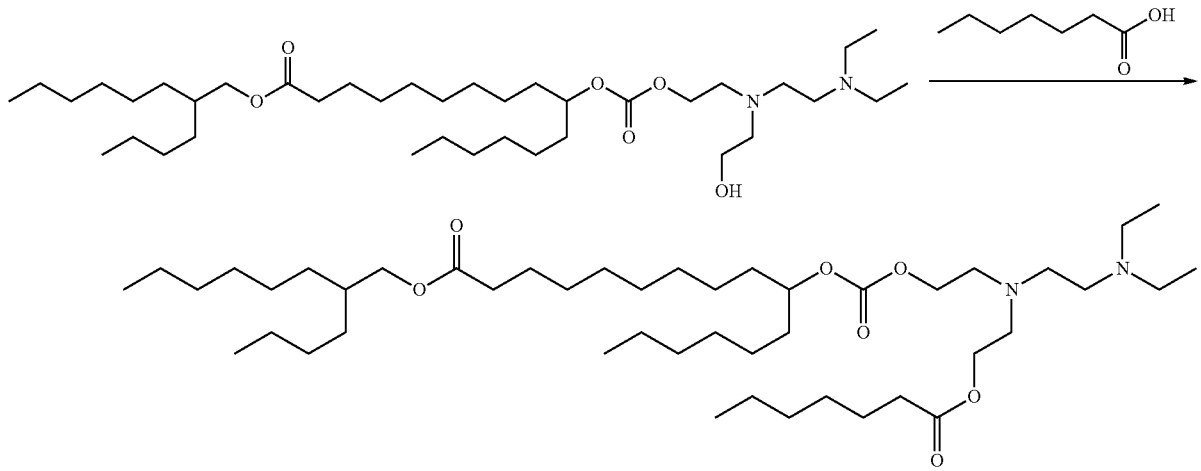

2-Butyloctyl 3-ethyl-6-(2-(heptanoyloxy)ethyl)-12-hexyl-10-oxo-9,11-dioxa-3,6-diazahenicosan-21-oate as a colorless oily substance was obtained by the same method as

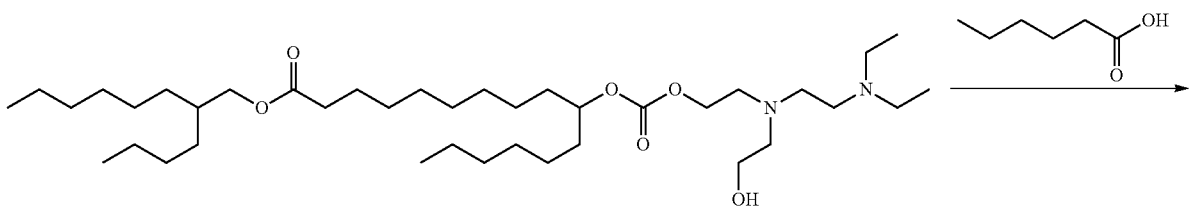

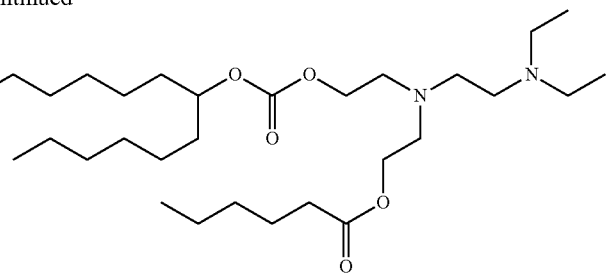

2-Butyloctyl 3-ethyl-6-(2-(hexanoyloxy)ethyl)-12-hexyl-10-oxo-9,11-dioxa-3,6-diazahenicosan-21-oate as a colorless oily substance was obtained by the same method as that in Example 86, except that hexanoic acid was used instead of dodecanoic acid in Example 86.

$^1$H-NMR (CDCl$_3$) δ: 4.73-4.61 (1H, m), 4.21-4.08 (4H, m), 3.97 (2H, d, J=5.4 Hz), 2.89-2.76 (4H, m), 2.72-2.62 (2H, m), 2.59-2.45 (6H, m), 2.30 (4H, t, J=8.1 Hz), 1.71-1.47 (9H, m), 1.40-1.19 (38H, m), 1.02 (6H, t, J=6.6 Hz), 0.94-0.82 (12H, m).

MS m/z (M+H): 770.

Example 106 that in Example 86, except that 2-butyloctyl 3-ethyl-12-hexyl-6-(2-hydroxyethyl)-10-oxo-9,11-dioxa-3,6-diazahexadecan-16-oate was used instead of 2-butyloctyl 3-ethyl-12-hexyl-6-(2-hydroxyethyl)-10-oxo-9,11-dioxa-3,6-diazahenicosan-21-oate in Example 86. $^1$H-NMR (CDCl$_3$) δ: 4.74-4.64 (1H, m), 4.21-4.07 (4H, m), 3.97 (2H, d, J=6.0 Hz), 2.89-2.76 (4H, m), 2.72-2.63 (2H, m), 2.58-2.46 (6H, m), 2.37-2.25 (4H, m), 1.74-1.50 (9H, m), 1.39-1.19 (40H, m), 1.02 (6H, t, J=6.6 Hz), 0.95-0.83 (12H, m).

MS m/z (M+H): 784.

Example 107

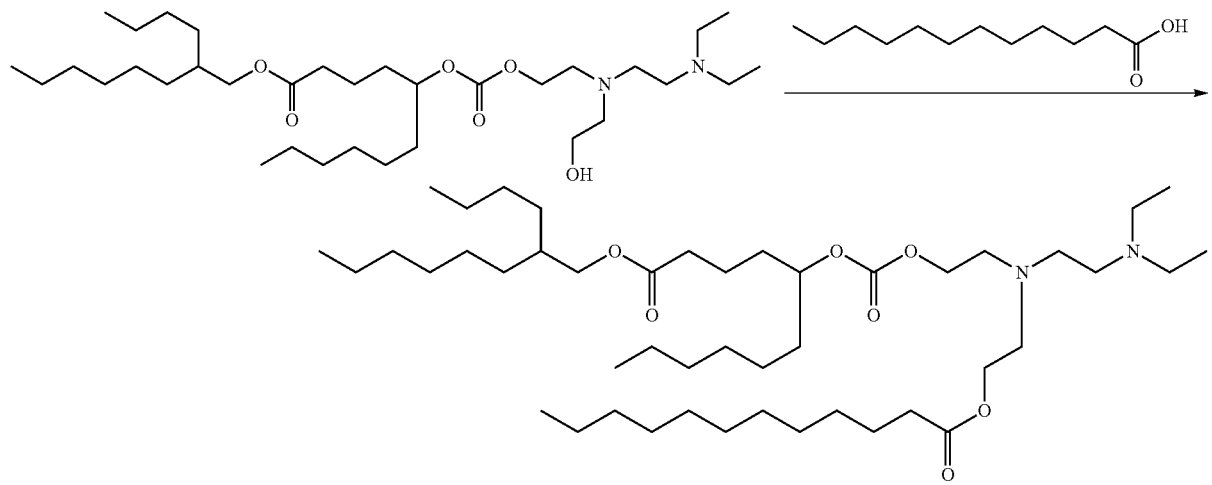

2-Butyloctyl 6-(2-(dodecanoyloxy)ethyl)-3-ethyl-12-hexyl-10-oxo-9,11-dioxa-3,6-diazahexadecan-16-oate as a colorless oily substance was obtained by the same method as

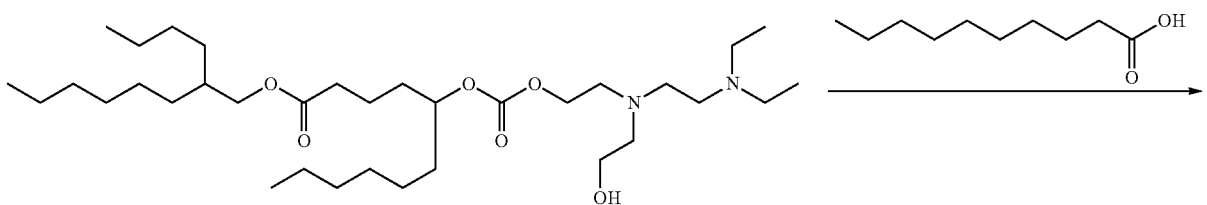

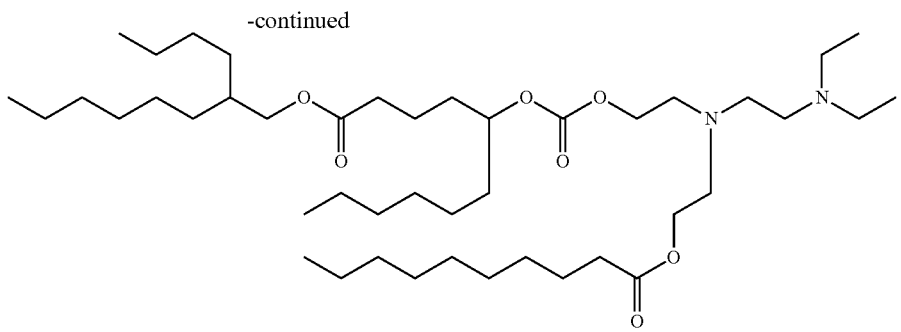

2-Butyloctyl 6-(2-(decanoyloxy)ethyl)-3-ethyl-12-hexyl-10-oxo-9,11-dioxa-3,6-diazahexadecan-16-oate as a colorless oily substance was obtained by the same method as that in Example 106, except that decanoic acid was used instead of dodecanoic acid in Example 106.

$^1$H-NMR (CDCl$_3$) δ: 4.74-4.64 (1H, m), 4.22-4.07 (4H, m), 3.97 (2H, d, J=6.0 Hz), 2.88-2.75 (4H, m), 2.72-2.62 (2H, m), 2.58-2.46 (6H, m), 2.37-2.25 (4H, m), 1.74-1.52 (9H, m), 1.40-1.19 (36H, m), 1.02 (6H, t, J=7.2 Hz), 0.94-0.82 (12H, m).

MS m/z (M+H): 756.

Example 108 less oily substance was obtained by the same method as that in Example 106, except that octanoic acid was used instead of dodecanoic acid in Example 106.

$^1$H-NMR (CDCl$_3$) δ: 4.74-4.64 (1H, m), 4.21-4.08 (4H, m), 3.97 (2H, d, J=6.0 Hz), 2.88-2.76 (4H, m), 2.72-2.62 (2H, m), 2.58-2.46 (6H, m), 2.37-2.27 (4H, m), 1.74-1.50 (9H, m), 1.40-1.19 (32H, m), 1.02 (6H, t, J=7.2 Hz), 0.95-0.83 (12H, m).

MS m/z (M+H): 728.

Example 109

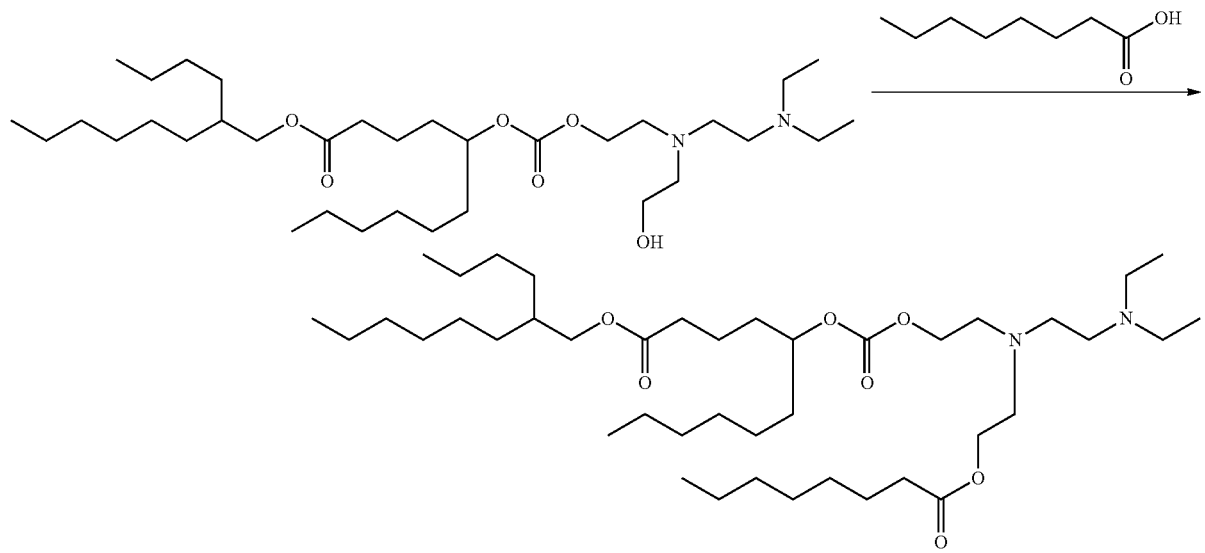

2-Butyloctyl 3-ethyl-12-hexyl-6-(2-(octanoyloxy)ethyl)-10-oxo-9,11-dioxa-3,6-diazahexadecan-16-oate as a color-

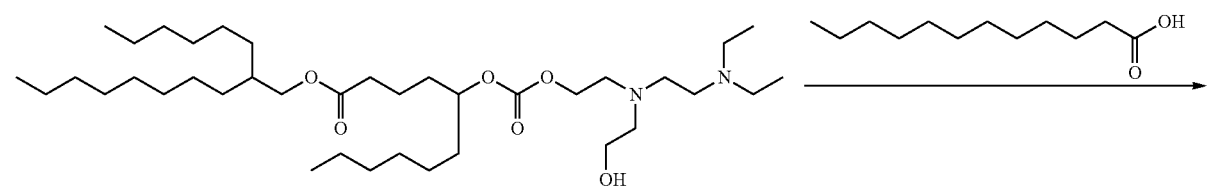

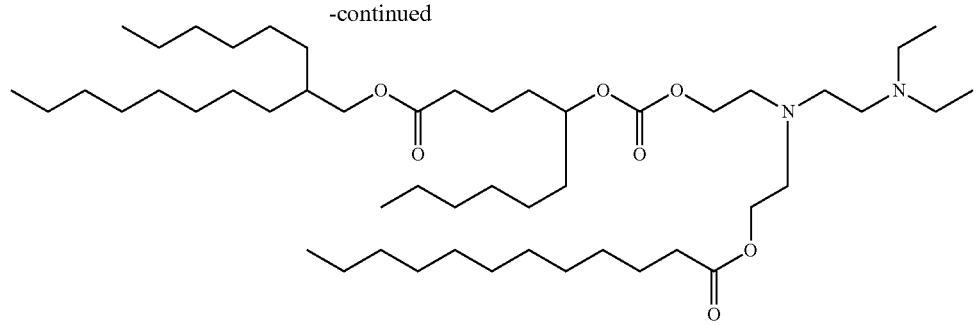

2-Hexyldecyl 6-(2-(dodecanoyloxy)ethyl)-3-ethyl-12-hexyl-10-oxo-9,11-dioxa-3,6-diazahexadecan-16-oate as a colorless oily substance was obtained by the same method as that in Example 86, except that 2-hexyldecyl 3-ethyl-12-hexyl-6-(2-hydroxyethyl)-10-oxo-9,11-dioxa-3,6-diazahexadecan-16-oate was used instead of 2-butyloctyl 3-ethyl-12-hexyl-6-(2-hydroxyethyl)-10-oxo-9,11-dioxa-3,6-diazahenicosan-21-oate in Example 86.

$^1$H-NMR (CDCl$_3$) δ: 4.74-4.64 (1H, m), 4.21-4.06 (4H, m), 3.97 (2H, d, J=5.4 Hz), 2.88-2.76 (4H, m), 2.71-2.63 (2H, m), 2.57-2.46 (6H, m), 2.36-2.25 (4H, m), 1.72-1.52 (9H, m), 1.39-1.20 (48H, m), 1.02 (6H, t, J=7.5 Hz), 0.95-0.81 (12H, m).

MS m/z (M+H): 840.

Example 110 colorless oily substance was obtained by the same method as that in Example 109, except that decanoic acid was used instead of dodecanoic acid in Example 109.

$^1$H-NMR (CDCl$_3$) δ: 4.75-4.63 (1H, m), 4.21-4.07 (4H, m), 3.97 (2H, d, J=5.7 Hz), 2.88-2.76 (4H, m), 2.71-2.62 (2H, m), 2.58-2.45 (6H, m), 2.36-2.26 (4H, m), 1.73-1.52 (9H, m), 1.38-1.19 (44H, m), 1.02 (6H, t, J=7.2 Hz), 0.95-0.81 (12H, m).

MS m/z (M+H): 812.

Example 111

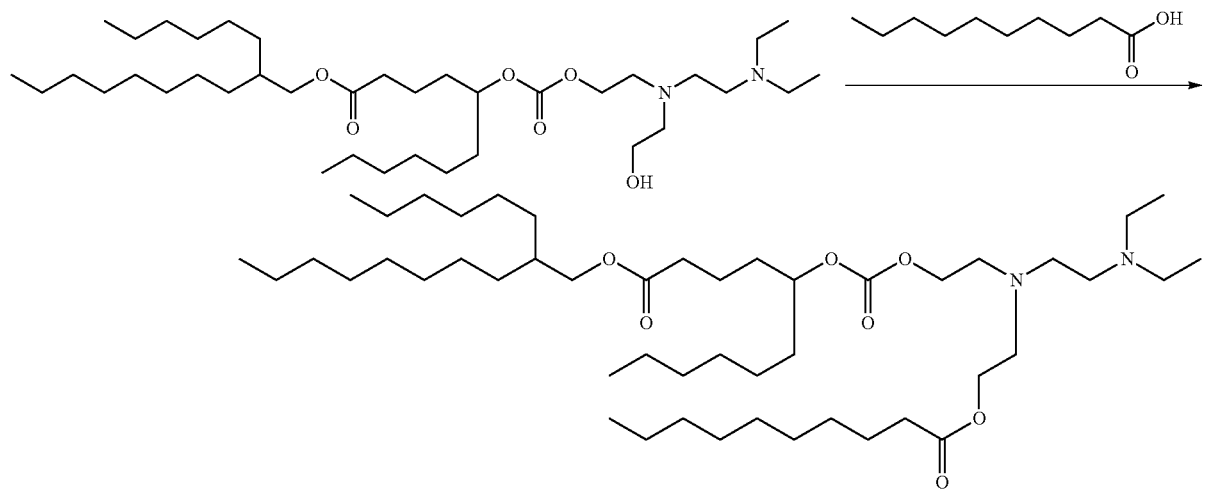

2-Hexyldecyl 6-(2-(decanoyloxy)ethyl)-3-ethyl-12-hexyl-10-oxo-9,11-dioxa-3,6-diazahexadecan-16-oate as a

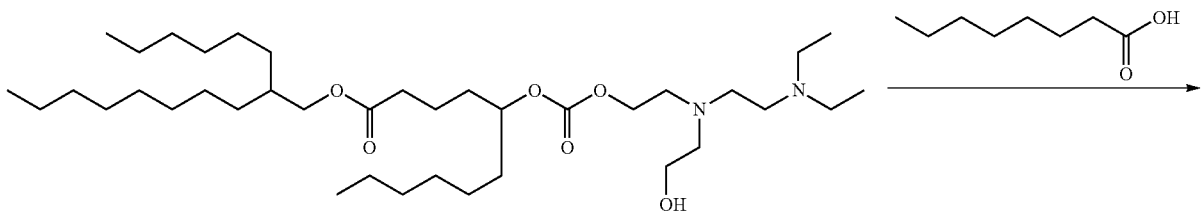

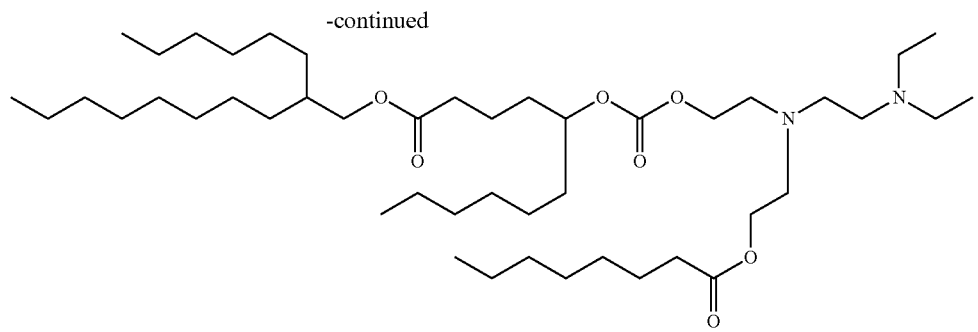

2-Hexyldecyl 3-ethyl-12-hexyl-6-(2-(octanoyloxy)ethyl)-10-oxo-9,11-dioxa-3,6-diazahexadecan-16-oate as a colorless oily substance was obtained by the same method as that in Example 109, except that octanoic acid was used instead of dodecanoic acid in Example 109.

$^1$H-NMR (CDCl$_3$) δ: 4.75-4.63 (1H, m), 4.22-4.07 (4H, m), 3.96 (2H, d, J=5.1 Hz), 2.88-2.76 (4H, m), 2.71-2.63 (2H, m), 2.58-2.45 (6H, m), 2.37-2.24 (4H, m), 1.74-1.52 (9H, m), 1.39-1.19 (40H, m), 1.02 (6H, t, J=6.6 Hz), 0.96-0.83 (12H, m).

MS m/z (M+H): 784.

Example 112

2-Decyltetradecyl 3-ethyl-12-hexyl-6-isopropyl-10-oxo-9,11-dioxa-3,6-diazahexadecan-16-oate as a colorless oily substance was obtained by the same method as that in (1) and (2) of Example 80, except that in (1) and (2) of Example 80, 2-decyltetradecan-1-ol was used instead of 2-butyloctan-1-ol, and 2-((2-(diethylamino)ethyl)(isopropyl)amino)ethan-1-ol was used instead of 2-((2-(diethylamino)ethyl)(ethyl)amino)ethan-1-ol.

$^1$H-NMR (CDCl$_3$) δ:4.75-4.63 (1H, m), 4.17-4.02 (2H, m), 3.96 (2H, d, J=5.4 Hz), 2.97-2.85 (1H, m), 2.68 (2H, t, J=6.6 Hz), 2.60-2.42 (8H, m), 2.32 (2H, t, J=7.2 Hz), 1.74-1.49 (7H, m), 1.39-1.17 (48H, m), 1.09-0.95 (12H, m), 0.94-0.81 (9H, m).

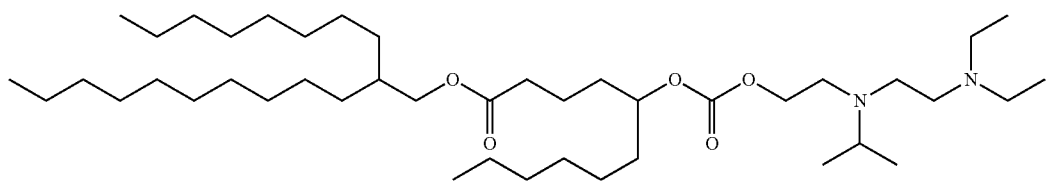 [SMILES: CCCCCCCCCCC(CCCCCCCC)COC(=O)CCCC(CCCCCC)OC(=O)OCCN(CCN(CC)CC)C(C)C]

2-Octyldodecyl 3-ethyl-12-hexyl-6-isopropyl-10-oxo-9,11-dioxa-3,6-diazahexadecan-16-oate as a colorless oily substance was obtained by the same method as that in (1) and (2) of Example 80, except that in (1) and (2) of Example 80, 2-octyldodecan-1-ol was used instead of 2-butyloctan-1-ol, and 2-((2-(diethylamino)ethyl)(isopropyl)amino)ethan-1-ol was used instead of 2-((2-(diethylamino)ethyl)(ethyl)amino)ethan-1-ol.

$^1$H-NMR (CDCl$_3$) δ: 4.75-4.63 (1H, m), 4.18-4.02 (2H, m), 3.96 (2H, d, J=6.0 Hz), 2.97-2.83 (1H, m), 2.68 (2H, t, J=7.2 Hz), 2.60-2.41 (8H, m), 2.32 (2H, t, J=6.6 Hz), 1.74-1.50 (7H, m), 1.39-1.16 (40H, m), 1.09-0.95 (12H, m), 0.93-0.80 (9H, m).

MS m/z (M+H): 712.

Example 113

MS m/z (M+H): 768.

Example 114

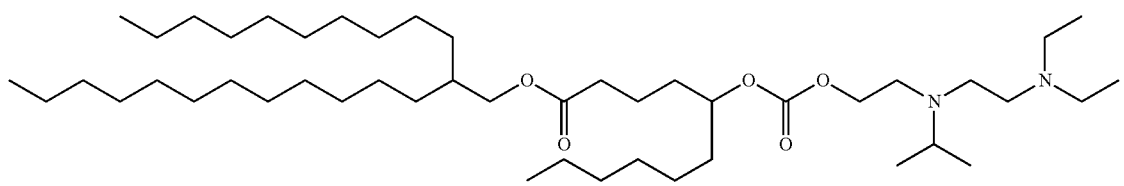 [SMILES: CCCCCCCCCCCCC(CCCCCCCCCC)COC(=O)CCCC(CCCCCC)OC(=O)OCCN(CCN(CC)CC)C(C)C]

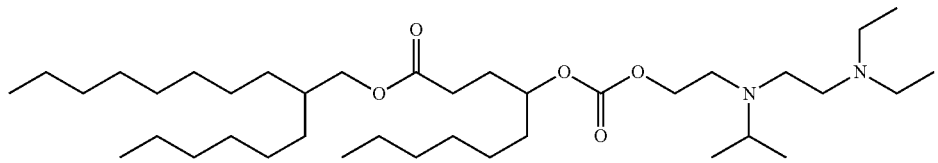 [SMILES: CCCCCCCCC(CCCCCC)COC(=O)CCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazapentadecan-15-oate as a colorless oily substance was obtained by the same method as that in (1) and (2) of Example 84, except that in (1) and (2) of Example 84, 4-ethoxy-4-oxobutanoic acid was used instead of 10-methoxy-10-oxodecanoic acid, and 2-hexyldecan-1-ol was used instead of 2-butyloctan-1-ol.

$^1$H-NMR (CDCl$_3$) δ: 4.77-4.67 (1H, m), 4.18-4.04 (2H, m), 3.97 (2H, d, J=5.4 Hz), 2.97-2.84 (1H, m), 2.68 (2H, t, J=7.5 Hz), 2.61-2.30 (10H, m), 2.02-1.78 (2H, m), 1.70-1.48 (3H, m), 1.41-1.17 (32H, m), 1.11-0.95 (12H, m), 0.94-0.81 (9H, m).

MS m/z (M+H): 642.

stance was obtained by the same method as that in (1) and (2) of Example 84, except that in (1) and (2) of Example 84, 7-ethoxy-7-oxoheptanoic acid was used instead of 10-methoxy-10-oxodecanoic acid, and 2-hexyldecan-1-ol was used instead of 2-butyloctan-1-ol.

$^1$H-NMR (CDCl$_3$) δ: 4.72-4.62 (1H, m), 4.17-4.03 (2H, m), 3.96 (2H, d, J=6.0 Hz), 2.97-2.85 (1H, m), 2.68 (2H, t, J=7.5 Hz), 2.60-2.41 (8H, m), 2.29 (2H, t, J=7.8 Hz), 1.68-1.48 (7H, m), 1.41-1.18 (36H, m), 1.08-0.95 (12H, m), 0.93-0.81 (9H, m).

MS m/z (M+H): 684.

Example 115

Example 117

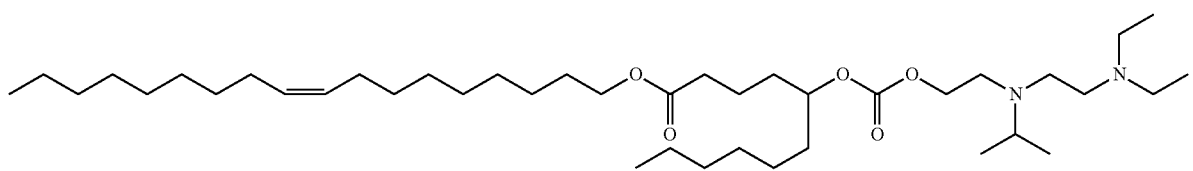 [SMILES: CCCCCCCC/C=C\CCCCCCCCOC(=O)CCCC(CCCCCC)OC(=O)OCCN(CCN(CC)CC)C(C)C]

(Z)-octadec-9-en-1-yl 3-ethyl-12-hexyl-6-isopropyl-10-oxo-9,11-dioxa-3,6-diazahexadecan-16-oate as a colorless oily substance was obtained by the same method as that in (1) and (2) of Example 80, except that in (1) and (2) of Example 80, (Z)-octadec-9-en-1-ol was used instead of 2-butyloctan-1-ol, and 2-((2-(diethylamino)ethyl)(isopropyl)amino)ethan-1-ol was used instead of 2-((2-(diethylamino)ethyl)(ethyl)amino)ethan-1-ol.

$^1$H-NMR (CDCl$_3$) δ: 5.41-5.26 (2H, m), 4.74-4.64 (1H, m), 4.15-4.01 (4H, m), 2.97-2.85 (1H, m), 2.68 (2H, t, J=6.6 Hz), 2.60-2.42 (8H, m), 2.31 (2H, t, J=7.2 Hz), 2.08-1.94 (4H, m), 1.74-1.50 (10H, m), 1.41-1.19 (28H, m), 1.07-0.95 (12H, m), 0.92-0.82 (6H, m).

MS m/z (M+H): 682.

Example 116

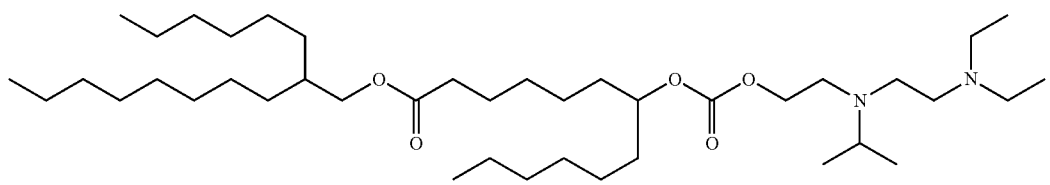 [SMILES: CCCCCCCCC(CCCCCC)COC(=O)CCCCCC(CCCCCC)OC(=O)OCCN(CCN(CC)CC)C(C)C]

2-Hexyldecyl 3-ethyl-12-hexyl-6-isopropyl-10-oxo-9,11-dioxaoctadecan-18-oate as a colorless oily sub-

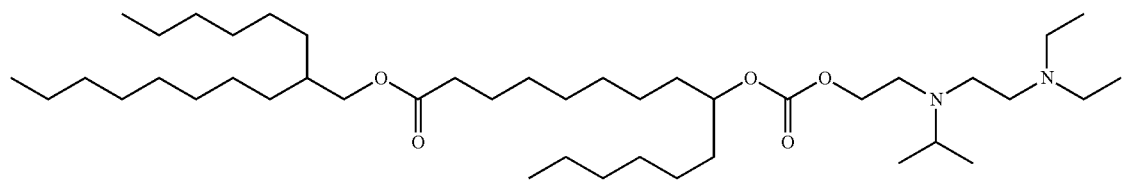 [SMILES: CCCCCCCCC(CCCCCC)COC(=O)CCCCCCCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazaicosan-20-oate as a colorless oily substance was obtained by the same method as that in (1) and (2) of Example 84, except that in (1) and (2) of Example 84, 9-methoxy-9-oxononanoic acid was used instead of 10-methoxy-10-oxodecanoic acid, and 2-hexyldecan-1-ol was used instead of 2-butyloctan-1-ol.

$^1$H-NMR (CDCl$_3$) δ: 4.73-4.61 (1H, m), 4.15-4.03 (2H, m), 3.96 (2H, d, J=5.1 Hz), 2.98-2.84 (1H, m), 2.68 (2H, t, J=6.6 Hz), 2.60-2.42 (8H, m), 2.29 (2H, t, J=7.2 Hz), 1.68-1.47 (7H, m), 1.40-1.19 (40H, m), 1.08-0.95 (12H, m), 0.93-0.81 (9H, m).

MS m/z (M+H): 712.

Example 118 less oily substance was obtained by the same method as that in Example 98, except that oleic acid was used instead of decanoic acid in Example 98.

$^1$H-NMR (CDCl$_3$) δ: 5.38-5.28 (2H, m), 4.71-4.61 (1H, m), 4.21-4.08 (4H, m), 3.96 (2H, d, J=6.0 Hz), 2.87-2.76 (4H, m), 2.71-2.63 (2H, m), 2.57-2.45 (6H, m), 2.29 (4H, t, J=7.2 Hz), 2.06-1.94 (4H, m), 1.67-1.49 (9H, m), 1.39-1.18 (62H, m), 1.02 (6H, t, J=7.2 Hz), 0.95-0.82 (12H, m).

MS m/z (M+H): 992.

Example 119

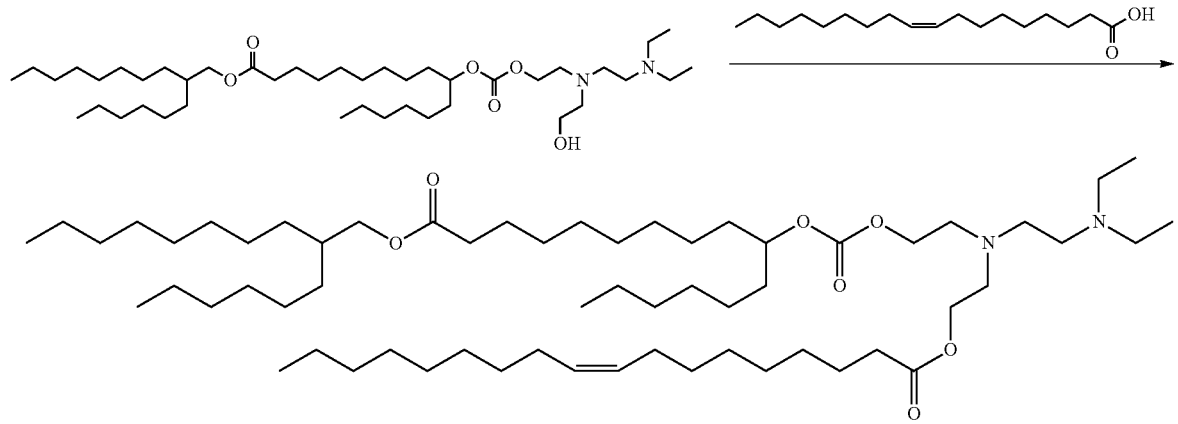

2-Hexyldecyl 3-ethyl-12-hexyl-6-(2-(oleoyloxy)ethyl)-10-oxo-9,11-dioxa-3,6-diazahenicosan-21-oate as a color-

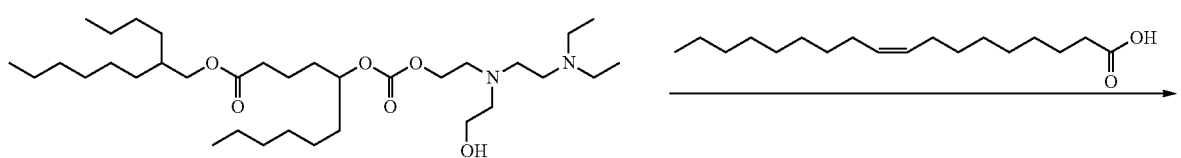

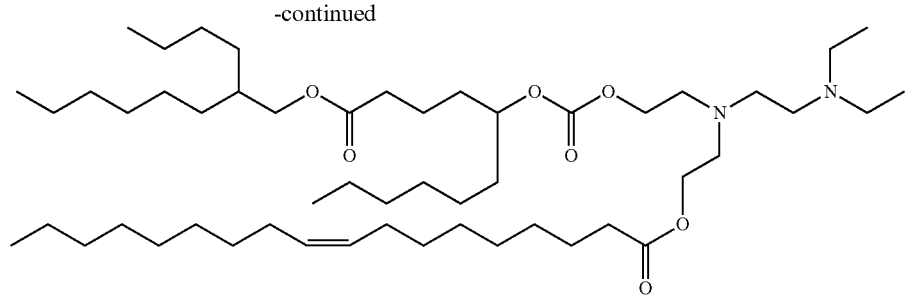

2-Butyloctyl 3-ethyl-12-hexyl-6-(2-(oleoyloxy)ethyl)-10-oxo-9,11-dioxa-3,6-diazahexadecan-16-oate as a colorless oily substance was obtained by the same method as that in Example 106, except that oleic acid was used instead of dodecanoic acid in Example 106.

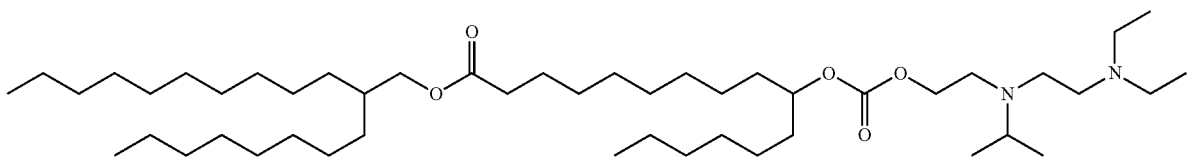 [SMILES: CCCCCCCCCCC(CCCCCCCC)COC(=O)CCCCCCCCC(CCCCCC)OC(=O)OCCN(CCN(CC)CC)C(C)C]

$^1$H-NMR (CDCl$_3$) δ: 5.40-5.28 (2H, m), 4.74-4.63 (1H, m), 4.22-4.07 (4H, m), 3.97 (2H, d, J=6.0 Hz), 2.88-2.76 (4H, m), 2.73-2.62 (2H, m), 2.59-2.45 (6H, m), 2.37-2.25 (4H, m), 2.08-1.94 (4H, m), 1.73-1.50 (9H, m), 1.41-1.18 (44H, m), 1.02 (6H, t, J=6.6 Hz), 0.96-0.82 (12H, m).

MS m/z (M+H): 866.

2-Hexyldecyl 3-ethyl-12-hexyl-6-(2-(oleoyloxy)ethyl)-10-oxo-9,11-dioxa-3,6-diazahexadecan-16-oate as a colorless oily substance was obtained by the same method as that in Example 109, except that oleic acid was used instead of dodecanoic acid in Example 109.

$^1$H-NMR (CDCl$_3$) δ: 5.40-5.28 (2H, m), 4.73-4.64 (1H, m), 4.21-4.07 (4H, m), 3.96 (2H, d, J=5.1 Hz), 2.88-2.76 (4H, m), 2.72-2.62 (2H, m), 2.58-2.45 (6H, m), 2.37-2.24 (4H, m), 2.07-1.94 (4H, m), 1.73-1.51 (9H, m), 1.39-1.19 (52H, m), 1.02 (6H, t, J=6.6 Hz), 0.94-0.81 (12H, m).

MS m/z (M+H): 922.

Example 121

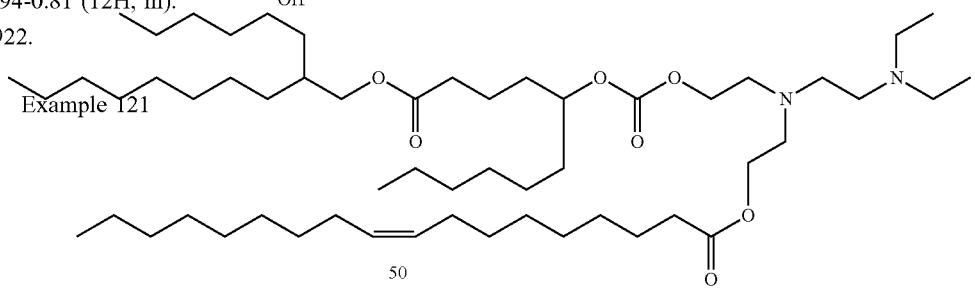

2-Octyldodecyl 3-ethyl-12-hexyl-6-isopropyl-10-oxo-9,11-dioxa-3,6-diazahenicosan-21-oate as a colorless oily substance was obtained by the same method as that in (1) and (2) of Example 84, except that 2-octyldodecan-1-ol was used instead of 2-butyloctan-1-ol in (1) and (2) of Example 84.

$^1$H-NMR (CDCl$_3$) δ: 4.73-4.61 (1H, m), 4.15-4.06 (2H, m), 3.96 (2H, d, J=6.0 Hz), 2.97-2.84 (1H, m), 2.68 (2H, t, J=6.6 Hz), 2.59-2.42 (8H, m), 2.29 (2H, t, J=8.1 Hz), 1.68-1.48 (7H, m), 1.38-1.19 (50H, m), 1.09-0.96 (12H, m), 0.93-0.82 (9H, m).

MS m/z (M+H): 782.

Example 122

(1)

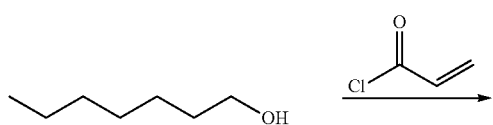

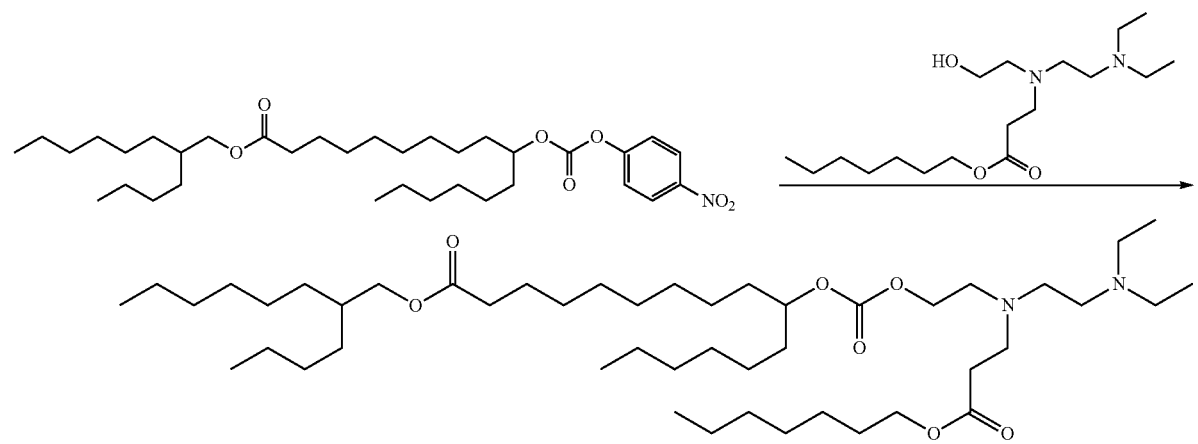

-continued

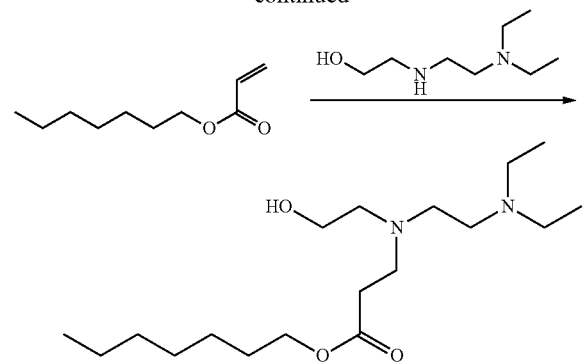

Acrylic acid chloride (0.45 mL) was added to a mixture of heptan-1-ol (0.86 mL), triethylamine (1.55 mL), and tetrahydrofuran (5.00 mL) under ice cooling, and the mixture was stirred at room temperature for 2 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining heptyl acrylate (0.57 g) as a colorless oily substance.

Triethylamine (1.24 mL) was added to a mixture of the obtained heptyl acrylate (0.57 g), 2-((2-(diethylamino)ethyl)amino)ethan-1-ol dihydrochloride (0.52 g), and tetrahydrofuran (10 mL), and the mixture was stirred and heated under reflux for 8 hours. The reaction mixture was cooled to room temperature, and the solvent was distilled away under reduced pressure. The obtained residue was purified by silica gel column chromatography (ethyl acetate-hexane, NH silica gel), thereby obtaining heptyl 3-((2-(diethylamino)ethyl)(2-hydroxyethyl)amino)propanoate (0.21 g) as a colorless oily substance.

MS m/z (M+H): 331.

(2)

2-Butyloctyl 3-ethyl-6-(3-(heptyloxy)-3-oxopropyl)-12-hexyl-10-oxo-9,11-dioxa-3,6-diazahenicosan-21-oate as a colorless oily substance was obtained by the same method as that in (2) of Example 84, except that heptyl 3-((2-(diethylamino)ethyl)(2-hydroxyethyl)amino)propanoate was used instead of 2-((2 (diethylamino)ethyl)(isopropyl)amino)ethan-1-ol in (2) of Example 84.

$^1$H-NMR (CDCl$_3$) δ: 4.72-4.61 (1H, in), 4.20-4.11 (2H, in), 4.06 (2H, t, J=6.6 Hz), 3.96 (2H, d, J=6.0 Hz), 2.87 (2H, t, J=6.6 Hz), 2.77 (2H, d, J=6.0 Hz), 2.64-2.41 (10H, in), 2.29 (2H, t, J=7.2 Hz), 1.66-1.50 (9H, in), 1.37-1.22 (42H, in), 1.02 (6H, t, J=6.6 Hz), 0.92-0.84 (12H, in).

MS m/z (M+H): 798.

Example 123

(1)

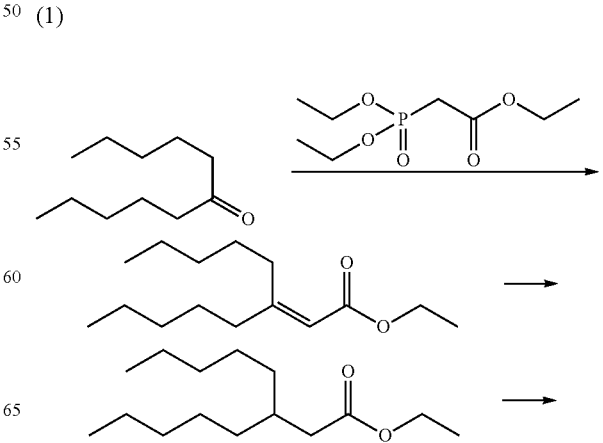

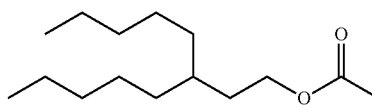

-continued

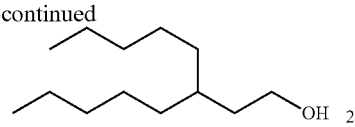

Ethyl 2-(diethoxyphosphoryl)acetate (18.8 mL) was added dropwise to a tetrahydrofuran (80 mL) suspension of 60% wt sodium hydride (3.3 g) under ice cooling, and the mixture was stirred at the same temperature for 30 minutes. Undecan-6-one (2.0 g) was added to the reaction mixture, and the reaction mixture was stirred and heated under reflux for 5 hours. The reaction mixture was cooled to room temperature and poured into ice water, and then ethyl acetate was added thereto. The organic layer was separated and washed with a saturated aqueous sodium chloride solution, the solvent was then distilled away under reduced pressure, and the obtained residue was purified by silica gel column chromatography (ethyl acetate-hexane), thereby obtaining ethyl 3-pentyloct-2-enoate (2.8 g) as a colorless oily substance.

$^{1}$H-NMR (CDCl$_{3}$) δ: 5.61 (1H, s), 4.14 (2H, q, J=6.6 Hz), 2.58 (2H, t, J=7.2 Hz), 2.12 (2H, t, J=7.2 Hz), 1.50-1.20 (15H, m), 0.89 (6H, t, J=6.6 Hz).

Ammonium formate (4.4 g) was added to a mixture of ethyl 3-pentyloct-2-enoate (2.8 g), 10% palladium-carbon (0.84 g), and methanol (56 mL), and the mixture was stirred and heated under reflux for 3 hours. The reaction mixture was cooled to room temperature, the insoluble matters were filtered off using celite, and then the solvent was distilled away under reduced pressure. The obtained residue was purified by silica gel column chromatography (ethyl acetate-hexane), thereby obtaining ethyl 3-pentyloctanoate (2.8 g) as a colorless oily substance.

$^{1}$H-NMR (CDCl$_{3}$) δ: 4.12 (2H, q, J=7.2 Hz), 2.22 (2H, t, J=6.6 Hz), 2.05-2.04 (1H, m), 1.34-1.20 (19H, m), 0.88 (6H, t, J=6.6 Hz).

A tetrahydrofuran (10 mL) solution of ethyl 3-pentyloctanoate (2.8 g) was added dropwise to a mixture of a 2.5 mol/L lithium aluminum hydride-tetrahydrofuran solution (9.3 mL) and tetrahydrofuran (50 mL) under ice cooling, and the mixture was stirred at the same temperature for 30 minutes and then stirred at room temperature for 2 hours. Ethyl acetate was added to the reaction mixture, the reaction mixture was poured into ice water under ice cooling, and then the insoluble matters were filtered off using celite. The organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 3-pentyloctan-1-ol (2.4 g) as a colorless oily substance.

$^{1}$H-NMR (CDCl$_{3}$) δ: 3.62 (2H, t, J=6.6 Hz), 1.55-1.20 (21H, m), 0.88 (6H, t, J=6.6 Hz).

(1) 3-Pentyloctyl 10-(((4-nitrophenoxy)carbonyl)oxy)hexadecanoate as a colorless oily substance was obtained by the same method as that in (1) of Example 84, except that 3-pentyloctan-1-ol was used instead of 2-butyloctan-1-ol in (1) of Example 84.

$^{1}$H-NMR (CDCl$_{3}$) δ: 8.31-8.25 (2H, m), 7.41-7.36 (2H, m), 4.86-4.77 (1H, m), 3.97 (2H, d, J=5.4 Hz), 2.30 (2H, t, J=7.5 Hz), 1.72-1.20 (43H, m), 0.92-0.85 (9H, m).

(2)

(3)

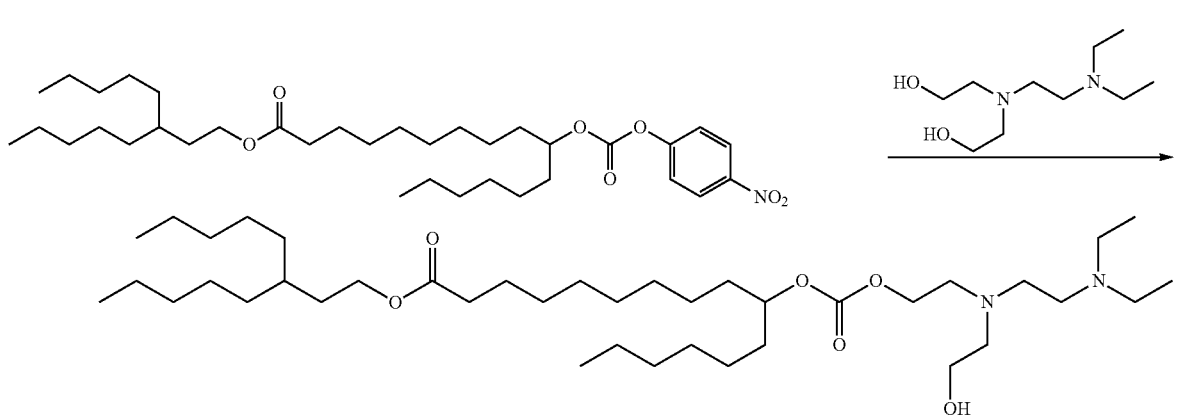

3-Pentyloctyl 3-ethyl-12-hexyl-6-(2-hydroxyethyl)-10-oxo-9,11-dioxa-3,6-diazahenicosan-21-oate as a colorless oily substance was obtained by the same method as that in (2) of Example 85, except that 3-pentyloctyl 10-(((4-nitrophenoxy)carbonyl)oxy)hexadecanoate was used instead of 2-butyloctyl 10-(((4-nitrophenoxy)carbonyl)oxy)hexadecanoate in (2) of Example 85.

$^{1}$H-NMR (CDCl$_{3}$) δ: 4.74-4.06 (1H, m), 4.20 (2H, t, J=6.0 Hz), 4.08 (2H, t, J=6.6 Hz), 3.54 (2H, t, J=4.5 Hz), 2.88 (2H, t, J=5.7 Hz), 2.75-2.63 (4H, m), 2.60-2.41 (6H, m), 2.28

(2H, t, J=7.8 Hz), 1.72-1.47 (8H, m), 1.44-1.14 (35H, m), 1.03 (6H, t, J=7.2 Hz), 0.94-0.81 (9H, m).

MS m/z (M+H): 686.

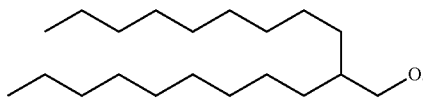

Example 124

(1)

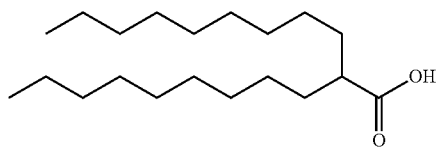 [SMILES: CCCCCCCCCC(CCCCCCCCC)C(=O)O]

2-Nonylundecanoate as a colorless oily substance was obtained by the same method as that in (1) of Example 74, except that in (1) of Example 74, undecanoic acid was used instead of decanoic acid, and 1-iodononane was used instead of 1-iodooctane.

$^1$H-NMR (CDCl$_3$) δ: 2.29-2.41 (1H, m), 1.68-1.20 (32H, m), 0.88 (6H, t, J=6.6 Hz).

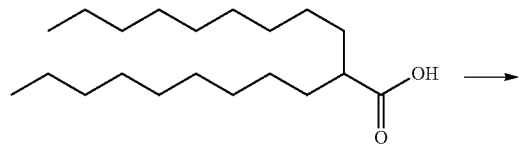

-continued

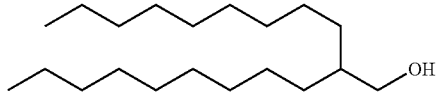

A tetrahydrofuran (10 mL) solution of 2-nonylundecanoate (3.0 g) was added dropwise to a mixture of a 2.5 mol/L lithium aluminum hydride-tetrahydrofuran solution (7.6 mL) and tetrahydrofuran (60 mL) under ice cooling, and the mixture was stirred at the same temperature for 30 minutes and then stirred at room temperature for 6 hours. Ethyl acetate was added to the reaction mixture, the reaction mixture was poured into ice water under ice cooling, and then the insoluble matters were filtered off using celite. The organic layer was separated, washed with a saturated aqueous sodium chloride solution, and then dried over anhydrous sodium sulfate, and the solvent was distilled off under reduced pressure. The obtained residue was purified by silica gel column chromatography (ethyl acetate-hexane), thereby obtaining 2-nonylundecan-1-ol (2.8 g) as a colorless oily substance.

$^1$H-NMR (CDCl$_3$) δ: 3.57-3.51 (2H, m), 1.50-1.20 (33H, m), 0.88 (6H, t, J=6.6 Hz).

MS m/z (M+H): 712.

Example 125

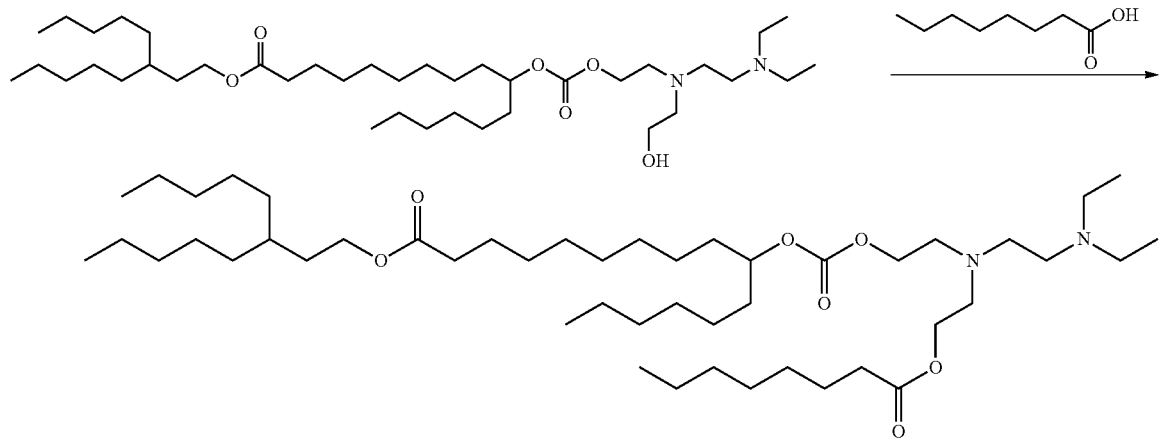

3-Pentyloctyl 3-ethyl-12-hexyl-6-(2-(octanoyloxy)ethyl)-10-oxo-9,11-dioxa-3,6-diazahenicosan-21-oate as a colorless oily substance was obtained by the same method as that in Example 86, except that in Example 86, 3-pentyloctyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and octanoic acid was used instead of dodecanoic acid.

$^1$H-NMR (CDCl$_3$) δ: 4.72-4.61 (1H, m), 4.21-4.02 (6H, m), 2.88-2.75 (4H, m), 2.71-2.62 (2H, m), 2.58-2.45 (6H, m), 2.34-2.22 (4H, m), 1.68-1.48 (10H, m), 1.44-1.17 (43H, m), 1.02 (6H, t, J=6.6 Hz), 0.94-0.81 (12H, m).

MS m/z (M+H): 812.

Example 126 of Example 84, a 1.0 mol/L pentyl magnesium bromide-tetrahydrofuran solution was used instead of a 1.0 mol/L hexyl magnesium bromide-diethyl ether solution, and 2-hexyldecan-1-ol was used instead of 2-butyloctan-1-ol.

$^1$H-NMR (CDCl$_3$) δ: 8.31-8.25 (2H, m), 7.41-7.35 (2H, m), 4.87-4.75 (1H, m), 3.96 (2H, d, J=6.0 Hz), 2.30 (2H, t, J=7.2 Hz), 1.72-1.20 (47H, m), 0.93-0.83 (9H, m).

(2)

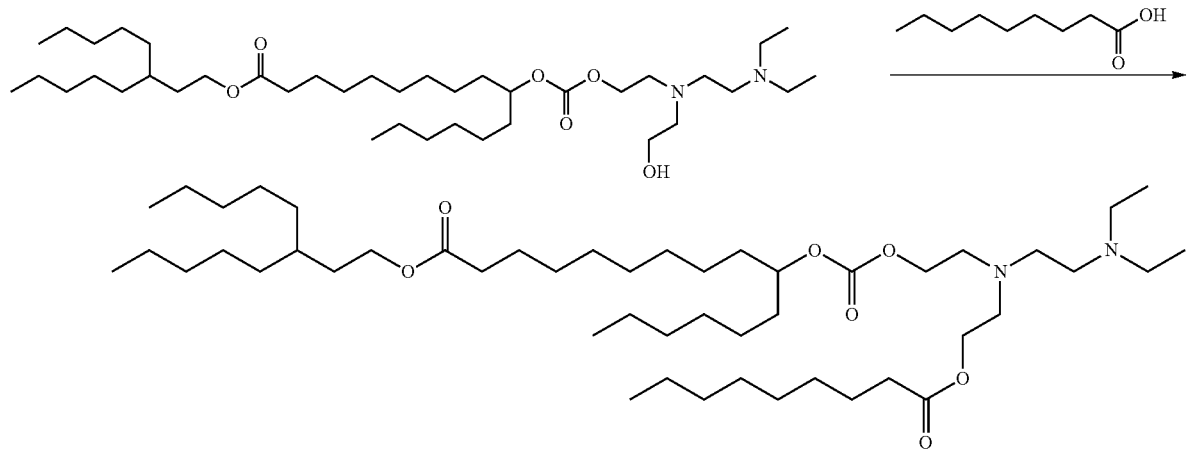

3-Pentyloctyl 3-ethyl-12-hexyl-6-(2-(nonanoyloxy)ethyl)-10-oxo-9,11-dioxa-3,6-diazahenicosan-21-oate as a colorless oily substance was obtained by the same method as that in Example 86, except that in Example 86, 3-pentyloctyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and nonanoic acid was used instead of dodecanoic acid.

$^1$H-NMR (CDCl$_3$) δ: 4.73-4.59 (1H, m), 4.23-4.01 (6H, m), 2.90-2.76 (4H, m), 2.72-2.62 (2H, m), 2.58-2.45 (6H, m), 2.35-2.22 (4H, m), 1.69-1.47 (10H, m), 1.44-1.18 (45H, m), 1.02 (6H, t, J=7.5 Hz), 0.96-0.80 (12H, m).

MS m/z (M+H): 826.

Example 127

(1)

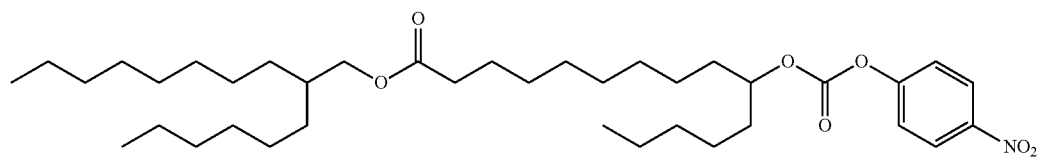 [SMILES: CCCCCCCCC(CCCCCC)COC(=O)CCCCCCCCC(CCCCC)OC(=O)Oc1ccc([N+](=O)[O-])cc1]

2-Hexyldecyl 10-(((4-nitrophenoxy)carbonyl)oxy)pentadecanate as a colorless oily substance was obtained by the same method as that in (1) of Example 84, except that in (1)

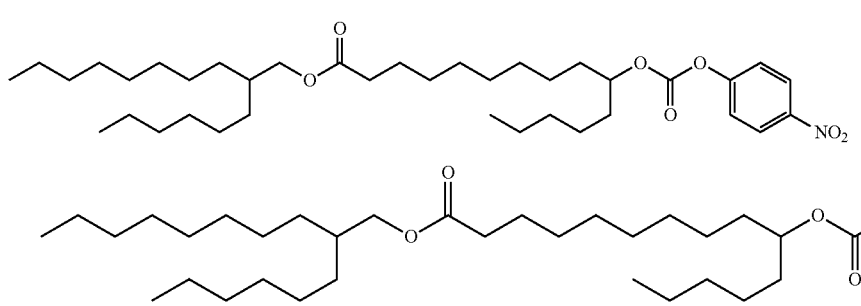

2-Hexyldecyl 3-ethyl-6-isopropyl-10-oxo-12-pentyl-9,11-dioxa-3,6-diazahenicosan-21-oate as a colorless oily substance was obtained by the same method as that in (2) of Example 84, except that 2-hexyldecyl 10-(((4-nitrophenoxy)carbonyl)oxy)pentadecanoate was used instead of 2-butyloctyl 10-(((4-nitrophenoxy)carbonyl)oxy)hexadecanoate in (2) of Example 84.

¹H-NMR (CDCl₃) δ: 4.72-4.62 (1H, m), 4.10 (2H, t, J=6.6 Hz), 3.96 (2H, d, J=6.0 Hz), 2.98-2.82 (1H, m), 2.68 (2H, t, J=6.6 Hz), 2.59-2.42 (8H, m), 2.29 (2H, t, J=7.2 Hz), 1.66-1.47 (7H, m), 1.40-1.18 (40H, m), 1.06-0.96 (12H, m), 0.92-0.84 (9H, m).

MS m/z (M+H): 712.

Example 128

(1)

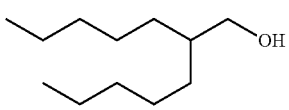

2-Pentylheptan-1-ol as a colorless oily substance was obtained by the same method as that in (2) of Example 124, except that 2-pentylheptanoate was used instead of 2-nonylundecanoate in (2) of Example 124.

¹H-NMR (CDCl₃) δ: 3.57-3.51 (2H, m), 1.50-1.20 (17H, m), 0.88 (6H, t, J=6.6 Hz).

(2)

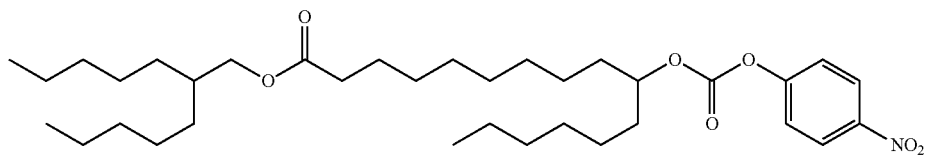 [SMILES: CCCCCCC(CCCCCCCCC(=O)OCC(CCCCC)CCCCC)OC(=O)Oc1ccc([N+](=O)[O-])cc1]

2-Pentylheptyl 10-(((4-nitrophenoxy)carbonyl)oxy)hexadecanoate as a colorless oily substance was obtained by the same method as that in (1) of Example 84, except that 2-pentylheptan-1-ol was used instead of 2-butyloctan-1-ol in (1) of Example 84.

¹H-NMR (CDCl₃) δ: 8.28 (2H, dd, J=7.2 Hz, 2.1 Hz), 7.39 (2H, dd, J=7.2 Hz, 2.1 Hz), 4.86-4.76 (1H, m), 3.97 (2H, d, J=6.0 Hz), 2.30 (2H, t, J=7.2 Hz), 1.74-1.20 (41H, m), 0.92-0.85 (9H, m).

(3)

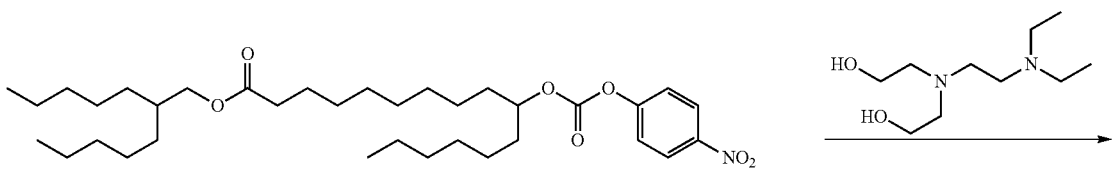

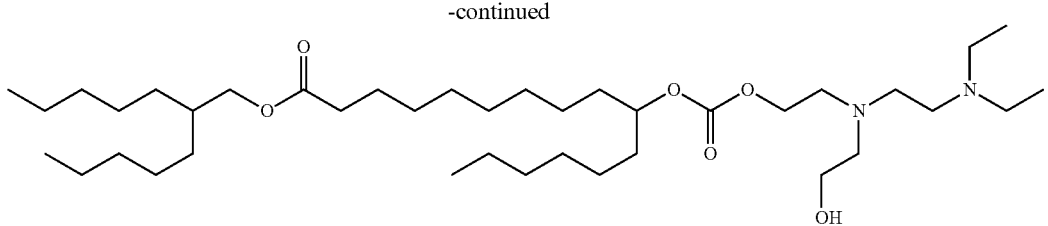

2-Pentylheptyl 3-ethyl-12-hexyl-6-(2-hydroxyethyl)-10-oxo-9,11-dioxa-3,6-diazahenicosan-21-oate as a colorless oily substance was obtained by the same method as that in (2) of Example 85, except that 2-pentylheptyl 10-(((4-nitrophenoxy)carbonyl)oxy)hexadecanoate was used instead of 2-butyloctyl 10-(((4-nitrophenoxy)carbonyl)oxy)hexadecanoate in (2) of Example 85.

$^1$H-NMR (CDCl$_3$) δ: 4.73-4.61 (1H, m), 4.20 (2H, t, J=6.0 Hz), 3.97 (2H, d, J=5.4 Hz), 3.54 (2H, t, J=4.5 Hz), 2.88 (2H, t, J=6.6 Hz), 2.74-2.64 (4H, m), 2.59-2.44 (6H, m), 2.29 (2H, t, J=7.2 Hz), 1.75-1.45 (7H, m), 1.40-1.19 (34H, m), 1.02 (6H, t, J=7.2 Hz), 0.92-0.84 (9H, m).

MS m/z (M+H): 672.

Example 129 that in Example 86, except that in Example 86, 2-pentylheptyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and octanoic acid was used instead of dodecanoic acid.

$^1$H-NMR (CDCl$_3$) δ: 4.73-4.61 (1H, m), 4.21-4.07 (4H, m), 3.97 (2H, d, J=5.4 Hz), 2.88-2.77 (4H, m), 2.72-2.62 (2H, m), 2.58-2.45 (6H, m), 2.29 (4H, t, J=7.2 Hz), 1.69-1.48 (9H, m), 1.41-1.18 (42H, m), 1.02 (6H, t, J=7.2 Hz), 0.94-0.82 (12H, m).

MS m/z (M+H): 798.

Example 130

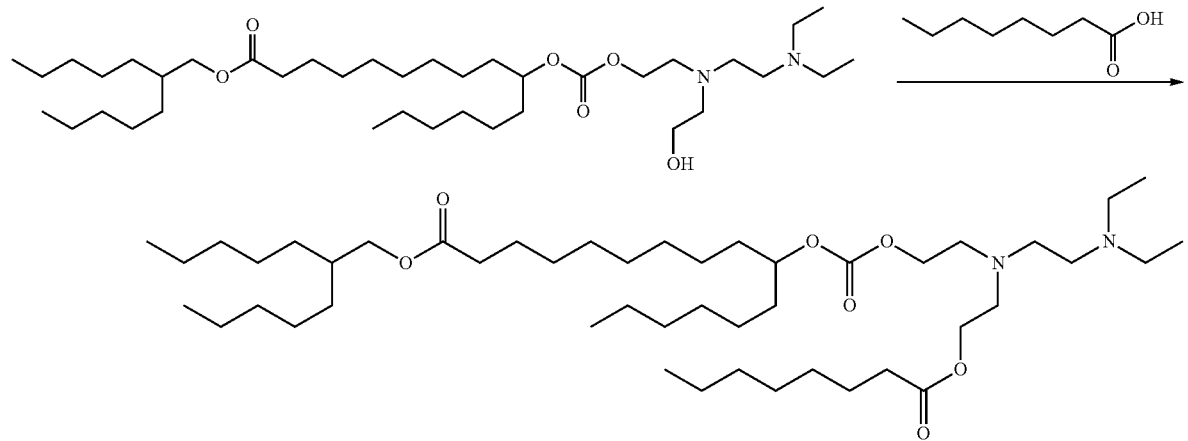

2-Pentylheptyl 3-ethyl-12-hexyl-6-(2-(octanoyloxy)ethyl)-10-oxo-9,11-dioxa-3,6-diazahenicosan-21-oate as a colorless oily substance was obtained by the same method as

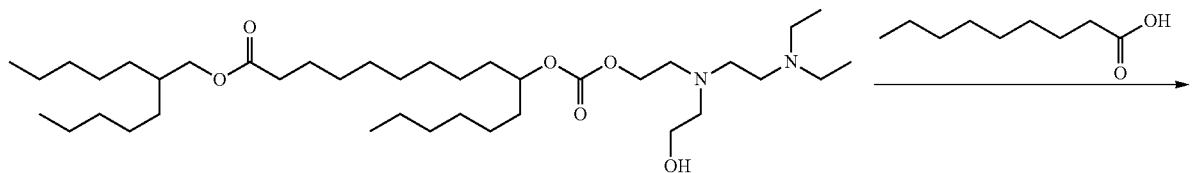

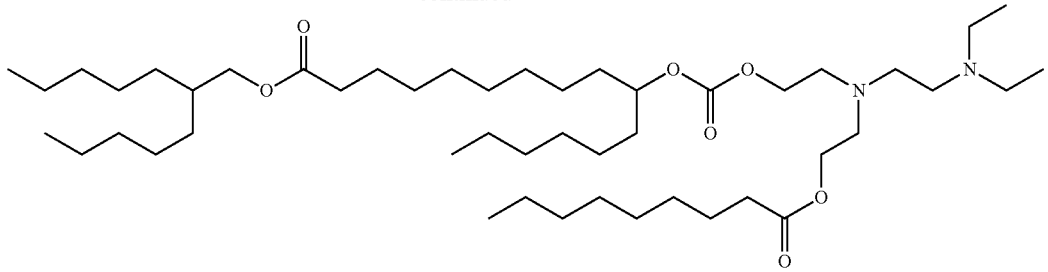

2-Pentylheptyl 3-ethyl-12-hexyl-6-(2-(nonanoyloxy)ethyl)-10-oxo-9,11-dioxa-3,6-diazahenicosan-21-oate as a colorless oily substance was obtained by the same method as that in Example 86, except that in Example 86, 2-pentylheptyl 3-ethyl-12-hexyl-6-(2-hydroxyethyl)-10-oxo-9,11-dioxa-3,6-diazahenicosane-21-oate was used instead of 2-butyloctyl 3-ethyl-12-hexyl-6-(2-hydroxyethyl)-10-oxo-9,11-dioxa-3,6-diazahenicosan-21-oate, and nonanoic acid was used instead of dodecanoic acid.

¹H-NMR (CDCl₃) δ: 4.72-4.61 (1H, m), 4.22-4.08 (4H, m), 3.97 (2H, d, J=6.0 Hz), 2.88-2.75 (4H, m), 2.72-2.62 (2H, m), 2.60-2.46 (6H, m), 2.29 (4H, t, J=7.5 Hz), 1.70-1.47 (9H, m), 1.41-1.18 (44H, m), 1.02 (6H, t, J=6.6 Hz), 0.95-0.81 (12H, m).

MS m/z (M+H): 812.

Example 131 oily substance was obtained by the same method as that in (2) of Example 85, except that 2-hexyldecyl 10-(((4-nitrophenoxy)carbonyl)oxy)pentadecanoate was used instead of 2-butyloctyl 10-(((4-nitrophenoxy)carbonyl)oxy)hexadecanoate in (2) of Example 85.

¹H-NMR (CDCl₃) δ: 4.74-4.62 (1H, m), 4.20 (2H, t, J=6.0 Hz), 3.96 (2H, d, J=5.7 Hz), 3.54 (2H, t, J=4.5 Hz), 2.89 (2H, t, J=6.0 Hz), 2.75-2.64 (4H, m), 2.60-2.43 (6H, m), 2.29 (2H, t, J=7.8 Hz), 1.67-1.49 (7H, m), 1.41-1.19 (40H, m), 1.02 (6H, t, J=7.2 Hz), 0.94-0.82 (9H, m).

MS m/z (M+H): 714.

Example 132

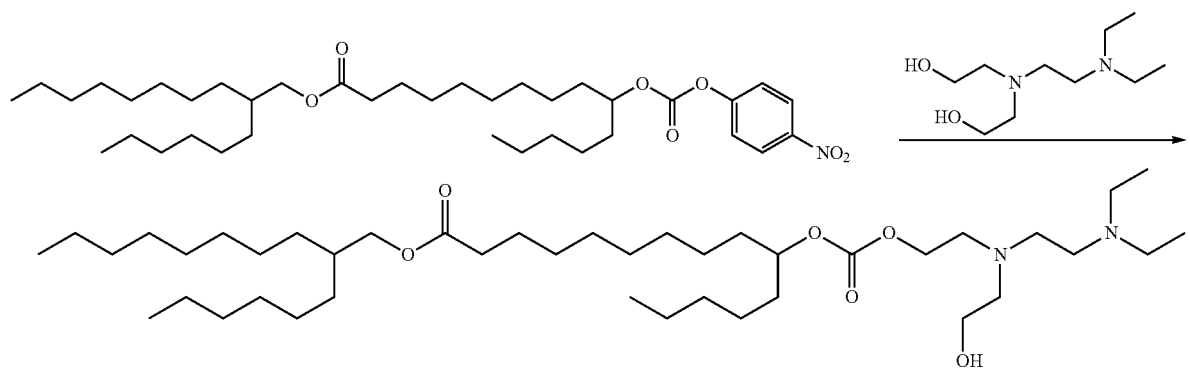

2-Hexyldecyl 3-ethyl-6-(2-hydroxyethyl)-10-oxo-12-pentyl-9,11-dioxa-3,6-diazahenicosan-21-oate as a colorless

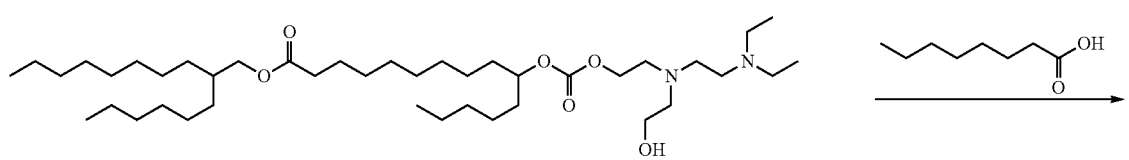

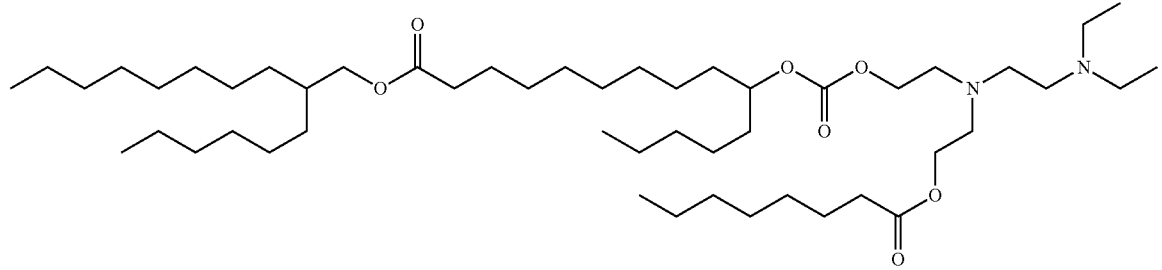

2-Hexyldecyl 3-ethyl-6-(2-(octanoyloxy)ethyl)-10-oxo-12-pentyl-9,11-dioxa-3,6-diazahenicosan-21-oate as a colorless oily substance was obtained by the same method as that in Example 86, except that in Example 86, 2-hexyldecyl 3-ethyl-6-(2-hydroxyethyl)-10-oxo-12-pentyl-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and octanoic acid was used instead of dodecanoic acid.

$^1$H-NMR (CDCl$_3$) δ: 4.72-4.61 (1H, m), 4.22-4.06 (4H, m), 3.96 (2H, d, J=6.0 Hz), 2.88-2.76 (4H, m), 2.72-2.62 (2H, m), 2.58-2.45 (6H, m), 2.29 (4H, t, J=7.2 Hz), 1.68-1.48 (9H, m), 1.39-1.18 (48H, m), 1.02 (6H, t, J=6.6 Hz), 0.94-0.82 (12H, m).

MS m/z (M+H): 840.

Example 133

(1)

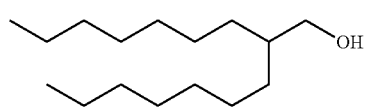 [SMILES: CCCCCCCC(CO)CCCCCCC]

2-Heptylnonan-1-ol as a colorless oily substance was obtained by the same method as that in (1) and (2) of Example 124, except that in (1) and (2) of Example 124, nonanoic acid was used instead of undecanoic acid, and 1-iodoheptane was used instead of 1-iodononane.

$^1$H-NMR (CDCl$_3$) δ: 3.57-3.51 (2H, m), 1.50-1.20 (25H, m), 0.88 (6H, t, J=6.6 Hz).

(2)

2-Heptylnonyl 3-ethyl-12-hexyl-6-isopropyl-10-oxo-9,11-dioxa-3,6-diazahenicosan-21-oate as a colorless oily substance was obtained by the same method as that in (1) and (2) of Example 84, except that 2-heptylnonan-1-ol was used instead of 2-butyloctan-1-ol in (1) and (2) of Example 84.

$^1$H-NMR (CDCl$_3$) δ: 4.72-4.62 (1H, m), 4.10 (2H, t, J=6.6 Hz), 3.96 (2H, d, J=6.0 Hz), 2.97-2.85 (1H, m), 2.68 (2H, t, J=6.9 Hz), 2.60-2.41 (8H, m), 2.29 (2H, t, J=7.2 Hz), 1.67-1.47 (7H, m), 1.39-1.19 (42H, m), 1.08-0.95 (12H, m), 0.94-0.82 (9H, m).

MS m/z (M+H): 726.

Comparative Example 8

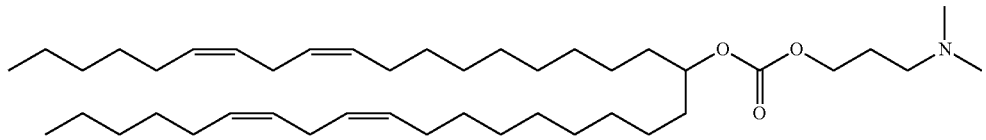

3-(Dimethylamino)propyl((6Z,9Z,28Z,31Z)-heptatriaconta-6,9,28,31-tetraen-19-yl)carbonate was obtained according to the method described in WO2015/005253.

$^1$H-NMR (CDCl$_3$) δ: 5.44-5.27 (8H, m), 4.73-4.62 (1H, m), 4.18 (2H, t, J=6.6 Hz), 2.77 (4H, t, J=6.0 Hz), 2.36 (2H, t, J=7.2 Hz), 2.22 (6H, s), 2.09-1.98 (8H, m), 1.90-1.79 (2H, m), 1.61-1.51 (4H, m), 1.41-1.20 (36H, m), 0.89 (6H, t, J=6.0 Hz).

MS m/z (M+H): 659.

Comparative Example 9

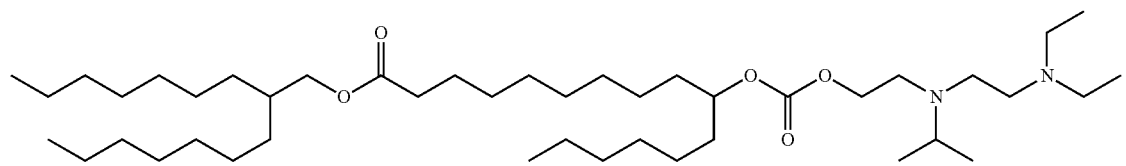 [SMILES: CCCCCCCC(CCCCCCC)COC(=O)CCCCCCCCC(CCCCCC)OC(=O)OCCN(CCN(CC)CC)C(C)C]

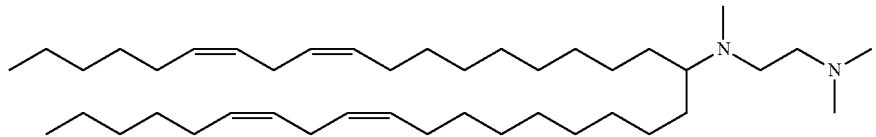 [SMILES: CCCCC/C=C\C/C=C\CCCCCCCCC(CCCCCCCC/C=C\C/C=C\CCCCC)N(C)CCN(C)C]

N1-((6Z,9Z,28Z,31Z)-heptatriaconta-6,9,28,31-tetraen-19-yl)-N1,N2,N2-trimethylethane-1,2-diamine was obtained according to the method described in WO2013/059496.

$^1$H-NMR (CDCl$_3$) δ: 5.43-5.28 (8H, m), 2.78 (4H, t, J=6.0 Hz), 2.53-2.46 (2H, m), 2.38-2.30 (3H, m), 2.24 (6H, s), 2.20 (3H, s), 2.09-2.01 (8H, m), 1.42-1.20 (40H, m), 0.89 (6H, t, J=6.6 Hz).

MS m/z (M+H): 614.

<Preparation of Lipid Particles>

The compounds described in Examples 1, 9, and 10,1,2-distearoyl-sn-glycero-3-phosphocholine (trade name: COATSOME® MC-8080; NOF corporation), cholesterol (trade name: Cholesterol HP; NIPPON FINE CHEMICAL CO., LTD.), and 1,2-dimyristoyl-rac-glycero-3-(methylpolyoxyethylene 2000) (hereinafter, called DMG-PEG2000) (trade name: SUNBRIGHT® GM-020; NOF corporation) were dissolved in ethanol at a molar ratio of 50/10/38.5/1.5 such that the total lipid concentration became 20 mmol/L, thereby obtaining an oil phase.

A 10 mmol/L acetate buffer having a pH of 4 was used as a water phase and mixed with the oil phase by a micromixer (see JP5288254B) using a syringe pump such that the volume ratio of water phase:oil phase became 6.7:3.3. The mixed solution was diluted 2× with a phosphate buffered saline (PBS), thereby obtaining a dispersion liquid of lipid particles. The dispersion liquid was dialyzed using a dialysis cassette (Slide-A-Lyzer G2, MWCO: 10 kD, Thermo Fisher Scientific) including PBS such that ethanol was removed, thereby obtaining lipid particles containing the compounds described in Examples 1, 9, and 10.

Measurement of Particle Size

By using the dispersion liquid of lipid particles as it was, the particle size of the lipid particles was measured using a zeta potential/particle size measurement system ELS-Z2 (Otsuka Electronics Co., Ltd.). The results are shown in Table 1.

TABLE 1

Data on particle size of lipid particles

| Used lipid | Particle size (nm) |
| --- | --- |
| Example 1 | 145.9 |
| Example 9 | 127.5 |
| Example 10 | 111.2 |

As is evident from the results in Table 1, the average particle size of the prepared lipid particles was 100 to 150 nm.

<Preparation of Nucleic Acid Lipid Particles>

The compounds described in Table 2, L-α-distearoylphosphatidylcholine (trade name: COATSOME® MC-8080; NOF corporation), cholesterol (trade name: Cholesterol HP; NIPPON FINE CHEMICAL CO., LTD.), and 1,2-dimyristoyl-rac-glycero-3-(methylpolyoxyethylene 2000) (hereinafter, called DMG-PEG2000) (trade name: SUNBRIGHT® GM-020; NOF corporation) were dissolved in ethanol at a molar ratio of 50/10/38.5/1.5 such that the total lipid concentration became 20 mmol/L, thereby obtaining an oil phase.

An aqueous nucleic acid solution obtained by dissolving 5 mg of Luc2-siRNA having the sequence described in Biomacromolecules (2013) 14, p. 3905 in 1 mL of sterile water was diluted with 10 mmol/L acetate buffer having a pH 4 such that the nucleic acid concentration became 19.7 μmol/L, thereby obtaining a water phase. Then, the water phase and the oil phase were mixed together by a micromixer (see JP5288254B) using a syringe pump such that the volume ratio of water phase:oil phase became 3:1 (final ratio of siRNA/lipid=339 (mol/mol)), and the mixed solution was diluted 2× with PBS, thereby obtaining a dispersion liquid of nucleic acid lipid particles. The dispersion liquid was dialyzed (Slide-A-Lyzer G2, MWCO: 10 kD, Thermo Fisher Scientific) using a phosphate buffered saline such that ethanol was removed, thereby obtaining nucleic acid lipid particles.

Measurement of Particle Size

The particle size of the nucleic acid lipid particles was measured by the same method as that in <Preparation of lipid particles>.

Evaluation of Encapsulation Rate of siRNA (Quantification of Total Nucleic Acid Concentration)

A 3 mol/L aqueous sodium acetate solution (30 μL) and 9 μL of glycogen were added to 60 μL of the lipid particles retaining nucleic acids, and then 1.5 mL of ethanol was added thereto such that only the nucleic acids were precipitated while the lipid was dissolved. Then, the supernatant was removed by centrifugation. After the precipitates were air-dried for 15 minutes or longer, water was added thereto such that the precipitates were redissolved, and the concentration thereof was measured using Nanodrop NF1000 (Thermo Fisher Scientific), thereby quantifying the total nucleic acid concentration.

(Quantification of Nucleic Acid Concentration in Outer Water Phase)

The nucleic acid concentration was quantified using a Quant-iT RiboGreen RNA Assay Kit (Thermo Fisher Scientific) according to the protocol. First, a 20×TE buffer included in the above kit was diluted with water, thereby obtaining a 1×TE buffer. TE represents Tris/EDTA (ethylenediaminetetraacetic acid). In order to quantify only the nucleic acid in the outer water phase, the dispersion liquid of lipid particles retaining nucleic acids was diluted 10,000× with the 1×TE buffer.

The 10,000× diluted dispersion liquid of lipid particles (100 μL) was put in a 96-well plate, then 100 μL of a RiboGreen reagent (reagent included in the Quanti-iT Ribogreen RNA Assay Kit described above) diluted 2000× with the 1×TE buffer was added to a sample, and fluorescence (excitation wavelength: 485 nm, fluorescence wavelength: 535 nm) was measured using a plate reader Infinit EF200 (TECAN), thereby quantifying the nucleic acid concentration in the outer water phase.

(Calculation of Encapsulation Rate)

By using the total nucleic acid concentration obtained through the above steps and the quantified nucleic acid concentration in the outer water phase, the nucleic acid encapsulation rate of the nucleic acid lipid particles was calculated according to the following Equation. Nucleic acid encapsulation rate (%)=(total nucleic acid concentration−nucleic acid concentration in outer water phase)/total nucleic acid concentration×100 The results are shown in Table 2.

TABLE 2

Data on nucleic acid encapsulation rate and particle size of nucleic acid-containing lipid particles

| Used compound | Particle size (nm) | Nucleic acid encapsulation rate |
| --- | --- | --- |
| Reference Example 1 | 69.6 | 81% |
| Reference Example 2 | 118.4 | 85% |
| Comparative Example 3 | 72.4 | 80% |
| Comparative Example 4 | 62.8 | 77% |
| Comparative Example 5 | 75.1 | 87% |
| Comparative Example 6 | 81.9 | 89% |
| Comparative Example 7 | 71.9 | 87% |
| Comparative Example 8 | 63.1 | 59% |
| Comparative Example 9 | 58.4 | 84% |
| Example 1 | 66.4 | 84% |
| Example 2 | 80.5 | 78% |
| Example 3 | 83.6 | 100% |
| Example 4 | 66.1 | 81% |
| Example 5 | 73.8 | 78% |
| Example 6 | 113.5 | 78% |
| Example 7 | 98.6 | 84% |
| Example 8 | 81.4 | 83% |
| Example 9 | 79.5 | 92% |
| Example 10 | 159.9 | 80% |
| Example 11 | 217.2 | 84% |
| Example 12 | 254.2 | 100% |
| Example 13 | 140.3 | 88% |
| Example 14 | 219.0 | 76% |
| Example 15 | 122.8 | 83% |
| Example 16 | 113.4 | 90% |
| Example 20 | 101.6 | 84% |
| Example 21 | 78.0 | 78% |
| Example 22 | 69.3 | 69% |
| Example 23 | 69.2 | 85% |
| Example 24 | 62.0 | 88% |
| Example 25 | 68.5 | 76% |
| Example 26 | 209.8 | 97% |
| Example 27 | 75.2 | 75% |
| Example 28 | 76.4 | 75% |
| Example 29 | 70.1 | 77% |
| Example 30 | 69.8 | 78% |
| Example 31 | 67.9 | 78% |
| Example 32 | 71.6 | 78% |
| Example 33 | 67.9 | 87% |
| Example 34 | 74.6 | 84% |
| Example 35 | 80.1 | 87% |
| Example 36 | 73.4 | 85% |
| Example 37 | 80.4 | 85% |
| Example 38 | 94.2 | 87% |
| Example 39 | 78.3 | 88% |
| Example 40 | 73.7 | 75% |
| Example 41 | 69.5 | 77% |
| Example 42 | 70 | 78% |
| Example 43 | 74.5 | 78% |
| Example 44 | 69.4 | 59% |
| Example 45 | 71.7 | 76% |
| Example 46 | 71 | 80% |
| Example 47 | 72.3 | 74% |
| Example 48 | 73.9 | 81% |
| Example 49 | 74.3 | 80% |
| Example 50 | 65.6 | 79% |
| Example 51 | 69 | 76% |
| Example 52 | 79.9 | 80% |
| Example 53 | 81 | 78% |
| Example 54 | 88.5 | 82% |
| Example 55 | 70.5 | 85% |
| Example 56 | 70.8 | 83% |
| Example 57 | 77.9 | 79% |
| Example 58 | 81.5 | 77% |
| Example 59 | 80.6 | 77% |
| Example 60 | 83.4 | 84% |
| Example 61 | 60.9 | 75% |
| Example 62 | 47.1 | 76% |
| Example 63 | 65.8 | 79% |
| Example 64 | 61.5 | 75% |
| Example 65 | 83.3 | 69% |
| Example 66 | 69.8 | 73% |
| Example 67 | 69.4 | 70% |
| Example 68 | 70.7 | 97% |
| Example 69 | 67.6 | 98% |
| Example 70 | 76.3 | 72% |
| Example 71 | 68.5 | 77% |
| Example 72 | 74.2 | 81% |
| Example 73 | 66.8 | 78% |
| Example 74 | 75.7 | 70% |
| Example 75 | 65.4 | 76% |
| Example 76 | 69.7 | 76% |
| Example 77 | 81.9 | 88% |
| Example 78 | 71.7 | 75% |
| Example 79 | 65.5 | 81% |
| Example 80 | 98.7 | 61% |
| Example 81 | 102.6 | 49% |
| Example 82 | 77 | 78% |
| Example 83 | 83.6 | 82% |
| Example 84 | 81 | 79% |
| Example 85 | 246.6 | 86% |
| Example 86 | 67.1 | 74% |
| Example 87 | 69.2 | 79% |
| Example 88 | 74.6 | 81% |
| Example 89 | 68.2 | 83% |
| Example 90 | 169.3 | 60% |
| Example 91 | 75.0 | 69% |
| Example 92 | 90.5 | 73% |
| Example 93 | 70.4 | 70% |
| Example 94 | 72.7 | 76% |
| Example 95 | 95.5 | 83% |
| Example 96 | 72.9 | 88% |
| Example 97 | 142 | 82% |
| Example 98 | 74.9 | 82% |
| Example 99 | 68.9 | 81% |
| Example 100 | 76.7 | 82% |
| Example 101 | 177.3 | 68% |
| Example 102 | 147.2 | 70% |
| Example 103 | 64.3 | 80% |
| Example 104 | 76.6 | 81% |
| Example 105 | 100 | 81% |
| Example 106 | 62.4 | 80% |
| Example 107 | 64.8 | 78% |
| Example 108 | 78.7 | 81% |
| Example 109 | 65.7 | 91% |
| Example 110 | 60.7 | 87% |
| Example 111 | 63.9 | 93% |
| Example 112 | 68.6 | 79% |
| Example 113 | 67.8 | 82% |
| Example 114 | 80.1 | 69% |
| Example 115 | 88.6 | 69% |
| Example 116 | 76.3 | 73% |
| Example 117 | 77.3 | 90% |
| Example 118 | 93.6 | 90% |
| Example 119 | 67.8 | 89% |
| Example 120 | 66.5 | 90% |
| Example 121 | 63.2 | 91% |
| Example 122 | 69.5 | 83% |
| Example 123 | 257 | 66% |
| Example 124 | 68.3 | 69% |
| Example 125 | 73.8 | 76% |
| Example 126 | 66.8 | 75% |
| Example 127 | 80.7 | 71% |
| Example 128 | 255 | 62% |
| Example 129 | 70.2 | 63% |
| Example 130 | 64.9 | 66% |
| Example 131 | 291 | 41% |

TABLE 2-continued

Data on nucleic acid encapsulation rate and particle size of nucleic acid-containing lipid particles

| Used compound | Particle size (nm) | Nucleic acid encapsulation rate |
|---|---|---|
| Example 132 | 98.4 | 76% |
| Example 133 | 75.8 | 78% |

As is evident from the results in Table 2, the prepared nucleic acid lipid particles contain siRINA encapsulated in the lipid particles (the encapsulation rate was 60%~, some of the particles had a high encapsulation rate that was equal to or higher than 70%, 80%, or 90%), and the average particle size thereof was about 50 to 250 nm.

<Evaluation of Target Reporter Protein Knockdown Rate in Cell>

The nucleic acid lipid particles prepared by the same method as that in <Preparation of nucleic acid lipid particles> by using the compounds described in Table 3 were evaluated by reporter assay by the following method.

[Transfection of Cell with Lipid Particles]

By using pGL4.50 Luc2 (E1310 Promega), DMS273 cells (human small cell lung cancer) (European Collection of Authenticated Cell Cultures) constantly expressing Luc were prepared. RPMI (Gibco) (10% FBS (Gibco), 1% Penicillin-Streptomycin (Gibco), and 200 µg/mL Hygromycin (Wako)) was used as a culture medium. DMS273 cells ($2.0 \times 10^3$) constantly expressing luciferase (Luc) were seeded in a 96-well plate and cultured in a 5% $CO_2$ incubator for 24 hours, and then the medium was replaced. Then, 10 µL of each of the dispersion liquids of lipid particles diluted with PBS (Gibco) to yield a concentration of 1 to 1,000 nmol/L was added to the 96-well plate, and the final concentration was adjusted to 0.1 to 100 nmol/L (total amount of liquid: 110 µl). Thereafter, the cells were cultured in a 5% $CO_2$ incubator for 24 hours, the medium was then replaced, and the cells were further cultured for 24 hours.

[Viable Cell Count]

After the culturing, the proportion of viable cells after the transfection was quantified using a Cell Counting Kit-8 (Dojindo) according to the protocol. The cell counting kit (10 µL) was added to each well, and the cells were cultured in a 5% $CO_2$ incubator for 4 hours. Then, the absorbance at 450 nm was measured using EnVision (PerkinElmer), thereby determining the viable cell count. The viability was calculated based on the following equation.

Cell viability (%) = absorbance of well administered with sample / absorbance of well adminstered with $PBS \times 100$

[Reporter Protein Assay]

After the viable cell count was determined, the expression amount of Luc was quantified using a Steady Glo assay kit (Promega), and the knockdown efficiency was calculated according to the following equation. Then, the IC50 concentration at which the expression amount of Luc was knocked down to 50% was calculated.

Knockdown efficiency (%) =

(expression amount of $Luc$ in transfection group/cell viability) / (expression amount of $Luc$ in untreated group/cell viability) $\times 100$ The results are shown in Table 3.

TABLE 3

Results of reporter protein assay

| Used compound | IC50(nmol/L) |
|---|---|
| Reference Example 1 | 47 |
| Reference Example 2 | 59 |
| Comparative Example 3 | >100 |
| Comparative Example 4 | >100 |
| Comparative Example 5 | >100 |
| Comparative Example 6 | >100 |
| Comparative Example 7 | >100 |
| Example 1 | 13 |
| Example 3 | 43 |
| Example 4 | 10 |
| Example 7 | 14 |
| Example 9 | 21 |
| Example 20 | 15 |
| Example 23 | 39 |
| Example 24 | 41 |
| Example 25 | 16 |
| Example 26 | 30 |
| Example 27 | 31 |
| Example 29 | 19 |
| Example 30 | 24 |
| Example 31 | 38 |
| Example 33 | 12 |
| Example 36 | 11 |
| Example 40 | 15 |
| Example 41 | 14 |
| Example 43 | 19 |
| Example 45 | 22 |
| Example 46 | 17 |
| Example 47 | 19 |
| Example 48 | 43 |
| Example 50 | 13 |
| Example 51 | 37 |
| Example 52 | 27 |
| Example 53 | 9 |
| Example 56 | 19 |
| Example 60 | 1 |
| Example 61 | 7 |
| Example 64 | 5 |
| Example 66 | 28 |
| Example 67 | 22 |
| Example 68 | 37 |
| Example 69 | 28 |
| Example 70 | 24 |
| Example 72 | 31 |
| Example 73 | 24 |
| Example 74 | 22 |
| Example 75 | 8 |
| Example 76 | 18 |
| Example 78 | 16 |
| Example 84 | 30 |
| Example 87 | 34 |
| Example 88 | 23 |
| Example 93 | 22 |
| Example 94 | 39 |
| Example 100 | 26 |
| Example 101 | 39 |
| Example 102 | 27 |
| Example 103 | 14 |
| Example 104 | 4 |
| Example 105 | 28 |
| Example 106 | 37 |
| Example 107 | 23 |
| Example 109 | 26 |
| Example 110 | 17 |
| Example 111 | 42 |
| Example 112 | 18 |
| Example 113 | 21 |
| Example 116 | 25 |

TABLE 3-continued

Results of reporter protein assay

| Used compound | IC50(nmol/L) |
|---|---|
| Example 118 | 35 |
| Example 119 | 31 |
| Example 120 | 27 |
| Example 121 | 39 |
| Example 122 | 19 |
| Example 129 | 41 |

From the results in Table 3, it as been revealed that the lipid particles using the compound according to an embodiment of the present invention have activity (IC50) appropriate for the lipid particles to be used as an inhibitor. That is, it has been revealed that the lipid particles containing the compound according to the embodiment of the present invention as a lipid can efficiently deliver nucleic acids into cells. This result shows that the lipid particles have the possibility of being used in drugs and the like.

<Measurement of Factor VII (FVII) Protein>

The Factor VII (FVII) protein was measured according to the method described in Nature Biotechnology (2010) 28, 172-176. C57BL6/J mice were randomly grouped (n=3). A dispersion liquid of nucleic acid lipid particles was prepared by the same method as that in <Preparation of nucleic acid lipid particles>, except that FVII-siRNA having the sequence described in Molecular Therapy (2009) 17, p. 878 was used instead of Luc-siRNA. The dispersion liquid was administered to the caudal vein of the mice at a dosage of 0.1 mg/kg. For comparison, PBS at the same volume was administered to the caudal vein of the mice. Twenty four hours after the administration, blood was collected from the caudal vena cava, thereby obtaining plasma. The amount of FVII protein was quantified using the obtained plasma and a Biophen FVII assay kit (Aniara).

The FVII amount in the plasma sample of each individual in the PBS administration group was regarded as 100%, and the ratio of the FVII amount in the plasma sample of each individual to 100% was adopted as a measurement value. The results are shown in Table 5.

TABLE 4

Data on particle size, nucleic acid encapsulation rate, FVII protein quantification of nucleic acid-containing lipid particles

| Used compound | Particle size (nm) | Nucleic acid encapsulation rate | Relative amount of FVII protein (%) |
|---|---|---|---|
| Comparative Example 8 | 63.4 | 78% | 58 |
| Comparative Example 9 | 60 | 71% | 44 |
| Example 23 | 75.4 | 57% | 39 |
| Example 24 | 66.2 | 67% | 24 |
| Example 30 | 73.6 | 88% | 5 |
| Example 31 | 73.5 | 80% | 14 |
| Example 37 | 74.5 | 100% | 17 |
| Example 38 | 67.9 | 100% | 16 |
| Example 40 | 66.6 | 75% | 3 |
| Example 41 | 74.2 | 74% | 18 |
| Example 42 | 68.1 | 70% | 9 |
| Example 43 | 75.3 | 87% | 11 |
| Example 45 | 71.5 | 79% | 16 |
| Example 46 | 68.4 | 84% | 18 |
| Example 47 | 79.4 | 82% | 11 |
| Example 48 | 70.1 | 84% | 20 |
| Example 50 | 65.4 | 84% | 11 |
| Example 51 | 71 | 84% | 19 |
| Example 52 | 73.1 | 83% | 19 |
| Example 56 | 72.5 | 79% | 3 |
| Example 58 | 78.6 | 82% | 14 |
| Example 59 | 72.9 | 79% | 10 |
| Example 61 | 67.7 | 78% | 8 |
| Example 62 | 72.2 | 85% | 3 |
| Example 64 | 65.7 | 86% | 10 |
| Example 65 | 88.9 | 100% | 11 |
| Example 66 | 85.4 | 98% | 17 |
| Example 67 | 82.2 | 86% | 5 |
| Example 68 | 84.5 | 91% | 9 |
| Example 69 | 86.8 | 97% | 6 |
| Example 70 | 85.7 | 98% | 6 |
| Example 71 | 80.1 | 92% | 4 |
| Example 72 | 72.4 | 85% | 6 |
| Example 73 | 71.2 | 82% | 1 |
| Example 74 | 76.7 | 79% | 4 |
| Example 75 | 79.1 | 83% | 17 |
| Example 76 | 73.4 | 80% | 4 |
| Example 77 | 81.2 | 76% | 3 |
| Example 78 | 74.2 | 78% | 10 |
| Example 83 | 85.4 | 88% | 13 |
| Example 86 | 69.2 | 88% | 15 |
| Example 87 | 69.3 | 87% | 3 |
| Example 88 | 78.7 | 83% | 2 |
| Example 89 | 77.3 | 94% | 8 |
| Example 91 | 66.5 | 76% | 9 |
| Example 93 | 67.8 | 73% | 7 |
| Example 94 | 86.1 | 75% | 8 |
| Example 98 | 68.3 | 76% | 2 |
| Example 99 | 72.3 | 79% | 3 |
| Example 100 | 85.1 | 80% | 2 |
| Example 103 | 69.8 | 79% | 2 |
| Example 104 | 85.8 | 69% | 1 |
| Example 105 | 102.4 | 73% | 7 |
| Example 106 | 66.4 | 85% | 2 |
| Example 107 | 70.6 | 83% | 1 |
| Example 108 | 78.8 | 90% | 3 |
| Example 109 | 62.7 | 86% | 3 |
| Example 110 | 66.1 | 85% | 2 |
| Example 111 | 70.5 | 88% | 2 |
| Example 112 | 74.2 | 100% | 3 |
| Example 113 | 66.1 | 100% | 4 |
| Example 117 | 85.4 | 89% | 12 |
| Example 118 | 80.5 | 64% | 9 |
| Example 119 | 66.3 | 69% | 5 |
| Example 120 | 68.1 | 66% | 6 |
| Example 121 | 65.8 | 70% | 10 |
| Example 122 | 80.7 | 84% | 3 |
| Example 124 | 73.4 | 84% | 8 |
| Example 125 | 77.8 | 80% | 5 |
| Example 126 | 74.2 | 85% | 9 |
| Example 129 | 76.4 | 58% | 4 |
| Example 130 | 74.1 | 68% | 9 |
| Example 133 | 75.8 | 78% | 16 |

As is evident from the above results, the lipid particles containing the compound according to an embodiment of the present invention showed a strong FVII inhibitory activity. Therefore, it has been revealed that the lipid particles containing the compound according to the embodiment of the present invention as a lipid can efficiently deliver nucleic acids into cells and are useful as nucleic acid lipid particles capable of inhibiting gene expression. This result shows that the lipid particles have the possibility of being used in drugs and the like.

What is claimed is:
1. Lipid particles comprising:
   a compound represented by Formula (1) or a salt thereof; and
   a nucleic acid,

(1)

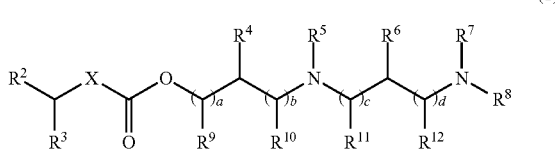

wherein in the formula, X represents —NR$^1$— or —O—, R$^1$ represents a hydrogen atom, a hydrocarbon group having 6 to 24 carbon atoms, or a group represented by R$^{21}$-L$^1$-R$^{22}$—, R$^{21}$ represents a hydrocarbon group having 1 to 24 carbon atoms, L$^1$ represents —O(CO)O—, —O(CO)—, —(CO)O—, —O—, or a group represented by the following formula,

R$^{22}$ represents a divalent hydrocarbon linking group having 1 to 18 carbon atoms, R$^2$ and R$^3$ each independently represent a hydrogen atom, a hydrocarbon group having 3 to 24 carbon atoms, or a group represented by R$^{31}$-L$^2$-R$^{32}$—, R$^{31}$ represents a hydrocarbon group having 1 to 24 carbon atoms, L$^2$ represents —O(CO)O—, —O(CO)—, —(CO)O—, —O—, or a group represented by the following formula,

R$^{32}$ represents a divalent hydrocarbon linking group having 1 to 18 carbon atoms, R$^4$, R$^5$, R$^6$, R$^7$, R$^8$, R$^9$, R$^{10}$, R$^{11}$, and R$^{12}$ each independently represent a hydrogen atom or an alkyl group having 1 to 18 carbon atoms that may be substituted, groups in any one or more pairs among R$^4$ and R$^5$, R$^{10}$ and R$^5$, R$^5$ and R$^{12}$, R$^4$ and R$^6$, R$^5$ and R$^6$, R$^6$ and R$^7$, R$^6$ and R$^{10}$, R$^{12}$ and R$^7$, and R$^7$ and R$^8$ may be linked to each other to form a 4- to 7-membered ring which may contain an O atom, a substituent on the alkyl group having 1 to 18 carbon atoms that may be substituted is a hydroxyl group, a carboxyl group, an amino group represented by —NR$^{45}$R$^{46}$, a substituted or unsubstituted aryl group, a substituted or unsubstituted heteroaryl group, or a group represented by —O(CO)O—R$^{41}$, —O(CO)—R$^{42}$, —(CO)O—R$^{43}$, or —O—R$^{44}$, R$^{41}$, R$^{42}$, R$^{43}$, R$^{44}$, R$^{45}$, and R$^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by —NR$^{45}$R$^{46}$, or a group represented by —O(CO)O—R$^{41}$, —O(CO)—R$^{42}$, —(CO)O—R$^{43}$, or —O—R$^{44}$, R$^{41}$, R$^{42}$, R$^{43}$, R$^{44}$, R$^{45}$, and R$^{46}$ each independently represent a hydrocarbon group having 1 to 18 carbon atoms, a, b, c, and d each independently represent an integer of 0 to 3, a+b is equal to or greater than 1, and c+d is equal to or greater than 1.

2. The lipid particles according to claim 1, further comprising a lipid.

3. The lipid particles according to claim 2, wherein the lipid is at least one kind of lipid selected from the group consisting of a neutral lipid and a lipid having a nonionic hydrophilic polymer.

4. The lipid particles according to claim 1, further comprising a sterol.

5. The lipid particles according to claim 1,
wherein X represents —NR$^1$—, and R$^1$ has the same definition as R$^1$ in claim 1.

6. The lipid particles according to claim 1,
wherein X represents —NR$^1$—, R$^1$ represents a hydrocarbon group having 6 to 24 carbon atoms, or a group represented by R$^{21}$-L$^1$-R$^{22}$—, R$^{21}$, L$^1$, and R$^{22}$ have the same definitions as R$^{21}$, L$^1$, and R$^{22}$ in claim 1 respectively;
one of R$^2$ and R$^3$ represents a hydrogen atom and the other represents a hydrocarbon group having 3 to 24 carbon atoms or a group represented by R$^{31}$-L$^2$-R$^{32}$—, and R$^{31}$, L$^2$, and R$^{32}$ have the same definitions as R$^{31}$, L$^2$, and R$^{32}$ in claim 1 respectively.

7. The lipid particles according to claim 1,
wherein the compound represented by Formula (1) is a compound represented by Formula (1-1), (1-1)

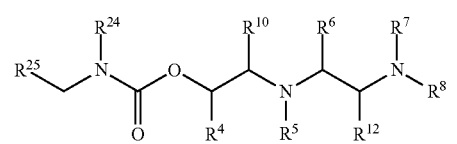

wherein R$^{24}$ represents a hydrogen atom, a hydrocarbon group having 6 to 24 carbon atoms, or a group represented by R$^{21}$-L$^1$-R$^{22}$—, R$^{21}$ represents a hydrocarbon group having 1 to 24 carbon atoms, L$^1$ represents —O(CO)O—, —O(CO)—, —(CO)O—, —O—, or a group represented by the following formula,

R$^{22}$ represents a divalent hydrocarbon linking group having 1 to 18 carbon atoms, R$^{25}$ represents a hydrogen atom, a hydrocarbon group having 3 to 24 carbon atoms, or a group represented by R$^{31}$-L$^2$-R$^{32}$—, R$^{31}$ represents a hydrocarbon group having 1 to 24 carbon atoms, L$^2$ represents —O(CO)O—, —O(CO)—, —(CO)O—, —O—, or a group represented by the following formula,

R$^{32}$ represents a divalent hydrocarbon linking group having 1 to 18 carbon atoms, $R^4$, $R^5$, $R^6$, $R^7$, $R^8$, $R^{10}$, and $R^{12}$ each independently represent a hydrogen atom or an alkyl group having 1 to 18 carbon atoms that may be substituted, groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other to form a 4- to 7-membered ring which may contain an O atom, a substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms.

8. The lipid particles according to claim 1,
wherein X represents —O—.

9. The lipid particles according to claim 1,
wherein X represents —O—,
$R^2$ and $R^3$ each independently represent a hydrocarbon group having 3 to 24 carbon atoms or a group represented by $R^{31}$-$L^2$-$R^{32}$—, and $R^{31}$, $L^2$, and $R^{32}$ have the same definitions as $R^{31}$, $L^2$, and $R^{32}$ in claim 1 respectively.

10. The lipid particles according to claim 1,
wherein $R^4$, $R^6$, $R^9$, $R^{10}$, $R^{11}$, and $R^{12}$ each represent a hydrogen atom.

11. The lipid particles according to claim 1,
wherein $R^2$ and $R^3$ each independently represent a hydrogen atom, a hydrocarbon group having 6 to 24 carbon atoms, or a group represented by $R^{31}$-$L^2$-$R^{32}$—.

12. The lipid particles according to claim 1,
wherein X represents —O—,
$R^2$, $R^3$, $R^{31}$, $L^2$, and $R^{32}$ have the same definitions as $R^2$, $R^3$, $R^{31}$, $L^2$, and $R^{32}$ in claim 1 respectively,
$R^4$, $R^5$, $R^6$, $R^7$, $R^8$, $R^9$, $R^{10}$, $R^{11}$, and $R^{12}$ each independently represent a hydrogen atom or an alkyl group having 1 to 18 carbon atoms that may be substituted,
a substituent on the alkyl group having 1 to 18 carbon atoms that may be substituted and the substituent on the substituted or unsubstituted aryl group and on the substituted or unsubstituted heteroaryl group have the same definitions as those in claim 1,
a+b is 1, and c+d is 1 or 2.

13. The lipid particles according to claim 1,
wherein the compound represented by Formula (1) is a compound represented by Formula (2),

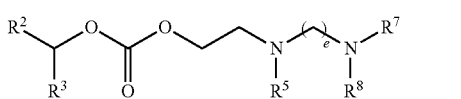

(2)

in the formula, $R^2$ and $R^3$ each independently represent a hydrogen atom, a hydrocarbon group having 3 to 24 carbon atoms, or a group represented by $R^{31}$-$L^2$-$R^{32}$—,
$R^{31}$ represents a hydrocarbon group having 1 to 24 carbon atoms,
$L^2$ represents —O(CO)O—, —O(CO)—, —(CO)O—, —O—, or a group represented by the following formula,

$R^{32}$ represents a divalent hydrocarbon linking group having 1 to 18 carbon atoms,
$R^5$ represents a hydrogen atom or an alkyl group having 1 to 18 carbon atoms that may be substituted,
$R^7$ and $R^8$ each independently represent a hydrogen atom or an alkyl group having 1 to 18 carbon atoms that may be substituted,
a substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, and e represents 2 or 3.

14. The lipid particles according to claim 13,
wherein $R^7$ and $R^8$ each independently represent a hydrogen atom or an alkyl group having 1 to 18 carbon atoms,
a substituent on the alkyl group having 1 to 18 carbon atoms that may be substituted is a hydroxyl group, a substituted or unsubstituted aryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$ and $R^{46}$ each independently represent a hydrocarbon group having 1 to 18 carbon atoms,
a substituent on the substituted or unsubstituted aryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$ and $R^{46}$ each independently represent a hydrocarbon group having 1 to 18 carbon atoms.

15. The lipid particles according to claim 13,
wherein $R^2$ and $R^3$ each independently represent a hydrocarbon group having 3 to 24 carbon atoms or a group represented by $R^{31}$-$L^2$-$R^{32}$—,
$L^2$ represents —O(CO)— or —(CO)O—,
$R^7$ and $R^8$ each independently represent a hydrogen atom or an alkyl group having 1 to 18 carbon atoms, a substituent on the alkyl group having 1 to 18 carbon atoms that may be substituted is an unsubstituted aryl group, —O(CO)—$R^{42}$, or —(CO)O—$R^{43}$, and $R^{42}$ and $R^{43}$ each independently represent a hydrocarbon group having 1 to 18 carbon atoms.

16. The lipid particles according to claim 13,
wherein $R^2$ and $R^3$ each independently represent a hydrogen atom or a hydrocarbon group having 3 to 24 carbon atoms,
$R^7$ and $R^8$ each independently represent a hydrogen atom or an alkyl group having 1 to 18 carbon atoms,
a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

17. The lipid particles according to claim 13,
wherein at least one of $R^2$ or $R^3$ represents a group represented by $R^{31}$-$L^2$-$R^{32}$—,
$L^2$ represents —O(CO)— or —(CO)O—,
$R^7$ and $R^8$ each independently represent a hydrogen atom or an alkyl group having 1 to 18 carbon atoms,
a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

18. The lipid particles according to claim 13,
wherein $R^2$ and $R^3$ each independently represent a group represented by $R^{31}$-$L^2$-$R^{32}$—,
$L^2$ represents —O(CO)— or —(CO)O—,
$R^7$ and $R^8$ each independently represent a hydrogen atom or an alkyl group having 1 to 18 carbon atoms,
a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

19. The lipid particles according to claim 13,
wherein one of $R^2$ and $R^3$ represents a group represented by $R^{31}$-$L^2$-$R^{32}$— and the other represents a hydrocarbon group having 3 to 24 carbon atoms,
$L^2$ represents —O(CO)— or —(CO)O—,
$R^7$ and $R^8$ each independently represent a hydrogen atom or an alkyl group having 1 to 18 carbon atoms,
a substituent on the alkyl group having 1 to 18 carbon atoms that may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

20. The lipid particles according to claim 13,
wherein one of $R^2$ and $R^3$ represents a group represented by $R^{31}$-$L^2$-$R^{32}$— and the other represents a hydrocarbon group having 6 carbon atoms,
$L^2$ represents —O(CO)— or —(CO)O—,
$R^7$ and $R^8$ each independently represent a hydrogen atom or an alkyl group having 1 to 18 carbon atoms,
a substituent on the alkyl group having 1 to 18 carbon atoms that may be substituted is a group represented by —O(CO)—$R^{42}$ or —(CO)O—$R^{43}$, and $R^{42}$ and $R^{43}$ each independently represent a hydrocarbon group having 1 to 18 carbon atoms.

21. The lipid particles according to claim 13,
wherein one of $R^2$ and $R^3$ represents a group represented by $R^{31}$-$L^2$-$R^{32}$— and the other represents a hydrocarbon group having 6 carbon atoms,
$L^2$ represents —O(CO)— or —(CO)O—,
$R^5$ represents a hydrogen atom or an alkyl group having 1 to 18 carbon atoms,
$R^7$ and $R^8$ each independently represent a hydrogen atom or an alkyl group having 1 to 18 carbon atoms.

22. The lipid particles according to claim 13,
wherein one of $R^2$ and $R^3$ represents a group represented by $R^{31}$-$L^2$-$R^{32}$— and the other represents a hydrocarbon group having 6 carbon atoms,
$L^2$ represents —O(CO)— or —(CO)O—,
$R^5$ represents a hydrogen atom or an alkyl group having 1 to 18 carbon atoms,
$R^7$ and $R^8$ each independently represent a hydrogen atom or an alkyl group having 1 to 18 carbon atoms,
e represents 2.

23. The lipid particles according to claim 13,
wherein one of $R^2$ and $R^3$ represents a group represented by $R^{31}$-$L^2$-$R^{32}$— and the other represents a hydrocarbon group having 3 to 5 carbon atoms,
$L^2$ represents —O(CO)— or —(CO)O—,
$R^5$ represents a hydrogen atom or an alkyl group having 1 to 18 carbon atoms,
$R^7$ and $R^8$ each independently represent a hydrogen atom or an alkyl group having 1 to 18 carbon atoms.

24. The lipid particles according to claim 13,
wherein one of $R^2$ and $R^3$ represents a group represented by $R^{31}$-$L^2$-$R^{32}$— and the other represents a hydrocarbon group having 6 carbon atoms,
$L^2$ represents —O(CO)— or —(CO)O—,
$R^5$ represents a hydrogen atom or an alkyl group having 1 to 18 carbon atoms that is substituted,
$R^7$ and $R^8$ each independently represent a hydrogen atom or an alkyl group having 1 to 18 carbon atoms,
a substituent on the alkyl group having 1 to 18 carbon atoms that is substituted is a group represented by —O(CO)—$R^{42}$ or —(CO)O—$R^{43}$, and $R^{42}$ and $R^{43}$ each independently represent a hydrocarbon group having 1 to 18 carbon atoms.

25. The lipid particles according to claim 13,
wherein one of $R^2$ and $R^3$ represents a group represented by $R^{31}$-$L^2$-$R^{32}$— and the other represents a hydrocarbon group having 6 carbon atoms,
$L^2$ represents —O(CO)— or —(CO)O—,
$R^5$ represents a hydrogen atom or an alkyl group having 1 to 18 carbon atoms that is substituted,
$R^7$ and $R^8$ each independently represent a hydrogen atom or an alkyl group having 1 to 18 carbon atoms,
a substituent on the alkyl group having 1 to 18 carbon atoms that is substituted is a group represented by —O(CO)—$R^{42}$ or —(CO)O—$R^{43}$, and $R^{42}$ and $R^{43}$ each independently represent a hydrocarbon group having 1 to 18 carbon atoms,
e represents 2.

26. The lipid particles according to claim 1, wherein the compound represented by Formula (1) is selected from the following compounds:

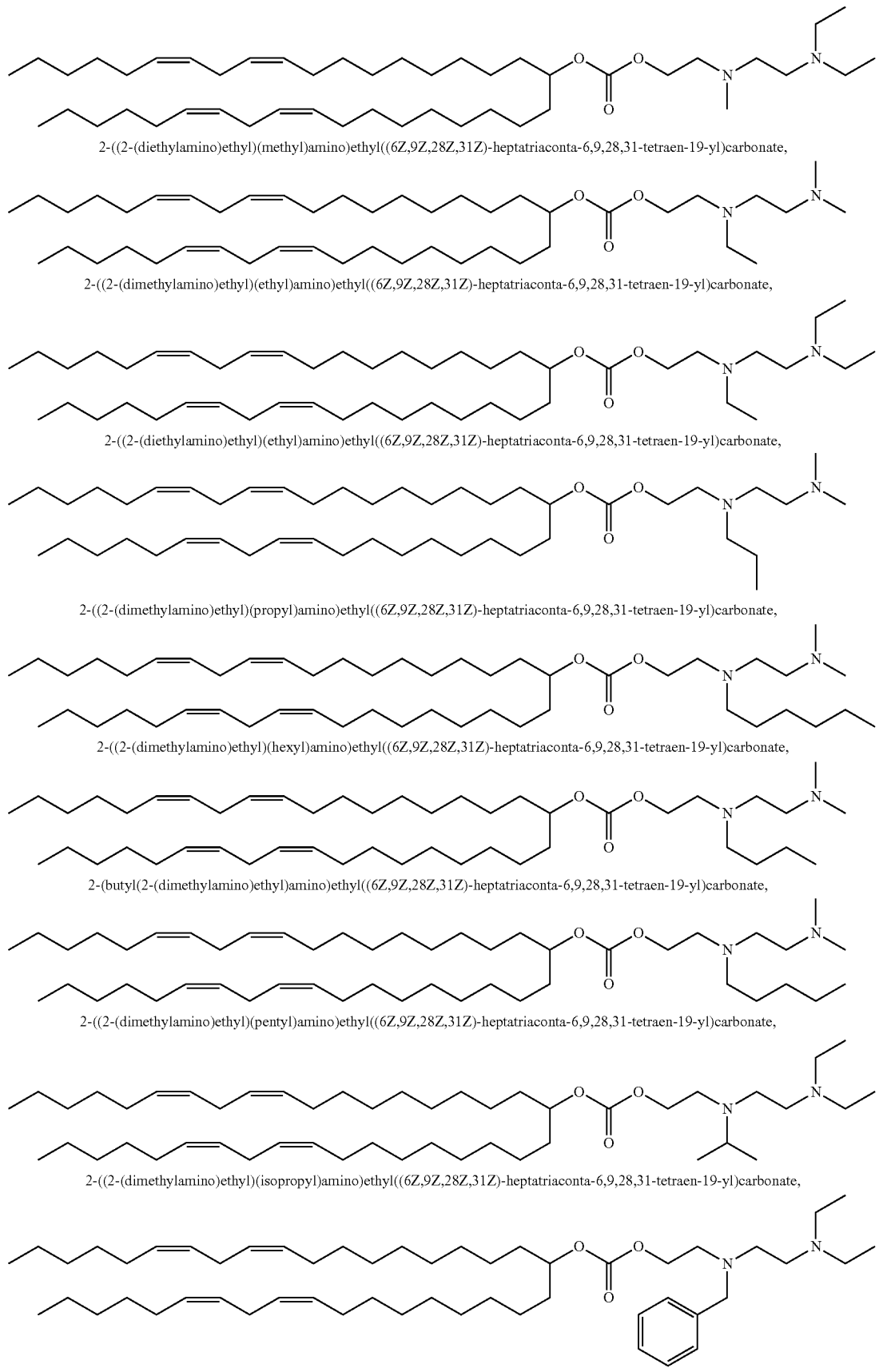

2-((2-(diethylamino)ethyl)(methyl)amino)ethyl((6Z,9Z,28Z,31Z)-heptatriaconta-6,9,28,31-tetraen-19-yl)carbonate, 2-((2-(dimethylamino)ethyl)(ethyl)amino)ethyl((6Z,9Z,28Z,31Z)-heptatriaconta-6,9,28,31-tetraen-19-yl)carbonate, 2-((2-(diethylamino)ethyl)(ethyl)amino)ethyl((6Z,9Z,28Z,31Z)-heptatriaconta-6,9,28,31-tetraen-19-yl)carbonate, 2-((2-(dimethylamino)ethyl)(propyl)amino)ethyl((6Z,9Z,28Z,31Z)-heptatriaconta-6,9,28,31-tetraen-19-yl)carbonate, 2-((2-(dimethylamino)ethyl)(hexyl)amino)ethyl((6Z,9Z,28Z,31Z)-heptatriaconta-6,9,28,31-tetraen-19-yl)carbonate, 2-(butyl(2-(dimethylamino)ethyl)amino)ethyl((6Z,9Z,28Z,31Z)-heptatriaconta-6,9,28,31-tetraen-19-yl)carbonate, 2-((2-(dimethylamino)ethyl)(pentyl)amino)ethyl((6Z,9Z,28Z,31Z)-heptatriaconta-6,9,28,31-tetraen-19-yl)carbonate, 2-((2-(dimethylamino)ethyl)(isopropyl)amino)ethyl((6Z,9Z,28Z,31Z)-heptatriaconta-6,9,28,31-tetraen-19-yl)carbonate, 2-(benzyl(2-(diethylamino)ethyl)amino)ethyl((6Z,9Z,28Z,31Z)-heptatriaconta-6,9,28,31-tetraen-19-yl)carbonate, 27. A nucleic acid drug, comprising the lipid particles according to claim 1.

28. A composition for delivery of a nucleic acid, comprising the lipid particles according to claim 1.

* * * * *